United States Patent
Jaykus et al.

(10) Patent No.: US 10,883,149 B2
(45) Date of Patent: Jan. 5, 2021

(54) APTAMERS WITH BINDING AFFINITY TO NOROVIRUS

(71) Applicant: North Carolina State University, Raleigh, NC (US)

(72) Inventors: Lee-Ann Jaykus, Durham, NC (US); Blanca Irene Escudero-Abarca, Raleigh, NC (US); Matthew D. Moore, Morrisville, NC (US); Helen Rawsthorne, Nottinghamshire (GB)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/379,952

(22) Filed: Apr. 10, 2019

(65) Prior Publication Data
US 2019/0233905 A1 Aug. 1, 2019

Related U.S. Application Data

(62) Division of application No. 15/317,002, filed as application No. PCT/US2015/035619 on Jun. 12, 2015, now Pat. No. 10,308,989.

(60) Provisional application No. 62/011,880, filed on Jun. 13, 2014.

(51) Int. Cl.
| | | |
|---|---|---|
| *C12Q 1/68* | (2018.01) | |
| *A61K 39/00* | (2006.01) | |
| *C12N 9/22* | (2006.01) | |
| *A61K 48/00* | (2006.01) | |
| *C12N 15/113* | (2010.01) | |
| *C12Q 1/70* | (2006.01) | |
| *B82Y 30/00* | (2011.01) | |
| *G01N 33/53* | (2006.01) | |
| *G01N 33/569* | (2006.01) | |
| *C12N 15/115* | (2010.01) | |
| *C12Q 1/6834* | (2018.01) | |

(52) U.S. Cl.
CPC .............. *C12Q 1/70* (2013.01); *B82Y 30/00* (2013.01); *C12N 15/115* (2013.01); *C12Q 1/6834* (2013.01); *G01N 33/5308* (2013.01); *G01N 33/56983* (2013.01); *C12N 2310/16* (2013.01)

(58) Field of Classification Search
CPC ............ C12Q 2545/101; C12Q 1/6851; C12Q 2521/301; C12Q 2525/301
See application file for complete search history.

(56) References Cited

U.S. PATENT DOCUMENTS

2012/0141980 A1   6/2012   Rossmanith et al.

FOREIGN PATENT DOCUMENTS

| WO | WO 2013/117746 A1 | 8/2013 |
| WO | WO2013117746 | * 8/2013 |

OTHER PUBLICATIONS

Atmar, R., et al., "Norovirus Vaccine against Experimental Human Norwalk Virus Illness," *The New England Journal of Medicine*, 2011, vol. 365(23), pp. 2178-2187.
Giamberardino, A., et al., "Ultrasensitive Norovirus Detection Using DNA Aptasensor Technology," *PLOS One*, 2013, vol. 8(11), pp. 1-9.
Lee, H., et al., "A sensitive method to detect *Escherichia coli* based on immumomagnetic separation and real-time PCR amplification of aptamers," *Biosensors and Bioelectronics*, 2009, vol. 24, pp. 3550-3555.
Song, K., et al., "Aptamers and Their Biological Applications," *Sensors*, 2012, vol. 12, pp. 612-631.

* cited by examiner

*Primary Examiner* — Barry A Chestnut
(74) *Attorney, Agent, or Firm* — Womble Bond Dickinson (US) LLP

(57) ABSTRACT

The instant disclosure provides norovirus-binding aptamers, compositions comprising such aptamers, and methods of using and producing such aptamers. The aptamers are useful, for example, for detecting the presence of norovirus in test samples, for capturing and/or concentrating norovirus from test samples, for evaluating the efficacy of therapeutic agents in patients diagnosed with a norovirus infection, and for evaluating the efficacy of norovirus vaccines.

15 Claims, 26 Drawing Sheets

Specification includes a Sequence Listing.

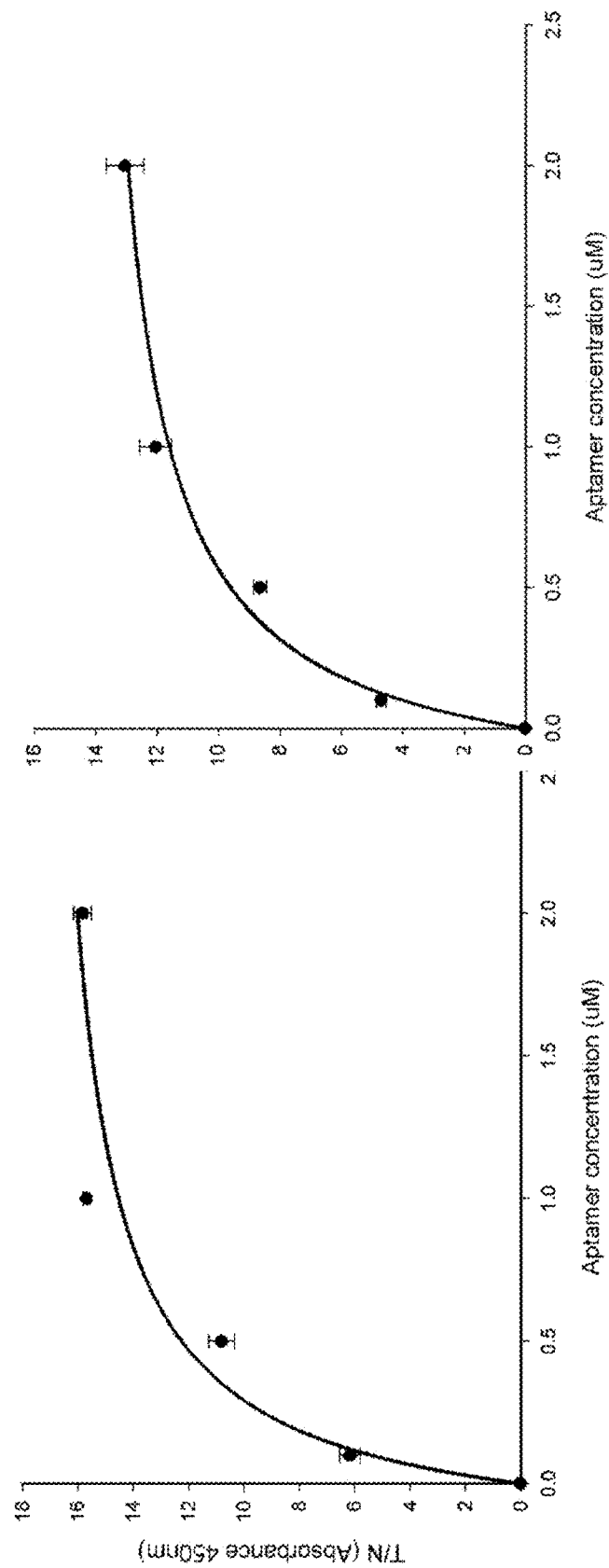
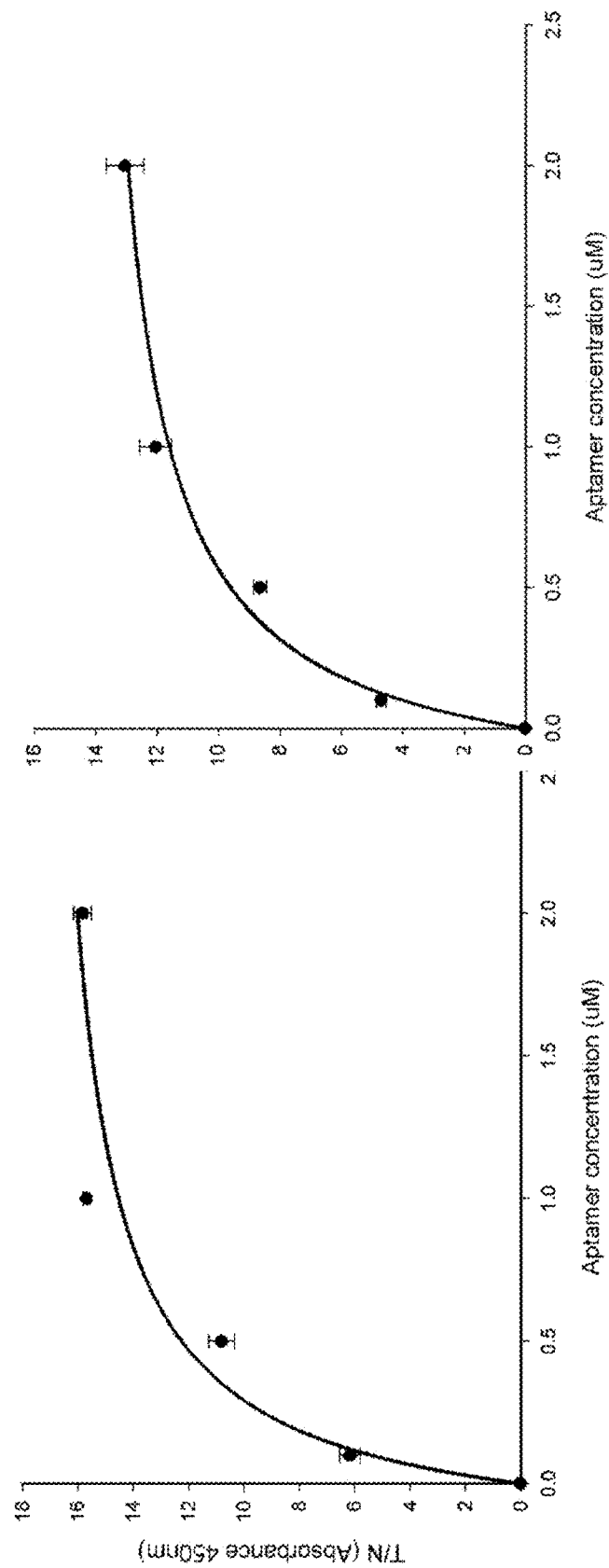
FIG. 5C
FIG. 5D

FIG. 9

APTAMERS WITH BINDING AFFINITY TO NOROVIRUS

CROSS REFERENCE TO RELATED APPLICATIONS

This application is a divisional application of U.S. application Ser. No. 15/317,002, which is a national stage filing under 35 U.S.C. 371 of PCT/US2015/035619 filed Jun. 12, 2015, which International Application was published by the International Bureau in English on Dec. 17, 2015, and application claims priority from U.S. Provisional Application No. 62/011,880, filed Jun. 13, 2014, which applications are hereby incorporated in their entirety by reference in this application.

FEDERALLY SPONSORED RESEARCH OR DEVELOPMENT

The present invention was made with United States Government support under grant number 2011-68003-30395 from USDA National Institute of Food and Agriculture, Agriculture and Food Research Initiative. The United States Government has certain rights in this invention.

SEQUENCE LISTING

A sequence listing is incorporated herein by reference in its entirety. The listing, in ASCII format, was created on Apr. 9, 2019, is named N61824_1450US_D1_-280_8_SEQLIST.txt and is 38.2 kilobytes in size.

BACKGROUND

Noroviruses are the most common cause of acute viral gastroenteritis worldwide (Glass et al., *N. Engl. J. Med.* 361:1776-1785 (2009)). These viruses, which are members of the Caliciviridae family, are transmitted by a variety of routes and frequently cause outbreaks in closed settings such as schools, nursing homes, and cruise ships. Noroviruses can also be transmitted through contaminated foods and water, and they are the leading cause of foodborne disease in the U.S. (Scallan et al., *Emerg. Infect. Dis.* 17:16-22 (2011)) and perhaps worldwide (Patel et al., *Emerg. Infect. Dis.* 14:1224-1231 (2008); Ahmed et al., *PLoS One* 8:e75922 (2013)). Low infectious dose, high virus concentrations in the feces and vomitus of infected individuals, lengthy environmental persistence, and resistance to many commonly used sanitizers and disinfectants all contribute to the high degree of transmissibility of noroviruses (Hall et al., *Emerg. Infect. Dis.* 19:1198-1205 (2013)).

Despite their public health significance, routine detection of noroviruses in community settings or in food and environmental samples is limited. First, there is no cell culture model to propagate these viruses. Second, noroviruses have tremendous antigenic diversity. This antigenic diversity has complicated the development of broadly reactive antibodies, meaning that enzyme immunoassays have poor sensitivity (Costantini et al., *J. Clin. Microbiol.* 48:2770-2778 (2010); Kele et al., *Diagn. Microbiol. Infect. Dis.* 70:475-478 (2011)). Detection of noroviruses in food and environmental samples is even more complicated because virus concentrations are so low in these samples that it is necessary to perform labor-intensive and inefficient pre-concentration steps prior to detection (Knight et al., *Crit. Rev. Microbiol.* 39:295-309 (2013)).

SUMMARY OF THE CLAIMED INVENTION

Compositions are provided comprising isolated norovirus-binding aptamers. Also provided are methods using norovirus-binding aptamers. Such methods include methods of detecting the presence of at least one norovirus strain in a test sample, methods of capturing at least one norovirus from a test sample, methods of evaluating the efficacy of a therapeutic agent in a patient diagnosed with a norovirus infection with at least one norovirus strain, and methods of evaluating the efficacy of a norovirus vaccine. Also provided are mixtures comprising isolated norovirus-binding aptamers and kits for detection of at least one norovirus strain comprising isolated norovirus-binding aptamers.

The invention provides methods of detecting the presence of at least one norovirus strain in a test sample, the methods comprising: (a) contacting said test sample with a norovirus-binding aptamer comprising a norovirus-binding motif and/or any one of SEQ ID NOS: 1-78 or variants thereof having at least 90% sequence identity and having norovirus-binding activity; and (b) detecting the presence of said norovirus-binding aptamer bound to norovirus in said test sample, wherein detection of bound aptamer indicates the presence of at least one norovirus strain. The invention provides methods of detecting the presence of at least one norovirus strain in a test sample, the methods comprising: (a) contacting said test sample with a norovirus-binding aptamer comprising a norovirus-binding motif and/or any one of SEQ ID NOS: 1-78 and 176-181 or variants thereof having at least 90% sequence identity and having norovirus-binding activity; and (b) detecting the presence of said norovirus-binding aptamer bound to norovirus in said test sample, wherein detection of bound aptamer indicates the presence of at least one norovirus strain. Optionally, the methods further comprise removing unbound norovirus-binding aptamer prior to detecting the presence of said norovirus-binding aptamer bound to norovirus in said test sample. Optionally, the detecting step comprises amplifying the bound aptamer.

Some methods further comprise comparing the presence of said norovirus-binding aptamer bound to norovirus in said test sample with the presence of said norovirus-binding aptamer bound to norovirus in a control sample, whereby increased presence of said norovirus-binding aptamer bound to norovirus in said test sample relative to said control sample indicates the presence of at least one norovirus strain in said test sample. Optionally, said control sample and said test sample are of the same type.

In any of the above methods, the test sample can be a clinical sample such as a fecal sample. In any of the above methods, the test sample can be an environmental sample. In any of the above methods, the test sample can be a food sample.

In some methods, the test sample comprises captured norovirus. Optionally, said captured norovirus was captured through an initial capturing step using a molecule that binds to said at least one norovirus strain at an epitope that is different from the epitope to which said norovirus-binding aptamer binds.

Some methods further comprise capturing said at least one norovirus strain from said test sample by substantially separating the aptamer-bound norovirus from the remainder of said test sample. Optionally, the concentration of the captured norovirus is higher than the concentration of said at least one norovirus strain in said test sample.

In some methods, said norovirus-binding aptamer preferentially binds to infectious norovirus particles. In some methods, said norovirus-binding aptamer preferentially binds to norovirus strains from multiple genogroups. In some methods, said norovirus-binding aptamer preferentially binds to norovirus strains from genogroup I; genogroup I, genotype 1; genogroup II; genogroup II, genotype 2; and/or genogroup II, genotype 4. In some methods, said norovirus-binding aptamer preferentially binds to an epitope within the VPg protein, the VP1 protein, the P domain of the VP1 protein, the P1 subdomain of the VP1 protein, the P2 subdomain of the VP1 protein, the S domain of the VP1 protein, and/or the VP2 protein of said at least one norovirus strain.

In some methods, said norovirus-binding aptamer is a single-stranded DNA aptamer. In some methods, said norovirus-binding aptamer comprises any one of the nucleic acid sequences of SMV-19 (SEQ ID NO: 25), SMV-21 (SEQ ID NO: 27), SMV-25 (SEQ ID NO: 30), SMV-26 (SEQ ID NO: 31), SMV-5 (S-7) (SEQ ID NO: 5), SMV-18 (SEQ ID NO: 6), SMV-22 (S-7) (SEQ ID NO: 7), SMV-5 (S-9) (SEQ ID NO: 12), SMV-17 (SEQ ID NO: 23), SMV-22 (S-9) (SEQ ID NO: 28), M1 (SEQ ID NO: 35), M6-2 (SEQ ID NO: 39), NV 1-1 (SEQ ID NO: 41), NV 1-15 (SEQ ID NO: 42), NV 1-24 (SEQ ID NO: 53), NV 2-9 (SEQ ID NO: 55), NV 2-3 (SEQ ID NO: 56), NV 2-1 (SEQ ID NO:62), N6 (SEQ ID NO: 66), N3 (SEQ ID NO: 67), N1 (SEQ ID NO: 68), N14 (SEQ ID NO: 69), N1-2 (SEQ ID NO: 70), N4-2 (SEQ ID NO: 71), N11-12 (SEQ ID NO: 72), N12-2 (SEQ ID NO: 73), T5 (SEQ ID NO: 74), T9 (SEQ ID NO: 75), T1-2 (SEQ ID NO: 76), T9-2 (SEQ ID NO: 77), and T10-2 (SEQ ID NO: 78). In some methods, said norovirus-binding aptamer comprises any one of the nucleic acid sequences of SMV-19 (SEQ ID NO: 25), SMV-21 (SEQ ID NO: 27), SMV-25 (SEQ ID NO: 30), SMV-26 (SEQ ID NO: 31), SMV-5 (S-7) (SEQ ID NO: 5), SMV-18 (SEQ ID NO: 6), SMV-22 (S-7) (SEQ ID NO: 7), SMV-5 (S-9) (SEQ ID NO: 12), SMV-17 (SEQ ID NO: 23), SMV-22 (S-9) (SEQ ID NO: 28), M1 (SEQ ID NO: 35), M9-2 (SEQ ID NO: 36), M12-2 (SEQ ID NO: 37), M13-2 (SEQ ID NO: 38), M6-2 (SEQ ID NO: 39), M5 (SEQ ID NO: 40), NV 1-1 (SEQ ID NO: 41), NV 1-15 (SEQ ID NO: 42), NV 1-24 (SEQ ID NO: 53), NV 2-9 (SEQ ID NO: 55), NV 2-3 (SEQ ID NO: 56), NV 2-1 (SEQ ID NO:62), N6 (SEQ ID NO: 66), N3 (SEQ ID NO: 67), N1 (SEQ ID NO: 68), N14 (SEQ ID NO: 69), N1-2 (SEQ ID NO: 70), N4-2 (SEQ ID NO: 71), N11-12 (SEQ ID NO: 72), N12-2 (SEQ ID NO: 73), T5 (SEQ ID NO: 74), T9 (SEQ ID NO: 75), T1-2 (SEQ ID NO: 76), T9-2 (SEQ ID NO: 77), T10-2 (SEQ ID NO: 78), AP1-GI (SEQ ID NO: 176), AP2-GI (SEQ ID NO: 177), AP3-GI (SEQ ID NO: 178), AP4-GI (SEQ ID NO: 179), AP5-GI (SEQ ID NO: 180), and AP6-GI (SEQ ID NO: 181). In some methods, said norovirus-binding motif comprises one or more of motifs 1-14 or SEQ ID NOS: 98-145 and 162-174. In some methods, said norovirus-binding motif comprises one or more of motifs 1-23 or SEQ ID NOS: 98-145, 162-174, and 182-199.

In some methods, said norovirus-binding aptamer binds to said at least one norovirus strain with an affinity characterized by a $K_d$ value from about 1 nM to about 999 nM. In some methods, said norovirus-binding aptamer is at least 20 nucleotides in length. Optionally, said norovirus-binding aptamer is 20 to 80 nucleotides in length.

In some methods, said norovirus-binding aptamer is tethered to a solid support. Optionally, said norovirus-binding aptamer is immobilized on a magnetic bead.

In some methods, said norovirus-binding aptamer further comprises a label. Optionally, said label is a fluorophore label or a biotin label. Optionally, said label is conjugated to the 5' end of the aptamer.

In some methods, said norovirus-binding aptamer comprises an aptamer mixture comprising a first aptamer and at least one different aptamer. Optionally, said first aptamer and said at least one different aptamer bind to different epitopes on the same norovirus strain. Optionally, said first aptamer and said at least one different aptamer preferentially bind to different norovirus strains, wherein detection of bound first aptamer and bound at least one different aptamer indicates the presence of at least two norovirus strains. Optionally, said first aptamer and said at least one different aptamer are differentially labeled.

The invention also provides methods of capturing at least one norovirus from a test sample, the methods comprising: (a) contacting said test sample with a norovirus-binding aptamer comprising a norovirus-binding motif and/or any one of SEQ ID NOS: 1-78 or variants thereof having at least 90% sequence identity and having norovirus-binding activity; and (b) substantially separating the aptamer-bound norovirus from the remainder of said test sample. The invention also provides methods of capturing at least one norovirus from a test sample, the methods comprising: (a) contacting said test sample with a norovirus-binding aptamer comprising a norovirus-binding motif and/or any one of SEQ ID NOS: 1-78 and 176-181 or variants thereof having at least 90% sequence identity and having norovirus-binding activity; and (b) substantially separating the aptamer-bound norovirus from the remainder of said test sample. Optionally, the concentration of the captured norovirus is higher than the concentration of said at least one norovirus in said test sample. Optionally, said norovirus-binding motif comprises one or more of motifs 1-14 or SEQ ID NOS: 98-145 and 162-174. Optionally, said norovirus-binding motif comprises one or more of motifs 1-23 or SEQ ID NOS: 98-145, 162-174, and 182-199. Optionally, said norovirus-binding aptamer binds to said at least one norovirus with an affinity characterized by a $K_d$ value from about 1 nM to about 999 nM.

The invention also provides compositions comprising an isolated aptamer comprising a norovirus-binding motif and/or any one of SEQ ID NOS: 1-78 or variants thereof having at least 90% sequence identity and having norovirus-binding activity, wherein said aptamer binds to at least one norovirus strain. The invention also provides compositions comprising an isolated aptamer comprising a norovirus-binding motif and/or any one of SEQ ID NOS: 1-78 and 176-181 or variants thereof having at least 90% sequence identity and having norovirus-binding activity, wherein said aptamer binds to at least one norovirus strain. Optionally, said isolated aptamer is a single-stranded DNA aptamer.

In some compositions, said isolated aptamer preferentially binds to norovirus strains from multiple genogroups. In some compositions, said isolated aptamer preferentially binds to norovirus strains from genogroup I; genogroup I, genotype 1; genogroup II; genogroup II, genotype 2; and/or genogroup II, genotype 4. In some compositions, binding of said isolated aptamer to said at least one norovirus strain is greater than binding of said isolated aptamer to hepatitis A virus and/or poliovirus. In some compositions, said isolated aptamer preferentially binds to infectious norovirus particles. In some compositions, said isolated aptamer preferentially binds to an epitope within the VPg protein, the VP1 protein, the P domain of the VP1 protein, the P1 subdomain of the VP1 protein, the P2 subdomain of the VP1 protein, the S domain of the VP1 protein, and/or the VP2 protein of said at least one norovirus strain.

In some compositions, said isolated aptamer comprises any one of the nucleic acid sequences of SMV-19 (SEQ ID NO: 25), SMV-21 (SEQ ID NO: 27), SMV-25 (SEQ ID NO: 30), SMV-26 (SEQ ID NO: 31), SMV-5 (S-7) (SEQ ID NO: 5), SMV-18 (SEQ ID NO: 6), SMV-22 (S-7) (SEQ ID NO: 7), SMV-5 (S-9) (SEQ ID NO: 12), SMV-17 (SEQ ID NO: 23), SMV-22 (S-9) (SEQ ID NO: 28), M1 (SEQ ID NO: 35), M6-2 (SEQ ID NO: 39), NV 1-1 (SEQ ID NO: 41), NV 1-15 (SEQ ID NO: 42), NV 1-24 (SEQ ID NO: 53), NV 2-9 (SEQ ID NO: 55), NV 2-3 (SEQ ID NO: 56), NV 2-1 (SEQ ID NO:62), N6 (SEQ ID NO: 66), N3 (SEQ ID NO: 67), N1 (SEQ ID NO: 68), N14 (SEQ ID NO: 69), N1-2 (SEQ ID NO: 70), N4-2 (SEQ ID NO: 71), N11-12 (SEQ ID NO: 72), N12-2 (SEQ ID NO: 73), T5 (SEQ ID NO: 74), T9 (SEQ ID NO: 75), T1-2 (SEQ ID NO: 76), T9-2 (SEQ ID NO: 77), and T10-2 (SEQ ID NO: 78). In some compositions, said isolated aptamer comprises any one of the nucleic acid sequences of SMV-19 (SEQ ID NO: 25), SMV-21 (SEQ ID NO: 27), SMV-25 (SEQ ID NO: 30), SMV-26 (SEQ ID NO: 31), SMV-5 (S-7) (SEQ ID NO: 5), SMV-18 (SEQ ID NO: 6), SMV-22 (S-7) (SEQ ID NO: 7), SMV-5 (S-9) (SEQ ID NO: 12), SMV-17 (SEQ ID NO: 23), SMV-22 (S-9) (SEQ ID NO: 28), M1 (SEQ ID NO: 35), M9-2 (SEQ ID NO: 36), M12-2 (SEQ ID NO: 37), M13-2 (SEQ ID NO: 38), M6-2 (SEQ ID NO: 39), M5 (SEQ ID NO: 40), NV 1-1 (SEQ ID NO: 41), NV 1-15 (SEQ ID NO: 42), NV 1-24 (SEQ ID NO: 53), NV 2-9 (SEQ ID NO: 55), NV 2-3 (SEQ ID NO: 56), NV 2-1 (SEQ ID NO:62), N6 (SEQ ID NO: 66), N3 (SEQ ID NO: 67), N1 (SEQ ID NO: 68), N14 (SEQ ID NO: 69), N1-2 (SEQ ID NO: 70), N4-2 (SEQ ID NO: 71), N11-12 (SEQ ID NO: 72), N12-2 (SEQ ID NO: 73), T5 (SEQ ID NO: 74), T9 (SEQ ID NO: 75), T1-2 (SEQ ID NO: 76), T9-2 (SEQ ID NO: 77), T10-2 (SEQ ID NO: 78), AP1-GI (SEQ ID NO: 176), AP2-GI (SEQ ID NO: 177), AP3-GI (SEQ ID NO: 178), AP4-GI (SEQ ID NO: 179), AP5-GI (SEQ ID NO: 180), and AP6-GI (SEQ ID NO: 181). In some compositions, said norovirus-binding motif comprises one or more of motifs 1-14 or SEQ ID NOS: 98-145 and 162-174. In some compositions, said norovirus-binding motif comprises one or more of motifs 1-23 or SEQ ID NOS: 98-145, 162-174, and 182-199.

In some compositions, the binding of said isolated aptamer to said at least one norovirus strain is characterized by a $K_d$ value from about 1 nM to about 999 nM. In some compositions, said isolated aptamer is at least 20 nucleotides in length. Optionally, said isolated aptamer is 20 to 80 nucleotides in length.

In some compositions, said isolated aptamer is tethered to a solid support. Optionally, wherein said isolated aptamer is immobilized on a magnetic bead. In some compositions, said isolated aptamer further comprises a label. Optionally, said label is a fluorophore label or a biotin label. Optionally, said label is conjugated to the 5' end of the aptamer.

The invention also provides aptamer mixtures comprising a first isolated aptamer as described above and at least one different isolated aptamer or aptamer mixtures comprising a first isolated aptamer and at least one different isolated aptamer, wherein said first isolated aptamer and said at least one different isolated aptamer are each isolated aptamers as described above. Optionally, said first isolated aptamer and said at least one different isolated aptamer bind to different epitopes on the same norovirus strain. Optionally, said first isolated aptamer and said at least one different isolated aptamer preferentially binds to different norovirus strains. Optionally, said at least one different isolated aptamer preferentially binds to a target other than a norovirus. Optionally, said first isolated aptamer and said at least one different isolated aptamer are differentially labeled.

The invention also provides kits for detection of at least one norovirus strain comprising an isolated aptamer as described above and written material describing a method for the kit's use. Optionally, the kits further comprise a positive control comprising a norovirus virus-like-particle suspension, viral RNA, or a surrogate virus. Optionally, the kits further comprise magnetic beads. Optionally, the kits further comprise primers and probes targeting a region of the genome of at least one norovirus strain.

The invention also provides methods of evaluating the efficacy of a therapeutic agent in a patient diagnosed with a norovirus infection with at least one norovirus strain, the methods comprising: (a) contacting a first clinical sample from said patient, obtained prior to treatment with said therapeutic agent, with a norovirus-binding aptamer comprising a norovirus-binding motif and/or any one of SEQ ID NOS: 1-78 or variants thereof having at least 90% sequence identity and having norovirus-binding activity; (b) detecting the presence of said norovirus-binding aptamer bound to norovirus in said first clinical sample; (c) contacting a second clinical sample from said patient, obtained following treatment with said therapeutic agent, with said norovirus-binding aptamer; (d) detecting the presence of said norovirus-binding aptamer bound to norovirus in said second clinical sample; and (e) comparing the presence of said norovirus-binding aptamer bound to norovirus in said first clinical sample with the presence of said norovirus-binding aptamer bound to norovirus in said second clinical sample, whereby decreased presence of said norovirus-binding aptamer bound to norovirus in said second clinical sample relative to said first clinical sample indicates that said therapeutic agent is effective in treating said norovirus infection in said patient. The invention also provides methods of evaluating the efficacy of a therapeutic agent in a patient diagnosed with a norovirus infection with at least one norovirus strain, the methods comprising: (a) contacting a first clinical sample from said patient, obtained prior to treatment with said therapeutic agent, with a norovirus-binding aptamer comprising a norovirus-binding motif and/or any one of SEQ ID NOS: 1-78 and 176-181 or variants thereof having at least 90% sequence identity and having norovirus-binding activity; (b) detecting the presence of said norovirus-binding aptamer bound to norovirus in said first clinical sample; (c) contacting a second clinical sample from said patient, obtained following treatment with said therapeutic agent, with said norovirus-binding aptamer; (d) detecting the presence of said norovirus-binding aptamer bound to norovirus in said second clinical sample; and (e) comparing the presence of said norovirus-binding aptamer bound to norovirus in said first clinical sample with the presence of said norovirus-binding aptamer bound to norovirus in said second clinical sample, whereby decreased presence of said norovirus-binding aptamer bound to norovirus in said second clinical sample relative to said first clinical sample indicates that said therapeutic agent is effective in treating said norovirus infection in said patient. Optionally, the methods further comprise administering said therapeutic agent to said patient. Optionally, said norovirus-binding motif comprises one or more of motifs 1-14 or SEQ ID NOS: 98-145 and 162-174. Optionally, said norovirus-binding motif comprises one or more of motifs 1-23 or SEQ ID NOS: 98-145, 162-174, and 182-199. Optionally, said norovirus-binding aptamer comprises an aptamer mixture comprising a first aptamer and at least one different aptamer. Optionally, said first aptamer and said at least one different aptamer preferentially bind to different norovirus strains.

Optionally, said first aptamer and said at least one different aptamer are differentially labeled.

The invention also provides methods of evaluating the efficacy of a norovirus vaccine, the methods comprising: (a) challenging one or more vaccinated subjects and one or more non-vaccinated subjects with norovirus; (b) contacting a first set of one or more clinical samples from said one or more vaccinated subjects with a norovirus-binding aptamer comprising a norovirus-binding motif and/or any one of SEQ ID NOS: 1-78 or variants thereof having at least 90% sequence identity and having norovirus-binding activity; (c) detecting the presence of said norovirus-binding aptamer bound to norovirus in said first set of one or more clinical samples; (d) contacting a second set of one or more clinical samples from said one or more non-vaccinated subjects with said norovirus-binding aptamer; (e) detecting the presence of said norovirus-binding aptamer bound to norovirus in said second set of one or more clinical samples; and (f) comparing the presence of said norovirus-binding aptamer bound to norovirus in said first set of one or more clinical samples with the presence of said norovirus-binding aptamer bound to norovirus in said second set of one or more clinical samples, whereby lower presence of said norovirus-binding aptamer bound to norovirus in said first set relative to said second set indicates that said norovirus vaccine is effective in preventing or reducing norovirus infection. The invention also provides methods of evaluating the efficacy of a norovirus vaccine, the methods comprising: (a) challenging one or more vaccinated subjects and one or more non-vaccinated subjects with norovirus; (b) contacting a first set of one or more clinical samples from said one or more vaccinated subjects with a norovirus-binding aptamer comprising a norovirus-binding motif and/or any one of SEQ ID NOS: 1-78 and 176-181 or variants thereof having at least 90% sequence identity and having norovirus-binding activity; (c) detecting the presence of said norovirus-binding aptamer bound to norovirus in said first set of one or more clinical samples; (d) contacting a second set of one or more clinical samples from said one or more non-vaccinated subjects with said norovirus-binding aptamer; (e) detecting the presence of said norovirus-binding aptamer bound to norovirus in said second set of one or more clinical samples; and (f) comparing the presence of said norovirus-binding aptamer bound to norovirus in said first set of one or more clinical samples with the presence of said norovirus-binding aptamer bound to norovirus in said second set of one or more clinical samples, whereby lower presence of said norovirus-binding aptamer bound to norovirus in said first set relative to said second set indicates that said norovirus vaccine is effective in preventing or reducing norovirus infection. Optionally, said norovirus-binding motif comprises one or more of motifs 1-14 or SEQ ID NOS: 98-145 and 162-174. Optionally, said norovirus-binding motif comprises one or more of motifs 1-23 or SEQ ID NOS: 98-145, 162-174, and 182-199. Optionally, said norovirus-binding aptamer comprises an aptamer mixture comprising a first aptamer and at least one different aptamer. Optionally, said first aptamer and said at least one different aptamer preferentially bind to different norovirus strains. Optionally, said first aptamer and said at least one different aptamer are differentially labeled.

BRIEF DESCRIPTION OF THE DRAWINGS

FIG. 5A-D shows equilibrium dissociation curves for aptamers SMV-19 (FIG. 5A), SMV-21 (FIG. 5B), SMV-25 (FIG. 5C), and SMV-26 (FIG. 5D), respectively, with SMV VLPs as demonstrated by ELASA.

FIG. 9 shows the performance (% capture efficiency, CE) of the AMC-RT-qPCR method as applied to SMV using aptamer SMV-17 as the capture ligand. The performance of immunomagnetic separation (IMS)-RT-qPCR was performed in tandem to provide comparison.

(FIG. 18A) and 65° C. (FIG. 18B) for different times.

FIG. 20A shows signal of SMV VLPs treated at 72° C. for different times as a percentage of untreated SMV VLPs. FIG. 20B shows signal of SMV VLPs at 70° C. for different times as a percentage of untreated SMV VLPs. Percentages have absorbance of completely denatured SMV subtracted.

FIG. 21A shows binding signals to GII.4 Sydney Virus VLPs treated at 68° C. for different times as a percentage of untreated GII.4 Sydney Virus VLPs. FIG. 21B shows binding signals to GII.4 Sydney Virus VLPs treated at 65° C. for different times as a percentage of untreated GII.4 Sydney Virus VLPs. Percentages have absorbance of completely denatured GII.4 Sydney Virus subtracted.

DETAILED DESCRIPTION

I. Overview

Figure 1:
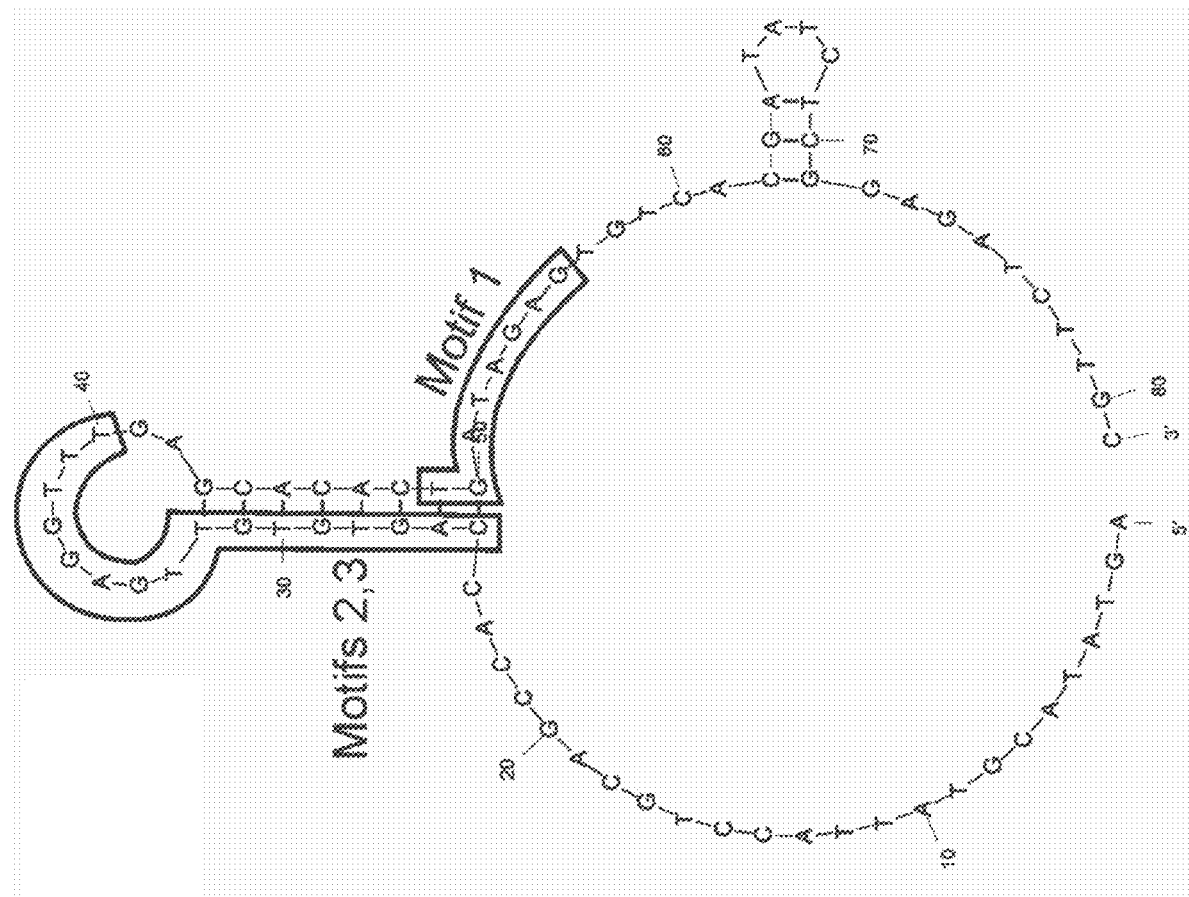
FIG. 1 shows the predicted structural folding of aptamer SMV-19 (SEQ ID NO: 79).
Figure 2:
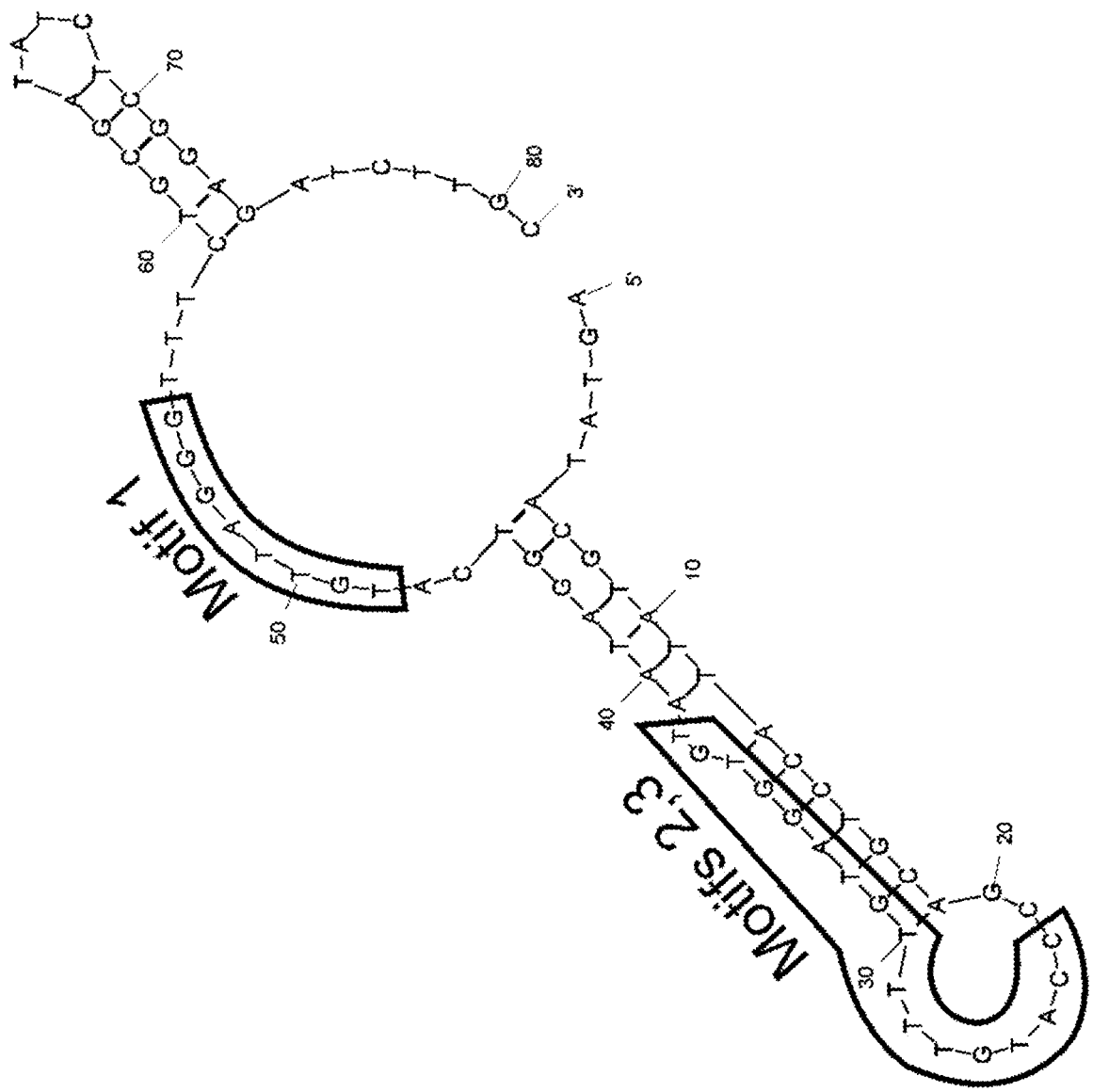
FIG. 2 shows the predicted structural folding of aptamer SMV-21 (SEQ ID NO: 80).
Figure 3:
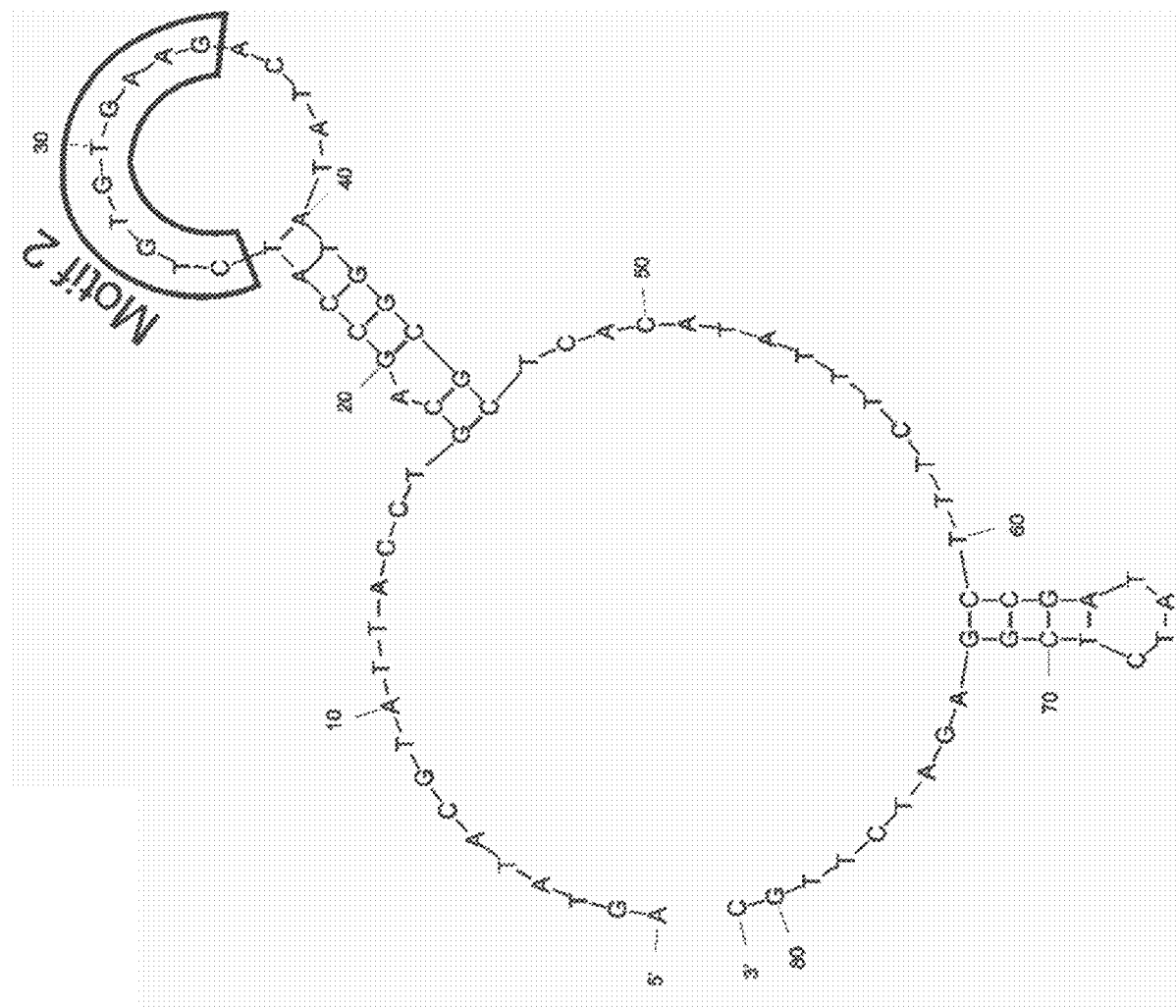
FIG. 3 shows the predicted structural folding of aptamer SMV-25 (SEQ ID NO: 81).
Figure 4:
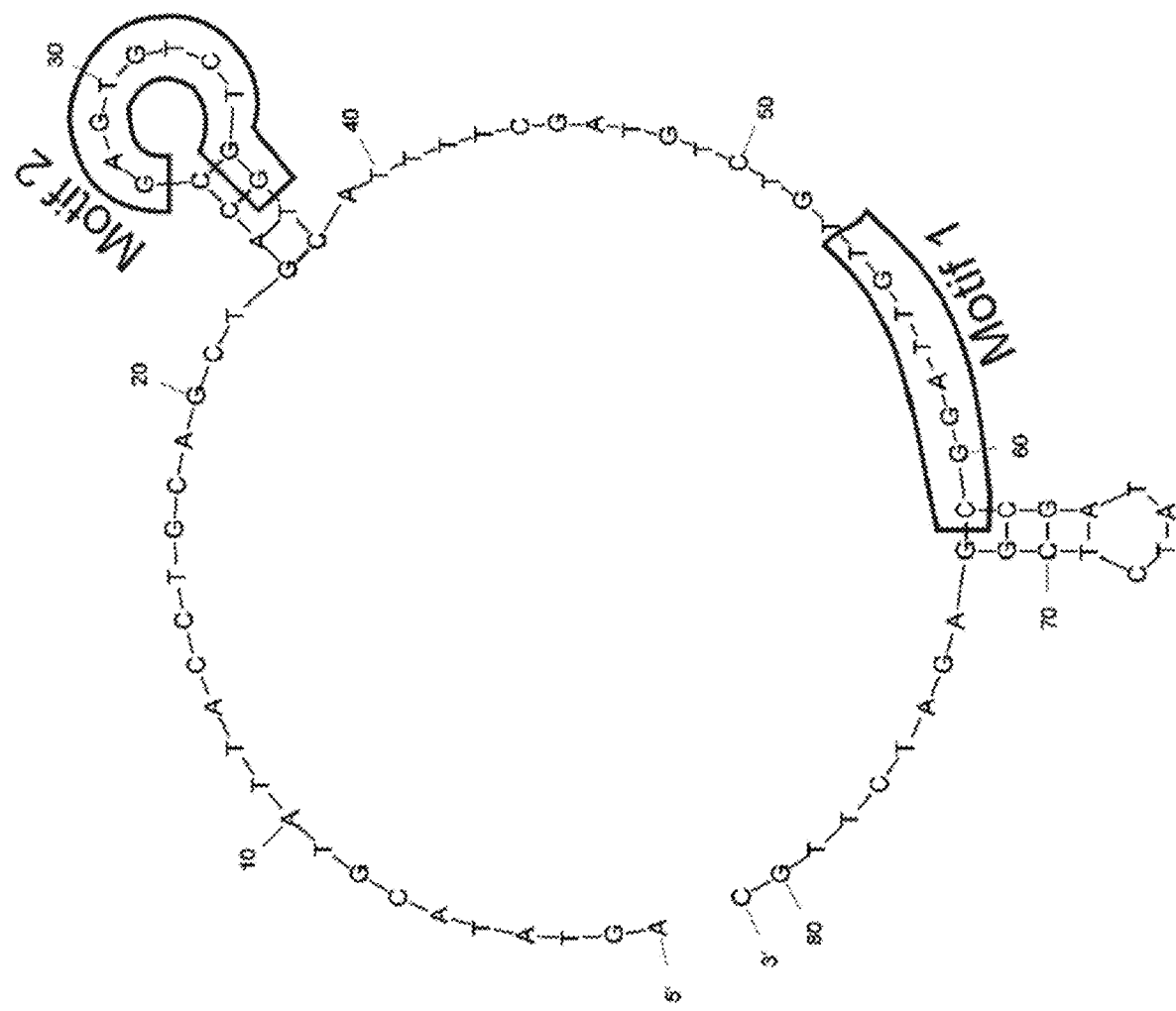
FIG. 4 shows the predicted structural folding of aptamer SMV-26 (SEQ ID NO: 82).
Figure 5A:
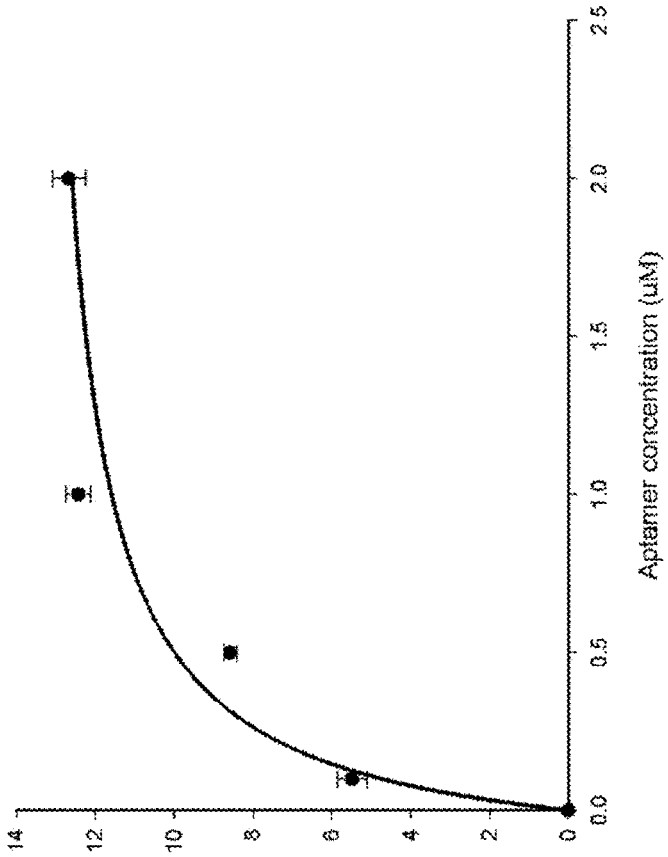
Figure 5B:
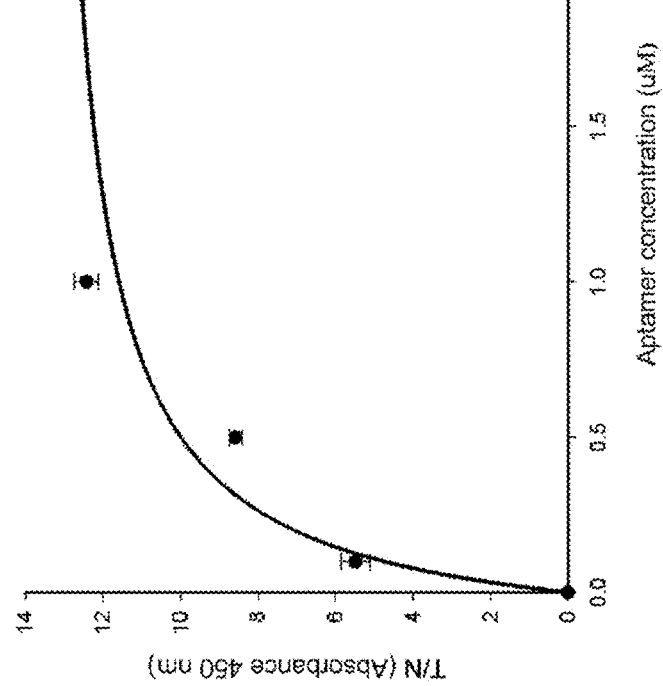

The instant disclosure provides norovirus-binding aptamers, isolated norovirus-binding aptamers, compositions comprising such aptamers, and methods for using and producing such aptamers. The norovirus-binding aptamers disclosed herein are useful, for example, for detecting the presence of norovirus in test samples such as clinical samples, environmental samples, and food samples, and for capturing and/or concentrating norovirus from test samples.

II. Aptamers

The ability of nucleic acids, and single-stranded nucleic acids in particular, to fold into specific and stable secondary structures has led to identification of nucleic acid sequences (i.e., aptamers) with structures that can bind preferentially to selected targets and also discriminate between subtle molecular differences within the target.

Unless otherwise apparent from context, the term "aptamer" refers to a nucleic acid molecule that naturally folds into specific and stable secondary structures that enable it to bind to a selected target. The term "nucleic acid" refers to single-stranded or double-stranded deoxyribonucleic acid (DNA) or ribonucleic acid (RNA) and any chemical modifications thereof. Such modifications can include, for example, modifications at cytosine exocyclic amines, substitution of 5-bromo-uracil, backbone modifications, methylations, unusual base-pairing combinations, and the like. In some cases, aptamers are isolated nucleic acids.

The term "isolated," when referring to an aptamer or a nucleic acid, means that the aptamer or nucleic acid is a predominant aptamer or nucleic acid species in a composition. An aptamer or nucleic acid can be considered to be a predominant aptamer or nucleic acid species in a composition if it represents at least about 5%, at least about 10%, at least about 20%, at least about 30%, at least about 40%, at least about 50%, at least about 60%, at least about 70%, at least about 80%, at least about 90%, at least about 95%, or 100% of the aptamers or nucleic acid species in the composition. This can be determined, for example, using analytical chemistry techniques such as polyacrylamide gel electrophoresis, high performance liquid chromatography, and the like.

The term "norovirus-binding aptamer" refers to any aptamer that preferentially binds to any norovirus (i.e., has norovirus-binding activity). The term "preferential binding" or "preferentially binds" means that an aptamer or other molecule binds with greater affinity, with greater avidity, more readily, and/or with greater duration to a target than it binds to at least one unrelated non-target. An aptamer or other molecule that preferentially binds to a first target may or may not preferentially bind to a second target. Thus, preferential binding does not require (although it can include) exclusive binding. Many assays can be used to qualitatively or quantitatively detect or measure binding of norovirus-binding aptamers to norovirus. For example, an Enzyme-Linked Aptamer Sorbent Assay (ELASA) can be used. Assays involving amplification of the bound aptamer (e.g., qPCR) or RNA from the aptamer-bound virus (e.g., qRT-PCR) can be used. Flow cytometry methods as described in U.S. Pat. No. 5,853,984 can be used. Microarrays, BIAcore assays, differential centrifugation, chromatography, electrophoresis, immunoprecipitation, optical biosensors, and other surface plasmon resonance assays can be used as described in WO 2011/061351. Other assays that can be used are calorimetric analysis and dot blot assays. Moreover, just as the enzyme-linked immunosorbent assay (ELISA) was adapted for aptamers in the ELASA assay, any other assays involving norovirus-binding antibodies can be adapted for use with the norovirus-binding aptamers disclosed herein in place of the antibodies. Such assays include immunometric assays such as radioimmunoassays, flow cytometry assays, blotting applications, anisotropy, membrane assays, biosensors, and the like. Any other assays known in the art can also be used or adapted to detect or measure binding of norovirus-binding aptamers to norovirus.

A. Structure and Examples of Norovirus-Binding Aptamers

The norovirus-binding aptamers disclosed herein can have discrete nucleic acid structures that facilitate preferential binding to norovirus targets. The primary sequence of a DNA is a specific string of nucleotides (A, C, G, or T) in one dimension. Likewise, the primary sequence of an RNA is a specific string of nucleotides (A, C, G, or U) in one dimension. The primary sequence dictates the three dimensional configuration of the aptamer. In some cases, the primary sequence of a norovirus-binding aptamer can be greater than 20 nucleotides. Optionally, it can be between about 20-200 nucleotides, between about 20-150 nucleotides, between about 20-100 nucleotides, between about 20-80 nucleotides, between about 20-50 nucleotides, between about 30-50 nucleotides, or between about 35-50 nucleotides. Representative primary sequences for the norovirus-binding aptamers disclosed herein include SEQ ID NOS: 1-78. Variants of SEQ ID NOS: 1-78 that retain norovirus-binding activity can include aptamers comprising a nucleic acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity with any one of SEQ ID NOS: 1-78. Other representative primary sequences for the norovirus-binding aptamers disclosed herein include SEQ ID NOS: 176-181. Variants of SEQ ID NOS: 176-181 that retain norovirus-binding activity can include aptamers comprising a nucleic acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity with any one of SEQ ID NOS: 176-181.

The secondary structure of a section of a DNA or RNA is represented by contact in two dimensions between specific nucleotides. Secondary structures can comprise Watson/Crick base pairs (A:U, A:T and C:G) and other base pairs of lower stability (e.g., G:U, G:T, A:C, G:A, U:U, and T:T). Secondary structures include stem loops, symmetric and asymmetric bulges, pseudoknots, and combinations of the same. In some cases, such structures can be formed in a nucleic acid sequence of no more than about 30 nucleotides. When nucleotides that are distant in the primary sequence and not thought to interact through Watson/Crick and non-Watson/Crick base pairs are in fact interacting, these interactions (which are often depicted in two dimensions) are also part of the secondary structure.

The tertiary structure of a DNA or RNA is the description in space of the atoms of the DNA or RNA. Primary sequences of aptamers limit the possible tertiary structures, as do the fixed secondary structures. Norovirus-binding aptamers have structures in three dimensions that are comprised of a collection of DNA or RNA motifs and secondary structures. DNA or RNA secondary and tertiary structures include all the ways in which it is possible to describe in general terms the most stable groups of conformations that a nucleic acid compound can form.

Families of norovirus-binding aptamers that bind to a particular norovirus target can be characterized by one or more norovirus-binding motifs held in common. Although such families of aptamers having norovirus-binding motifs in common may include a relatively large number of potential members, the family members are capable of preferential binding to one or more particular norovirus targets.

The term "norovirus-binding motif" refers to any motif that is within an aptamer and is predicted to contribute to preferential binding of the aptamer to a norovirus. Motifs can be primary sequences of nucleotides, secondary structures or portions thereof, or tertiary structures or portions thereof. Examples of norovirus-binding motifs include motifs 1-14 and SEQ ID NOS: 98-145 and 162-174 as disclosed herein. Other examples of norovirus-binding motifs include motifs 15-23 and SEQ ID NOS: 182-199 as disclosed herein. Yet other examples of norovirus-binding motifs include any nucleic acid sequences contributing to any of the secondary structures (e.g., stem loops, symmetric and asymmetric bulges, pseudoknots, and the like) in a norovirus-binding aptamer, such as those shown in FIGS. 1-4, 12-14, and 23-28. Other examples of norovirus-binding motifs include nucleic acid sequences of at least about 3, at least about 4, at least about 5, at least about 6, at least about 7, at least about 8, at least about 9, at least about 10 nucleotides, at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, or at least about 20 nucleotides that share at least about 40%, at least about 50%, at least about 60%, at least about 70%, at least about 80%, at least about 90%, at least about 95%, at least about 96%, at least about 97%, at least about 98%, at least about 99%, or 100% sequence identity with each other and are present in two or more norovirus-binding aptamers.

When comparing aptamer sequences, percentage sequence identities are determined with aptamer sequences maximally aligned. After alignment, if a subject aptamer region (e.g., a putative norovirus-binding motif) is being compared with the same region of a reference aptamer, the percentage sequence identity between the subject and reference aptamer regions is the number of positions occupied by the same nucleotide in both the subject and reference aptamer regions divided by the total number of aligned positions of the two regions, with gaps not counted, multiplied by 100 to convert to percentage.

One family of norovirus-binding aptamers comprises motif 1. Motif 1 is characterized by the sequence T-G-$N_1$-$N_2$-A-G-$N_3$-$N_4$ (SEQ ID NO: 98), where $N_1$, $N_2$, $N_3$, and $N_4$ can be any nucleotide. Optionally, one or more of the nucleotides in the motif can be modified. In some cases, $N_1$ can be T or A. In some cases, $N_2$ can be T or G. In some cases, $N_3$ can be G, C, or A. In some cases, $N_4$ can be G or C. In some cases, $N_1$ can be T or A, $N_2$ can be T or G, $N_3$ can be G, C, or A, $N_4$ can be G or C, and the motif has the sequence of T-G-W-K-A-G-V-S(SEQ ID NO: 162) using IUPAC nomenclature, where W can be A or T, K can be G or T, V can be A or G or C, and S can be G or C. In one example of motif 1, $N_1$ is A, $N_2$ is T, $N_3$ is A, and $N_4$ is G, and the motif has the sequence of T-G-A-T-A-G-A-G (SEQ ID NO: 112). In another example of motif 1, $N_1$ is T, $N_2$ is T, $N_3$ is G, and $N_4$ is G, and the motif has the sequence of T-G-T-T-A-G-G-G (SEQ ID NO: 113). In yet another example of motif 1, $N_1$ is T, $N_2$ is T, $N_3$ is G, and $N_4$ is C, and the motif has the sequence of T-G-T-T-A-G-G-C(SEQ ID NO: 114). Examples of norovirus-binding aptamers comprising motif 1 include SMV-19 (SEQ ID NO: 25), SMV-21 (SEQ ID NO: 27), and SMV-26 (SEQ ID NO: 31).

Another family of norovirus-binding aptamers comprises motif 2. Motif 2 is characterized by the sequence $N_1$-$N_2$-$N_3$-T-G-T-$N_4$-$N_5$-$N_6$-G (SEQ ID NO: 99), where $N_1$, $N_2$, $N_3$, $N_4$, $N_5$, and $N_6$ can be any nucleotide. Optionally, one or more nucleotides in the motif can be modified. In some cases, $N_1$ can be C or G. In some cases, $N_2$ can be A, T, or C. In some cases, $N_3$ can be G or A. In some cases, $N_4$ can be G, T, or C. In some cases, $N_5$ can be T or A. In some cases, $N_6$ can be T, G, or A. In some cases, $N_1$ can be C or G, $N_2$ can be A, T, or C, $N_3$ can be G or A, $N_4$ can be G, T, or C, $N_5$ can be T or A, $N_6$ can be T, G, or A, and the motif has the sequence of S-H-R-T-G-T-B-W-D-G (SEQ ID NO: 163) using IUPAC nomenclature, where S can be G or C, H can be A or C or T, R can be G or A, B can be G or C or T, W can be A or T, and D can be A or G or T. In one example of motif 2, $N_1$ is C, $N_2$ is A, $N_3$ is G, $N_4$ is G, $N_5$ is T, and $N_6$ is T, and the motif has the sequence of C-A-G-T-G-T-G-T-T-G (SEQ ID NO: 115). In another example of motif 2, $N_1$ is C, $N_2$ is C, $N_3$ is A, $N_4$ is T, $N_5$ is T, and $N_6$ is T, and the motif has the sequence of C-C-A-T-G-T-T-T-T-G (SEQ ID NO: 116). In yet another example of motif 2, $N_1$ is C, $N_2$ is T, $N_3$ is G, $N_4$ is G, $N_5$ is A, and $N_6$ is A, and the motif has the sequence of C-T-G-T-G-T-G-A-A-G (SEQ ID NO: 117). In yet another example of motif 2, $N_1$ is G, $N_2$ is A, $N_3$ is G, $N_4$ is C, $N_5$ is T, and $N_6$ is G, and the motif has the sequence of G-A-G-T-G-T-C-T-G-G (SEQ ID NO: 118). Examples of norovirus-binding aptamers comprising motif 2 include SMV-19 (SEQ ID NO: 25), SMV-21 (SEQ ID NO: 27), SMV-25 (SEQ ID NO: 30), and SMV-26 (SEQ ID NO: 31).

Another family of norovirus-binding aptamers comprises motif 3. Motif 3 is characterized by the sequence A-G-G-T-N-T (SEQ ID NO: 100), where N can be any nucleotide. Optionally, one or more nucleotides in the motif can be modified. In some cases, N can be T or G, and the motif has the sequence of A-G-G-T-K-T (SEQ ID NO: 164) using IUPAC nomenclature, where K can be G or T. In one example of motif 3, N is T, and the motif has the sequence of A-G-G-T-T-T (SEQ ID NO: 119). In another example of motif 3, N is G, and the motif has the sequence of A-G-G-T-G-T (SEQ ID NO: 120). Examples of norovirus-binding aptamers comprising motif 3 include SMV-19 (SEQ ID NO: 25) and SMV-21 (SEQ ID NO: 27).

Another family of norovirus-binding aptamers comprises motif 4. Motif 4 is characterized by the sequence T-G-G-G-N-A (SEQ ID NO: 101), where N can be any nucleotide. Optionally, one or more nucleotides in the motif can be modified. In some cases, N can be G or A, and the motif has the sequence of T-G-G-G-R-A (SEQ ID NO: 165) using IUPAC nomenclature, where R can be G or A. In one example of motif 4, N is G, and the motif has the sequence of T-G-G-G-G-A (SEQ ID NO: 121). In another example of motif 4, N is A, and the motif has the sequence of T-G-G-G-A-A (SEQ ID NO: 122). Examples of norovirus-binding aptamers comprising motif 4 include M1 (SEQ ID NO: 35) and M6-2 (SEQ ID NO: 39).

Another family of norovirus-binding aptamers comprises motif 5. Motif 5 is characterized by the sequence G-$N_1$-G-A-$N_2$-A-A (SEQ ID NO: 102), where N can be any nucleotide. Optionally, one or more nucleotides in the motif can be modified. In some cases, $N_1$ can be G or T. In some cases, $N_2$ can be T or C. In some cases, $N_1$ can be G or T, $N_2$ can be T or C, and the motif has the sequence of G-K-G-A-Y-A-A (SEQ ID NO: 166) using IUPAC nomenclature, where K can be G or T and Y can be T or C. In one example of motif 5, $N_1$ is G, $N_2$ is T, and the motif has the sequence of G-G-G-A-T-A-A (SEQ ID NO: 123). In another example of motif 5, $N_1$ is T, $N_2$ is C, and the motif has the sequence of G-T-G-A-C-A-A (SEQ ID NO: 124). Examples of norovirus-binding aptamers comprising motif 5 include M1 (SEQ ID NO: 35) and M5 (SEQ ID NO: 40).

Another family of norovirus-binding aptamers comprises motif 6. Motif 6 is characterized by the sequence T-G-G-G-$N_1$-$N_2$-G (SEQ ID NO: 103), where $N_1$ and $N_2$ can be any nucleotide. Optionally, one or more nucleotides in the motif can be modified. In some cases, $N_1$ can be G or A. In some cases, $N_2$ can be G or A. In some cases, $N_1$ can be G or A, $N_2$ can be G or A, and the motif has the sequence of T-G-G-G-R-R-G (SEQ ID NO: 167) using IUPAC nomenclature, where R can be G or A. In one example of motif 6, $N_1$ is G, $N_2$ is G, and the motif has the sequence of T-G-G-G-G-G-G (SEQ ID NO: 125). In another example of motif 6, $N_1$ is A, $N_2$ is A, and the motif has the sequence of T-G-G-G-A-A-G (SEQ ID NO: 126). Examples of norovirus-binding aptamers comprising motif 6 include M5 (SEQ ID NO: 40) and M6-2 (SEQ ID NO: 39).

Another family of norovirus-binding aptamers comprises motif 7. Motif 7 is characterized by the sequence T-C-$N_1$-$N_2$-G-T-A (SEQ ID NO: 104), where $N_1$ and $N_2$ can be any nucleotide. Optionally, one or more nucleotides in the motif can be modified. In some cases, $N_1$ can be G or C. In some cases, $N_2$ can be T or G. In some cases, $N_1$ can be G or C, $N_2$ can be T or G, and the motif has the sequence of T-C-S-K-G-T-A (SEQ ID NO: 168) using IUPAC nomenclature, where S can be G or C and K can be G or T. In one example of motif 7, $N_1$ is C, $N_2$ is T, and the motif has the sequence of T-C-G-T-G-T-A (SEQ ID NO: 127). In another example of motif 7, $N_1$ is C, $N_2$ is G, and the motif has the sequence of T-C-C-G-G-T-A (SEQ ID NO: 128). Examples of norovirus-binding aptamers comprising motif 7 include M1 (SEQ ID NO: 35) and M6-2 (SEQ ID NO: 39).

Another family of norovirus-binding aptamers comprises motif 8. Motif 8 is characterized by the sequence G-G-T-N-C-G-G-T (SEQ ID NO: 105), where N can be any nucleotide. Optionally, one or more nucleotides in the motif can be modified. In some cases, N can be G or C, and the motif has the sequence of G-G-T-S-C-G-G-T (SEQ ID NO: 169), where S can be G or C. In one example of motif 8, N is G, and the motif has the sequence of G-G-T-G-C-G-G-T (SEQ ID NO: 129). In another example of motif 8, N is C, and the motif has the sequence of G-G-T-C-C-G-G-T (SEQ ID NO: 130). Examples of norovirus-binding aptamers comprising motif 8 include M5 (SEQ ID NO: 40) and M6-2 (SEQ ID NO: 39).

Another family of norovirus-binding aptamers comprises motif 9. Motif 9 is characterized by the sequence T-A-A-A-$N_1$-G-$N_2$-A (SEQ ID NO: 106), where $N_1$ and $N_2$ can be any nucleotide. Optionally, one or more nucleotides in the motif can be modified. In some cases, $N_1$ can be C or T. In some cases, $N_2$ can be T or C. In some cases, $N_1$ can be C or T, $N_2$ can be T or C, and the motif has the sequence of T-A-A-A-Y-G-Y-A (SEQ ID NO: 170) using IUPAC nomenclature, where Y can be T or C. In one example of motif 9, $N_1$ is C, $N_2$ is T and the motif has the sequence of T-A-A-A-C-G-T-A (SEQ ID NO: 131). In another example of motif 9, $N_1$ is T, $N_2$ is C, and the motif has the sequence of T-A-A-A-T-G-C-A (SEQ ID NO: 132). Examples of norovirus-binding aptamers comprising motif 9 include M1 (SEQ ID NO: 35) and M6-2 (SEQ ID NO: 39).

Another family of norovirus-binding aptamers comprises motif 10. Motif 10 is characterized by the sequence T-G-T-T-$N_1$-$N_2$-$N_3$-G-G-G-$N_4$-A-T-$N_5$-A-A (SEQ ID NO: 107), where $N_1$, $N_2$, $N_3$, $N_4$, and $N_5$ can be any nucleotide. Optionally, one or more nucleotides in the motif can be modified. In some cases, $N_1$ can be T or A. In some cases, $N_2$ can be A or G. In some cases, $N_3$ can be T or G. In some cases, $N_4$ can be G or A. In some cases, $N_5$ can be T or A. In some cases, $N_1$ can be T or A, $N_2$ can be A or G, $N_3$ can be T or G, $N_4$ can be G or A, $N_5$ can be T or A, and the motif has the sequence of T-G-T-T-W-R-K-G-G-G-R-A-T-W-A-A (SEQ ID NO: 171) using IUPAC nomenclature, where W can be A or T, R can be G or A, and K can be G or T. In one example of motif 10, $N_1$ is T, $N_2$ is A, $N_3$ is T, $N_4$ is G, and $N_5$ is A, and the motif has the sequence of T-G-T-T-T-A-T-G-G-G-G-A-T-A-A-A (SEQ ID NO: 133). In another example of motif 10, $N_1$ is A, $N_2$ is A, $N_3$ is G, $N_4$ is A, and $N_5$ is T, and the motif has the sequence of T-G-T-T-A-A-G-G-G-G-A-A-T-T-A-A (SEQ ID NO: 134). In another example, $N_1$ is A, $N_2$ is G, $N_3$ is G, $N_4$ is A, and $N_5$ is T, and the motif has the sequence of T-G-T-T-A-G-G-G-G-A-A-T-T-A-A (SEQ ID NO: 135). Examples of norovirus-binding aptamers comprising motif 10 include M1 (SEQ ID NO: 35), M9-2 (SEQ ID NO: 36), and M12-2 (SEQ ID NO: 37).

Another family of norovirus-binding aptamers comprises motif 11. Motif 11 is characterized by the sequence T-A-A-T-$N_1$-C-G-T-$N_2$-T-A-C-T-A-A-T-C-A (SEQ ID NO: 108), where $N_1$ and $N_2$ can be any nucleotide. Optionally, one or more nucleotides in the motif can be modified. In some cases, $N_1$ can be T or C. In some cases, $N_2$ can be G or C. In some cases, $N_1$ can be T or C, $N_2$ can be G or C, and the motif has the sequence of T-A-A-T-Y-C-G-T-S-T-A-C-T-A-A-T-C-A (SEQ ID NO: 172) using IUPAC nomenclature, where Y can be T or C and S can be G or C. In one example of motif 11, $N_1$ is T and $N_2$ is G, and the motif has the sequence of T-A-A-T-T-C-G-T-G-T-A-C-T-A-A-T-C-A (SEQ ID NO: 136). In another example of motif 11, $N_1$ is C and $N_2$ is C, and the motif has the sequence of T-A-A-T-C-C-G-T-C-T-A-C-T-A-A-T-C-A (SEQ ID NO: 137). Examples of norovirus-binding aptamers comprising motif 11 include M1 (SEQ ID NO: 35) and M9-2 (SEQ ID NO: 36).

Another family of norovirus-binding aptamers comprises motif 12. Motif 12 is characterized by the sequence T-G-G-G-$N_1$-$N_2$-G-$N_3$-G-G-T-$N_4$-C-G-G-T (SEQ ID NO: 109), where $N_1$, $N_2$, $N_3$, and $N_4$ can be any nucleotide. Optionally, one or more of the nucleotides in the motif can be modified. In some cases, $N_1$ can be G or A. In some cases, $N_2$ can be G or A. In some cases, $N_3$ can be T or A. In some cases, $N_4$ can be G or C. In some cases, $N_1$ can be G or A, $N_2$ can be G or A, $N_3$ can be T or A, $N_4$ can be G or C, and the motif has the sequence of T-G-G-G-R-R-G-W-G-G-T-S-C-G-G-T (SEQ ID NO: 173) using IUPAC nomenclature, where R can be G or A, W can be A or T, and S can be G or C. In one example of motif 12, $N_1$ is G, $N_2$ is G, $N_3$ is T, and $N_4$ is G, and the motif has the sequence of T-G-G-G-G-G-G-T-G-G-T-G-C-G-G-T (SEQ ID NO: 138). In another example of motif 12, $N_1$ is A, $N_2$ is A, $N_3$ is A, and $N_4$ is C, and the motif has the sequence of T-G-G-G-A-A-G-A-G-G-T-C-C-G-G-T (SEQ ID NO: 139). Examples of norovirus-binding aptamers comprising motif 12 include M5 (SEQ ID NO: 40), M6-2 (SEQ ID NO: 39), and M13-2 (SEQ ID NO: 38).

Another family of norovirus-binding aptamers comprises motif 13. Motif 13 is characterized by the sequence T-G-G-G-$R_1$-$R_2$-K (SEQ ID NO: 110) using IUPAC nomenclature, where R can be A or G and K can be G or T. Optionally, one or more nucleotides in the motif can be modified. In one example of motif 13, $R_1$ is G, $R_2$ is A, K is T, and the motif has the sequence of T-G-G-G-G-A-T (SEQ ID NO: 140). In another example of motif 13, $R_1$ is G, $R_2$ is G, K is G, and the motif has the sequence of T-G-G-G-G-G-G (SEQ ID NO: 141). In another example of motif 13, $R_1$ is A, $R_2$ is A, K is G, and the motif has the sequence of T-G-G-G-A-A-G (SEQ ID NO: 142). Examples of norovirus-binding aptamers comprising motif 13 include M1 (SEQ ID NO: 35), M5 (SEQ ID NO: 40), and M6-2 (SEQ ID NO: 39).

Another family of norovirus-binding aptamers comprises motif 14. Motif 14 is characterized by the sequence T-G-G-G-$R_1$-$R_2$-$K_1$-W-$R_3$-$R_4$-$Y_1$-S-$Y_2$-$R_5$-$K_2$-$Y_3$ (SEQ ID NO: 111) using IUPAC nomenclature, where R can be A or G, K can be G or T, W can be A or T, Y can be C or T, and S can be G or C. In some cases, $K_1$ can be G, $R_3$ can be G, $R_4$ can be G, $Y_1$ can be T, $Y_2$ can be C, $R_5$ can be G, $K_2$ can be G, and $Y_3$ can be T, and the motif has the sequence of T-G-G-G-$R_1$-$R_2$-G-W-G-G-T-S-C-G-G-T (SEQ ID NO: 174) using IUPAC nomenclature, where R can be G or A, W can be A or T or A, and S can be G or C. In one example of motif 14, $R_1$ is G, $R_2$ is A, $K_1$ is T, W is A, $R_3$ is A, $R_4$ is A, $Y_1$ is C, S is G, $Y_2$ is T, $R_5$ is A, $K_2$ is T, $Y_3$ is C, and the motif has the sequence T-G-G-G-G-A-T-A-A-A-C-G-T-A-T-C (SEQ ID NO: 143). In another example of motif 14, $R_1$ is G, $R_2$ is G, $K_1$ is G, W is T, $R_3$ is G, $R_4$ is G, $Y_1$ is T, S is G, $Y_2$ 1 S C, $R_5$ is G, $K_2$ is G, $Y_3$ is T, and the motif has the sequence T-G-G-G-G-G-G-T-G-G-T-G-C-G-G-T (SEQ ID NO: 144). In another example of motif 14, $R_1$ is A, $R_2$ is A, $K_1$ is G, W is A, $R_3$ is G, $R_4$ is G, $Y_1$ is T, S is C, $Y_2$ is C, $R_5$ is G, $K_2$ is G, $Y_3$ is T, and the motif has the sequence T-G-G-G-A-A-G-A-G-G-T-C-C-G-G-T (SEQ ID NO: 145). Examples of norovirus-binding aptamers comprising motif 14 include M1 (SEQ ID NO: 35), M5 (SEQ ID NO: 40), M6-2 (SEQ ID NO: 39), and M13-2 (SEQ ID NO: 38).

Another family of norovirus-binding aptamers comprises motif 15. Motif 15 is characterized by the sequence A-C-G-A-A-T-G (SEQ ID NO: 182). Optionally, one or more nucleotides in the motif can be modified. Examples of norovirus-binding aptamers comprising motif 15 include AP2-GI (SEQ ID NO: 177) and AP3-GI (SEQ ID NO: 178).

Another family of norovirus-binding aptamers comprises motif 16. Motif 16 is characterized by the sequence A-C-G-G-A-T (SEQ ID NO: 183). Optionally, one or more nucleotides in the motif can be modified. Examples of norovirus-binding aptamers comprising motif 16 include AP3-GI (SEQ ID NO: 178).

Another family of norovirus-binding aptamers comprises motif 17. Motif 17 is characterized by the sequence C-G-A-A-G-G-G-A-C (SEQ ID NO: 184). Optionally, one or more nucleotides in the motif can be modified. Examples of norovirus-binding aptamers comprising motif 17 include AP2-GI (SEQ ID NO: 177) and AP4-GI (SEQ ID NO: 179).

Another family of norovirus-binding aptamers comprises motif 18. Motif 18 is characterized by the sequence C-G-A-A-G-T-G-T-A-C (SEQ ID NO: 185). Optionally, one or more nucleotides in the motif can be modified. Examples of norovirus-binding aptamers comprising motif 18 include AP4-GI (SEQ ID NO: 179).

Another family of norovirus-binding aptamers comprises motif 19. Motif 19 is characterized by the sequence G-G-N-G-A-G-C-G (SEQ ID NO: 186), where N can be any nucleotide. Optionally, one or more nucleotides in the motif can be modified. In some cases, N can be A or T, and the motif has the sequence G-G-W-G-A-G-C-G (SEQ ID NO: 191) using IUPAC nomenclature, where W can be A or T. In one example of motif 19, W is A, and the motif has the sequence of G-G-A-G-A-G-C-G (SEQ ID NO: 192). In another example of motif 19, W is T, and the motif has the sequence of G-G-T-G-A-G-C-G (SEQ ID NO: 193). Examples of norovirus-binding aptamers comprising motif 19 include AP5-GI (SEQ ID NO: 180) and AP6-GI (SEQ ID NO: 181).

Another family of norovirus-binding aptamers comprises motif 20. Motif 20 is characterized by the sequence $N_1$-G-T-$N_2$-G-G (SEQ ID NO: 187), where $N_1$ and $N_2$ can be any nucleotide. Optionally, one or more nucleotides in the motif can be modified. In some cases, $N_1$ and $N_2$ can each be A or T, and the motif has the sequence $W_1$-G-T-$W_2$-G-G (SEQ ID NO: 194) using IUPAC nomenclature, where W can be A or T. In one example of motif 20, $W_1$ is A and $W_2$ is A, and the motif has the sequence of A-G-T-A-G-G (SEQ ID NO: 195). In another example of motif 20, $W_1$ is T and $W_2$ is T, and the motif has the sequence of T-G-T-T-G-G (SEQ ID NO: 196). Examples of norovirus-binding aptamers comprising motif 20 include AP3-GI (SEQ ID NO: 178) and AP6-GI (SEQ ID NO: 181).

Another family of norovirus-binding aptamers comprises motif 21. Motif 21 is characterized by the sequence $N_1$-G-G-T-$N_2$-G (SEQ ID NO: 188), where $N_1$ and $N_2$ can be any nucleotide. Optionally, one or more nucleotides in the motif can be modified. In some cases, $N_1$ and $N_2$ can each be A or C, and the motif has the sequence $M_1$-G-G-T-$M_2$-G (SEQ ID NO: 197) using IUPAC nomenclature, where M can be A or C. In one example of motif 21, $M_1$ is A and $M_2$ is A, and the motif has the sequence of A-G-G-T-A-G (SEQ ID NO: 198). In another example of motif 20, $M_1$ is C and $M_2$ is C, and the motif has the sequence of C-G-G-T-C-G (SEQ ID NO: 199). Examples of norovirus-binding aptamers comprising motif 21 include AP2-GI (SEQ ID NO: 177) and AP6-GI (SEQ ID NO: 181).

Another family of norovirus-binding aptamers comprises motif 22. Motif 22 is characterized by the sequence G-G-A-T-T-A-G (SEQ ID NO: 189). Optionally, one or more nucleotides in the motif can be modified. Examples of norovirus-binding aptamers comprising motif 22 include AP1-GI (SEQ ID NO: 176) and AP5-GI (SEQ ID NO: 180).

Another family of norovirus-binding aptamers comprises motif 23. Motif 23 is characterized by the sequence G-G-A-A-T-A-G (SEQ ID NO: 190). Optionally, one or more nucleotides in the motif can be modified. Examples of norovirus-binding aptamers comprising motif 23 include AP1-GI (SEQ ID NO: 176).

Some norovirus-binding aptamers comprise one or more of motifs 1-14. Other norovirus-binding aptamers comprise norovirus-binding motifs other than motifs 1-14. Other norovirus-binding aptamers comprise one or more of motifs 1-14 in combination with other norovirus-binding motifs. Some norovirus-binding aptamers comprise one or more of motifs 1-23. Other norovirus-binding aptamers comprise norovirus-binding motifs other than motifs 1-23. Other norovirus-binding aptamers comprise one or more of motifs 1-23 in combination with other norovirus-binding motifs.

B. Targets of Norovirus-Binding Aptamers

The norovirus-binding aptamers disclosed herein preferentially bind to norovirus targets. In some cases, the norovirus-binding aptamers have little cross-reactivity with other viruses, such as hepatitis A virus (HAV) or enteroviruses such as poliovirus. The term "norovirus" includes intact noroviruses (aggregated or not aggregated) from all genogroups, genotypes, and strains of norovirus; norovirus virus-like particles; and parts or combinations of parts of intact noroviruses or norovirus virus-like particles. Noroviruses are a group of small, genetically diverse viruses belonging to the genus Norovirus, family Caliciviridae. Noroviruses can be segregated genetically into at least five genogroups, I to V, based on the molecular characterization of the capsid gene sequences (see Zheng et al., *Virology* 346:312-323 (2006)). The genogroups are further divided into more than 30 genotypes. Genotypes can further be divided into strains or variants. Strains of three genogroups—GI, GII, and GIV—are found in humans, and the GIII and GV genogroups are found in cows and mice, respectively. The GII genogroup, and more specifically variants of the GII.4 genotype, comprise the epidemic strains and cause the majority of outbreaks. However, other strains cause outbreaks as well and many of these are foodborne. Examples of norovirus strains include Snow Mountain virus (SMV; prototypical GII.2 norovirus), Norwalk virus (NV; prototypical GI.1 norovirus), Houston virus (HOV; a GII.4 strain), and Grimbsy virus (GRV; a GII.4 strain).

An intact norovirus or norovirus particle is a norovirus that is not disassembled in any significant way. In natural environments, norovirus particles are frequently aggregated. See Teunis et al., *J. Med. Viral.* 80:1468-1476 (2008). The term "virus-like particle" or "VLP" refers to a structure that in at least one attribute resembles a virus but which is non-infectious and non-replicating. Virus-like particles are typically multiprotein structures that mimic the organization and conformation of a native virus capsid, making them morphologically and antigenically similar to a native virus, but are non-infectious because they lack viral genetic material sufficient to replicate. The expression of viral structural proteins can result in the self-assembly of virus-like particles. A "part" of a norovirus or norovirus VLP can include, for example, a portion of a norovirus (e.g., the viral capsid); a component of the norovirus such as a particular norovirus protein; a domain or subdomain within such a protein; an epitope within such a protein, domain, or subdomain; or an epitope spanning two or more proteins, domains, or subdomains. The term "target" or "target molecule" refers to any compound or molecule of interest to which binding of a norovirus-binding aptamer is desired.

Norovirus-binding aptamers can preferentially bind to various norovirus targets. In some cases, aptamers can preferentially bind to a particular genogroup, genotype, or strain of norovirus or a target specific to a particular genogroup, genotype, or strain of norovirus. For example, the target genogroup can be genogroup I, genogroup II, and/or other genogroups, or the target genotype can be genogroup I, genotype 1; genogroup I, genotype 7; genogroup II, genotype 1; genogroup II, genotype 2; genogroup II, genotype 4; genogroup II, genotype 7; and/or other norovirus genotypes. Similarly, aptamers can preferentially bind to infectious norovirus particles or a target specific to infectious norovirus particles. As used herein, an "infectious" norovirus particle is a norovirus that has the capacity to invade an animal host and replicate. In other cases, targets can be any combination of genogroups, genotypes, or strains of norovirus of or common to any combination of genogroups, genotypes, or strains of norovirus and/or common to infectious and non-infectious norovirus particles.

Norovirus-binding aptamers typically bind to their designated norovirus target with an affinity characterized by an equilibrium dissociation constant ($K_d$) of less than about $10^{-4}$, less than about $10^{-5}$, less than about $10^{-6}$, less than about $10^{-7}$, less than about $10^{-8}$, less than about $10^{-9}$, less than about $10^{-10}$, less than about $10^{-11}$, or less than about $10^{-12}$ M. For example, some norovirus-binding aptamers can have an affinity characterized by an equilibrium dissociation constant value from about 0.001 nM to about 100 μM, from about 0.1 nM to about 999 nM, from about 1 nM to about 999 nM, from about 1 nM to about 500 nM, or from about 1 nM to about 300 nM.

Although smaller molecules such as proteins are typically used as targets for aptamers, complex heterogeneous targets such as whole cells, viruses, or virus-like particles are also employable for the generation of aptamers (see WO 2011/097420; Ohuchi, *BioRes. Open Access* 1:265-271 (2012)). Thus, in some cases, the target can be a norovirus virus-like particle, an intact norovirus, an intact human norovirus, or an infectious norovirus particle. This interaction can enable selection of norovirus-binding aptamers against these norovirus targets in their native conformation and physiological environment. Furthermore, norovirus-binding aptamers can be identified that preferentially bind to multiple norovirus surface targets in their native conformations and physiological environments, which can lead to candidate norovirus-binding aptamers with different levels of specificity (e.g., genogroups, genotypes, or strains) or even the ability to discriminate between different physiological states (e.g., infectious or non-infectious).

Norovirus targets can also comprise norovirus proteins or any other part or combination of parts of an intact norovirus, intact human norovirus, infectious norovirus particle, or a norovirus virus-like particle. Major and minor norovirus capsid proteins include VP1 and VP2, respectively (see Karst, *Viruses* 2:748-781 (2010); Hardy, *FEMS Microbiol. Lett.* 253:1-8 (2005)). VP1 can range from about 530-555 amino acids, and VP2 can range from about 208-268 amino acids. Norovirus capsids can be formed from 180 copies (90 dimers) of VP1 arranged with T=3 icosahedral symmetry and one or two copies of VP2 (see Hardy, *FEMS Microbiol. Lett.* 253:1-8 (2005); Taube et al., *J. Virol.* 84:5695-5705 (2010)). VP1 can self-assemble into virus-like particles (VLPs) in baculovirus, mammalian, and plant expression systems. The VP1 protein forms two domains: P (protruding, P1 and P2) and S (shell). The norovirus genome also encodes a nonstructural polyprotein, which can then be cleaved into at least six different nonstructural proteins, including VPg, p48, p22, an NTPase, a protease, and an RNA-dependent RNA polymerase.

In some cases, the norovirus target to which a norovirus-binding aptamer preferentially binds can be the viral capsid, the VPg protein or any other nonstructural protein, the VP1 protein, the VP2 protein, an epitope within any of the above, an epitope spanning both capsid proteins, or a region of one of the VPg, VP1, or VP2 proteins necessary for a particular functionality. For example, the target can be the S domain, the P domain, the P1 subdomain, or the P2 subdomain within the VP1 protein, or an epitope within any of these domains or subdomains or spanning two or more of these domains or subdomains.

The term "epitope" refers to a site on a target to which an aptamer binds. For example, an epitope on a protein target can be formed from contiguous amino acids or noncontiguous amino acids juxtaposed by tertiary folding of one or more proteins. Epitopes formed from contiguous amino acids are typically retained on exposure to denaturing solvents, whereas epitopes formed by tertiary folding are typically lost on treatment with denaturing solvents. An epitope typically includes at least about 2, at least about 3, at least about 5, or at least about 8-10 amino acids. Such amino acids can be in a specific spatial conformation. Methods of determining spatial conformation of epitopes include, for example, X-ray crystallography and two-dimensional nuclear magnetic resonance. See, e.g., Epitope Mapping Protocols, in Methods in Molecular Biology, Vol. 66, Glenn E. Morris, Ed. (1996). Thus, a norovirus target can be, for example, an epitope comprising at least about 2, at least about 3, at least about 5, or at least about 8-10 amino acids from the P2 subdomain of the P domain of the VP1 protein.

In some cases, only one norovirus target is selected, and the norovirus-binding aptamer preferentially binds to that target. In other cases, more than one target molecule is selected. When more than one target is selected, the targets can be from the same genogroup, genotype, or strain of norovirus, or from different genogroups, genotypes, or strains of norovirus. In other cases, targets can also include norovirus targets and non-norovirus targets.

In some cases, norovirus targets to which norovirus-binding aptamers preferentially bind are necessary for the function of the intact norovirus such that aptamers binding to such targets will affect a function of those molecules and/or a function of the intact norovirus. Such functions might include facilitating colonization of a niche in the host (e.g., adhesion of norovirus to host cells such as enterocytes, macrophages, and dendritic cells), evasion of the host's immune response, entry into or exit out of host cells, or production of apoptotic or other toxic responses in host cells. For example, association of the norovirus with histo-blood group antigens (HBGAs), which are neutral carbohydrates linked to proteins or lipids on cell surfaces, can be blocked. Many of the cellular interactions and immune recognition features may be located in the norovirus VP1 protein, and in particular the P2 subdomain, which is a subdomain that extends above the viral surface and has the most sequence divergence in the genome. Thus, the P2 subdomain can contain sites for antigenicity, immune-driven evolution, and cell binding. In some cases, such sites can be used as targets selected to affect corresponding functions of the norovirus.

Another example of a norovirus target necessary for the function of the intact norovirus is the VPg protein. The VPg protein is covalently bound to HuNoV genomic and subgenomic RNA and can be involved in translation of viral RNA and in initiating transcription. The VPg protein has been found to be necessary for HuNoV replication (see Guix et al., *J. Virology* 81(22):12238-12248 (2007)). As such, it can be required for HuNoV to be infectious. Thus, the VPg protein can be selected as a norovirus target to affect these functions.

C. Modifications of Norovirus-Binding Aptamers

The norovirus-binding aptamers disclosed herein can contain modified nucleic acids or other chemical or physical modifications. Such modifications can be made, for example, in order to increase the in vivo stability of the aptamer, to enhance or mediate the delivery of the aptamer, or to reduce clearance rate of the aptamer from the body. For example, aptamers can be pretreated with an anti-nuclease before use. Such modifications can also include those which provide other chemical groups that incorporate additional charge, polarizability, hydrogen bonding, electrostatic interaction, and fluxionality to the nucleic acid bases or to the aptamer as a whole. Modifications can also be made to make the aptamer as small as possible while still retaining norovirus-binding activity, to increase specificity for the target, to confer resistance to degradation, to provide capability to cross various tissue or cell membrane barriers, or any other accessory properties that do not significantly interfere with affinity for the target (see, e.g., U.S. Pat. No. 5,496,938).

Examples of such modifications include nucleotide substitutions, as well as chemical substitutions at the deoxyribose/ribose and/or phosphate and/or base positions of a given nucleotide sequence (see, e.g., WO 92/03568; U.S. Pat. Nos. 5,118,672; 5,660,985; 6,090,932). Aptamers can include one or more substitute internucleotide linkages, altered sugars, altered bases, or combinations thereof (see, e.g., WO 2011/061351). For example, such aptamers can contain one or more nucleotides with 2'-position sugar modifications such as 2'-amino (2'-NH$_2$), 2'-O-methyl (2'-OMe), and/or 2'-fluoro (2'-F) groups. Such aptamers can also contain nucleotide derivatives chemically modified at the 5' and 2' positions of pyrimidines or at the 8' position of purines (see U.S. Pat. Nos. 5,660,985 and 5,580,737). Other modifications include modifications at exocyclic amines, substitution of 5-bromo-uracil or 5-iodo-uracil, substitution of 4-thiouridine, backbone modifications, methylations, unusual base-pairing combinations such as the isobases isocytidine and isoguanidine, and the like. Modifications can also include 3' and 5' modifications such as capping. Some specific modifications include the 5'-5' inversion, 5'-cholesteryl, 5'-liposome, 3'-3' inversion, 3'-T capping, 3'-biotin, mirror-design, phosphorothioate replacement, mehtylphosphonate replacement, N3'-P5', locked nucleic acid (LNA), unlocked nucleic acid (UNA), hexitol nucleic acid (HNA), 2'-O-methyl-4'-thio, 5-N-(6-aminohexyl) carbamoyl-2'-deoxyuridine, 4'-C-(aminoethyl) thymidine, and 4'-thio modifications described in Wang et al., *Curr. Med. Chem.* 18:4126-4138 (2011).

The norovirus-binding aptamers disclosed herein can also be coupled to other elements. Such elements can, for example, add independent affinity for the target, enhance the affinity of the aptamer to the target, direct or localize the aptamer to the desired location in vivo, or utilize the specificity of the aptamer to the target to effect some additional reaction at that location.

Some norovirus-binding aptamers are chimeric aptamers. Such aptamers, and methods for making them, are described in U.S. Pat. No. 5,637,459. Chimeric aptamers are aptamers with two or more functionalities. Chimeric norovirus-binding aptamers can comprise two or more component aptamers. In some cases, the component aptamers are 3'-3'-linked. Some chimeric norovirus-binding aptamers preferentially bind to different epitopes of the same norovirus target. For example, a chimeric norovirus-binding aptamer can comprise one component norovirus-binding aptamer targeting a first epitope within the P1 domain of a norovirus and a second component norovirus-binding aptamer targeting a second epitope within the P1 domain of a norovirus. Other chimeric norovirus-binding aptamers preferentially bind to epitopes on two different targets on the same norovirus. For example, a chimeric norovirus-binding aptamer can comprise one component norovirus-binding aptamer targeting the VP1 protein of a norovirus and a second component norovirus-binding aptamer targeting the VP2 protein of a norovirus. Other chimeric norovirus-binding aptamers preferentially bind to an epitope on a target norovirus and an epitope on a non-norovirus molecule.

Some norovirus-binding aptamers are blended aptamers. Such aptamers, and methods for making them, are described in U.S. Pat. No. 5,683,867. Blended norovirus-binding aptamers comprise a norovirus-binding aptamer coupled to at least one other functional unit. The functional unit can be coupled to the 5' end of the aptamer, the 3' end of the aptamer, or any other location within the norovirus-binding aptamer that does not affect a desired functionality of the norovirus-binding aptamer. Some examples of functional units include peptides, amino acids, aliphatic groups and lipid chains, or peptide motifs. In some cases, the functional units are recognizable by the norovirus target. For example, the functional unit may fit into a specific binding pocket on the norovirus target to form tight binding via hydrogen bonds, salt bridges, or van der Waals interactions. Some functional units guide the norovirus-binding aptamers to specific sites on the target.

Other functional units add functionality to the norovirus-binding aptamer, for example, to increase RNA hydrophobicity and enhance binding, membrane partitioning, and/or permeability, or to add reporter molecules or labels, such as biotin- or fluorescence-tagged reporter oligonucleotides. Examples of such labels include radiolabels, fluorophores, chromophores, and affinity tags. Such labels can be radiolabels used for medical imaging (e.g., technetium-99m (tc99m) or iodine-123 (1123)), or spin labels used for nuclear magnetic resonance (NMR) imaging or magnetic resonance imaging (MRI), such as iodine-123, iodine-131, indium-111, fluorine-19, carbon-13, nitrogen-15, oxygen-17, gadolinium, manganese, or iron. Examples of fluorophores include fluorescein, rhodamine, Cy5 reactive dye, Cy3 reactive dye, allophycocyanin, peridinine chlorophyll-a protein (PerCP), phycoerythrin, Alexa Fluor, and green fluorescent protein (GFP). Other labels include quantum dots (QDs), which are nanocrystals made of semiconductor materials that function like fluorophores. Functional groups can also comprise chemical groups which covalently react and couple the norovirus-binding aptamer to the norovirus target.

Several approaches can be used to create chimeric or blended norovirus-binding aptamers. Such approaches include conjugation approaches involving 3' or 5' primary amines coupled to various other molecules during chemical synthesis of nucleic acids, or classic carbodiimide, aldehyde, diazonium, or other approaches which take advantage of the greater chemical reactivity or primary alkyl amine tags versus aryl amines on the nucleotides themselves. Such approaches, as well as several types of aptamer-drug and aptamer-toxin conjugates, are described in Bruno, *Pharmaceuticals* 6:340-357 (2013).

The norovirus-binding aptamers disclosed herein can be coupled to other elements through direct covalent conjugation. Direct conjugation can be achieved, for example, by construction of a polynucleotide fusion through genetic fusion of two component aptamers so that they exist as a single polynucleotide. Direct conjugation can also be achieved by formation of a covalent bond between a reactive group on a norovirus-binding aptamer and a corresponding group or acceptor on a coupled element. Direct conjugation can also be achieved by modification of one of the two molecules to be conjugated to include a reactive group that forms a covalent attachment to the other molecule to be conjugated under appropriate conditions. For example, methods for covalent conjugation of nucleic acids to proteins are known (e.g., photocrosslinking, see, e.g., Zatsepin et al., *Russ. Chem. Rev.* 74:77-95 (2005)).

Coupling may also be performed using a variety of linkers. Linkers can be any suitable spacer moiety. For example, suitable linker groups include polynucleotides, PEG, polyvinyl alcohol, polyacrylates, and polypeptides. In some cases, the linkage is cleavable. Examples of suitable cleavable linkages include photochemically labile linkers, disulfides, and carbonates. The linkage can also be cleavable with enzymes, such as DNAses and proteinases. Linkers that release the linked element under acidic or reducing conditions can also be employed.

The norovirus-binding aptamers disclosed herein can also be tethered to a solid support. For example, the aptamers can be immobilized on magnetic beads. This can be achieved, for example, on P(HPMA/EGDMA)-g-p(GMA) magnetic beads via glutaraldehyde linking (see Ozalp et al., *Anal. Biochem.* 447:119-125 (2014) or using biotinylated aptamers and streptavidin paramagnetic particles. Norovirus-binding aptamers can also be immobilized on gold electrode chips (see Kim et al., *Biosensors and Bioelectronics* 54:195-198 (2014)) or on any other solid support that is suitable for a desired application, such as a method of detection, capture, or concentration of norovirus.

D. Combinations Comprising Norovirus-Binding Aptamers

Norovirus-binding aptamers disclosed herein can also be combined with but not physically coupled to other aptamer(s) and/or element(s) in one mixture. Optionally, the norovirus-binding aptamer and other aptamer(s) and/or element(s) can be differentially labeled. The term "differentially labeled" indicates that the norovirus-binding aptamer and other aptamer(s) and/or molecule(s) can be distinguished from each other because each is coupled to a different label.

In some cases, a mixture of norovirus-binding aptamers may be generated in which the different component aptamers preferentially bind to the same norovirus target(s). The component norovirus-binding aptamers may, for example, preferentially bind to different epitopes on the same norovirus target. In some cases, the ability of a mixture of norovirus-binding aptamers to bind to different epitopes on the same norovirus target will result in increased binding affinity to the norovirus target compared to norovirus-binding aptamers binding to only one epitope.

In other cases, a mixture of norovirus-binding aptamers may be generated in which the different component aptamers preferentially bind to different norovirus targets. For example, such mixtures can include one or more norovirus-binding aptamers that preferentially bind to one or more genogroups of noroviruses and one or more other norovirus-binding aptamers that preferentially bind to one or more different genogroups of noroviruses. Similarly, such mixtures can include one or more norovirus-binding aptamers that preferentially bind to one or more genotypes of noroviruses and one or more other norovirus-binding aptamers that preferentially bind to one or more different genotypes of noroviruses. Likewise, such mixtures can include one or more norovirus-binding aptamers that preferentially bind to one or more strains of norovirus and one or more other norovirus-binding aptamers that preferentially bind to one or more different strains of norovirus.

In yet other cases, a mixture of aptamers may be generated in which one or more component aptamers are norovirus-binding aptamers that preferentially bind to a norovirus target and one or more other aptamers preferentially bind to a non-norovirus target. For example, such mixtures can include one or more aptamers that preferentially bind to noroviruses and one or more other aptamers that preferentially bind to another type of virus or bacteria. In some cases, the other type of virus or bacteria is a pathogenic virus or bacteria, and the one or more aptamers that preferentially bind to noroviruses and the one or more other aptamers that preferentially bind to another type of virus or bacteria are differentially labeled such that the noroviruses and the other type of virus or bacteria can be differentially detected.

The norovirus-binding aptamers disclosed herein can also be combined with but not physically coupled to one or more other non-aptamer molecules in a mixture. In some cases, the other non-aptamer molecules preferentially bind to norovirus targets. In other cases, the other non-aptamer molecules preferentially bind to non-norovirus targets. In some cases, the other non-aptamer molecules can be norovirus-binding molecules, such as antibodies or peptide aptamers. Such other non-aptamer molecules can bind to the same target as the norovirus-binding aptamer. For example, the norovirus-binding aptamer can bind to one epitope on the norovirus target, and the other non-aptamer molecule can bind to another epitope on the same norovirus target. Such other non-aptamer molecules can also bind to a different norovirus target or a non-norovirus target. For example, such mixtures can include norovirus-binding aptamers that preferentially bind to one or more genogroups of noroviruses and other non-aptamer molecules that preferentially bind to one or more different genogroups of noroviruses. Similarly, such mixtures can include norovirus-binding aptamers that preferentially bind to one or more genotypes of noroviruses and other non-aptamer molecules that preferentially bind to one or more different genotypes of noroviruses. Likewise, such mixtures can include norovirus-binding aptamers that preferentially bind to one or more strains of norovirus and other non-aptamer molecules that preferentially bind to one or more different strains of norovirus.

III. Methods for Detecting Presence of, Capturing, and/or Concentrating Norovirus The norovirus-binding aptamers disclosed herein can be used for specifically, qualitatively, and/or quantitatively detecting norovirus from any source in the context of clinical diagnosis, treatment, and/or research based on preferential binding of the aptamer to the norovirus. For example, the aptamers can be used for detecting norovirus in a test sample as an indication that the test sample contains norovirus.

Different types of test samples can be used. The term "test sample" refers to any clinical sample, environmental sample, food sample, or any other type of sample that is being assayed for the presence of norovirus. A test sample can be taken or derived from anything or anywhere susceptible to contain norovirus. Some test samples can be used directly. Other test samples can be subjected to purifying protocols or other processing, such as coating on plates.

Some test samples can comprise captured or pre-concentrated norovirus. The term "captured norovirus" refers to norovirus that has been substantially separated from a test sample. For example, a test sample can be contacted with a norovirus-binding aptamer disclosed herein or any other norovirus-binding molecule, and the bound norovirus can then be substantially separated from the remainder of the test sample. The norovirus that has been substantially separated from the remainder of the test sample is the captured norovirus. Both the captured norovirus and the original test sample from which the captured norovirus was substantially separated are considered to be test samples.

As used herein, the term "substantially separating" refers to removing a molecule of interest (e.g., a norovirus) so that it is at least partially free of one or more other components with which it was previously associated. For example, a norovirus of interest can be at least partially free of some non-norovirus components with which it was previously associated but not other non-norovirus components. In some cases, the molecule of interest is at least about 30%, at least about 40%, at least about 50%, at least about 60%, at least about 70%, at least about 80%, at least about 90%, or 100% free of one or more other components with which it was previously associated. For example, substantially separating aptamer-bound norovirus from a test sample means that the aptamer-bound norovirus (aggregated or not aggregated) is at least about 30%, at least about 40%, at least about 50%, at least about 60%, at least about 70%, at least about 80%, at least about 90%, or 100% free of one or more other components present in the test sample.

The term "clinical sample" refers to a sample of biological material within or obtainable from a patient or any other biological source, such as another human or mammalian subject. Such samples can include, for example, organs, organelles, tissues, sections of tissues, bodily fluids, peripheral blood, blood plasma, blood serum, fecal matter, vomitus, urine, sputum, saliva, bronchial aspirate, cells, molecules such as proteins and peptides, and any parts or combinations derived therefrom. The term clinical sample can also encompass any material derived by processing the sample. Derived material can include cells or their progeny. Processing of the clinical sample may involve one or more of filtration, distillation, extraction, concentration, fixation, inactivation of interfering components, and the like. In certain cases, clinical samples are blood, fecal matter, vomitus, or any bodily fluid sample taken from a patient suffering or suspected to be suffering from norovirus infection.

The term "environmental sample" refers to a sample taken or derived from any particular environment. For example, an environmental sample can be taken or derived from water (e.g., freshwater, salt water, waste water, and drinking water), soil, sewage, sludge, or an organism or tissue from an organism, such as a shellfish, that is a potential reservoir for a norovirus. An environmental sample can also be a sample taken or derived from a particular surface or object ("fomite") in a specific location, such as a restaurant, cruise ship, hospital, nursing home, school, or other location. In certain cases, an environmental sample is taken or derived from a particular environment suspected to be a source of norovirus.

The term "food sample" refers to a sample taken or derived from any food or beverage product. Examples of such food or beverage products include fresh produce, deli meats, salad bars, prepared foods (e.g., sandwiches, meat salads, casseroles), raw and cooked molluscan shellfish, and highly acidic foods such as orange juice and frozen raspberries. In certain cases, a food sample is taken from a food or beverage product suspected to be a source of norovirus.

Some methods of detecting norovirus comprise contacting a test sample with a norovirus-binding aptamer disclosed herein, and detecting the presence of the norovirus-binding aptamer bound to norovirus in the test sample. Detection of bound aptamer can indicate the presence of at least one norovirus strain. In some such methods, unbound aptamer is removed before detecting the presence of the norovirus-binding aptamer bound to norovirus in the test sample. In some such methods, the norovirus-binding aptamers disclosed herein can be labeled with fluorescent molecules, spin-labeled molecules, enzymes, radioisotopes, or similar labels, and they can also be provided in the form of a kit with all the necessary reagents to perform the assay for detection of norovirus.

In some methods of detecting norovirus, a test sample is contacted with a norovirus-binding aptamer disclosed herein under conditions and for an amount of time sufficient to permit the norovirus-binding aptamer to bind to the norovirus. For example, a test sample can be incubated with at least about 10 nM, at least about 100 nM, at least about 500 nM, at least about 1 or at least about 2 µM of norovirus-binding aptamer. In some cases, the incubation can be done at room temperature. In other cases, it can be done at 4° C. In some cases, the incubation can be overnight. In other cases, the incubation can be for at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours, at least about 12 hours, or at least about 24 hours.

In some methods of detecting norovirus, unbound aptamer is removed after contacting the test sample with the norovirus-binding aptamer. Unbound aptamer may be removed (e.g., by washing one or more times with, for example, a buffer) under conditions such that some of the norovirus-binding aptamer that is bound to norovirus will remain bound to the norovirus. For example, unbound aptamer can be removed by washing one or more times with a buffer. In some cases, substantially all of the norovirus-binding aptamer that is bound to norovirus will remain bound to the norovirus.

Many assays can be used to qualitatively or quantitatively detect binding of the norovirus-binding aptamers disclosed herein to norovirus. For example, an Enzyme-Linked Aptamer Sorbent Assay (ELASA) can be used. Assays involving amplification of the bound aptamer (e.g. qPCR) or RNA from the aptamer-bound virus (e.g., qRT-PCR) can be used. Flow cytometry methods as described in U.S. Pat. No. 5,853,984 can be used. Microarrays, BIAcore assays, differential centrifugation, chromatography, electrophoresis, immunoprecipitation, optical biosensors, and other surface plasmon resonance assays can be used as described in WO 2011/061351. Other assays that can be used are calorimetric analysis and dot blot assays. Moreover, just as the enzyme-linked immunosorbent assay (ELISA) was adapted for aptamers in the ELASA assay, any other assays involving norovirus-binding antibodies can be adapted for use with the norovirus-binding aptamers disclosed herein in place of the antibodies. Such assays include immunometric assays such as radioimmunoassays, flow cytometry assays, blotting applications, anisotropy, membrane assays, biosensors, and the like. Any other assays known in the art can also be used or adapted.

Methods of detecting norovirus using the norovirus-binding aptamers disclosed herein can also be combined with other methods of detecting norovirus. For example, methods of detecting norovirus using the norovirus-binding aptamers disclosed herein can be combined with sample concentration and amplification of viral RNA as described in U.S. Pat. No. 7,205,112, or any methods utilizing norovirus-binding antibodies, including immunometric assays such as enzyme-linked immunosorbent assays (ELISAs), radioimmunoassays, flow cytometry assays, blotting applications, anisotropy, membrane assays, biosensors, and the like.

Methods for detecting norovirus can have varying degrees of inclusivity and exclusivity. In some cases, the norovirus-binding aptamers used are exclusive, wherein only noroviruses of one or more particular genogroups, genotypes, or strains can be detected. In other cases, the norovirus-binding aptamers used are more inclusive, wherein noroviruses of a wide range of genogroups, genotypes, or strains of norovirus can be detected. If multiple genogroups, genotypes, or strains can be detected, particular genogroups, genotypes, or strains may be preferentially detected due to a higher binding affinity of the norovirus-binding aptamer(s) to those particular genogroups, genotypes, or strains. Methods of detecting norovirus can also be specific for infectious norovirus particles or alternatively can detect both infectious and non-infectious norovirus particles.

In some cases, only infectious norovirus particles can be detected. For example, norovirus-binding aptamers can be used that preferentially bind to intact norovirus capsids, VPg, or another protein whose function is required for norovirus to be infectious.

Some methods of detecting norovirus can differentially detect two or more genogroups, genotypes, or strains of norovirus or can differentially detect infectious and non-infectious norovirus. For example, a mixture of norovirus-binding aptamers can be used, wherein the first norovirus-binding aptamer preferentially binds to one or more genogroups, genotypes, or strains of norovirus and one or more other norovirus-binding aptamers preferentially bind to one or more different genogroups, genotypes, or strains of norovirus. The different norovirus-binding aptamers can be differentially labeled, and detection of bound first aptamer and bound other aptamers can indicate the presence of at least two norovirus genogroups, genotypes, or strains in a test sample. Comparable methods of detecting two or more genogroups, genotypes, or strains of norovirus involve use of a norovirus-binding aptamer disclosed herein that preferentially binds to one or more genogroups, genotypes, or strains of norovirus, and one or more other detection compounds (e.g., peptide aptamers, antibodies, or the like) that detect one or more different genogroups, genotypes, or strains of norovirus.

Some methods of detecting norovirus can further detect non-norovirus targets as well. For example, a norovirus-binding aptamer disclosed herein can be used with one or more other detection compounds (e.g., nucleic acid aptamers, peptide aptamers, antibodies, or the like) that preferentially bind to other types of viruses or bacteria, such as hepatitis A virus or *Listeria monocytogenes* (see, e.g., U.S. Pat. No. 7,645,582). In some cases, the other types of viruses or bacteria detected with the one or more other detection compounds can cause symptoms in a patient that are similar to those caused by norovirus infection. The norovirus-binding aptamer and the other detection compound(s) can be differentially labeled so that detection of bound aptamer can indicate norovirus infection whereas detection of binding of the other detection compound(s) can indicate a different type of infection or condition.

Binding of the aptamers in a test sample can be compared to binding of the aptamers in a control sample. The term "control sample" refers to a test sample, clinical sample, environmental sample, or food sample not known or suspected to include norovirus, or not known or suspected to include norovirus of a given genogroup, genotype, or strain. Such samples can be obtained at the same time as a test sample, clinical sample, environmental sample, or food sample suspected to include norovirus, or they can be obtained on a different occasion. Such samples can be obtained from the same source or from different sources. The control sample can be the same type of sample as the test sample, clinical sample, environmental sample, or food sample to which it is being compared. For example, if the clinical sample comprises fecal matter, then the control sample can comprise fecal matter. Similarly, if the food sample comprises lettuce, then the control sample can comprise lettuce.

Multiple test samples and multiple control samples can be evaluated on multiple occasions to protect against random variation independent of the differences between the samples. A direct comparison can then be made between the test samples and the control samples to determine whether aptamer binding (i.e., the presence of norovirus) in the test samples is increased, decreased, or the same relative to aptamer binding in the control samples. Increased binding of the aptamer in the test samples relative to the control samples indicates the presence of at least one strain of norovirus in the test samples. In some instances, increased binding is statistically significant relative to the control sample. For example, statistical significance can mean $p \leq 0.1$, $p \leq 0.05$, $p \leq 0.01$, or $p \leq 0.001$. In some cases, the term "increased binding" refers to aptamer binding in a test sample that is at least about 1.5-fold, at least about 2-fold, at least about 3-fold, at least about 4-fold, at least about 5-fold, at least about 10-fold, or at least about 20-fold higher than aptamer binding in a control sample.

The norovirus-binding aptamers disclosed herein can also be used for capturing, purifying, and/or concentrating norovirus from test samples. Such methods can comprise contacting a test sample with a norovirus-binding aptamer disclosed herein and then substantially separating the aptamer-bound norovirus from the remainder of the test sample. For example, norovirus can be captured with nanomagnetic streptavidin beads using biotinylated aptamers.

The norovirus that was substantially separated from the remainder of the test sample (i.e., the captured norovirus) can be in a more concentrated form than the norovirus in the original test sample. For example, the concentration of the captured norovirus can be at least about 1.5-fold, at least about 2-fold, at least about 3-fold, at least about 4-fold, at least about 5-fold, at least about 10-fold, at least about 20-fold, at least about 25-fold, at least about 30-fold, at least about 40-fold, at least about 50-fold, at least about 75-fold, or at least about 100-fold higher than the norovirus concentration in the original test sample. Norovirus concentration can be calculated, for example, in terms of genomic copies of viral RNA per liter or per gram of sample (e.g., using qRT-PCR).

Captured and/or concentrated norovirus can be used to facilitate detection using molecular amplification methods. For example, an aptamer bound to the captured norovirus can be used for subsequent qPCR amplification as an indirect method of detecting the norovirus. Other molecular amplification methods that can be used include viral RNA extraction and subsequent real-time RT-PCR. Other nucleic acid amplification methods such as RT-LAMP (Reverse Transcription-Loop Mediated Isothermal Amplification), RPA (Recombinase Polymerase Amplification), and others could also be used.

Methods of capturing and/or concentrating norovirus using the norovirus-binding aptamers disclosed herein can be combined with other norovirus concentration and purification schemes. Such other schemes can be based on sample manipulations that capitalize on the behavior of enteric viruses to be released from particulates at high pH and salt concentration (elution), to act as proteins in solutions (precipitation using polyethylene glycol), to co-sediment by simple centrifugation when adsorbed to larger particles, and to remain infectious at pH extremes or in the presence of organic solvents. Filtration and ultracentrifugation can also be used. Other schemes that can be used involve capture by antibodies or carbohydrate ligands. Examples of ligands that can be used include porcine gastric mucin, histo-blood group antigens (HBGAs), HBGA-like substances, and human plasma protein components.

Similarly, methods of capturing and/or concentrating norovirus using the norovirus-binding aptamers disclosed herein can be combined with norovirus detection schemes such as antibody-based detection, or methods of detecting norovirus using the norovirus-binding aptamers disclosed herein can be combined with other virus capturing and/or concentrating schemes. One example of a method of detecting norovirus using the norovirus-binding aptamers disclosed herein combined with another virus capturing scheme is the two-site binding sandwich qPCR assay. In such assays, any aptamer-based or non-aptamer-based methods of capturing norovirus can be used prior to exposing a norovirus-binding aptamer disclosed herein to the captured norovirus. In some such assays, the molecule(s) used for the initial capture of the norovirus can bind to an epitope on the norovirus that is different from the epitope to which the norovirus-binding aptamer binds. After exposing the captured norovirus to the norovirus-binding aptamer, the bound norovirus-binding aptamer can be detected. For example, the bound norovirus-binding aptamer can be amplified by qPCR.

IV. Methods for Identification and Selection of Aptamers

Methods are provided herein for the identification and selection of aptamers that preferentially bind to norovirus targets. Some such methods comprise the Systematic Evolution of Ligands by EXponential Enrichment (SELEX) method or modifications thereof. SELEX is a method for selecting high affinity ligands of a target. The SELEX method is described in detail elsewhere. See, e.g., U.S. Pat. Nos. 5,270,163; 5,567,588; 5,696,249; and 5,853,984, herein incorporated by reference in their entirety for all purposes.

A SELEX process for identifying norovirus-binding aptamers can comprise contacting a candidate mixture of nucleic acids with a selected norovirus target and partitioning the nucleic acids with relatively higher affinity to the target from the nucleic acids with relatively lower affinity to the target. In some cases, the nucleic acids that preferentially bind to the selected target can then be amplified. Any combination of the steps can be repeated as desired until the desired number and affinity of norovirus-binding aptamers is achieved. By repeating the partitioning and amplifying steps, the newly formed candidate mixture may contain fewer and fewer unique sequences, and the average degree of affinity of the nucleic acids to the norovirus target can increase. The SELEX process can yield a candidate mixture containing one or a small number of unique nucleic acid sequences representing those nucleic acids from the original candidate mixture, or portions thereof, having the highest affinity to the norovirus target.

The term "candidate mixture" refers to a mixture of nucleic acids of differing sequence from which to select a desired norovirus-binding aptamer that binds to a norovirus target with greater affinity than that of the bulk population of nucleic acids or a desired norovirus-binding aptamer that binds to a norovirus target with greater affinity than the average binding affinity of all of the nucleic acids in the candidate mixture. The source of a candidate mixture can be from naturally occurring nucleic acids or fragments thereof, chemically synthesized nucleic acids, enzymically synthesized nucleic acids, or nucleic acids made by a combination of these techniques. The candidate mixture may contain nucleic acids with one or more types of modified nucleotides. Alternatively, modified nucleotides may be incorporated into norovirus-binding aptamers that were identified by SELEX using a candidate mixture of nucleic acids not containing modified nucleotides.

The term "partitioning" refers to any process whereby norovirus-binding aptamers bound to norovirus targets (hereinafter referred to as aptamer-target pairs) can be separated from nucleic acids not bound to norovirus targets. Because only a small number of sequences (and possibly only one molecule of nucleic acid) corresponding to the highest affinity nucleic acids may exist in the candidate mixture, it can be desirable to select partitioning criteria so that an appropriate amount of the nucleic acids in the candidate mixture (about 5-50%) can be retained during partitioning, providing a greater number of norovirus-binding aptamers. Partitioning can be accomplished by various methods known in the art. For example, nucleic acid-protein pairs can be bound to nitrocellulose filters while unbound nucleic acids are not. Columns that specifically retain aptamer-target pairs (or specifically retain bound aptamer complexed to an attached norovirus target) can be used for partitioning. Liquid-liquid partition can also be used as well as filtration gel retardation and density gradient centrifugation. The choice of partitioning method will depend on properties of the norovirus target and of the aptamer-target pairs and can be made according to principles and properties known to those of ordinary skill in the art.

The term "amplifying" refers to any process or combination of steps that increases the amount or number of copies of a molecule or class of molecules. Any reaction or combination of reactions known in the art can be used for amplifying as appropriate, including direct DNA replication, direct RNA amplification, and the like. The amplification method should result in the proportions of the amplified mixture being representative of the proportions of different sequences in the initial mixture.

Some methods for identification and selection of norovirus-binding aptamers comprise the counter-SELEX method or modifications thereof. See U.S. Pat. Nos. 5,580,737 and 6,376,190, hereby incorporated by reference in their entirety for all purposes. Counter-SELEX can increase specificity of SELEX pools and can decrease the number of SELEX selection rounds required to identify a norovirus-binding aptamer specific for a norovirus target. Further, it provides a methodology for identifying a norovirus-binding aptamer that does not cross-react with other molecules, including closely related molecules.

A method of using the SELEX and counter-SELEX processes to identify norovirus-binding aptamers can be done in sequential steps. In SELEX, a candidate mixture of nucleic acids is placed in contact with a selected norovirus target, partitioning the nucleic acids with relatively higher affinity to the norovirus target from the nucleic acids with relatively lower affinity to the norovirus target, and amplifying the former. In counter-SELEX, a nucleic acid pool is placed in contact with a sample containing one or more non-target molecules, and the nucleic acids binding to these non-targets are removed. The resulting non-bound nucleic acid mixture is then preferentially amplified. Any combination of SELEX and counter-SELEX steps can be repeated as desired until the desired number and affinity of norovirus-binding aptamers is achieved.

Any combination of rounds of SELEX and rounds of counter-SELEX can be used in any order. Thus, in some cases, SELEX and counter-SELEX rounds are not done in sequence. For example, one or more rounds of SELEX can be performed, followed by one or more rounds of counter-SELEX, or vice versa.

Examples of non-target molecules that can be used to enhance norovirus-binding aptamer specificity are a matrix used to immobilize the virus during the SELEX process (e.g., antibody-bound beads), glutathione sepharose 4B, clinical samples such as human stool specimens that are negative for norovirus, food samples negative for norovirus, environmental samples negative for norovirus, bacteria derived from clinical samples (e.g., fecal matter), bacteria derived from food samples, bacteria derived from environmental samples, or unrelated viruses such as hepatitis A virus or an enterovirus such as poliovirus.

There are many potential applications of the SELEX and counter-SELEX processes. For example, the selected norovirus target can correspond to proteins or protein structures that must be intact or complete in order for a norovirus particle to be infectious and the non-target molecules can be those lacking the necessary structure(s), thereby producing norovirus-binding aptamers that preferentially bind to infectious norovirus particles. Non-infectious viral particles can potentially be generated, for example, through thermal inactivation of norovirus, chemical inactivation (e.g., 2% trisodium phosphate, 2% glutaraldehyde, 1,000-5,000 ppm chlorine, etc.), electron beam inactivation, UV irradiation, gamma irradiation, high pressure processing, use of ozone, and pH inactivation (see Richards, *Food Environ. Virol.* 4:6-13 (2012)). In certain cases, thermal inactivation can be achieved by treatment at a temperature of at least 60° C., at least 65° C., at least 70° C., at least 75° C., or at least 80° C. In some cases, thermal inactivation can be achieved at a temperature of 63° C. or at a temperature of 65° C. In some cases, the thermal inactivation treatment occurs over a period of at least 0.5 minutes, at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes, or at least 30 minutes.

In other cases, the selected target can be norovirus strains from a target genogroup and/or genotype, and the non-target molecules can be norovirus strains from other genogroups and/or genotypes, thereby producing norovirus-binding aptamers that preferentially bind to the target genogroup and/or genotype. For example, the target genogroup can be genogroup I, genogroup II, and/or other genogroups, or the target genotype can be genogroup I, genotype 1; genogroup I, genotype 7; genogroup II, genotype 1; genogroup II, genotype 2; genogroup II, genotype 4; genogroup II, genotype 7; and/or other norovirus genotypes. The selected target can also be a particular norovirus strain, with the non-target molecules being any other norovirus strain, thereby producing norovirus-binding aptamers that preferentially bind to the target norovirus strain. In other cases, the target can be a particular part of a norovirus, thereby producing norovirus-binding aptamers that preferentially bind to the target part of the norovirus. For example, the target could be the VPg protein or any other nonstructural protein, the VP1 protein, the P domain within the VP1 protein, the P1 subdomain within the VP1 protein, the P2 subdomain within the VP1 protein, the S domain within the VP1 protein, or the VP2 protein. The target can also be a defined epitope within any of the above proteins, domains, or subdomains, thereby producing norovirus-binding aptamers that preferentially bind to that epitope. The non-target molecules could then be, for example, any protein, domain, subdomain, or epitope other than the target protein, domain, subdomain, epitope.

A variation of the SELEX process is a method that uses graphene or a derivative thereof, such as graphene oxide. Because graphene and its derivative graphene oxide have useful properties such as the ability to adsorb ssDNA and to release that DNA in the presence of specific targets of the DNA, graphene and its derivatives, such as graphene oxide, can be used with SELEX to provide an immobilization-free platform for screening of aptamers that bind to their target with high affinity and specifcity. For example, a pool of aptamers can be incubated with graphene oxide so that they adsorb. The unadsorbed aptamers are then discarded, and the adsorbed aptamers can be incubated with a selected norovirus target for specific desorption of the aptamers.

Secondary selection methods can be combined with SELEX and/or counter-SELEX to select for additional functionality, such as ability to modify a norovirus target function upon binding to selected norovirus-binding aptamers. For example, such methods can include selections or screens for inhibition, alteration of substrate binding, loss of functionality, disruption of structure, and the like. Those of ordinary skill in the art are able to select from among various alternatives those selection or screening methods that are compatible with the methods described herein.

V. Methods for Assessing Efficacy of Therapeutic Agents or Vaccines

The instant disclosure further provides methods of evaluating the efficacy of a therapeutic agent in a patient diagnosed with a norovirus infection. A "patient" includes a human or other mammalian subject that receives either prophylactic or therapeutic treatment. Treatment is considered prophylactic if administered to an individual susceptible to or otherwise at risk of norovirus infection. Treatment is considered therapeutic if administered to an individual suspected of having, or already suffering from, norovirus infection.

An individual is at increased risk of norovirus infection if the individual has at least one known risk factor placing individuals with that risk factor at a statistically significant greater risk of developing an infection than individuals without the risk factor. Genetic risk factors such as histo-blood group antigen type or fucosyl transferase secretor status can mediate inherent susceptibility. Other risk factors can include, for example, presence on cruise ships or at other vacation settings, restaurants, hospitals, nursing homes, schools, or other locations where others have experienced norovirus infection or where a norovirus outbreak is suspected. Infected individuals can remain contagious up to 48-72 hours after symptoms subside and perhaps longer. Some infections are asymptomatic, but infected individuals who are asymptomatic may still spread the virus. As few as 10 to 100 virus particles are sufficient to cause infection, and the virus can survive under varying temperatures for days to months. Transmission is primarily through the fecal-oral route, direct person-to-person contact, by exposure to ill individuals experiencing vomiting, or by touching contaminated surface, objects, or substances. Risk factors can also include being exposed to clinical, food, or environmental samples potentially contaminated with norovirus. Food-related norovirus outbreaks have been associated with multiple products, such as fresh produce, deli meats, salad bars, prepared foods, raw and cooked molluscan shellfish, highly acidic foods such as orange juice and frozen raspberries, and other food products. Fecal- or vomitus-contaminated food or water is a major source of infection. Other risk factors can include having an impaired immune system, living with a child who attends a school or child care center, or being an infant or elderly individual.

Such methods can comprise contacting a first clinical sample from a patient, obtained prior to treatment with the therapeutic agent, with a norovirus-binding aptamer; detecting the presence of the norovirus-binding aptamer bound to norovirus in the clinical sample; contacting a second clinical sample from the patient, obtained following treatment with the therapeutic agent, with the norovirus-binding aptamer; detecting the presence of the norovirus-binding aptamer bound to norovirus in the second clinical sample; and then comparing the presence of the norovirus-binding aptamer bound to norovirus in the first and second clinical samples. Decreased binding in the second clinical sample relative to the first clinical sample can indicate that the therapeutic agent is effective in treating norovirus infection in the patient.

Such methods can be used in the context of a clinical setting to determine if a patient is responding to an approved therapeutic agent for norovirus infection or in a preclinical or clinical trial setting to assess whether a candidate therapeutic agent is therapeutically effective in treating norovirus infections.

In some cases, mixtures of norovirus-binding aptamers are used comprising a first norovirus-binding aptamer and at least one different norovirus-binding aptamer. In some cases, the first norovirus-binding aptamer and the one or more other norovirus-binding aptamers bind to different epitopes on the same norovirus genogroup, genotype, or strain. In some cases, the first norovirus-binding aptamer and the one or more other norovirus-binding aptamers preferentially bind to different norovirus genogroups, genotypes, or strains. In some cases, the first norovirus-binding aptamer and the one or more other norovirus-binding aptamers are differentially labeled.

A clinical sample from a patient diagnosed with norovirus infection can first be evaluated to establish a baseline for the binding of one or more norovirus-binding aptamers disclosed herein in the sample (i.e., a baseline for the presence of norovirus in the sample) before commencing therapy with the therapeutic agent. In some instances, multiple clinical samples from the patient are evaluated to establish both a baseline and measure of random variation independent of treatment. A therapeutic agent can then be administered in a regime. The regime may include multiple administrations of the therapeutic agent over a period of time. Optionally, binding of the aptamers (i.e., presence of norovirus) is evaluated on multiple occasions in multiple clinical samples from the patient, both to establish a measure of random variation and to show a trend in response to therapy. The various assessments of aptamer binding to the clinical samples can then be compared. If only two assessments are made, a direct comparison can be made between the two assessments to determine whether aptamer binding (i.e., presence of norovirus) has increased, decreased, or remained the same between the two assessments. If more than two measurements are made, the measurements can be analyzed as a time course starting before treatment with the therapeutic agent and proceeding through the course of therapy. In patients for whom aptamer binding in clinical samples has decreased (i.e., the concentration of norovirus has decreased), it can be concluded that the therapeutic agent was effective in treating the norovirus infection in the patient. The decrease in aptamer binding can be statistically significant. Optionally, binding decreases by at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100%.

Assessment of aptamer binding can be made in conjunction with assessing other symptoms of norovirus infection. The term "symptom" refers to a subjective evidence of a disease as perceived by a patient or objective evidence of a disease as observed by a physician. Relevant improvements or deteriorations in symptoms of norovirus infection can be those which in a physician's judgment are more likely than not due to the treatment rather than random variation in the patient's condition or the infection having run its natural course. Symptoms of norovirus infection include nausea, acute onset vomiting, watery non-bloody diarrhea, abdominal cramps, dehydration, low-grade fever, myalgia, malaise, muscle pain, and headache. Onset of such symptoms typically occurs about 12-48 hours post-exposure, and such symptoms typically last for about 18-72 hours.

The binding of aptamers (i.e., presence of norovirus) can be evaluated in multiple patients, some who have been treated with the therapeutic agent and some who have not, to establish the efficacy of the therapeutic agent in a population of patients. Such a population can be sufficiently large as to include at least one patient in whose clinical samples aptamer binding decreases in response to treatment with the therapeutic agent and at least one individual in whose clinical samples aptamer binding increases or remains the same after treatment. Optionally, the population includes at least about 2, at least about 5, at least about 10, at least about 50, at least about 100, or at least about 1000 subjects. Optionally, binding of the aptamers (i.e., presence of norovirus) is evaluated on multiple occasions in multiple clinical samples from multiple patients, some who have been treated with the therapeutic agent and some who have not, both to establish a measure of variation in a population and to establish on average how long the norovirus infection takes to run its course with and without the therapeutic agent.

Depending on the outcome of the comparison of aptamer binding (i.e., presence of norovirus) before treatment with the therapeutic agent and after treatment, different patients may receive different subsequent treatment regimes. In patients in whose clinical samples the aptamer binding has decreased, it can be concluded that the first regime was successful. The decrease in aptamer binding can be statistically significant. Optionally, binding decreases by at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100%. Such subjects can thereafter receive a second regime, which can be the same as the first regime (because it was successful) or can involve continued administration of the same therapeutic agent as in the first regime but at reduced dosage and/or frequency, or no further treatment. For example, in the second regime the dosage and/or frequency can be reduced by a factor of at least about 1.5, at least about 2, or at least about 1.5-5. In patients in whose clinical samples aptamer binding has remained the same or increased, it can be concluded that the first regime was unsuccessful or at least less than optimally successful. Such subjects thereafter can receive a second regime involving administering the same therapeutic agent as in the first regime but at an increased dosage and/or frequency. For example, the dosage and/or frequency can be increased by a factor of at least about 1.5, at least about 2, or at least about 1.5-5. The second regime can also include administering a different therapeutic agent than in the first regime.

The instant disclosure further provides methods of evaluating the efficacy of a norovirus vaccine in one or more subjects. The term "subject" includes humans or mammals.

Such methods can comprise challenging one or more vaccinated subjects and one or more non-vaccinated subjects with norovirus; contacting a first set of one or more clinical samples from the one or more vaccinated subjects with a norovirus-binding aptamer; detecting the presence of the norovirus-binding aptamer bound to norovirus in the clinical samples; contacting a second set of clinical samples from the one or more non-vaccinated subjects with a norovirus-binding aptamer; detecting the presence of the norovirus-binding aptamer bound to norovirus in the clinical samples; and then comparing the presence of the norovirus-binding aptamer bound to norovirus in the first and second sets of clinical samples. Decreased binding in the first set of clinical samples relative to the second set of clinical samples can indicate that the vaccine is effective in preventing or reducing norovirus infection.

The population of subjects can include at least about 2, at least about 5, at least about 10, at least about 50, at least about 100, or at least about 1000 subjects, some who have received the vaccine and some who have not. Optionally, binding of the aptamers (i.e., presence of norovirus) is evaluated on multiple occasions in multiple clinical samples from multiple subjects, some who have been vaccinated and some who have not, to establish a measure of variation in a population.

In some cases, mixtures of norovirus-binding aptamers are used comprising a first norovirus-binding aptamer and at least one different norovirus-binding aptamer. In some cases, the first norovirus-binding aptamer and the one or more other norovirus-binding aptamers bind to different epitopes on the same norovirus genogroup, genotype, or strain. In some cases, the first norovirus-binding aptamer and the one or more other norovirus-binding aptamers preferentially bind to different norovirus genogroups, genotypes, or strains. In some cases, the first norovirus-binding aptamer and the one or more other norovirus-binding aptamers are differentially labeled.

In some cases, clinical samples from the subjects can be evaluated prior to challenge with norovirus to establish a baseline for the binding of one or more norovirus-binding aptamers disclosed herein in the samples (i.e., a baseline for the presence of norovirus in the sample) before commencing challenge with norovirus. In some instances, multiple clinical samples from the subjects are evaluated to establish both a baseline and a measure of random variation independent of treatment. The subjects can then be challenged with norovirus. Optionally, binding of the aptamers (i.e., presence of norovirus) is evaluated on multiple occasions in multiple clinical samples from the subjects, both to establish a measure of random variation and to show a trend in response to challenge with norovirus. If more than two measurements are made, the measurements can be analyzed as a time course starting before challenge with norovirus proceeding through the challenge with norovirus and post-symptomatically. If aptamer binding in clinical samples is lower (i.e., the concentration of norovirus is lower) in vaccinated subjects post-norovirus challenge compared to non-vaccinated subjects post-norovirus challenge, it can be concluded that the vaccine was effective in preventing or reducing norovirus infection. The difference in aptamer binding between clinical samples from vaccinated subjects and clinical samples from non-vaccinated subjects can be statistically significant. Optionally, binding is at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100% lower in clinical samples from vaccinated subjects than in clinical samples from non-vaccinated subjects.

Assessment of aptamer binding can be made in conjunction with assessing other symptoms of norovirus infection. Relevant symptoms can include, for example, nausea, acute onset vomiting, watery non-bloody diarrhea, abdominal cramps, dehydration, low-grade fever, myalgia, malaise, muscle pain, and/or headaches.

VII. Kits

Also provided are kits including a norovirus-binding aptamer disclosed herein and instructions for use. Such kits can be used for, e.g., performing the detection and diagnostic methods described above. A kit can also include a label. Kits also typically contain labeling providing directions for use of the kit. Labeling generally refers to any written or recorded material that is attached to, or otherwise accompanies, a kit at any time during its manufacture, transport, sale or use. For example, the term labeling encompasses advertising leaflets and brochures, packaging materials, instructions, audio or video cassettes, computer discs, as well as writing imprinted directly on kits. Such kits may also provide a positive control, for example, a norovirus virus-like-particle in suspension, viral RNA, or a surrogate virus to be used as a process control. Such kits may further provide a solid support to which the aptamers can be tethered, such as magnetic beads. Such kits may further provide primers and probes targeting a region of the genome of at least one norovirus strain or targeting the aptamer itself.

Compositions or methods "comprising" or "including" one or more recited elements may include other elements not specifically recited. For example, a composition that "comprises" or "includes" an aptamer may contain the aptamer alone or in combination with other ingredients.

Designation of a range of values includes all integers within or defining the range, and all subranges defined by integers within the range.

Unless otherwise apparent from the context, the term "about," when referring to a value, is meant to encompass variations of +/−50%, +/−20%, +/−10, +/−5%, +/−1%, +/−0.5%, or +/−0.1% from the specified amount, as such variations are appropriate to perform the disclosed methods or employ the disclosed compositions.

The singular forms of the articles "a," "an," and "the" include plural references unless the context clearly indicates otherwise. For example, the term "an aptamer" or "at least one aptamer" can include a plurality of aptamers, including mixtures thereof.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

TABLE 1

Brief Description of the Sequences

| SEQ ID NO | Description |
|---|---|
| 1 | SMV aptamer |
| 2 | SMV aptamer |
| 3 | SMV aptamer |
| 4 | SMV aptamer |
| 5 | SMV aptamer: SMV-5 (S-7) |
| 6 | SMV aptamer: SMV-18 |
| 7 | SMV aptamer: SMV-22 (S-7) |
| 8 | SMV aptamer |
| 9 | SMV aptamer |
| 10 | SMV aptamer |
| 11 | SMV aptamer |
| 12 | SMV aptamer: SMV-5 (S-9) |
| 13 | SMV aptamer |
| 14 | SMV aptamer |
| 15 | SMV aptamer |
| 16 | SMV aptamer |
| 17 | SMV aptamer |
| 18 | SMV aptamer |
| 19 | SMV aptamer |
| 20 | SMV aptamer |
| 21 | SMV aptamer |
| 22 | SMV aptamer |
| 23 | SMV aptamer: SMV-17 |
| 24 | SMV aptamer |
| 25 | SMV aptamer: SMV-19 |
| 26 | SMV aptamer |
| 27 | SMV aptamer: SMV-21 |
| 28 | SMV aptamer: SMV-22 (S-9) |
| 29 | SMV aptamer |
| 30 | SMV aptamer: SMV-25 |
| 31 | SMV aptamer: SMV-26 |
| 32 | SMV aptamer |
| 33 | SMV aptamer |

TABLE 1-continued Brief Description of the Sequences

| SEQ ID NO | Description |
|---|---|
| 34 | SMV aptamer |
| 35 | GII.4 P Aptamer: M1 |
| 36 | GII.4 P Aptamer: M9-2 |
| 37 | GII.4 P Aptamer: M12-2 |
| 38 | GII.4 P Aptamer: M13-2 |
| 39 | GII.4 P Aptamer: M6-2 |
| 40 | GII.4 P Aptamer: M5 |
| 41 | NV Aptamer: NV 1-1 |
| 42 | NV Aptamer: NV 1-15 |
| 43 | NV Aptamer |
| 44 | NV Aptamer |
| 45 | NV Aptamer |
| 46 | NV Aptamer |
| 47 | NV Aptamer |
| 48 | NV Aptamer |
| 49 | NV Aptamer |
| 50 | NV Aptamer |
| 51 | NV Aptamer |
| 52 | NV Aptamer |
| 53 | NV Aptamer: NV 1-24 |
| 54 | NV Aptamer |
| 55 | NV Aptamer: NV 2-9 |
| 56 | NV Aptamer: NV 2-3 |
| 57 | NV Aptamer |
| 58 | NV Aptamer |
| 59 | NV Aptamer |
| 60 | NV Aptamer |
| 61 | NV Aptamer |
| 62 | NV Aptamer: NV 2-1 |
| 63 | NV Aptamer |
| 64 | NV Aptamer |
| 65 | NV Aptamer |
| 66 | NV VPg Aptamer: N6 |
| 67 | NV VPg Aptamer: N3 |
| 68 | NV VPg Aptamer: N1 |
| 69 | NV VPg Aptamer: N14 |
| 70 | NV VPg Aptamer: N1-2 |
| 71 | NV VPg Aptamer: N4-2 |
| 72 | NV VPg Aptamer: N11-2 |
| 73 | NV VPg Aptamer: N12-2 |
| 74 | TV VPg Aptamer: T5 |
| 75 | TV VPg Aptamer: T9 |
| 76 | TV VPg Aptamer: T1-2 |
| 77 | TV VPg Aptamer: T9-2 |
| 78 | TV VPg Aptamer: T10-2 |
| 79 | SMV-19 with constant regions |
| 80 | SMV-21 with constant regions |
| 81 | SMV-25 with constant regions |
| 82 | SMV-26 with constant regions |
| 83 | M-1 with constant regions |
| 84 | M6-2 with constant regions |
| 85 | NV 2-1 with constant regions |
| 86 | NV 2-9 with constant regions |
| 87 | NV 2-3 with constant regions |
| 88 | NV 1-1 with constant regions |
| 89 | NV 1-24 with constant regions |
| 90 | NV 1-15 with constant regions |
| 91 | SMV-5 (S-7) with constant regions |
| 92 | SMV-18 with constant regions |
| 93 | SMV-22 (S-7) with constant regions |
| 94 | SMV-5 (S-9) with constant regions |
| 95 | SMV-22 (S-9) with constant regions |
| 96 | SMV-17 with constant regions |
| 97 | M5 with constant regions |
| 98 | Motif 1 |
| 99 | Motif 2 |
| 100 | Motif 3 |
| 101 | Motif 4 |
| 102 | Motif 5 |
| 103 | Motif 6 |
| 104 | Motif 7 |
| 105 | Motif 8 |
| 106 | Motif 9 |
| 107 | Motif 10 |
| 108 | Motif 11 |
| 109 | Motif 12 |
| 110 | Motif 13 |
| 111 | Motif 14 |
| 112 | Motif 1, version 1 |
| 113 | Motif 1, version 2 |
| 114 | Motif 1, version 3 |
| 115 | Motif 2, version 1 |
| 116 | Motif 2, version 2 |
| 117 | Motif 2, version 3 |
| 118 | Motif 2, version 4 |
| 119 | Motif 3, version 1 |
| 120 | Motif 3, version 2 |
| 121 | Motif 4, version 1 |
| 122 | Motif 4, version 2 |
| 123 | Motif 5, version 1 |
| 124 | Motif 5, version 2 |
| 125 | Motif 6, version 1 |
| 126 | Motif 6, version 2 |
| 127 | Motif 7, version 1 |
| 128 | Motif 7, version 2 |
| 129 | Motif 8, version 1 |
| 130 | Motif 8, version 2 |
| 131 | Motif 9, version 1 |
| 132 | Motif 9, version 2 |
| 133 | Motif 10, version 1 |
| 134 | Motif 10, version 2 |
| 135 | Motif 10, version 3 |
| 136 | Motif 11, version 1 |
| 137 | Motif 11, version 2 |
| 138 | Motif 12, version 1 |
| 139 | Motif 12, version 2 |
| 140 | Motif 13, version 1 |
| 141 | Motif 13, version 2 |
| 142 | Motif 13, version 3 |
| 143 | Motif 14, version 1 |
| 144 | Motif 14, version 2 |
| 145 | Motif 14, version 3 |
| 146 | Generic combinatorial DNA library sequence |
| 147 | Forward constant region primer |
| 148 | Reverse constant region primer |
| 149 | JJV2F primer |
| 150 | COG2R primer |
| 151 | RING2-TP probe |
| 152 | GII4 P domain forward |
| 153 | GII4 P domain reverse |
| 154 | T7GII.4F |
| 155 | GII.4R2 |
| 156 | P493 |
| 157 | P494 |
| 158 | Norwalk VPg forward |
| 159 | Norwalk VPg reverse |
| 160 | Tulane VPg forward |
| 161 | Tulane VPg reverse |
| 162 | Motif 1, version 4 |
| 163 | Motif 2, version 5 |
| 164 | Motif 3, version 3 |
| 165 | Motif 4, version 3 |
| 166 | Motif 5, version 3 |
| 167 | Motif 6, version 3 |
| 168 | Motif 7, version 3 |
| 169 | Motif 8, version 3 |
| 170 | Motif 9, version 3 |
| 171 | Motif 10, version 4 |
| 172 | Motif 11, version 3 |
| 173 | Motif 12, version 3 |
| 174 | Motif 14, version 4 |
| 175 | COG2R primer, version 2 |
| 176 | Aptamer AP1-GI |
| 177 | Aptamer AP2-GI |
| 178 | Aptamer AP3-GI |
| 179 | Aptamer AP4-GI |
| 180 | Aptamer AP5-GI |
| 181 | Aptamer AP6-GI |
| 182 | Motif 15 |
| 183 | Motif 16 |
| 184 | Motif 17 |
| 185 | Motif 18 |

TABLE 1-continued

Brief Description of the Sequences

| SEQ ID NO | Description |
|---|---|
| 186 | Motif 19 |
| 187 | Motif 20 |
| 188 | Motif 21 |
| 189 | Motif 22 |
| 190 | Motif 23 |
| 191 | Motif 19, version 1 |
| 192 | Motif 19, version 2 |
| 193 | Motif 19, version 3 |
| 194 | Motif 20, version 1 |
| 195 | Motif 20, version 2 |
| 196 | Motif 20, version 3 |
| 197 | Motif 21, version 1 |
| 198 | Motif 21, version 2 |
| 199 | Motif 21, version 3 |

EXAMPLES

Example 1: Selection, Characterization and Application of Nucleic Acid Aptamers for the Capture and Detection of Human Norovirus Strains Materials and Methods
Viruses and Virus-Like Particles (VLPs)
  Viruses.

Snow Mountain virus (SMV), the prototype genogroup II, genotype 2 (GII.2) human norovirus (HuNoV) and the target for aptamer selection, and Norwalk (NV), the prototype genogroup I, genotype1 HuNoV, were obtained as stool specimens originating from a human challenge study. Pre-challenge stool samples confirmed (by RT-qPCR) as negative for HuNoV were used for counter selection and as negative controls in some studies. Additional fecal specimens associated with previously confirmed HuNoV outbreaks (representing strains GI.6, GII.1, GII.3, GII.4, GII.7 and an untypable GII) were also used in detection assays. All stool samples were suspended 20% in phosphate buffered saline (PBS). In some cases, these suspensions were used without further purification, designated as crude suspensions. In other cases, the suspensions were partially purified using chloroform extraction (Shin & Sobsey, Water Res. 42:4562-4568 (2008)). Hepatitis A virus HM175 (cell culture adapted) and poliovirus 1 were partially purified (chloroform extracted) from cell culture lysates and used in exclusivity studies. All virus suspensions were stored at −80° C. until use.

Virus-Like Particles (VLPs).

Self-assembled non-infectious Virus-Like Particles (VLPs), produced using the recombinant expression of HuNoV capsid proteins, were used as purified candidate proteins for the characterization of aptamer binding affinity. The VLP panel consisted of representatives of genogroup I (GI.1 (Norwalk virus), GI.4, GI.6, GI.7 and GI.8)) and genogroup II (GII.1, GII.2 (SMV), GII.3, GII.4 (Houston and Grimsby virus), GII.6, GII.7, GII.12 and GII.17) HuNoV. VLPs were stored at 4° C. until use.
Selection of Aptamers Using SELEX (Systematic Evolution of Ligands by EXponential Enrichment)
  Preparation of the DNA Library.

An 81-base combinatorial DNA library consisting of 40-mer random regions flanked by forward and reverse constant regions (5'-AGTATACGTATTACCTGCAGC-(N)$_{40}$—CGATATCTCGGAGATCTTGC-3') (SEQ ID NO: 146) was used. Preparation of the dsDNA library for SELEX was done in accordance with the method of Dwivedi et al., Appl. Microbiol. Biotechnol. 87:2323-2334 (2010). Specifically, the library was amplified using a fluorescein (FAM)-labeled forward constant region primer (5'-56-FAM/-AGTATACGTATTACCTGCAGC-3') (SEQ ID NO: 147) and a biotinylated reverse constant region primer (5'-/5Bios/-GCAAGATCTCCGAGATATCG-3') (SEQ ID NO: 148). Briefly, a 50 µl reaction master mix containing 5 µl of aptamer library (10 µM), 1×GOTAQ buffer (Promega Corp., Madison, Wis.), 0.2 mM GENEAMP dNTPmix (Applied Biosystems, Foster City, Calif.), 5 U GOTAQ DNA polymerase (Promega), and 500 nM of each primer were amplified as follows: 95° C. for 5 min, followed by 30 cycles of 95° C. (1 min), 55° C. (1 min), and 72° C. (1 min), and a final extension at 72° C. for 10 min, using a DNA Engine (PTC-200) Peltier Thermal Cycler-200 (MJ Research/Bio-Rad Laboratories, Hercules, Calif.). The labeled dsDNA library was conjugated to Streptavidin MAGNESPHERE paramagnetic particles (SA-PMPs) (Promega) according to manufacturer instructions and harvested with an MPC-M magnetic particle concentrator (Invitrogen Dynal A.S., Oslo, Norway). The library magnetic bead conjugate was washed three times in 0.1×SSC. The FAM-labeled ssDNA moieties were then separated from the immobilized biotinylated strands by alkaline denaturation using 50 µl of 0.15M NaOH for 7 min at room temperature (RT), followed by magnetic separation of the beads. The supernatant obtained was mixed with 1 ml of nuclease free water followed by filtration to remove residual NaOH using a MICROCON YM-30 filter device (Millipore, Billerica, Mass.). It was then purified by ethanol precipitation with resuspension in 50 µl of nuclease free water. The presence of FAM-labeled DNA was confirmed using a fluorescent plate reader (Tecan Safire, Tecan Group Ltd., Männedorf, Switzerland) and its concentration determined using a NanoPhotometer Pearl (Implen GMBH, Munich, Germany).

Preparation of the Target for SELEX.

The target for SELEX was produced by immobilizing SMV to antibody-bead conjugates. Briefly, M-280 Tosylactivated DYNABEADS (Invitrogen Dynal) were cross-linked to mouse monoclonal antibodies against SMV (Abeam, Cambridge, Mass.) as per manufacturer instructions. One hundred µl of the partially purified SMV stock (consisting of about $10^5$-$10^6$ RT-qPCR amplifiable units/nil) was mixed with 10 µl of the antibody-bead conjugate suspended in 500 µl of binding buffer (consisting of phosphate buffered saline (pH 7.1) supplemented with 100 mg/L $CaCl_2$, 100 mg/L $MgCl_2$ and 0.05% Tween 20) followed by RT incubation for 2 h. After washing thrice with PBS supplemented with 0.05% Tween 20 (PBST), the conjugate was resuspended in 20 µl of PBS and used for SELEX.

SELEX.

An aliquot of 300-500 pmoles of FAM-ssDNA pool suspended in 500 µl of binding buffer was added to 10 µl immobilized SMV target followed by gentle rotation for 45 min at RT. Aptamer-bound SMV was recovered by magnetic capture, washed thrice in PBST, and the aptamers eluted from the bead-bound virus particles with 200 µl of nuclease free water followed by heating at 90° C. for 5 min. The resulting aptamer pool was purified by ethanol precipitation, re-amplified using the labeled constant region primers, and the FAM-ssDNA aptamers were recovered as described above. This constituted one selection round and a total of up to nine such iterations of the selection process were performed. To avoid non-specific amplification of the recovered aptamer pool, single-stranded binding protein (Promega) at a concentration of 0.1 µg/µl was added to the PCR reactions and the pool was amplified using the appropriate annealing temperatures (obtained by running a temperature gradient within a range of 55° C. to 65° C. on the recovered aptamer pool).

Counter-SELEX.

Two sequential counter-SELEX rounds were done after each round of SELEX to impart specificity to the aptamer candidates against (1) the components of a 20% HuNoV-negative human stool suspension; and (2) the bead-antibody complex (without SMV). In counter-SELEX, exposure of the aptamer pools to the negative stool specimens or bead-antibody complex was done as described above, but in this case, the aptamers bound to the complex were discarded, while the unbound aptamer pool (supernatant) was recovered. This was purified by ethanol precipitation, reamplified by PCR, and used in another round of SELEX.

Identification of Aptamer Sequences.

After the $4^{th}$, $7^{th}$, and $9^{th}$ rounds of sequential SELEX and counter-SELEX, final PCR product was cleaned using the QIAquick PCR purification kit (Qiagen, Valencia, Calif.) and ligated into a pCR2.1 TOPO vector (Invitrogen, Carlsbad, Calif.) according to manufacturer instructions. Products were electroporated into *E. coli* Top10 cells (Invitrogen) and transformants selected as white colonies on (Luria Broth)-Xgal agar plates containing 50 µg/ml kanamycin. The selected transformants were grown overnight in Luria Broth with kanamycin (50 µg/ml) and the plasmid DNA was extracted using the QlAprep spin plasmid miniprep kit (Qiagen). The plasmid DNA was sent to Genewiz (South Plainfield, N.J.) for sequencing. The unique aptamers were identified by sequence analysis.

Characterization of Aptamer Candidates

Dissociation Constant and Structural Analysis of Aptamers.

An ELISA-like assay (Enzyme-Linked Aptamer Sorbent Assay, or ELASA, described below) was used to determine equilibrium dissociation constants ($K_d$) for the candidate aptamers (see, e.g., Friguet et al., *J Immunol. Methods* 77:305-319 (1985); Fuch et al., *J. Immunol. Methods* 188:197-208 (1995)). This was done using SMV VLPs (3 µg/ml) and different concentrations (10 nM, 100 nM, 500 nM, 1 µM, 2 µM) of each aptamer. To estimate $K_d$, plots of the ratio between absorbance of Test samples/absorbance of Negative controls (T/N ratios, Y axis) as a function of the aptamer concentration (X axis) were generated using a non-interacting binding sites model in Sigma Plot (Jandel, San Rafael, Calif.). Common sequence motifs were identified using the online MEME server, which can be found at the website located at meme.sdsc.edu. Structural folding analyses of the selected aptamers were done using the DNA Mfold online server, which can be found at the website located at mfold-d.rna.albany.edu/?q=mfold/DNA-Folding-Form (Zuker, *Nucleic Acids Res.* 31:3406-3415 (2003)).

Binding Affinity Studies Using Enzyme-Linked Aptamer Sorbent Assay (ELASA).

Binding affinity studies were performed with candidate aptamers and VLPs using a protocol adapted from a previously reported ELISA-based antigen detection assay (Rogers et al., *J. Clin. Microbiol.* 51:1803-1808 (2013)). In this case, the antibody was replaced with an aptamer and the resulting procedure termed Enzyme-Linked Aptamer Sorbent Assay (ELASA). For this assay, the selected aptamers were labeled with a 5' biotin moiety. One hundred µl of pure VLP suspension (3 µg/ml) was placed in each well of a covered, flat-bottomed polystyrene 96-well plate (Costar 3591, Fisher, Pittsburgh, Pa.) and incubated overnight at 4° C. After coating the wells with VLPs, the plates were blocked with 200 µl of 5% skim milk in PBST containing non-related DNA sequences (i.e., *L. monocytogenes* primers hlyQF/R and L23 SQF/R) (Rodriguez-Lazaro et al., *FEMS Microbiol. Lett.* 233:257-267 (2004)), followed by overnight incubation at 4° C. After washing three times with PBST, 100 µl of biotinylated aptamer (1 µM) was added to each well and the plate was incubated for an hour at RT with gentle mixing. After removing excess aptamers, the plates were washed three times with PBST. One-hundred µl of ELISA-grade streptavidin-horse radish peroxidase conjugate (1 mg/ml, 1:5000, Invitrogen) was added to the plate and incubated at RT for 15 min. The unbound conjugate was removed and the plate was washed five times with PBST before applying 100 µl of 3,3'5,5'tetramethylbenzidine (TMB) peroxidase substrate (KPL, Gaithersburg, Md.) to each well. The plate was incubated for 5 min at RT after which 100 µl of 1M phosphoric acid was added to stop the reaction. Absorbance at 450 nm was recorded using a microplate reader (Tecan Infiniti M200pro). Negative controls consisted of no VLPs. As per convention (Ebel et al., *Emerg. Infect. Dis.* 8:979-982 (2002)), binding affinity was interpreted based on the ratio between the absorbance readings for the test samples (to which labeled aptamer had been added) versus those for the negative control (PBS alone), (T/N ratios). Ratios <2.0 were considered negative by convention (Ebel et al., *Emerg. Infect. Dis.* 8:979-982 (2002)). Ratios between 2.0 and 5.0; >5.0 and 10.0; and >10.0 were interpreted as low, medium or strong binding, respectively. Ratios obtained for the negative control were in the range of 0.1-0.3.

To evaluate binding inclusivity, ELASA was performed using 1 µM (100 µl) of each candidate aptamer as applied to a panel of virus-like particles (VLPs) corresponding to genogroup I (GI.1 (Norwalk virus), GI.4, GI.6, GI.7 and GI.8)) and genogroup II (GII.1, GII.2 (SMV), GII.3, GII.4 (Houston and Grimsby), GII.6, GII.7, GII.12 and GII.17) HuNoV. Exclusivity analyses were done by ELASA using hepatitis A virus (HAV) and poliovirus. In all cases, PBS and SMV-VLPs were included as negative and positive controls, respectively.

Application of Aptamers for Detection of HuNoV in Clinical and Food Samples

Detection of HuNoV in Outbreak-Derived Stool Samples.

The ELASA assay was used to assess the performance of select aptamer candidates for detection of HuNoV in outbreak-derived fecal suspensions. Specimens evaluated included those representing strains GI.1 (Norwalk), GI.6, GII.1, GII.2 (SMV), GII.3, GII.4, GII.7 and an untypable GII. Briefly, 100 µl of ten-fold serially diluted partially purified fecal suspensions were used to coat plates followed by incubation overnight at 4° C. After three washes with PBST, the ELASA assay was done as described above. PBS alone and fecal suspensions derived from uninfected individuals were used as negative controls. Due to limited availability of SMV VLPs, we used GII.4 (Houston) VLPs, which were also highly reactive to aptamer 25, as the positive control.

Detection of HuNoV in Artificially Contaminated Lettuce Samples Using a Combined Pre-Concentration-Aptamer Magnetic Capture (AMC)-RT-qPCR.

Three g of lettuce (about 3×3 cm square) was disinfected by UV light and inoculated with 200 µl of serially diluted crude GII.4 virus stock suspension (due to limited availability of SMV) at inoculum concentrations ranging from 1-5 $\log_{10}$ RNA copies per lettuce sample. The inoculum was allowed to dry for 30 min. Virus pre-concentration was done using a previously reported elution-concentration method (Leggitt & Jaykus, *J. Food Prot.* 63:1738-1744 (2000)). Briefly, the samples were mixed with 25 ml of 0.5 M glycine-0.14 M NaCl buffer (pH 9.0), placed in sterile Whirl-Pak-filter bags (Nasco, Fort Atkinson, Wis.) and stomached (Stomacher 400 Circulator, Seward, Norfolk, UK) at 230 rpm for one min. The recovered filtrate (containing the eluted viruses) was adjusted to 0.9M NaCl and supplemented with 1% bovine serum albumin (Sigma Aldrich, St. Louis, Mo.), after which 12% polyethylene glycol (PEG) MW 8,000 (Sigma Aldrich) was added. After incubation for 2 h at 4° C., samples were centrifuged at 10,000×g for 20 min at 8° C. and the recovered pellet was resuspended in 1 ml of PBST.

The resuspended pellet was incubated with 1 µM of biotinylated aptamer for an hour at RT with rotation. This was followed by the addition of 10 µl of Streptavidin (SA)-C1 magnetic beads (from 10 mg/ml stock solution) (Invitrogen Dynal AS) previously blocked overnight with 5% skim milk in PBST followed by incubation for 25 min at RT. The bead-aptamer-virus conjugates were recovered using the magnetic particle concentrator. The conjugates were washed twice with PBST, suspended in 100 µl PBS, and the RNA extracted using the NUCLISENS EASYMAG automated system (bioMerieux SA, Marcy l'Etoile, France) according to manufacturer's instructions. The viral RNA was eluted in 40 µl of proprietary elution buffer and stored at −80° C. until used for amplification.

RT-qPCR was carried out using the SUPERSCRIPT III PLATINUM One-Step RT-qPCR system (Invitrogen) according to manufacturer instructions. Briefly, 25 µl RT-qPCR reactions consisted of 12.5 µl of 2× reaction mix, 5.5 µl DNase-RNase free water, 200 nM of each primer (JJV2F (5'-CAAGAGTCAATGTTTAGGTGGATGAG-3') (SEQ ID NO: 149) and COG2R (5'-TCGACGCCATCTTCATT-CACA-3') (SEQ ID NO: 150)), and probe RING2-TP (5'-56-FAM TGGGAGGGCGATCGCAATCT-3BHQ-3') (SEQ ID NO: 151) (Jothikumar et al., *Appl. Environ. Microbiol.* 71:1870-1875 (2005); Kageyama et al., *J. Clin. Microbiol.* 41:1548-1557 (2003)), 0.5 µl of the enzyme mix (SUPER-SCRIPT III RT/PLATINUM Taq Mix) and 5 µl of the RNA template. Amplification was done under the following conditions: 50° C. for 15 min, 95° C. for 2 min followed by 45 cycles of 95° C. for 15 sec, 54° C. for 30 sec, and 72° C. for 30 sec in a SmartCycler (Cepheid, Sunnyvale, Calif.). The RNA copy number was extrapolated from a standard curve based on Ct values obtained by RT-qPCR amplification of serially diluted synthetic RNA as previously reported (Escudero et al., *J. Food Prot.* 75:927-935 (2012)). Capture efficiency, expressed as a percentage, was estimated from the standard curve and calculated as the ratio of the extrapolated RNA copies (after capture and detection by RT-qPCR) to the total input RNA copies per sample, multiplied by 100 (Joshi et al., *Mol. Cell. Probes* 23:20-28 (2009)). Negative controls consisted of capture by blocked beads in the absence of aptamer.

Statistical Analysis

Data were expressed as mean±standard deviation of three replicates of each experiment. The data were analyzed by one-way analysis of variance (ANOVA) with the Tukey's multiple comparison test using GraphPad Prism ver. 5.0 d (San Diego, Calif.) or by Student's t-test. Values of $p<0.05$ were considered statistically significant.

ssDNA Aptamer Selection

After 4, 7, and 9 rounds of sequential SELEX and counter-SELEX, 34 unique aptamer candidates were identified from a total of 80 clones sequenced. All sequences are provided in Table 2. Candidates designated as SMV-19, SMV-21, SMV-25 and SMV-26 were selected for further analysis as they were the most abundant in the identified aptamer pool (identified between 5-10 times) and showed strong preliminary binding affinity for SMV, genogroup I.1 (Norwalk), and genogroup 11.4 (Houston) VLPs using the ELASA assay (data not shown). FIGS. 1-4 show the predicted structural folding of aptamers SMV-19, SMV-21, SMV-25 and SMV-26, respectively, with the forward and reverse constant regions included. Other aptamers identified included SMV-5 (S-7) (dG=−4.74 Kcal/mol), SMV-18 (dG=−4.92 Kcal/mol), SMV-22 (S-7) (dG=−6.41 Kcal/mol), SMV-5 (S-9) (dG=−6.75 Kcal/mol), SMV-22 (S-9) (dG=−8.62 Kcal/mol), and SMV-17 (dG=−6.19 Kcal/mol). SMV-5 (S-7), SMV-18, and SMV-22 (S-7) have binding affinities characterized by equilibrium dissociation constant values of 40 nM, 45 nM, and 142 nM, respectively, as determined by ELASA. These are similar to $K_d$ values (0.040 µM) obtained for antibodies against norovirus using the same methodology.

TABLE 2

Aptamer Sequences Obtained from $4^{th}$, $7^{th}$ and $9^{th}$ Rounds of SELEX for SMV

| Round of SELEX | Random Region Sequence | SEQ ID NO | # Repeats | Aptamer Identifier |
|---|---|---|---|---|
| 4 | TGTTGGATTTTACGAAAAACGTGCTTACTTCATAGCGGCC | 1 | 1 | |
| 4 | GGTTGGGTAAGGGGGTCTGGTCAGGTAGGGCGGGGGGGG | 2 | 1 | |
| 4 | TCGTAAACCCCTTATCCGTGAACCTTCAGCGGTAGACGCT | 3 | 2 | |
| 4 | CTCCCTCCAGCCTGCCTATTTTGCTTGGTTACGCATCTGT | 4 | 1 | |
| 7 | CCAGCGAAGGAAAGTCTTGGTTGGTCTAGTTTTTCGTGTG | 5 | 2 | SMV-5 (S-7) |
| 7 | CTACGTGTGCGTTCCGATTGTTTAAATTGCTCAATGTATG | 6 | 2 | SMV-18 |
| 7 | CACACCACCTGAATTCCAGCACACTGGCGGCCGTTACTAG | 7 | 2 | SMV-22 (S-7) |
| 9 | CACTCGACCTTCAGGGCGGCTTCTCAGCGTGTAGTGGTGA | 8 | 1 | |
| 9 | CTCGACTGATAGACCTAGCGTCAATCCTCATTGTTCGCTG | 9 | 1 | |

TABLE 2-continued

Aptamer Sequences Obtained from 4th, 7th and 9th Rounds of SELEX for SMV

| Round of SELEX | Random Region Sequence | SEQ ID NO | # Repeats | Aptamer Identifier |
|---|---|---|---|---|
| 9 | CCAGTATTAGAGTCCTACTTTACACCGCTCTTGGCATCGT | 10 | 1 | |
| 9 | CACATGATAAGGTCGCGTGACTGTGAGTTAGTTGTTACAC | 11 | 2 | |
| 9 | TCGGCATAGGTCAAGTCGCTTCATTTGGATTAAGTTGAGG | 12 | 1 | SMV-5 (S-9) |
| 9 | CACATACCAAAGTATTGGTCGCTAACTTTCGCCCAATTGA | 13 | 1 | |
| 9 | CTACGAGGTGGTTATAAGAGAACTTATCCGTGTTGGTTGC | 14 | 1 | |
| 9 | TGGTAGTGGGATATAGTTTTTCCAAGCGTACCCAGTTCTG | 15 | 2 | |
| 9 | CTATCAGCCATGAATTGCATTACCTTTGTTCTCCCCTTGC | 16 | 1 | |
| 9 | CCCCTCGGAAGATAGATTTTGCGAGAGTCTTGGGTTGAGG | 17 | 1 | |
| 9 | CCAGATAGCAGCACCTAATCTTATCCCTTTTATTTTTGGT | 18 | 2 | |
| 9 | TCGGGGGAGGAGGGGAATGGGAAGAAGGAGGTCGAGGG | 19 | 1 | |
| 9 | TGGATTACACGGCTAACTTCCCTGGTTCTTTTCTTTGATG | 20 | 2 | |
| 9 | TGGACGTTATTTGCACTCGTCGAACCCTATCATGCCTCCT | 21 | 1 | |
| 9 | CCTCATGCACAAAGGCTTATTACGGTCTAATTCTTTATAA | 22 | 1 | |
| 9 | TCGACATTATGTTTGACATCGATTGTTAATGTTTCTTTGC | 23 | 2 | SMV-17 |
| 9 | CCCCTACACAGTAAAATTCTTTAACACCTAGATCTTCGAC | 24 | 2 | |
| 7, 9 | CACCAGTGTGTTGAGGTTTGAGCACACTGATAGAGTGTCA | 25 | 9 | SMV-19 |
| 9 | TGAGCCTCCGTTTTAGTGATCAGAAGGGATGTGTGGCGTA | 26 | 1 | |
| 9 | CCATGTTTTGTAGGTGTAATAGGTCATGTTAGGGTTTCTG | 27 | 9 | SMV-21 |
| 9 | CGAGGGATACATGCTGACTATGGAATTATTTGAATTCCCA | 28 | 4 | SMV-22 (S-9) |
| 9 | CTACAGGAGTTCATCTGGGAGAGTGTAAAGGATGAGGTGG | 29 | 2 | |
| 7, 9 | CATCTGTGTGAAGACTATATGGCGCTCACATATTTCTTTC | 30 | 10 | SMV-25 |
| 9 | TGACCGAGTGTCTGGTCATTTTCGATGTCTGTTGTTAGGC | 31 | 7 | SMV-26 |
| 9 | CCCTCCTTATCTCTGCTAATGGTTGATCCGTGTCCCGTAC | 32 | 1 | |
| 9 | CCCTGTTATCCTTATCCAACGAGCTTAATGTAACTTGGAC | 33 | 2 | |
| 9 | TGGGGGAGTGGTAGGTGTGCTGTGAAGGGGAGGGTTGGGG | 34 | 1 | |

Characterization of ssDNA Aptamer Candidates

The structural folding for SMV-19, SMV-21, SMV-25, and SMV-26 demonstrated a dominant loop and two protruding hairpins (FIGS. 1-4). Three motifs were observed when comparing the random sequence regions of the four aptamers using the MEME program (see Bailey & Elkan, Proc. Int. Conf. Intell. Syst. *Mol. Biol.* 2:28-36 (1994)). The motifs are identified in Tables 3 and 4 and in the boxes in FIGS. 1-4. In Table 3, motif 1 is bolded and underlined, motif 2 is underlined, and motif 3 is bolded. Motif 1 (TGNNAGNN; SEQ ID NO: 98) was found near the 3' end of the aptamers and was found in aptamers SMV-19, SMV-21, and SMV-26. Motif 2 (NNNTGTNNNG; SEQ ID NO: 99) was found in all four aptamers, and is involved in notable stem-loops in all four of the aptamers, which may imply a conserved interaction site with human noroviruses. Motif 3 (AGGTNT; SEQ ID NO: 100) was found in aptamers SMV-19 and SMV-21 immediately downstream of motif 2, possibly as one larger motif between the two with the exception of an insertion of a thymine residue in aptamer SMV-21. These motif 2-3 segments are involved in the formation of similar stem-loops in both of the aptamers (see FIGS. 1 and 2). Such secondary structures have been considered as possible putative binding epitopes on aptamers (Kato et al., *Nucleic Acids Res.* 28:1963-1968 (2000)), so these stem-loops may be involved in aptamer binding to norovirus.

TABLE 3

Positions of Motifs 1, 2, and 3 in Aptamers SMV-19, SMV-21, SMV-25, and SMV-26

| Aptamer Identifier | Sequence | SEQ ID NO |
|---|---|---|
| SMV-19 | CAC<u>CAGTGTGTTG</u>AGGTTTGAGCACACTGATAGAGTGTCA | 25 |
| SMV-21 | <u>CCATGTTTTG</u>AGGTGTAATAGGTCATGTTAGGGTTTCTG | 27 |
| SMV-25 | CAT<u>CTGTGTGAAG</u>ACTATATGGCGCTCACATATTTCTTTC | 30 |
| SMV-26 | TGACC<u>GAGTGTCTGG</u>TCATTTTCGATGTCTGTTGTTAGGC | 31 |

TABLE 4

Motifs 1, 2, and 3 in Aptamers SMV-19, SMV-21, SMV-25, and SMV-26

| Aptamer Identifier | Motif 1 | Motif 2 | Motif 3 |
|---|---|---|---|
| SMV-19 | TGATAGAG (SEQ ID NO: 112) | CAGTGTGTTG (SEQ ID NO: 115) | AGGTTT (SEQ ID NO: 119) |
| SMV-21 | TGTTAGGG (SEQ ID NO: 113) | CCATGTTTTG (SEQ ID NO: 116) | AGGTGT (SEQ ID NO: 120) |
| SMV-25 | n/a | CTGTGTGAAG (SEQ ID NO: 117) | n/a |
| SMV-26 | TGTTAGGC (SEQ ID NO: 114) | GAGTGTCTGG (SEQ ID NO: 118) | n/a |

Equilibrium dissociation constant ($K_d$) values approximated for the aptamers were 191 nM for aptamer SMV-19; 101 nM for SMV-21; 232 nM for SMV-25; and 281 nM for SMV-26. FIG. 5A-D shows the corresponding equilibrium dissociation ($K_d$) curves for SMV-19, SMV-21, SMV-25, and SMV-26, respectively, generated using the one site binding model. The equilibrium dissociation curves were generated by ELASA with SMV VLPs (3 µg/ml) and various concentrations of aptamer (10 nM, 100 nM, 500 nM, 1 µM, and 2 µM). To estimate $K_d$, plots of the T/N ratios (absorbance at 450 nm) as a function of the aptamer concentration were fitted to a non-interacting binding sites model with the equation Y=Bmax X/Kd+X "T" represents absorbance readings for the test sample, and "N" represents absorbance readings for the negative control. The regression coefficients ($R^2$) associated with this model ranged from 0.95 to 0.99.

Signal intensity ratios (T/N) in ELASA as evaluated for aptamers SMV-19, SMV-21, SMV-25 and SMV-26 using a panel of VLPs ranged from a low of 1.3 to a high of 18.1 (Table 5). T/N values in Table 5 indicate the ratio of absorbance readings for the test sample (T) versus negative control (N) using ELASA. Per convention (Ebel et al., *Emerg. Infect. Dis.* 8:979-982 (2002)), results less than 2.0 were considered negative (−). Low (+/−), medium (+) or strong (++) binding were interpreted for ratios between 2 and 5; >5 and 10; and >10, respectively. All experiments were done in triplicate. Aptamer SMV-21 demonstrated medium to high binding affinity with VLPs corresponding to GI.7, GII.1, GII.2, GII.3, GII.4 (both VLPs), GII.7, GII.12, and GII.17 (T/N ratios ranging from 6.4 to 18.1). Aptamer SMV-25 reacted positively with VLPs corresponding to GI.4, GI.8, GII.1, GII.2, GII.3, GII.4 (both VLPs), GII.6, and GII.7 (T/N ratios ranged from 5.4 to 12.4). Aptamers SMV-19 and SMV-26 were less broadly reactive. In general, T/N ratios were higher for GII VLPs than for GI VLPs. Although all four aptamers showed variable binding affinity to different genotypes in genogroups I and II, binding affinity was highest for the GII.2 VLP, which is represented by SMV, the target used for the aptamer selection. Binding affinity was also quite high for GII.4 Houston VLPs. Relative to exclusivity analysis, binding affinity (T/N) of the four aptamers to the non-target virus poliovirus was in the range of 3.2-4.4, and for HAV, from 2.8-3.4. These values were statistically significantly lower (p<0.05) as compared to the positive control (GII.2 (SMV) VLPs) (see FIG. 8 and above).

TABLE 5

Binding Affinity of Selected Aptamers Against a Broad Panel of HuNoV VLPs

| VLPs Genogroup | Aptamers | | | | | | | |
|---|---|---|---|---|---|---|---|---|
| | SMV-19 | | SMV-21 | | SMV-25 | | SMV-26 | |
| | T/N | Binding | T/N | Binding | T/N | Binding | T/N | Binding |
| GI.1 (Norwalk) | 5.4 ± 0.9 | (+) | 2.4 ± 0.1 | (+/−) | 3.0 ± 0.4 | (+/−) | 2.6 ± 0.5 | (+/−) |

TABLE 5-continued

Binding Affinity of Selected Aptamers Against a Broad Panel of HuNoV VLPs

| VLPs | Aptamers | | | | | | | |
|---|---|---|---|---|---|---|---|---|
| | SMV-19 | | SMV-21 | | SMV-25 | | SMV-26 | |
| Genogroup | T/N | Binding | T/N | Binding | T/N | Binding | T/N | Binding |
| GI.4 | 1.7 ± 0.3 | (−) | 4.3 ± 0.2 | (+/−) | 5.6 ± 0.2 | (+) | 1.1 ± 0.2 | (−) |
| GI.6 | 3.7 ± 1.3 | (+/−) | 3.8 ± 0.1 | (+/−) | 2.4 ± 0.1 | (+/−) | 1.5 ± 0.4 | (−) |
| GI.7 | 10.3 ± 0.6 | (++) | 8.1 ± 0.1 | (+) | 3.5 ± 0.4 | (+/−) | 1.8 ± 0.8 | (−) |
| GI.8 | 1.7 ± 0.2 | (−) | 4.6 ± 0.3 | (+/−) | 6.2 ± 0.1 | (+) | 1.2 ± 0.1 | (−) |
| GII.1 | 7.1 ± 0.3 | (+) | 8.6 ± 0.3 | (+) | 9.4 ± 0.1 | (+) | 2.1 ± 0.3 | (+/−) |
| GII.2 (SMV) | 12.9 ± 5.1 | (++) | 18.1 ± 3.2 | (++) | 12.4 ± 1.1 | (++) | 4.1 ± 0.8 | (+/−) |
| GII.3 | 1.7 ± 0.9 | (−) | 11.8 ± 2.7 | (++) | 5.4 ± 0.1 | (+) | 2.4 ± 0.5 | (+/−) |
| GII.4 (Grimsby) | 9.6 ± 4.8 | (+) | 6.4 ± 1.9 | (+) | 10.4 ± 0.8 | (++) | 3.2 ± 0.3 | (+/−) |
| GII.4 (Houston) | 12.5 ± 4.2 | (++) | 11.3 ± 1.2 | (++) | 11.0 ± 1.1 | (++) | 2.8 ± 0.4 | (+/−) |
| GII.6 | 1.8 ± 1.0 | (−) | 3.0 ± 0.2 | (+/−) | 7.3 ± 0.7 | (+) | 2.8 ± 0.3 | (+/−) |
| GII.7 | 4.0 ± 1.9 | (+/−) | 13.5 ± 1.4 | (++) | 9.1 ± 2.1 | (+) | 2.8 ± 0.8 | (+/−) |
| GII.12 | 1.5 ± 0.4 | (−) | 6.6 ± 0.1 | (+) | 1.9 ± 0.1 | (−) | 2.4 ± 0.5 | (+/−) |
| GII.17 | 3.0 ± 1.6 | (+/−) | 12.2 ± 0.3 | (++) | 2.0 ± 0.1 | (+/−) | 1.3 ± 0.1 | (−) |

Despite the targeting of a single virus (SMV) in SELEX, two of the identified aptamers (candidates SMV-21 and SMV-25) showed binding affinity to a panel of HuNoV VLPs, demonstrating the efficacy of SELEX in identifying aptamers with binding inclusivity to HuNoV strains. The binding inclusivity of aptamer SMV-25 was further confirmed by the detection of HuNoV strains in outbreak-derived fecal samples by ELASA (see above). The performance of aptamer SMV-25 with outbreak stool specimens containing GII.1, GII.2, GII.3, and GII.4 HuNoV is consistent with the VLP binding data, all of which gave positive signals with ELASA. Likewise, poor performance of aptamer SMV-25 with an outbreak specimen corresponding to GI.6 is consistent with the low degree of binding to that VLP. Binding of stool specimens containing GI.1 virus was less consistent with VLP data, as was lack of binding to GII.7 specimens. Such inconsistency between VLP binding assays and application to outbreak-derived stool specimens could be a function of residual matrix-associated aptamer binding (or interference with aptamer binding) or potential differences between the behavior of VLPs and native virus, which has been discussed amongst experts in the field.

In general, the ELASA T/N ratios were higher for GII strains than for GI strains. This is not unexpected as major capsid protein (VP1) amino acid sequences for GII strains differ from those for GI strains by over 61.4% (Zheng et al., Virology 346:312-323 (2006)), and our SELEX target (SMV) was a GII strain. Nonetheless, different VLP binding patterns for the four characterized aptamers indicate that they may bind to slightly different regions of the viral capsid. The more broadly reactive aptamers could also bind to more highly conserved areas of the virus, such as the shell or P2 domains (Lindesmith et al., PLoS Med 5:e31 (2008)). Of the three common motifs identified in this study, motif 2 was found in all four aptamers, and this may imply a conserved interaction site with HuNoV. Secondary structures have been considered as possible putative binding epitopes on aptamers (Kato et al., Nucleic Acids Res. 28:1963-1968 (2000)).

Antibodies, the most frequently used ligands for HuNoV capture and detection (Yao et al., Lett. Appl. Microbiol. 49:173-178 (2009); Park et al., Appl. Environ. Microbiol. 74:4226-4230 (2008); Lee et al., J. Food Prot. 76:707-711 (2013)), tend to lack broad reactivity, meaning that subsequent assays developed with these antibodies lack analytical sensitivity (Costantini et al., J. Clin. Microbiol. 48:2770-2778 (2010)). Having an alternative ligand type showing broad reactivity to multiple HuNoV strains provides another tool upon which capture and detection assays may be based. So, for example, aptamers SMV-19, SMV-21, and SMV-25 could be used as a polyvalent cocktail to impart a high level of inclusivity for HuNoV capture and detection. They could also be used in combination with other ligands such as antibodies or peptides (Rogers et al., J. Clin. Microbiol. 51:1803-1808 (2013)).

Figure 6:
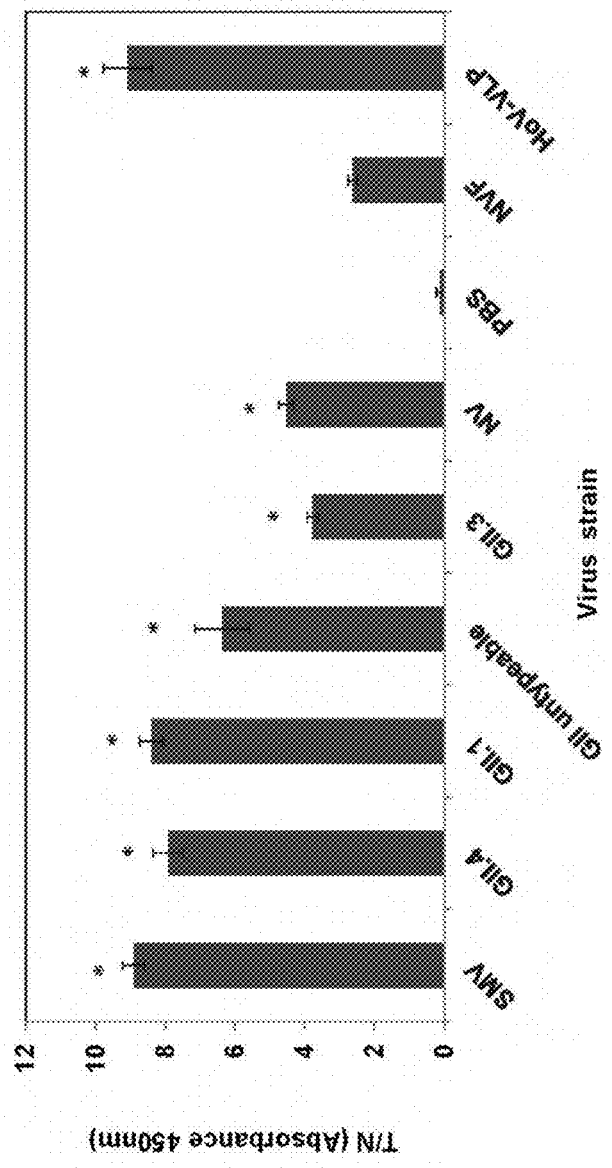
FIG. 6 shows binding of aptamer SMV-25 to HuNoV stool specimens as demonstrated by ELASA using PBS and HuNoV-negative human stool suspensions (NVF) as negative controls. Statistically significant differences between the positive stool specimens and the HuNoV-negative human stool suspensions are designated with an asterisk ($p<0.05$)

Application of Aptamers for Capture and Detection of HuNoV in Human Stool and Lettuce Samples ELASA assays using aptamer SMV-25 were performed on serially diluted partially purified outbreak-derived stool specimens. The 10-20% stool suspensions were chloroform-extracted, diluted, and tested using ELASA. Experiments were done in triplicate. Statistically significant differences between the ratios obtained from the virus-containing stool specimens and the NVF (HuNoV-negative human stool suspensions) are designated with an asterisk (p<0.05). Results are expressed as ratios between absorbance readings for test sample versus negative control (T/N). The T/N ratios corresponding to GI.1 (Norwalk), GII.1, GII.2 (SMV), GII.3, GII.4, and GII untypable outbreak specimens were all statistically significantly higher (p<0.05) when compared to the ratios obtained for either negative control samples (i.e., HuNoV-negative human stool suspensions (NVF) and no aptamer controls (PBS alone)) (FIG. 6). T/N ratios were higher for GII.2 (SMV), GII.1 and GII.4 outbreak specimens relative to GI.1 (Norwalk), GII.3, and GII untypable. Positive ELASA signals were not obtained for outbreak specimens corresponding to GI.6 and GII.7 HuNoV strains (data not shown).

Figure 7:
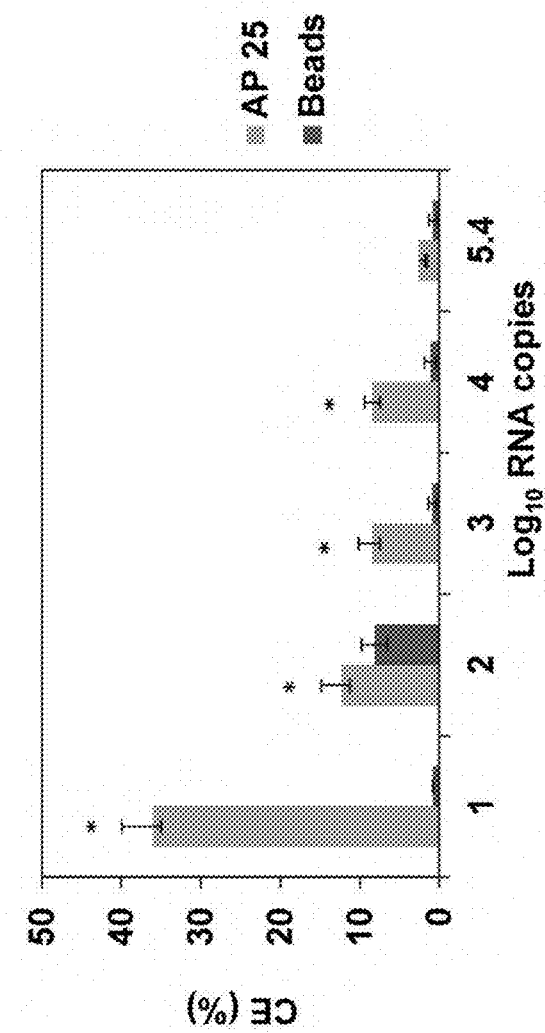
FIG. 7 shows the performance of the AMC-RT-qPCR method using aptamer SMV-25 applied to lettuce samples artificially inoculated with HuNoV GII.4 fecal stock. Statistically significant differences between test samples and negative controls (virus capture done using blocked beads without aptamer) are designated with an asterisk ($p<0.05$).

AMC-RT-qPCR using aptamer SMV-25 was performed on 3 g lettuce samples artificially inoculated with different concentrations of GII.4 fecal stock. The negative controls consisted of the samples containing blocked beads in the absence of the aptamer. Experiments were done in triplicate. Statistically significant differences are designated with an asterisk (p<0.05). When virus on artificially contaminated lettuce samples (inoculated with GII.4 at levels ranging from 1-5 $\log_{10}$ RNA copies per sample) were pre-concentrated, used in AMC with aptamer SMV-25, and detected after RNA extraction using RT-qPCR, a detection limit of about 1 $\log_{10}$ RNA copies per 3 g lettuce was obtained (FIG. 7). Over this inoculum range, the capture efficiency of the combined pre-concentration-AMC-RT-qPCR assay ranged from 2.5-36%. Capture efficiency (CE) was significantly higher ($p<0.05$) than the negative controls which consisted of blocked beads in the absence of aptamer. Capture efficiency increased with decreasing virus concentration.

Using the ELASA assay, we were able to approximate the SMV aptamer $K_d$ values to be in the 100-200 nM range (see above). This is similar to most commercial antibodies, which have $K_d$ values in the low µM to nM range (examples can be found at the website located at www.Abcam.com). In binding studies specifically with Norwalk virus VLPs, monoclonal antibodies have been shown to have $K_d$ values in the low nM range (Chen et al., *J. Virol.* 87:9547-9557 (2013)), and $K_d$ values for enteric virus binding protein as applied to HuNoV VLPs was similarly in the range of 210-240 nM (Imai et al., *BMC Biotechnol.* 11:123 (2011)). Using dilution series experiments (data not shown), we found the detection limits of the ELASA method to be about 2 $\log_{10}$ genomic copies better than commercial enzyme immunoassays that have previously been applied to fecal samples (Costantini et al., *J. Clin. Microbiol.* 48:2770-2778 (2010); Kele et al., *Diagn. Microbiol. Infect. Dis.* 70:475-478 (2011)).

Aptamer SMV-25 performed quite well when applied to a virus concentrate derived from an artificially contaminated model food product using a combined virus pre-concentration followed by AMC-qPCR assay format. Use of aptamers for pre-concentration of microbes has been reported recently by others (Ozalp et al., *Anal. Biochem.* 447:119-125 (2014)). Comparatively speaking, the detection limit and capture efficiency of this method, at 10 RNA copies and 36%, respectively, were comparable to those for HuNoV immunomagnetic separation-RT-qPCR assays applied to artificially contaminated fresh produce items (Park et al., *Appl. Environ. Microbiol.* 74:4226-4230 (2008); Lee et al., *J. Food Prot.* 76:707-711 (2013)) and clinical specimens (Yao et al., *Lett. Appl. Microbiol.* 49:173-178 (2009)). Our detection limits were also similar if not better than those for other capture approaches that use more non-specific ligands such as histo-blood group antigens (Tian et al., *Int. J. Food Microbiol.* 147:223-227 (2011); Morton et al., *Appl. Environ. Microbiol.* 75:4641-4643 (2009); Pan et al., *Food Microbiol.* 30:420-426 (2012)) and porcine gastric mucin (Tian et al., *Appl. Environ. Microbiol.* 74:4271-4276 (2008)).

Binding Exclusivity Analysis for Aptamers SMV-19, SMV-21, SMV-25, and SMV-26

Figure 8:
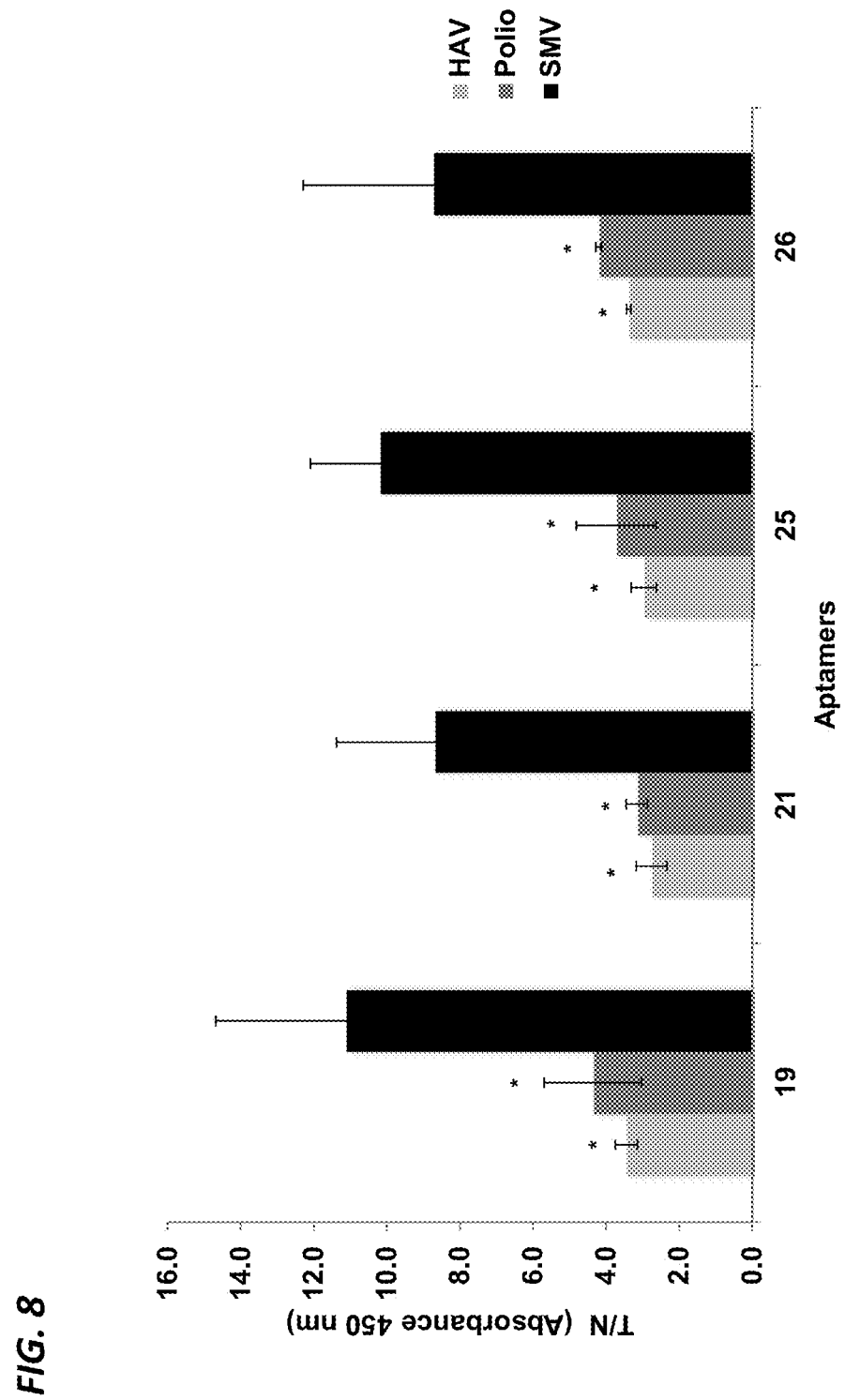
FIG. 8 shows binding of aptamers SMV-19, SMV-21, SMV-25, and SMV-26 to hepatitis A virus (HAV), poliovirus, and SMV VLPs as demonstrated by ELASA. Statistically significant differences between the positive control (SMV) and HAV or poliovirus are designated with an asterisk ($p<0.05$).

Binding of aptamers SMV-19, SMV-21, SMV-25, and SMV-26 to hepatitis A virus (HAV) and poliovirus was measured to analyze binding exclusivity. Virus suspensions (cell culture lysates) were chloroform-extracted prior to use in ELASA. SMV-VLPs were used as positive controls. The values of absorbance at 450 nm for the negative controls (PBS) were 0.1±0.045. Experiments were done in triplicate. Results are expressed as ratios between absorbance readings for test sample versus negative control (T/N). Statistically significant differences are designated with an asterisk ($p<0.05$). The T/N ratios corresponding to SMV were all statistically significantly higher ($p<0.05$) when compared to the ratios obtained for either HAV or poliovirus, indicating that aptamers SMV-19, SMV-21, SMV-25, SMV-26 have little cross-reactivity with other viruses (FIG. 8).

Example 2: Capture and Detection of Norovirus by Target Specific Nucleic Acid Aptamers Materials and Methods Norovirus-Specific ssDNA Aptamers The 81-mer ssDNA aptamer candidates (designated SMV-17 and SMV-22 (S-9)), previously selected against SMV (genogroup 11.2 human NoV strain) using a whole-virus SELEX approach were used in this study. These were selected from a larger aptamer candidate pool because of their apparent high binding affinities ($K_d$) and low free energies (dG) (Suh et al., Capture and Detection of a Representative Human Norovirus Strain using Target-Specific Nucleic Acid Aptamers: Proof of Concept, IAFP, Charlotte, N.C. (2013)), as previously evaluated using an Enzyme-linked Aptamer Sorbent assay (ELASA) (Bruno et al., *J. Biomol. Tech.* 22:27-36 (2011)) and the on-line software DNA Mfold version 3.2 (found at the website located at mfold.bioinfo.rpi.edu/cgi-bin/dna-forml.cgi) (Zuker, *Nucleic Acids Res.* 31:3406-3415 (2003)), respectively.

Prototype Assay Development

Two different approaches were used for aptamer-based capture and detection of SMV. The first assay design, called aptamer magnetic capture (AMC), used ssDNA aptamers as capture ligands, with subsequent detection using virus-specific RT-qPCR. In the second assay, a sandwich-based format, SMV was captured using antibody-bound beads, which were then exposed to SMV-specific, ssDNA aptamer. Detection was achieved by amplification of the SMV-specific aptamer using qPCR.

Method 1: Aptamer Magnetic Capture (AMC)-RT-qPCR.

One hundred µl of 10-fold serial dilutions of SMV (corresponding to 1-4 $\log_{in}$ genome equivalent copies or GEC) were suspended in 1 ml PBS and exposed to a 2 µM solution of biotinylated aptamer SMV-17. After incubation at room temperature for 45 min, immobilization of the suspended aptamer-bound SMV was done by exposure to 20 µl of streptavidin-coated magnetic beads (M-280, Invitrogen-Dynal A.S., Oslo, Norway) previously blocked with SUPERBLOCK buffer (Thermo Scientific, Rockford, Ill.). The aptamer-bead-bound SMV complexes were washed twice with 1×PBS and resuspended in 50 µl of DEPC-treated water.

The viral RNA was released by heat at 95° C. for 5 min prior to amplification by RT-qPCR using primers targeting the GII HuNoV ORF1/ORF2 junction (JJV2F (5'-CAAGAGTCAATGTTTAGGTGGATGAG-3') (SEQ ID NO: 149) and COG2R (5'-GACGCCATCTTCATTCACA-3') (SEQ ID NO: 175), and TAQMAN probe Ring 2P (5'/56-FAM-TGGGAGGGCGATCGCAATCT-3/BHQ_1-3') (SEQ ID NO: 151)) as previously described (Jothikumar et al., *Appl. Environ. Microbiol.* 71:1870-1875 (2005); Kageyama et al., *J. Clin. Microbiol.* 41:1548-1557 (2003)). Quantification of RNA copies was extrapolated from a standard curve based on Ct values obtained by RT-qPCR amplification of serially diluted synthetic RNA (SMV genomic location 5003-5424) (Escudero et al., *J. Food Prot.* 75:927-935 (2012)). The highest dilution providing a quantifiable RT-qPCR value was equated to one (1) Genome Equivalent Copy (GEC). The capture efficiency was expressed as the ratio of GEC detected in the sample after aptamer capture and subsequent RT-qPCR, compared to the input GEC concentration (all estimated using the standard curve), multiplied by 100.

Method 2: Two-Site Binding Sandwich qPCR (Sandwich Method).

Anti-HuNoV GII.2 antibody was conjugated to DYNABEADS M-280 Tosylactivated (Invitrogen-Dynal) as per manufacturer instructions, followed by extensive washing and blocking with 0.5% bovine serum albumin (Sigma-Aldrich, St. Louis, Mo.). A 50 µs aliquot of antibody-conjugated beads was used to capture virus in one ml volumes of 10-fold serially diluted SMV (corresponding to 1-4 $\log_{in}$ genome equivalent copies or GEC). The mixture was incubated for 2 h at room temperature with gentle rotation, followed by subsequent washings and magnetic pull-down to remove unbound or nonspecifically-bound viruses. The virus-bound beads were then blocked by the addition of a 5% skim milk-PBS-Tween solution containing 10 µM of ssDNA 20-mers. After blocking overnight at 4° C. with gentle rotation, the beads were washed again in PBS-Tween, concentrated by magnet, and supplemented with 10 nM of SMV-specific, ssDNA aptamer SMV-22 (S-9). The aptamer binding reaction was carried out for 1 h at room temperature with rotation, after which the aptamer-virus-bead complexes were washed sequentially with PBS-Tween and resuspended in 50 µl of DEPC-treated water.

The ssDNA aptamers were the target for subsequent qPCR detection, which was done using the SYBR Green PCR Master Mix (Applied Biosystems, Warrington, UK) and primers targeting the constant regions of aptamer SMV-22 (S-9) (Forward: 5'-AGTATACGTATTACCTGCAGC-3' (SEQ ID NO: 147), Reverse: 5'-GCAAGATCTCCGAGATATCG-3') (SEQ ID NO: 148) (Dwivedi et al., *Appl. Microbiol. Biotechnol.* 87:2323-2334 (2010)). Each reaction tube contained 12.5 µl of 2×SYBR Green Master Mix (Applied Biosystems), 9.6 µl of PCR-grade water, 0.2 µl of a 10 µM concentration of primer set, and 2.5 µl of template DNA in a 25 µl PCR mixture. The PCR amplification was performed in a SmartCycler using a two-step thermal protocol of initial denaturation at 95° C. for 10 min followed by 45 cycles of denaturation at 95° C. for 15 sec and annealing/extension at 60° C. for 60 sec. Fluorescence signals were measured once per cycle at the end of the extension step. After PCR amplification, $T_m$ curve analysis was performed by adding the analysis of fluorescence from 60° C. to 95° C. (0.2° C./sec).

The two-site binding sandwich assay was compared to immunomagnetic separation (IMS) without the subsequent aptamer binding step. Briefly, 50 µg of magnetic beads to which anti-NoV GII.2 antibody was conjugated were exposed to serially diluted SMV. After capture, the samples were washed, viral RNA released by heat, and downstream detection performed using RT-qPCR targeting the virus ORF1-ORF2 junction.

Statistical Methods

One-way analysis of variance (ANOVA) with the Tukey's multiple comparison test (p<0.05) was used to analyze the AMC assay data. For the two-site binding sandwich assay format and IMS, comparisons between groups were performed using t-tests. Values of p<0.05 were considered statistically significant. All statistical analyses were done using GraphPad Prism ver. 5.0d (San Diego, Calif.).

Results and Discussion

Aptamer Magnetic Capture (AMC)-RT-qPCR Method

Figure 9:
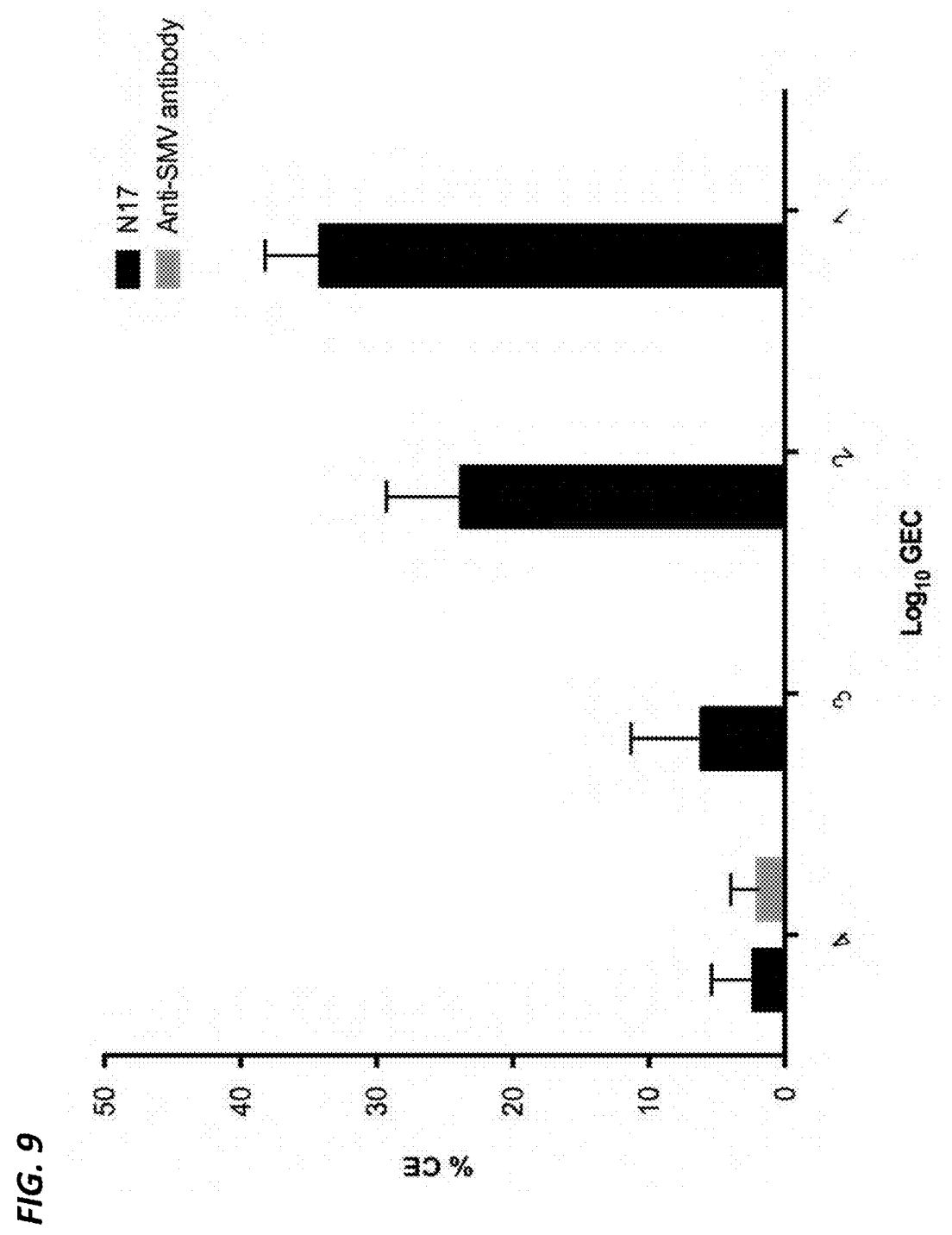

The lower limit of detection (LoD) of the combined AMC-RT-qPCR assay using aptamer SMV-17 was approximately 1 $\log_{10}$ GEC SMV/1 ml (FIG. 9). The mean capture efficiency (%) of aptamer SMV-17 as applied to serially diluted SMV stock ranged from 2.5%-34%, and increased (improved) as virus titer decreased (from 4 $\log_{10}$-1 $\log_{10}$ GEC/ml). The parallel IMS-RT-qPCR performed in this study showed limit of detection about 4 $\log_{10}$ GEC/ml with less than 2.5% of capture efficiency.

Two-Site Binding Sandwich qPCR Method

Figure 10:
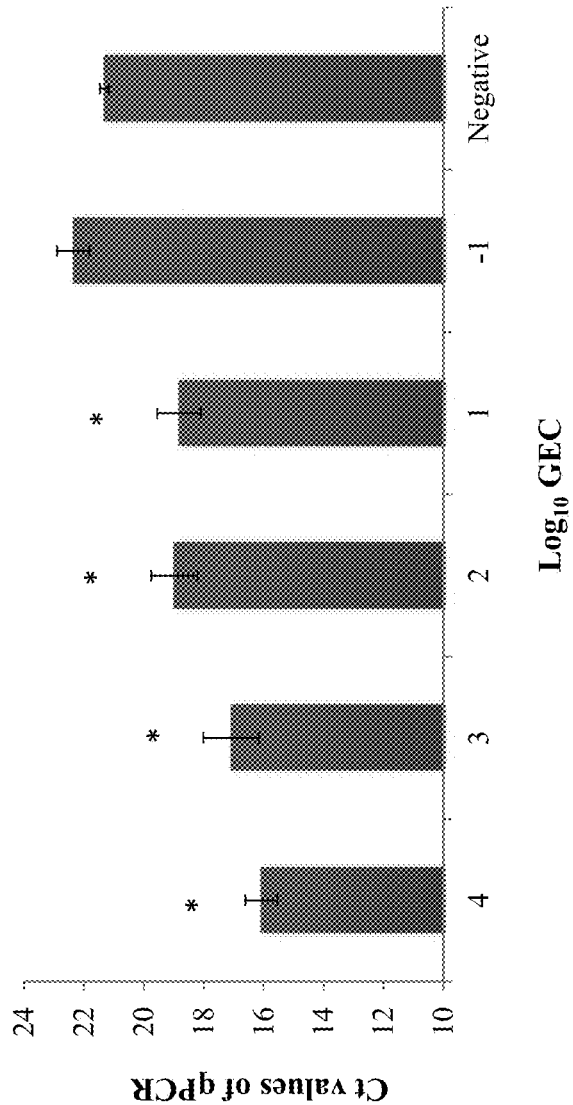
FIG. 10 shows the performance of the two-site binding sandwich qPCR method as applied to serially diluted SMV using amplification of aptamer SMV-22 (S-9) to achieve detection. An asterisk designates statistical significance ($p<0.05$) when comparing the Ct values of samples containing SMV to that of the negative control which did not contain SMV.

The relationship between initial SMV concentration (prior to the antibody capture step) and the Ct values obtained after amplification of aptamer SMV-22 (S-9) sequence is shown in FIG. 10. The x-axis represents the initial input of SMV, and the y-axis represents the qPCR Ct value (mean±standard deviation). Experiments were done by triplicate. An asterisk designates statistical significance (p<0.05) when comparing the Ct values of samples containing SMV to that of the negative control which did not contain SMV. As expected, the Ct values of samples containing high concentrations of SMV (≥4 $\log_{10}$ GEC) were very low (<18), and these Ct values gradually increased as the concentration of SMV decreased. The negative control sample (no SMV exposure during antibody capture but exposure to the aptamer) had a Ct value of approximately 21.5, indicating a relatively high degree of non-specific binding of the aptamer to the antibody-coated magnetic beads. In cases such as these, assay positivity is usually established at values >2-3 times the standard deviation associated with the negative control samples. This criteria was met for samples containing between 1 $\log_{10}$ and 4 $\log_{10}$ GEC SMV/1 ml, equating to a lower limit of detection of 1 $\log_{10}$ (10) GEC SMV.

Figure 11:
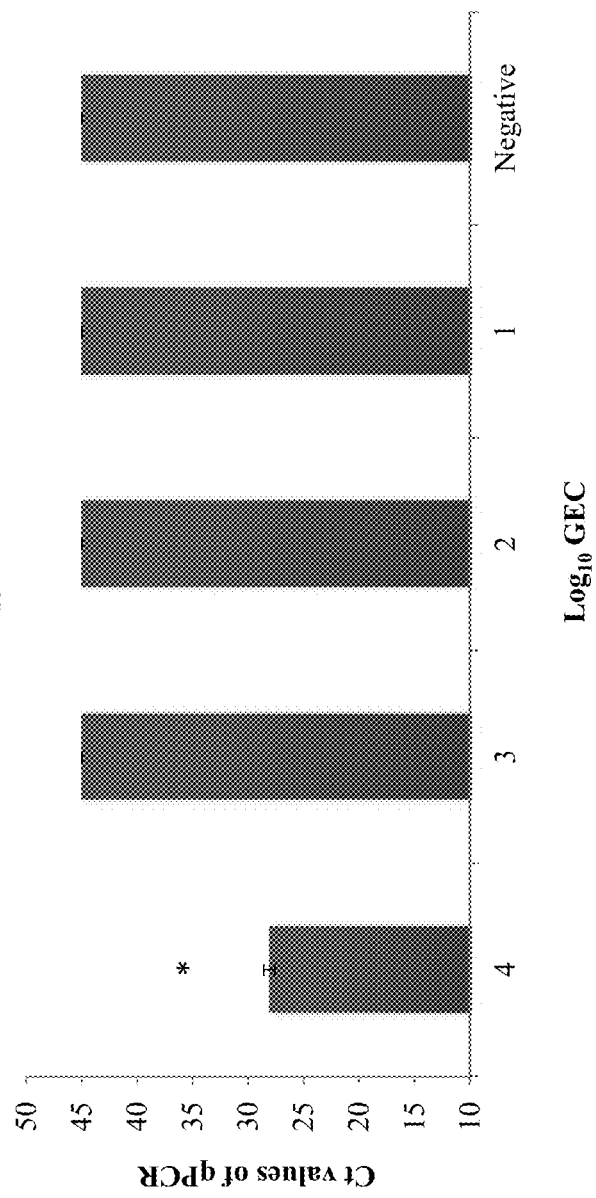
FIG. 11 shows the performance of the IMS-RT-qPCR method as applied to serially diluted SMV. An asterisk designates statistical significance ($p<0.05$) when comparing the Ct values of samples containing SMV to that of the negative control which did not contain SMV.

To better understand the dynamics of the antibody capture step of the two-site binding sandwich qPCR method, simple IMS/RT-qPCR assays targeting the viral genome were performed (FIG. 11). In this case, the x-axis represents the initial input $\log_{10}$ GEC of SMV, and the y-axis represents the Ct value as a result of RT-qPCR (mean±standard deviation) after antibody capture. For statistical comparison purposes, samples (1-3 $\log_{10}$ GEC) that were non-detectable by RT-qPCR were designated with a Ct value of 45. Experiments were done by triplicate. An asterisk designates statistical significance (p<0.05) when comparing the Ct values of samples containing SMV to that of the negative control which did not contain SMV. As expected, Ct values were much higher when the initial SMV concentration was 4 $\log_{10}$ GEC (Ct approx. 28). This also constituted the limit of detection of the assay, as samples having <3 $\log_{10}$ GEC SMV were not detectable (Ct>45) by RT-qPCR. The capture efficiency of IMS/RT-qPCR (calculated as ((GEC of detected SMV by IMS-RT-qPCR)/(input GEC of SMV)× 100)) was 1.7% at 4 $\log_{10}$ GEC in 1 ml.

Discussion

Both the AMC-RT-qPCR method and the two-site binding sandwich-qPCR method had lower limits of detection approximating 1 $\log_{10}$ (10) GEC SMV. For the AMC assay, the efficiency with which the aptamer-bound magnetic beads captured SMV improved with decreased virus titer, probably as a function of saturation. Each assay design has its own advantages and disadvantages. The two-site binding sandwich assay in particular has potential utility as a screening tool. Specifically, this method (i) is non-destructive of the target organism (virus); (ii) results in capture of the target for subsequent confirmatory analyses, if desired; and (iii) has the potential, with additional optimization, to be a more sensitive by virtue of the fact that more aptamers (which are about one-fourth the size of antibodies) can bind to each target virus. In our assay design, we used qPCR amplification in place of the enzyme-substrate reaction of sandwich ELISA. As PCR produces exponential amplification of the target, this may be a yet more sensitive means by which to amplify signal intensity. It should be noted that the antibody capture step of the two-site binding sandwich method was the limiting aspect of the assay, as antibody-mediated capture efficiency was quite low (<2%). This step also has disadvantages because HuNoV antibodies tend to have a high degree of specificity and hence lack broad reactivity. The capture efficiency and perhaps the assay sensitivity and reactivity could be improved if a more universal and efficient initial capture step were used. Ligands such as porcine gastric mucin, histo-blood group antigens (HBGAs) and HBGA-like substances, and/or human plasma protein components can be useful alternatives to antibodies in this assay design.

Example 3: Generation and Characterization of Nucleic Acid Aptamers Targeting the Capsid P Domain of a Human Norovirus GII.4 Strain Human noroviruses (NoV) are the most common cause of acute viral gastroenteritis worldwide (Glass et al., *N. Engl. J. Med.* 361:1776-1785 (2009)) and the leading cause of foodborne illness in the United States (Scallan et al., *Emerg. Infect. Dis.* 17:7-15 (2011)). Despite their public health significance, the availability of routine detection methods for these viruses is limited, in part due to the absence of an in vitro cultivation method. While molecular amplification (specifically reverse transcriptase quantitative PCR or RT-qPCR) is usually used for NoV detection by the public health sector, it is not commonly used in clinical diagnostics. Perhaps because of sample complexity (fecal matrix), ligand-based detection methods are more appealing for clinical diagnostics.

Unfortunately, human NoV are genetically and antigenically diverse, complicating the identification of broadly reactive ligands that can be used for virus capture and/or detection. For example, antibodies are well documented to lack completely broad reactivity (Burton-MacLeod et al., *J. Clin. Microbiol.* 42:2587-2595 (2004); Shiota et al., *J. Virol.* 81:12298-12306 (2007)), and for this reason, enzyme immunoassays display rather poor sensitivity Costantini et al., *J. Clin. Microbiol.* 48:2770-2778 (2010); Kele et al., *Diagn. Microbiol. Infect. Dis.* 70:475-478 (2011). Other candidate NoV ligands have been explored, such as putative NoV infection co-factors known as histo-blood group antigens (HBGAs; Cannon et al., *Appl. Environ. Microbiol.* 74:6818-6819 (2008); Harrington et al., *J. Virol.* 78:3035-3045 (2004)) and porcine gastric mucin, which contains some HBGAs (Pan et al., *Food Microbiol.* 30:420-426 (2012); Tian et al., *Appl. Environ. Microbiol.* 74:4271-4276 (2008)); peptides (Rogers et al., *J. Clin. Microbiol.* 51:1803-1808 (2013)); and single chain antibodies (Huang et al., *Protein Eng. Des. Sel.* 27:339-349 (2014)). While some of these can react with multiple human NoV strains or VLPs, none bind to all those tested.

For pathogen capture and purification, nucleic acid aptamers are a promising alternative ligand. Aptamers are short (20-80mer) single-stranded DNA or RNA sequences that interact (bind) to their target through their three-dimensional structures. They offer advantages over antibody-based affinity molecules in their ease of production, purification and modification, stability, and lower cost (Brody & Gold, *Rev. Mol. Biotechnol.* 74:5-13 (2000); Murphy, *Nucleic Acids Res.* 31:e110 (2003); Tombelli et al., *Biomol. Eng.* 24:191-200 (2007)). Nucleic acid aptamers are selected in vitro based on affinity for a target molecule, protein, virus, or cell using a molecular-based iterative enrichment method called SELEX (Systematic Evolution of Ligands by EXponential enrichment).

In the absence of a robust in vitro cultivation method, the only source of whole viruses for ligand selection is stool samples from infected individuals. As infectious virus in stool is a difficult sample to obtain and work with, virus-like particles (VLPs) are frequently used instead for many types of studies, from disinfection to immune response characterization (Cheetham et al., *J. Virol.* 81:3535-3544 (2007); Lou et al., *Appl. Environ. Microbiol.* 78:5320-5327 (2012); Nilsson et al., *Glycoconj. J.* 26:1171-1180 (2009); Souza et al., *J. Virol.* 81:9183-9192 (2007); Vongpunsawad et al., *J. Virol.* 87:4818-4825 (2013)). VLPs demonstrate similar binding behavior to HBGAs as human NoV particles (Huang et al. 2003; White et al. 1996); however, their production and purification can be costly, time consuming, and variable (Koho et al., *J. Virol. Methods* 179:1-7 (2012)). An alternative is to focus selection on a portion of the human NoV major capsid protein or VP1. Unlike VLPs for which the entire capsid (all 180 copies of the major capsid protein (VP1)) assembles as "ghosts," "P domain proteins" consist of a set of proteins where the outermost domain of VP1 capsid proteins is expressed. Like VLPs and human NoVs, these proteins retain their antigenicity, can still bind to histo-blood group antigens and have been used for structural, binding, and vaccination studies (Cao et al., *J. Virol.* 81:5949-5957 (2007); Koho et al., *J. Virol. Methods* 179:1-7 (2012); Tan et al., *Procedia Vaccinol.* 4:19-26 (2011)). P domain proteins can be produced in a bacterial system (Tan and Jiang 2005) relatively easily, and expressed and purified at low cost and with high yield, making them an attractive target for ligand selection. In this study, we describe the production of single stranded (ss)DNA aptamers with binding affinity to a representative human NoV strain by SELEX using a P domain protein. Once isolated and characterized, promising aptamer candidates were further tested for their degree of reactivity with a broad panel of human NoV VLPs. They were then used to develop prototype methods to capture and/or detect GII.4 human NoV in outbreak-associated fecal specimens.

Materials and Methods

Viruses, Virus-Free Fecal Specimens, Virus-Like Particles (VLPs), and Virus Capsid Protein A GII.4 outbreak-derived human clinical (fecal) sample (sequence-confirmed to be the "2006b" cluster of GII.4 epidemic strains (Tsai et al., *J. Med. Virol.* 86:335-346 (2014); Yang et al., *J. Virol.* 84:9595-9607 (2010)) was suspended 20% in phosphate-buffered saline (PBS). Human NoV-negative stool samples (confirmed negative by RT-qPCR) derived pre-exposure from individuals participating in a human challenge study were also used. In some instances, stool suspensions were used without further processing. In other cases, the suspensions were partially purified by chloroform extraction (Shin & Sobsey, *Water Res.* 42:4562-4568 (2008)). All suspensions were stored at −80° C. until use in experiments. The following virus-like particles (VLPs), which consisted of purified virus capsid without the viral genome, were available for this study: GI.1, GI.4, GI.6, GI.7, GI.8, GII.1, GII.2, GII.3, GII.4 (2 strains), GII.6, GII.7, GII.12, and GII.17.

Preparation of P Proteins

Viral P proteins were selected as targets for SELEX. The genomic RNA from the GII.4 clinical outbreak stool specimen was extracted using the phenol-chloroform-ethanol precipitation method. Reverse transcription polymerase chain reaction (RT-PCR) was performed using the commonly used, broadly reactive JJV2F (Jothikumar et al., *Appl. Environ. Microbiol.* 71:1870-1875 (2005)) and G2SKR (Kojima et al., *J. Virol. Methods* 100:107-114 (2002)) primers. The two step RT-PCR was completed using a DNA Engine (PTC-200) Peltier Thermal Cycler 200 (MJ Research/Bio-Rad Laboratories, Hercules, Calif.) with a 50° C. reverse transcription step for 30 min followed by enzyme inactivation by treatment at 94° C. for 15 min. Amplification consisted of 35 cycles of 94° C. for 30 sec, 58° C. for 50 sec, 72° C. for 60 sec, and a single 72° final extension step for 5 min. Amplified cDNA was purified with the QIAquick PCR Purification Kit (Qiagen, Valencia, Calif.) and sequenced by Genewiz, Inc. (South Plainfield, N.J.). RT-PCR amplification and sequencing confirmed that the clinical outbreak stool specimen used for creation of the P domain belonged to the 2006b GII.4 cluster. Primers specific to the P domain region (nt 5744-6704), which included flanking BamHI and NotI restriction enzyme sites, were designed using the GII.4 2006b sequence (Accession Number: JN400603; Tsai et al., *J. Med. Virol.* 86:335-346 (2014)) based on the locations of previously reported primers without a hinge (Tan & Jiang, *J. Virol.* 79:14017-14030 (2005)), and (Table 6). These were used to produce cDNA using the RETROscript kit (Ambion/Applied Biosystems) and amplified in PCR with the designed primers (GII.4 P Domain Forward/Reverse, Table 6) and the Platinum Taq system (Invitrogen). Reactions were cycled at 95° C. for 90 sec, followed by 40 cycles of 95° C. for 30 sec, 55° C. for 40 sec, 68° C. for 90 sec, and a single final extension step of 68° C. for 5 min. The products were then cleaned with the QIAquick PCR purification kit (Qiagen). After cleaning, 410 ng of the product was restriction digested with BamHI and NotI (New England BioLabs, Ipswtich, Mass.). This was ligated into a similarly digested pGEX-4T-1 plasmid (GE Healthcare, Piscataway, N.J.) containing an N-terminal glutathione-S-transferase (GST) tag with a 2:1 insert:vector ratio. The vector was then electroporated into electrocompetent *E. coli* BL21 (DE3) cells, which were plated on brain heart infusion (BHI) agar plates with 100 µg/ml ampicillin and incubated at 37° C. for 24-48 h. Successful transformants were screened by colony PCR and confirmed by sequencing (Genewiz, Inc.).

TABLE 6

Oligonucleotides Used in Selection and Characterization of Aptamers with Binding Affinity to Noroviruses

| Name | Sequence (5'-3') | SEQ ID NO |
|---|---|---|
| DNA Aptamer Library Sequence | AGTATACGTATTACCTGCAGC-(N)$_{40}$-CGATATCTCGGAGATCTTGC | 146 |
| FAM-Forward Constant Region | FAM-AGTATACGTATTACCTGCAGC | 147 |
| Biotin-Reverse Constant Region | Biotin-GCAAGATCTCCGAGATATCG | 148 |
| Forward Constant Region | AGTATACGTATTACCTGCAGC | 147 |
| Reverse Constant Region | GCAAGATCTCCGAGATATCG | 148 |
| GII.4 P Domain Forward* | GCAC<u>GGATCC</u>TCAAGAACTAAACCATTTACTGTC | 152 |
| GII.4 P Domain Reverse* | GGAC<u>GCGGCCGC</u>TTATAAAGCACGTCTACGCCC | 153 |
| JJV2F | CAAGAGTCAATGTTTAGGTGGATGAG | 149 |
| COG2R | TCGACGCCATCTTCATTCACA | 150 |
| Ring 2P Probe | 56-FAM TGGGAGGGCGATCGCAATCT-3BHQ | 151 |
| T7GII.4F | TAATACGACTCAACTATAGCAAGAGTCAATGTTTAGGTGGATGAG | 154 |
| GII.4R2 | GTTGGGAAATTCGGTGGGACTG | 155 |

*The underlined bases are restriction enzyme recognition sites.

P domain-GST fusion protein and GST-only cultures were grown overnight in 2× yeast extract tryptone ampicillin (YTA) broth incubated at 37° C. Thereafter, the bacteria were pelleted, reconstituted in 2×YTA, and used to seed a larger 2×YTA culture that was grown at 37° C. to an OD$_{600}$ of 0.6-0.9. The cultures were then induced with 1.0 mM isopropyl β-D-1-thiogalactopyranoside (IPTG) and left overnight at 25° C. with gentle shaking. Cells were purified by centrifugation and lysed by bead beating. For further purification, the lysate was incubated 1:1 (v/v) in 50% glutathione sepharose 4B agarose bead solution (GE Healthcare) for 30-45 min at room temperature, followed by centrifugation and washing of the bead-protein complexes. Elution from the fusion protein was done using 50 mM Tris-HCl/10 mM reduced glutathione buffer (pH 8.0) mixed 1:1 with the bead volume and incubated for 15-20 min at room temperature followed by centrifugation. The presence of the P domain protein in the lysate and eluate was confirmed by Western blotting on nitrocellulose membranes using anti-GST primary antibody (Thermo Fisher Scientific, Waltham, Mass.) and anti-GII.4 primary antibody (ab80024, Abcam, Cambridge, England).

Aptamer Selection (SELEX) and Characterization

Preparation of DNA Library.

An 81-base combinatorial DNA library having a 40 nt variable region was prepared for SELEX by producing an 81 bp double-stranded (ds) DNA molecule that was unlabeled at the 5' end and labeled at 3' end with biotin by PCR using a Forward Constant Region primer and a biotinylated Reverse Constant Region primer (Table 6), as described previously by Dwivedi et al., *Appl. Microbiol. Biotechnol.* 87:2323-2334 (2010). For separating the biotinylated DNA strand from its complementary strand, the labeled dsDNA was coupled with Streptavidin MAGNESPHERE paramagnetic particles (Promega), and captured by magnet (MPC-M magnetic particle concentrator, Dynal A.S. Oslo, Norway). The captured dsDNA was denatured by treatment with 0.15 M sodium hydroxide and after three washes with Tris-EDTA, the immobilized biotinylated strand was released by incubating beads in 28% ammonium hydroxide at 85° C. for 10 min. Removal of residual ammonium hydroxide was achieved using Vivaspin 500 filters (10,000 molecular weight cut-off, Sartorius Stedim Biotech, Cedex, France) with two washes of nuclease-free water. The purified ssDNA was stored in −80° C. until use.

Selection of Aptamers Using GII.4 HuNoV P Protein.

SELEX and counter SELEX were done using the P domain-GST fusion protein and the GST tag with NoV-negative human stool and bead matrix as targets, respectively. Briefly, 300-500 pmol of library was pre-heated at 90° C. for 10 min and cooled on ice for 10 min. For counter SELEX, the library was exposed to a 125 µl bed volume of the GST beads for 1 h at room temperature with end-over-end mixing. The mixture was centrifuged at 500×g for 5 min and the supernatant reserved. DNA was purified by phenol:chloroform:isoamyl alcohol (25:24:1) extraction and ethanol precipitation (10% (v/v) 3 M sodium acetate, 200% (v/v) 100% ethanol, and 50 µg/ml Ambion GlycoBlue (Life Technologies, Grand Island, N.Y.)) with reconstitution of the pellet in 25 µl DEPC-treated water. The DNA concentration was adjusted to 20-40 ng/µl and amplified by PCR using 2 µl of the template and the PCR primers described in Table 6. The reactions of 50 µl contained 1×GOTAQ Buffer (Promega), 500 nM of Conserved Forward Primer, 500 nM biotinylated Conserved Reverse Primer, 0.2 mM Promega-PCR Nucleotide mix (Promega), 0.5 µs single-stranded DNA binding protein (Promega), and 2 U GOTAQ DNA polymerase (Promega). A Bio-Rad T100 Thermal Cycler was used for the PCR (Bio-Rad Laboratories, Hercules, Calif.) with an initial 95° C. step for 2 min; 30 cycles of 95° C. for 30 s, 50-65° C. for 30 s (see below), and 72° C. for 15 s; and a final extension at 72° C. for 5 min. After each round of SELEX and counter-SELEX, an initial annealing gradient (from 50-65° C.) using the cycling conditions above was used to determine the optimal annealing temperature prior to the larger regeneration of the remaining pool. This temperature optimization was required to reduce concatamers and primer dimers. The amplified pool was then made into biotin-labeled ssDNA as described above.

The initial counter-SELEX was followed by seven rounds of positive selection, which were performed in the same manner as the counter-SELEX described above except that the P domain-GST fusion protein lysate was used instead of the GST lysate; unbound sequences were removed by washing; and the protein-aptamer complexes were eluted from the beads using a glutathione elution buffer (50 mM Tris-HCl/10 mM reduced glutathione buffer (pH 8.0)) followed by phenol-chloroform extraction and ethanol precipitation. Prior to sequencing, another counter-SELEX round was performed using GST lysate and human NoV-negative human stool. The amplified pool was then resolved on a 2% agarose gel and purified with the QIAquick Gel Extraction Kit (Qiagen). The purified pool was cloned via electroporation using the TOPO TA Cloning Kit (Invitrogen). Colonies were selected, grown, plasmid-extracted, and screened by PCR. Selected colony plasmids were then sequenced (Genewiz, Inc.).

Analysis of Aptamer Sequences, Structural Folding, and Stability.

Usable aptamer sequences obtained were grouped into identical/similar sequences, and the proportion of each sequence in the pool determined. Structural folding analysis and ΔG prediction of the candidate aptamer sequences was performed using the DNA Mfold online server using 0.5 mM magnesium, 1 mM sodium, and 23° C. as input parameters (Zucker, *Nucleic Acids Res.* 31:3406-3415 (2003)). Candidate sequences from the pool were selected on the basis of how many times they repeated in the pool, low ΔG value (stability), and uniqueness and formation of loops in the secondary structure. Common sequence identification of the random regions of the aptamers in the sequence pool was conducted using the MEME server for analysis of only the input aptamer strands with a minimum motif length of 6 bases (Bailey & Elkan, *Proc. Int. Conf. Intell. Syst. Mol. Biol.* 2:28-36 (1994); Bailey et al., *Nucleic Acids Res.* 37:W202-W208 (2009)). Motif analysis was conducted for four representative random regions (M1, M5, M6-2, and M9-2; see Table 7), to exclude some random regions that contained slight base substitutions and/or additions that would have generated redundant memes. Additionally, a MEME analysis was run comparing only the two sequence random regions chosen for further characterization (M1 and M6-2). Motifs identified by MEME analysis were considered as potential motifs if they contained no more than two mismatches within at least a set of six bases between two or more sequences.

Evaluation of Aptamer Binding Using an Enzyme-Linked Aptamer Sorbent Assay (ELASA)

Binding affinity assays were done using the candidate aptamers and a panel of virus-like particles (VLPs) corresponding to genogroup I (GI.1 (Norwalk virus), GI.2, GI.4, GI.6, GI.7 and GI.8) and genogroup II (GII.1, GII.2 (SMV), GII.3, GII.4 (Houston and Grimsby), GII.6, GII.7, GII.12 and GII.17) HuNoV, and also for chloroform-extracted 20% stool suspensions derived from a patient confirmed to have GII.4 New Orleans infection. This was done using a previously reported ELISA-like method (Escudero-Abarca et al., *PLoS One* 9:e106805 (2014); Moe et al., *Clin. Diagn. Lab. Immunol.* 11:1028-1034 (2004); Rogers et al., *J. Clin. Microbiol.* 51:1803-1808 (2013)). We refer to this assay as Enzyme-Linked Aptamer Sorbent Assay (ELASA). Briefly, VLP suspensions (1.3-4.3 mg/ml) were adjusted to a concentration of 3 µg/ml in PBS; in the case of whole virus, 10-fold serial dilutions of chloroform-extracted 20% GII.4 New Orleans stool solutions were made. One hundred µl aliquots of VLP or diluted stool were placed on the bottom of a flat-bottom, polystyrene 96-well plates (Costar 3591, Fisher, Pittsburgh, Pa.) along with 100 µl PBS in other no-VLP-control wells, and plates were incubated overnight at 4° C. After removal of the fluid, the wells were blocked with 200 µl of 5% skim milk in PBS-Tween 20 (0.05%) (PBST) with a 10 nM mix of unrelated DNA oligonucleotides (*Listeria monocytogenes* primers hlyQF/R and L23 SQF/R (Rodriguez-Lázaro et al., *Appl. Environ. Microbiol.* 70:1366-1377 (2004)) for 2 h at room temperature with gentle shaking. Blocking solution was discarded, and three washes of 200 µl PBST per well were performed. Next, 100 µl of biotinylated aptamer (1 µM) was added to each well, and the plate was incubated for 1 h at room temperature with gentle shaking. After removal of the liquid, the plates were washed 4 times with PBST. One hundred µl of ELISA-grade streptavidin-horseradish peroxidase (1 mg/ml, 1:5000, Invitrogen, Carlsbad, Calif.) was added per well with incubation for 15 min at room temperature with shaking. After removing the unbound enzyme and rewashing with PBST, 100 µl of 3,3',5,5'-Tetramethylbenzidine (TMB) microwell peroxidase substrate system (solution A:B (1:1), KPL, Gaithersburg, Md.) was added for color development, and absorbance at 450 nm was recorded using a microplate reader (Tecan Infinite M200pro, Tecan Group Ltd., Mannedorf, Switzerland).

Plate Data Analysis

All ELASAs were replicated on three separate occasions with at least three wells per replicate. Results were expressed as the ratio between the absorbance values for test samples divided by those for the negative control (no VLP). As per convention (Ebel et al., *Emerg. Infect. Dis.* 8:979-982 (2002); Escudero-Abarca et al., *PLoS One* 9:e106805 (2014); Hirneisen & Kniel, *J. Virol. Methods* 186:14-20 (2012)), a VLP/no VLP ratio of less than 2.0 was considered to be low-to-no binding (−); a ratio from 2.0 to 5.0 was considered to be low binding (+/−); 5.0 to 10.0 was considered to be medium binding (+); and ≥10.0 to be strong binding (++). Means and standard deviations for ratios associated with replicate experiments were calculated using Microsoft Excel. For the plates containing positive and negative chloroform-extracted stool, statistical comparison was performed using a one-way analysis of variance (ANOVA) with Tukey's multiple comparison using Graph-Pad Prism version 5.0d.

Aptamer Magnetic Capture (AMC) and RT-qPCR

Biotinylated aptamers were used to concentrate human NoV from stool samples. Thirty µg of DYNABEADS MYONE Streptavidin C1 magnetic beads (Invitrogen-Dynal AS, Oslo, Norway) were diluted in 1 ml PBS+0.05% PBST, mixed, and recaptured using the Dynal MPC-M magnetic particle concentrator (Invitrogen-Dynal). The beads were resuspended in 1 ml of 5% skim milk and blocked overnight at 4° C. with rotation. The beads were then washed with 500 µl PBST twice, resuspended in 50 µl PBST, and stored at 4° C. until use. These beads will hereafter be referred to as "blocked beads."

Aptamer Magnetic Capture of Human Norovirus from Stool Specimens.

Aptamer capture of human NoV from stool was performed based on the protocol of Cannon et al., *Appl. Environ. Microbiol.* 74:6818-6819 (2008) with substitute of aptamers for purified histo-blood group antigens (HBGAs). Ten-fold serial dilutions of a previously aliquoted 20% GII.4 stool suspension were prepared in PBS, and 100 µl of each dilution was placed into a dedicated tube containing 900 µl PBST and 15 µl of biotinylated aptamer (100 µM, ~5.9 ng total). The contents were mixed by end-over-end rotation for 1 h at room temperature. Fifty µl of the blocked beads were then added, and the tubes incubated for another hour with flipping at room temperature. Beads were magnetically recovered and washed once with 500 µl PBST followed by one wash with 500 µl PBS. Beads were resuspended in 100 µl PBS and stored at −80° C. until RNA extraction. Negative controls consisted of tubes containing 450 µl PBST, 450 µl Superblock T20 (Thermo Fisher Scientific, Waltham, Mass.), 100 µl of diluted sample, and 500 of blocked beads. RNA extraction was done using the NUCLISENS EASY-MAG system (bioMerieux SA, Marcy l'Etoile, France) according to the manufacturer's instructions with a 40 µl final elution volume. The eluted RNA was immediately stored at −80° C. until use in RT-qPCR (below).

Quantification of Viral Recovery by RT-qPCR

RNA was amplified by one step RT-qPCR using the SUPERSCRIPT III PLATINUM One-Step kit (Invitrogen). Reactions of 25 µl were made containing 12.5 µl 2× Reaction Mix, 0.5 µl SUPERSCRIPT III Reverse Transcriptase/PLATINUM Taq mix, 200 nM JJV2F primer, 200 nM COG2R primer, 200 nM Ring2P probe (Jothikumar et al., *Appl. Environ. Microbiol.* 71:1870-1875 (2005)), 5.5 µl nuclease-free water, and 50 µl template. Reverse transcription was done at 50° C. for 15 minutes, followed by enzyme inactivation at 95° C. for 2 minutes. Amplification was done for 45 cycles of 95° C. for 15 seconds, 54° C. for 30 seconds; and 72° C. for 30 seconds. Quantification of genomic copies was based upon a standard curve using an in vitro transcribed GII.4 New Orleans amplicon covering a 460 nt range of the genome containing the JJV2F-COG2R primer target region. The amplicon was quantified using a nanodrop, serially diluted, and used to construct a standard curve to estimate genomic copies. Amplifiable RT-qPCR units were estimated based on a standard curve of Ct values from serial 100 µl dilutions of the 20% GII.4 New Orleans stool isolate used for the AMC assay that had their genome RNA extracted and amplified using RT-qPCR as described above.

Aptamer Candidate Selection

Figure 12:
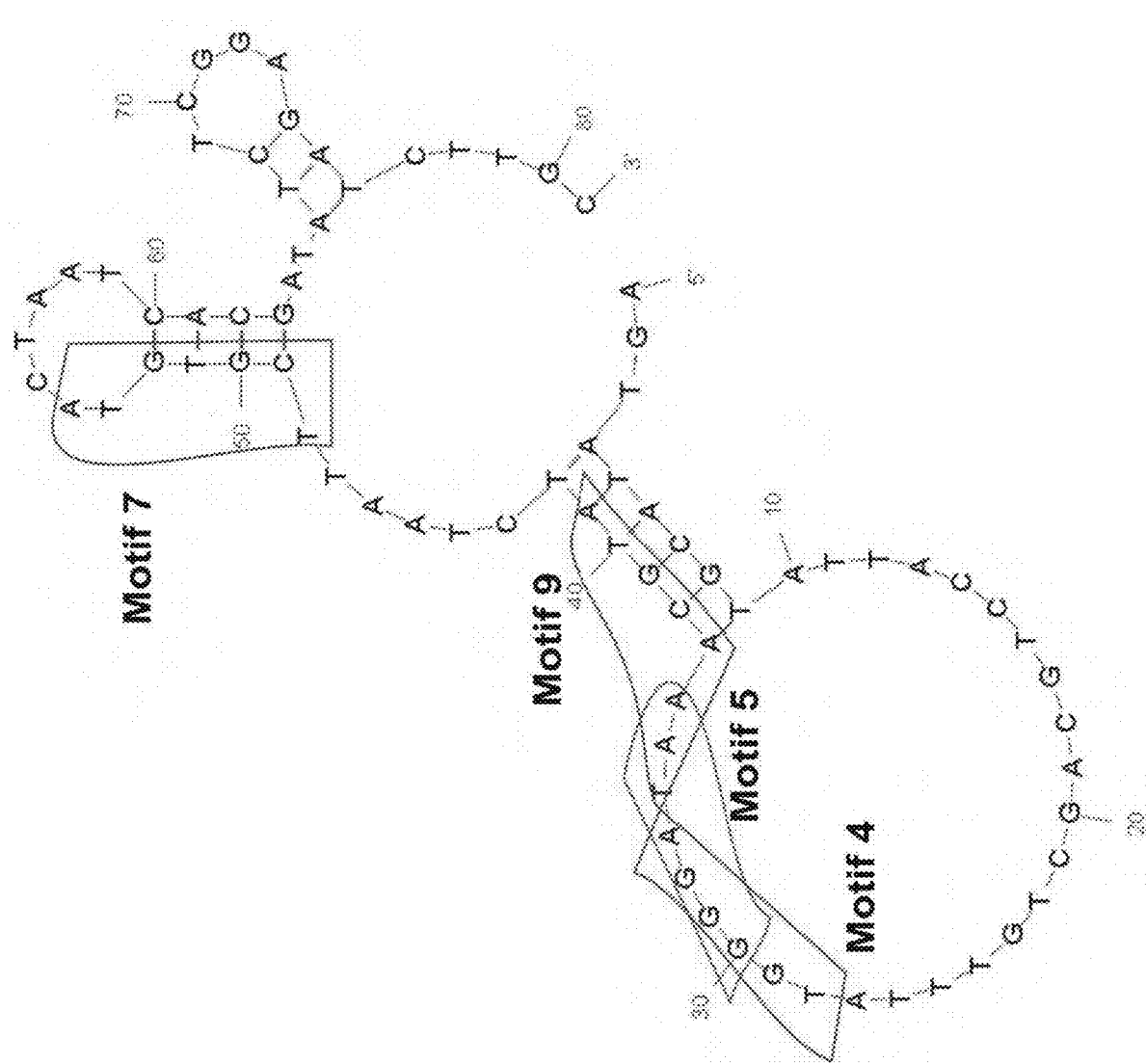
FIG. 12 shows the predicted structural folding of aptamer M1 (SEQ ID NO: 83).
Figure 13:
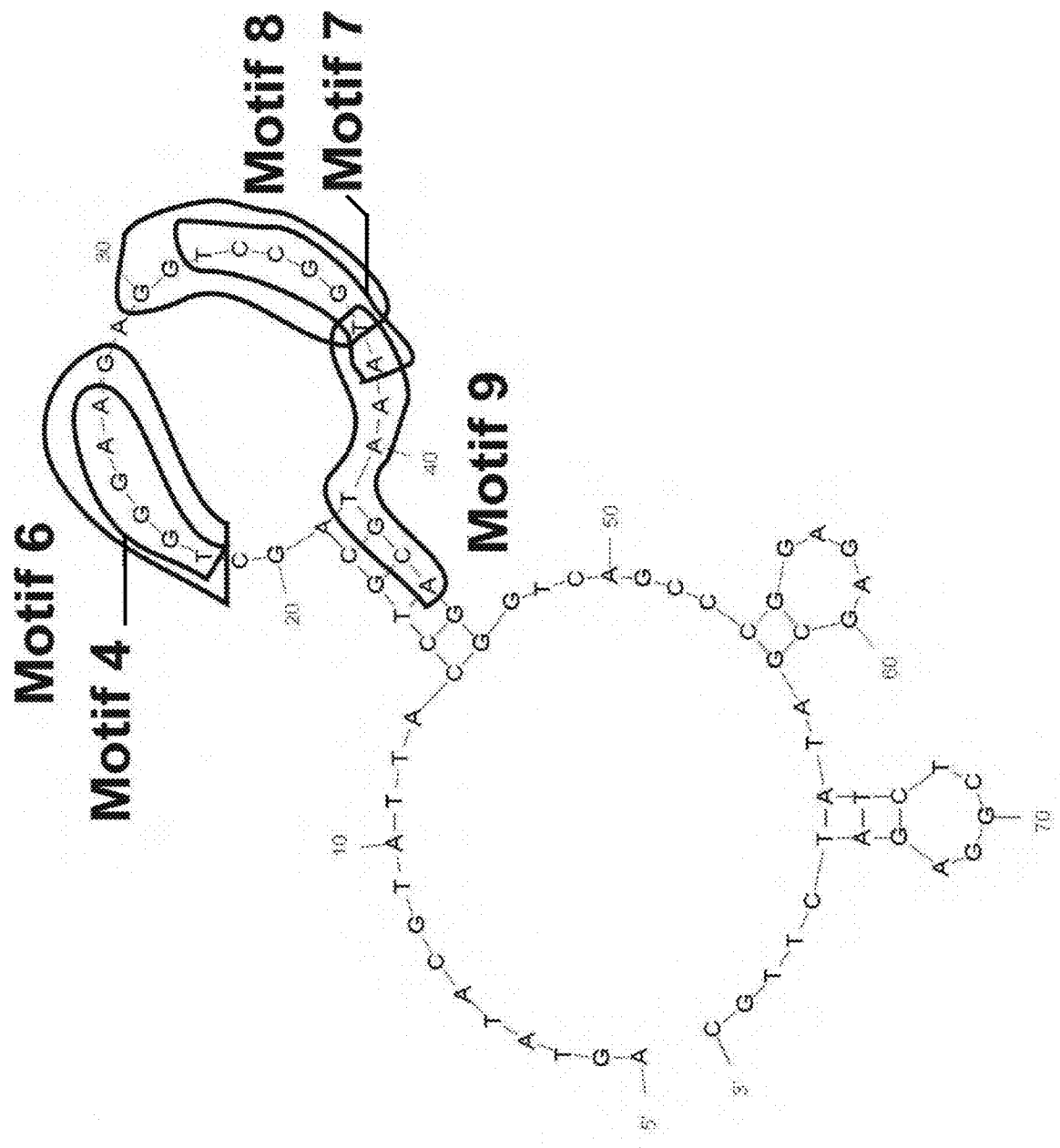
FIG. 13 shows the predicted structural folding of aptamer M6-2 (SEQ ID NO: 84).
Figure 14:
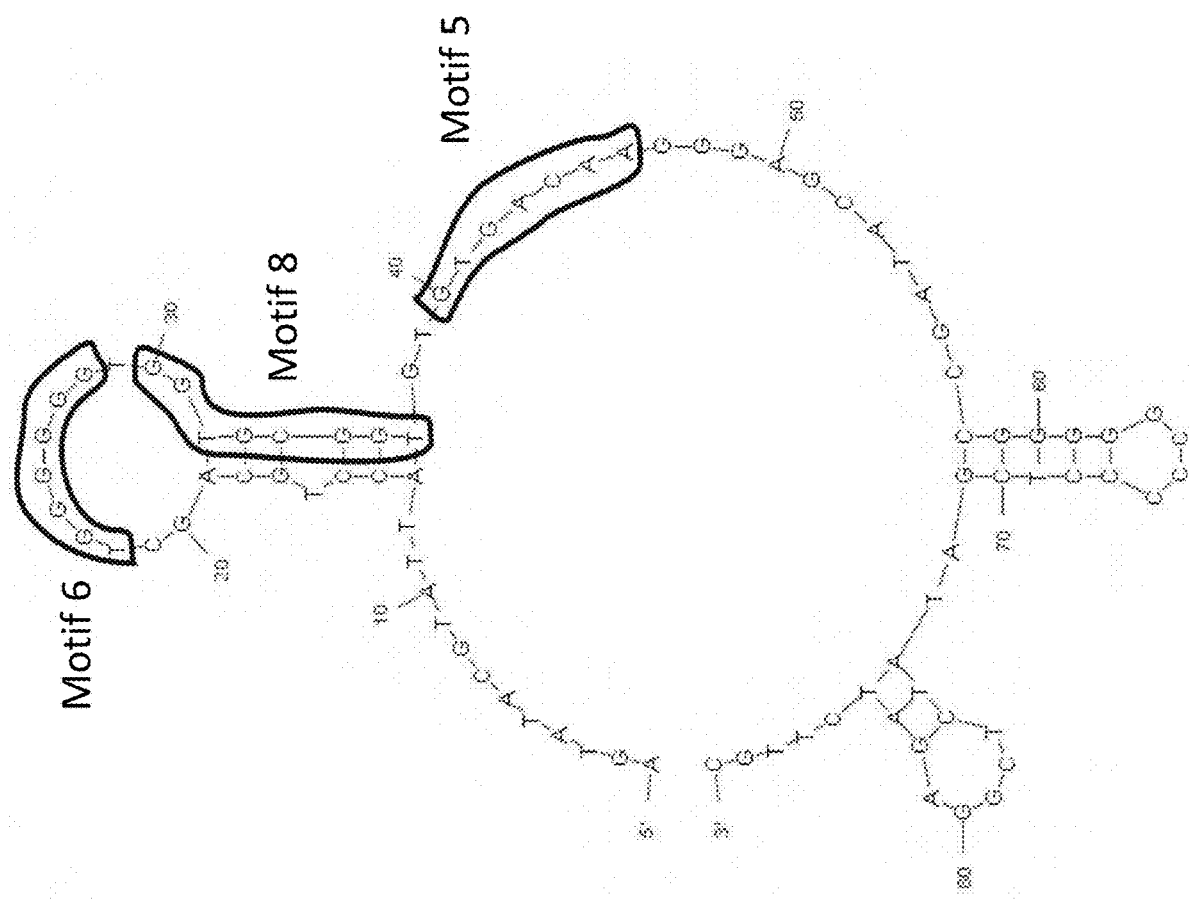
FIG. 14 shows the predicted structural folding of aptamer M5 (SEQ ID NO: 97).

After seven rounds of SELEX and two rounds of counter-SELEX, aptamer pools were sequenced, resulting in a pool of 11 sequences and leading to the identification of six unique aptamer candidates. All are detailed in Table 7. Candidates M1 and M6-2 were selected for further characterization based on the number of times the sequence occurred in the pool of sequences (3/11 and 1/11, respectively), low dG values (dG=−7.11 Kcal/mol and dG=−8.33 Kcal/mol for M1 and M6-2, respectively), and similarities in secondary structure. Candidates M1 and M6-2 have secondary structures containing multiple loops; however, both have some loops that contain conserved library primer regions involved in formation of stem-loops (FIGS. 12 and 13, respectively). FIG. 14 shows the predicted structural folding of aptamer M5 (dG=−6.43 Kcal/mol) with constant regions attached.

TABLE 7

Representative Aptamer Sequences Obtained from 7th Round of SELEX Against GII.4 P Domain and Two Rounds of Counter-SELEX Against GST-Beads and Negative Human Stool

| Round of SELEX | dG | Random Region Sequence[a] | SEQ ID NO | # Repeats | Aptamer Identifier |
|---|---|---|---|---|---|
| 7 | −7.11 | TGTTTATGGGGATAAACGTATCTAATTCGTGTACTAATCA | 35 | 3/11 | M1[ab] |
| 7 | −4.12 | TGTTAAGGGGAATTAATAATGATAATCCGTCTACTAATCA | 36 | 2/11 | M9-2 |

TABLE 7-continued

Representative Aptamer Sequences Obtained from 7th Round of
SELEX Against GII.4 P Domain and Two Rounds of Counter-SELEX
Against GST-Beads and Negative Human Stool

| Round of SELEX | dG | Random Region Sequence[a] | SEQ ID NO | # Repeats | Aptamer Identifier |
|---|---|---|---|---|---|
| 7 | -3.95 | TGTTAGGGGGAATTAATAATGGATAATCCGTCTACTAATCA | 37 | 1/11 | M12-1 |
| 7 | -8.13 | TGGGGGGTGGTGCGGTGTGTGGCAGGGGAGCATAGCCGGGGGCCCCT | 38 | 1/11 | M13-2 |
| 7 | -8.33 | TGGGAAGAGGTCCGGTAAATGCAGGGTCAGCCCGGAGAG | 39 | 1/11 | M6-2[ab] |
| 7 | -6.43 | TGGGGGGTGGTGCGGTGTGTGACAAGGGAGCATAGCCGGGGGCCCCCT | 40 | 3/11 | M5[b] |

[a]Candidate aptamers selected for further characterization
[b]Chosen for MEME analysis using MEME 4.9.1

MEME analysis showed multiple overlapping motifs involved in loop regions or the formation of loop regions. Sequence motif analysis of three aptamer random regions from the pool (which excluded random regions that were nearly identical to another region with the exception of one or two base substitutions/additions) as well as the two selected aptamers (M1 and M6-2) yielded several potential motifs (motifs 4-9) of at least 6 bases shared between different pairs of aptamers, allowing two mismatches. Other motifs were identified through further analysis. Motif 4 was shared between aptamers M1 and M6-2 and contained the sequence TGGGNA (SEQ ID NO: 101). The motif occurs near the beginning of the random regions of both of the aptamers and is involved in major loops in both of the aptamers. This is potentially a binding/interactive site, as stem-loop structures are targeted as potential binding sites on aptamers when screening to create truncated aptamers (Kaur et al., *PLoS One* 7:e31196 (2012)). Interestingly, this same motif region is also shared with M5, though the arbitrary cut-off of no more than two base mismatches in a motif means it could not be combined to be shared by all three aptamers (the motif shared by all three aptamers would be TGGGRRK using IUPAC nomenclature, which defines R as A or G and K as G or T) (motif 13; SEQ ID NO: 110). Motif 6 (TGGGNNG; SEQ ID NO: 103) is shared between M5 and M6-2, and occurs in a similar position on the two aptamers. Motif 6 is involved in loop regions on both aptamers, like motif 4. This suggests that the two similar motifs (4 and 6; TGGGRRK) comprise a sequence important for binding to HuNoV. Motif 5 (GNGANAA, SEQ ID NO: 102) is shared between M1 and M5, and occurs in the same loop region affected by the aforementioned conserved TGGGRRK loop sequence for M1. Motif 7 (TCNNGTA; SEQ ID NO: 104) is shared between M1 and M6-2. It occurs in the same loop as the conserved TGGGRRK sequence in M6-2, but appears as part of a separate stem-loop region in M1. Motif 7 occurs near the beginning of the random regions of both aptamers and is involved in their major loops. Motif 8 (GGTNCGGT; SEQ ID NO: 105) is shared between M5 and M6-2 at the same location and is involved in the major predicted stem-loops of both structures. It is also located near the conserved TGGGRRK sequence of both aptamers, but the resulting loops appear notably different based in secondary structure position in Mfold. Motif 9 (TAAANGNA; SEQ ID NO: 106) occupies similar positions on both M1 and M6-2. It is involved in forming the end of the stem and beginning of the conserved TGGGRRK loops of both of the aptamers. Motif 9 is involved in the stem-loop regions for the major loop of both aptamers.

It is interesting to note that many of the observed motifs occur in the loop regions of the aptamers, and many different motifs overlap. This might imply that different common sequence elements were conserved in the SELEX pool, but occur at different positions on the three different aptamers. M6-2 contains many overlapping motifs, all involved in a major stem loop, suggesting that the sequence was selected because it contained an "amalgamation" of different selected binding elements seen on the other two aptamers. The overlapping motifs are possibly the result of these conserved yet slightly different elements seen in different locations of the aptamers. If less stringent base mismatches were allowed, then a large sequence could be created that is shared between the three aptamers. For example, if the same base in two out of the three aptamers at each base position were the minimum, then the following sequence would be present in aptamers M1, M5, M6-2, and M13-2: TGG-GRRKWRRYSYRKY (R=A or G; K=G or T; W=A or T; Y=C or T; S=G or C) (motif 14; SEQ ID NO: 111). If restricted to just the conserved motif among M5, M6-2, and M13-2, a motif could be constructed that would have the sequence TGGGRRGWGGTSCGGT (SEQ ID NO: 174).

Notable sequence similarity between M1, M9-2, and M12-2 was detected. M1, M9-2, and M12-2 have very similar sequences in bases 1-16 and 23-40 of their random regions, indicating that these regions may be important for aptamer binding. These sequences have been designated motifs 10 and 11, respectively. Motif 10 has the sequence TGTTNNNGGGNATNAA (SEQ ID NO: 107), and motif 11 has the sequence TAATNCGTNTACTAATCA (SEQ ID NO: 108).

Aptamer Binding Inclusivity

Both aptamer candidates (M1 and M6-2) exhibited relatively stronger binding to VLPs representing GII human NoV genotypes over GI genotypes (Table 8). In Table 8, the values indicate the ratio between absorbance readings for the test sample versus negative control (VLP wells absorbance/ no VLP wells absorbance) for each aptamer. Results less than 2.0 are considered to be negative (−) per convention for determining assay detection limits and hence binding affinity; results in between 2.0-5.0 are considered low binding (+/−); results in between 5.0 and 10.0 are considered medium binding (+), and results >10.0 are considered strong binding (++). Values obtained for the negative control were in the range of 0.1-0.4. All experiments were done with at least three wells per replicate in triplicate. For aptamer M1, strong binding (++) was observed for GII.2 and GII.4 (Houston) while medium binding (+) was observed for GI.7, GII.4 (Grimsby), and GII.7 VLPs. For aptamer M6-2, strong binding (++) was seen for GII.2 and both GII.4 VLPs, and GI.7, GII.7, GII.12, and GII.17 VLPs bound to the aptamer with medium intensity. Based on an absorbance ratio cutoff of 2.0, aptamer M6-2 exhibited broader reactivity compared to aptamer M1, with some degree of binding to all of the VLPs tested. Positive signals were quite low for GI.6 and GII.3 VLPs. On the other hand, aptamer M1 did not appear to bind to GI.6, and had relatively low signals for GI.8, GII.3, and GII.6 VLPs. Overall, M6-2 also had higher VLP/No VLP ratios compared to M1. As expected, assays using GII.4 VLPs provided some of the highest signal ratios. Interestingly, both aptamers also had GII.2 ratios about as high as the GII.4 (highest) VLPs.

TABLE 8

Binding Affinity of Selected Aptamers Against a Broad Panel of Norovirus VLPs

| | VLPs Average VLP Pos/No VLP Ratio (Std. Dev.)[a] Aptamers | |
|---|---|---|
| Genogroup | M1 | M6-2 |
| GI.1 (Norwalk) | 3.40 (0.67) (+/−) | 4.28 (0.52) (+/−) |
| GI.4 | 3.17 (0.43) (+/−) | 3.36 (0.24) (+/−) |
| GI.6 | 1.98 (0.38) (−) | 2.75 (0.45) (+/−) |
| GI.7 | 7.32 (2.41) (+) | 7.56 (2.45) (+) |
| GI.8 | 2.61 (0.26) (+/−) | 4.55 (0.81) (+/−) |
| GII.1 | 3.59 (1.55) (+/−) | 4.52 (0.44) (+/−) |
| GII.2 (Snow Mountain) | 10.68 (0.70) (++) | 12.00 (1.10) (++) |
| GII.3 | 2.94 (1.90) (+/−) | 3.16 (0.72) (+/−) |
| GII.4 (Grimsby) | 7.59 (0.46) (+) | 11.54 (1.70) (++) |
| GII.4 (Houston) | 10.41 (1.23) (++) | 12.98 (1.76) (++) |
| GII.6 | 2.38 (0.78) (+/−) | 4.40 (0.85) (+/−) |
| GII.7 | 7.47 (1.15) (+) | 8.02 (1.99) (+) |
| GII.12 | 4.47 (0.54) (+/−) | 5.55 (0.10) (+) |
| GII.17 | 3.94 (1.03) (+/−) | 5.24 (0.75) (+) |

[a]Values indicate the ratio between absorbance readings for test VLP sample versus negative control (VLP wells absorbance/No VLP wells absorbance) for each aptamer.

Different binding patterns for these two aptamers indicate that they may bind to different regions of the P protein and hence the viral capsid. For example, it is possible that aptamer M1 binds the P2 subregion of the P domain because it is not as broadly reactive as aptamer M6-2. The P2 subregion can be involved in host cell binding and can be hypervariable, responsible for antigenic drift of GII.4 strains (Lindesmith et al., PLoS Med 5:e31 (2008)). Further, aptamer M6-2 showed higher signal intensity for all VLPs to which the two aptamers bound, and much higher intensity for the two GII.4 VLPs (Houston and Grimsby). Both aptamers bound well to the more recent GII.4 Houston strain, but aptamer M1 appears to have a noticeably lower affinity to the GII.4 Grimsby strain relative to M6-2. The target of SELEX was a GII.4 strain from 2007, thus higher binding to the Houston strain may be expected as Houston (2001) has less evolutionary distance from the 2006b target than Grimsby (1996; (Glass et al., N. Engl. J. Med. 361: 1776-1785 (2009); Shanker et al., J. Virol. 85:8635-8645 (2011).

Interestingly, both M1 and M6-2 aptamers bound GII.2 Snow Mountain VLPs about as well as the GII.4 strains. It may be possible that the aptamers are binding a conserved region between GII.4 and GII.2 Snow Mountain virus (SMV). This is further supported by the fact that aptamers produced against SMV also exhibited strong binding to Houston and Grimsby VLPs (see Example 1). However, it is also possible that the similar binding may be related to the preparation or characteristics of the VLPs, as the same VLP panel was used in both studies.

Figure 15:
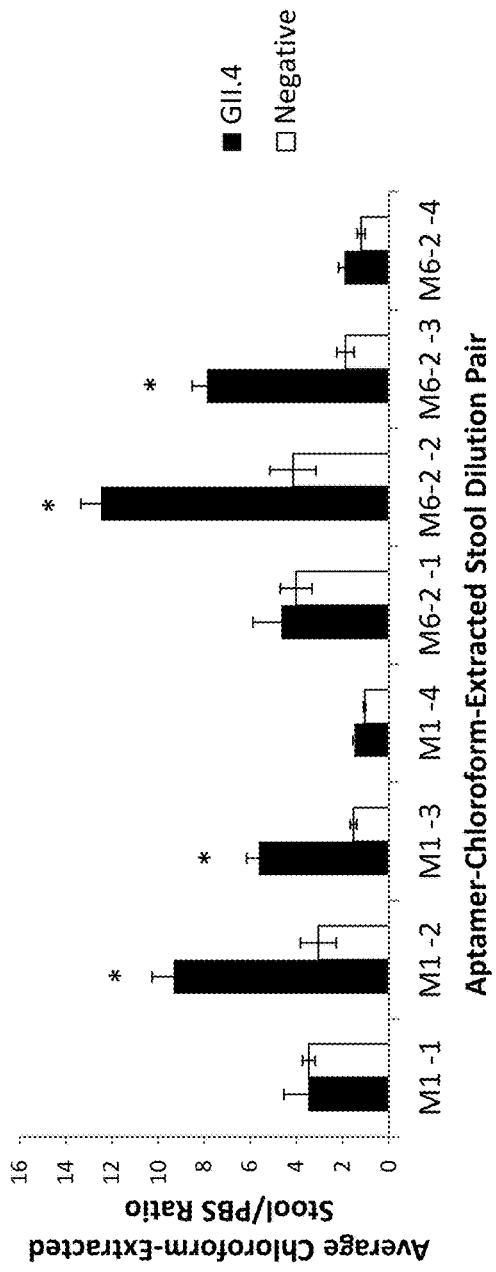
FIG. 15 shows binding ratios of partially purified, serially diluted 20% GII.4 and human NoV-negative stool samples to selected aptamers by ELASA. Data are presented as ratio of absorbance for test samples (serially diluted stool) vs. PBS negative control wells. The asterisk indicates a statistically significant difference ($p<0.05$) between GII.4 positive stool and stool confirmed negative for human NoV. Error bars represent one standard deviation above/below the mean. X axis is labeled by aptamer designation and dilution of stool.

Aptamers Bind to Partially Purified Human Stool Samples Obtained from Infected Individuals Both the M1 and M6-2 aptamers exhibited binding to serially diluted partially purified 20% stool specimens obtained from infected individuals (FIG. 15). Binding was statistically significant (p<0.05) relative to human NoV negative stool when the samples were diluted $10^{-2}$ or $10^{-3}$. These differences were not statistically significant for the $10^{-1}$ dilutions of stool, likely due to matrix-associated non-specific binding. When stool samples were diluted $10^{-4}$ or more, signal was lost, presumably because of dilution-associated depletion of virus, approaching the assay limit of detection.

Figure 16:
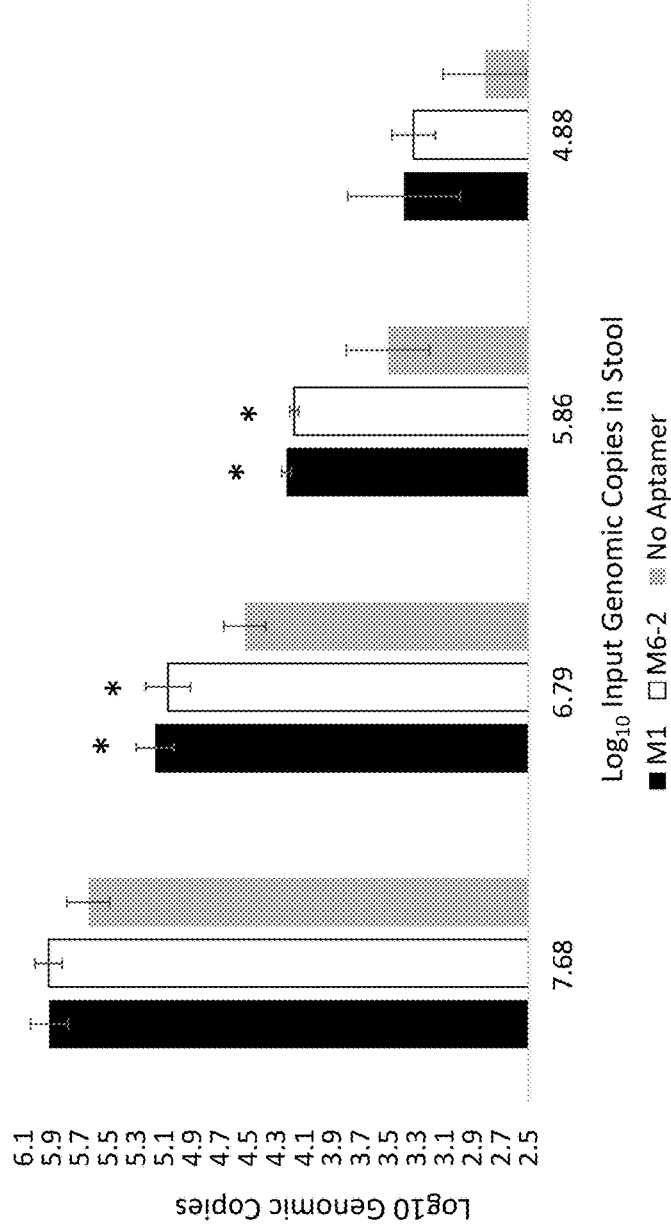
FIG. 16 shows capture and subsequent detection of GII.4 New Orleans from human stool using combined AMC-RT-qPCR. Negative controls consisted of beads without the aptamer conjugates. An asterisk designates statistical significance ($p<0.05$) when comparing aptamer and no aptamer controls.
Figure 17:
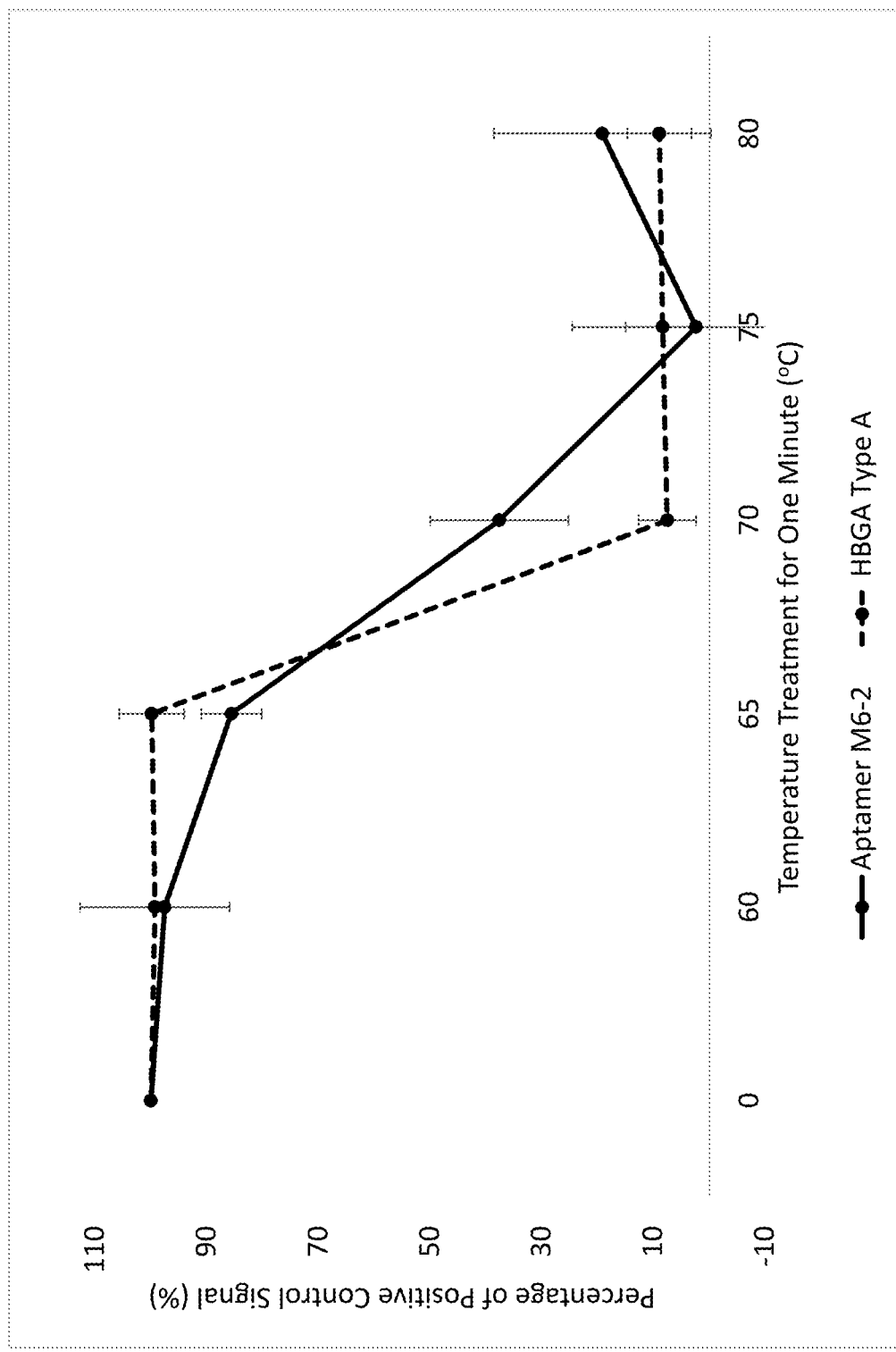
FIG. 17 shows binding of aptamer M6-2 and HBGA Type A to GII.4 Houston Virus VLPs at different temperatures.
Figure 18A:
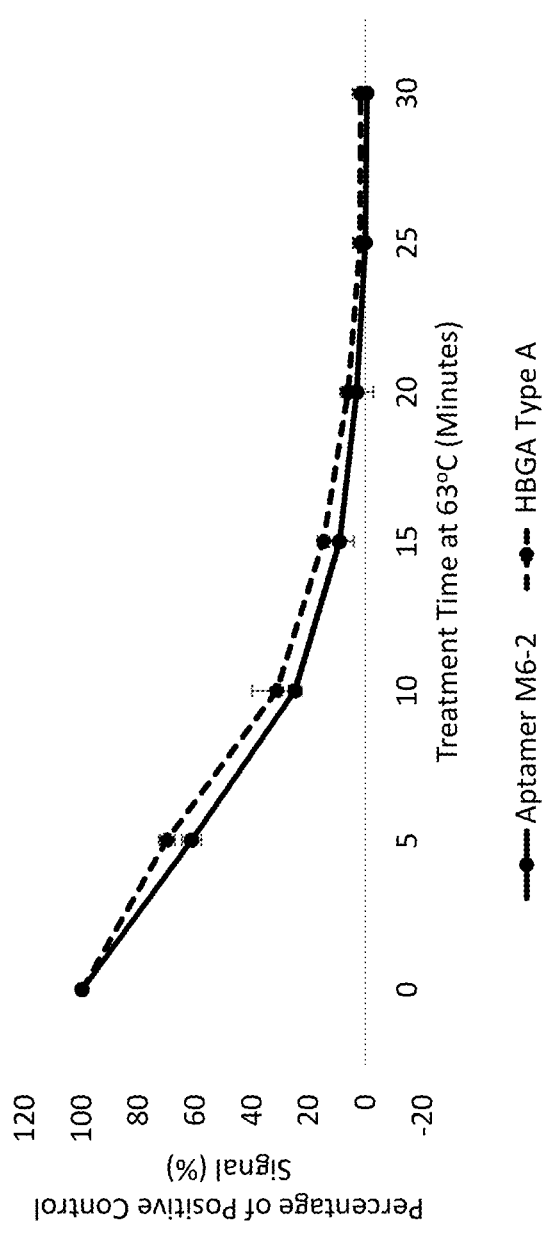
FIG. 18A-B shows binding of aptamer M6-2 and HBGA Type A to GII.4 Houston Virus VLPs at 63° C.
Figure 18B:
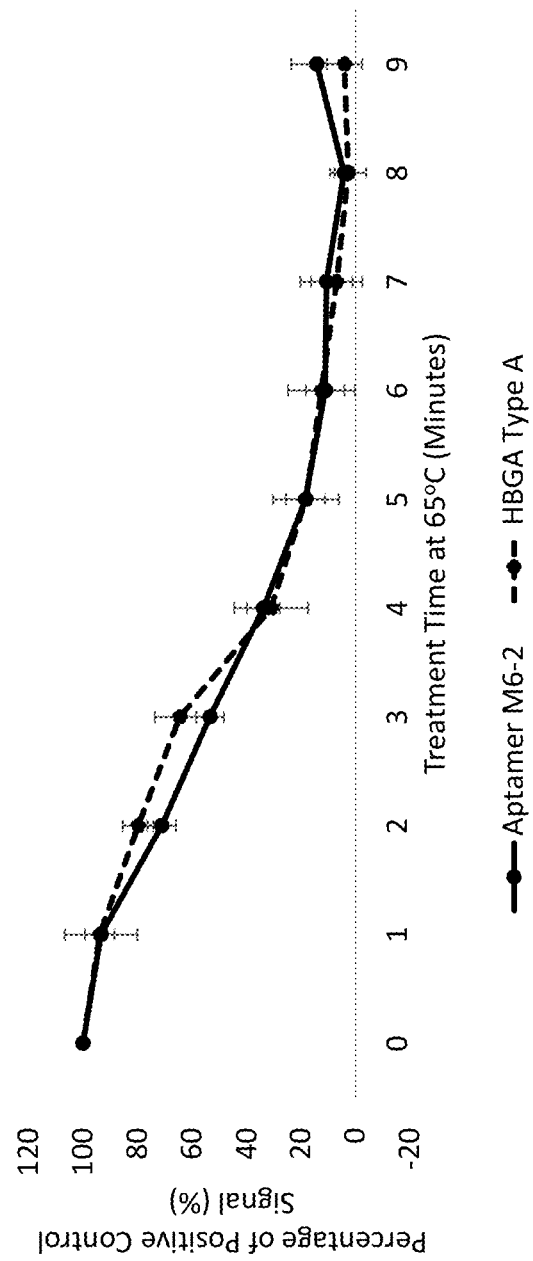

Aptamer Magnetic Capture (AMC) Coupled to RT-qPCR Applied to Outbreak Stool Specimens Aptamers M1 or M6-2 were used to concentrate HuNoV from diluted GII.4 New Orleans clinical stool isolates using magnetic nanoparticles. Concentrated viruses were then quantified by RT-qPCR (FIG. 16). Negative controls consisted of beads without the aptamer conjugates. An asterisk designates statistical significance (p<0.05) when comparing aptamer and no aptamer controls. Both aptamers concentrated significantly more virus (p<0.05) than no aptamer controls at concentrations of 5.86 and 6.79 $\log_{10}$ human NoV genomic units per ml of stool. At virus concentrations lower than this, the aptamers failed to produce statistically significant differences compared to the controls, although this could be due to increased variability at lower virus concentrations.

Use of the cloned P domain as a target for SELEX has potential benefit for the development of future diagnostics. With HuNoV capsid protein under constant selective pressure, a cost-effective, rapid, and easily implemented method for the creation of large quantities of binding ligands with high affinity to emerging strains could speed the development of detection assays. The generally low cost and instrumental requirements of cloning and expressing the P domain in the E. coli model produced an abundant source of target without the need for specialized equipment, or access to human stool from infected individuals; all that would be needed is capsid sequence information. Furthermore, demonstration of rapid, microfluidic SELEX processes may further facilitate the rapid identification of ligands specific to protein targets, which might include the P domain of HuNoV (Huang et al., Biosens. Bioelectron. 25:1761-1766 (2010); Lou et al., Proc. Nat'l Acad. Sci. U.S.A. 106:2989-2994 (2009)).

Discussion

In this example, the P domain cloned and expressed from the genome of a 2007 GII.4 human NoV clinical stool isolate was used as the target in SELEX for production of ssDNA aptamers. A GII.4 strain was considered relevant because it belongs to the epidemic genotype that has been causing the largest numbers of outbreaks and cases over the last two decades (Bok et al., J. Virol. 83:11890-11901 (2009); Noel et al., J. Infect. Dis., 179:1334-1344 (1999)). Furthermore, the P2 subdomain of the P domain is thought to be involved in host cell binding, is hypervariable, and likely responsible for antigenic drift of GII.4 strains (Lindesmith et al., *PLoS Med* 5:e31 (2008)). Given these features, the aptamers produced in this study did not strongly bind to all human NoV VLPs screened. However, they did exhibit binding to a majority of the VLPs tested, with generally better binding demonstrated for GII versus GI VLPs. A notable difference between aptamers M1 and M6-2 was observed for GI.8, GII.6, and GII.17 VLPs (Table 8). Different binding patterns for these two aptamers suggest that they may bind to different regions of the P domain. It could be hypothesized that aptamer M1 binds a less conserved region of the P domain because it was not as broadly reactive as M6-2, and overall showed lower signal intensity. As expected, both aptamers bound well to the GII.4 VLPs, as the aptamer target was a GII.4 2006b strain. Also as expected, both aptamers displayed stronger binding to the more recent and sequentially similar GII.4 Houston strain (2001) compared to the older and less sequentially similar GII.4 Grimsby (1996) strain (Glass et al., *N. Engl. J. Med.* 361:1776-1785 (2009); Shanker et al., *J. Virol.* 85:8635-8645 (2011)). Interestingly, M6-2 showed some degree of binding to all of the VLPs tested, suggesting that it likely binds a part of the P1 subdomain of NoV, where other fairly broadly reactive antibodies have been found to bind (Kitamoto et al., *J. Clin. Microbiol.* 40:2459-2465 (2002); Parker et al., *J. Virol.,* 79:7402-7409 (2005); Shiota et al., *J. Virol.* 81:12298-12306 (2007)).

Multiple common sequence motifs within the variable region of aptamers M1 and M6-2 were identified. Many of these motifs are involved in stem-loop or loop structures (FIGS. 12 and 13, respectively) and may be implicated in aptamer binding to human NoV, as loop and stem-loop structures are often involved in binding (Kato et al., *Nucleic Acids Res.* 28:1963-1968 (2000); Kaur et al., *PLoS One* 7:e31196 (2012)). Such motif analysis can inform future studies. For example, characterization of the nature of the aptamer binding domain(s) could be further investigated using nucleotide substitution. Further, identification of common motifs in aptamers M1 and M6-2, in addition to other aptamers might allow the production of truncated aptamers that could be combined into a chimeric aptamer (Kanwar et al., *Crit. Rev. Biochem. Mol. Biol.* 46:459-477 (2011)) to create an even more effective broadly reactive ligand.

Recently, three studies have reported the development of DNA aptamers having binding affinity to NoV. Giamberardino et al., *PLoS One* 8:E79087 (2013) produced aptamers targeting the murine norovirus (MNV) surrogate using whole virus SELEX, finding that one also bound GII.3 NoV VLPs; this aptamer was used as a recognition element in a voltammetry-based biosensor. Beier et al., *FEMS Microbiol. Lett.* 351:162-169 (2014) created DNA aptamers using an unspecified GII.4 strain's entire major capsid protein (VP1) by a different SELEX process than ours. The report of that work focused primarily on innovations in bioinformatic analysis and protein-aptamer modeling rather than the functional binding characterization reported here. Interestingly, the aptamers produced by Giamberardino et al. (2013) and Beier et al. (2014) had ΔG values similar to M1 and M6-2, but the sequences and secondary structures differed from ours. In both papers, the aptamers produced were never applied for capture or detection of human NoV in outbreak-derived stool specimens, and aptamer binding to the intact capsid of only one genotype of human NoV was confirmed for any of the reported aptamers.

In another study (see Example 1 and Escudero-Abarca et al., *PLoS One* 9:e106805 (2014) created aptamers using partially purified infectious GII.2 Snow Mountain virus from stool (whole virus SELEX), as juxtaposed to the GII.4 P domain target in this example. The aptamers described in that study, as well as those reported in this example, exhibited similar broad reactivity and high signal-to-noise ratios, despite the differences in target. The aptamers also had similar ΔG values and motifs that also occurred in stem-loops. Likewise, similar binding signals were observed using partially-purified GII.4 stool isolate in the ELASA assay. Aptamers M1 and M6-2 exhibited lower capture efficiencies in AMC-RT-qPCR compared to aptamer 25 reported by Escudero-Abarca et al. (2014) (Example 1). This may be a function of differences in the counter-selection process, as Escudero-Abarca et al (2014) (see Example 1) performed more counter-SELEX rounds against a greater number of targets, which likely reduced nonspecific aptamer binding to magnetic particles and stool components. Nonetheless, the aptamers M1 and M6-2 displayed a reasonably good capture efficiency at a range of 4.88-6.79 $\log_{10}$ input genomic copies of virus. Because of the similar performance of the M1, M6-2, and the Escudero-Abarca et al. (2014) aptamers (see Example 1) by ELASA and AMC-RT-qPCR, it is possible that they all bind to a conserved region, but further analysis would be necessary to support this hypothesis. The limit of detection of the AMC-RT-qPCR assay was 4.88 $\log_{10}$ input genomic copies, which corresponded to about 2-3 $\log_{10}$ RT-qPCR amplifiable units in the input stool sample.

Unlike any of the previous reports of aptamer generation to NoV, this paper is the first report of aptamers developed with a biotin label. Label modifications made after the development of aptamers have the potential to reduce aptamer binding affinity (Jiang et al., *Anal. Chem.* 76:5230-5235 (2004); Wang et al., *Anal. Chem.* 77:3542-3546 (2005)); thus selection using a functional biotin label allows for many downstream diagnostic and detection applications with less risk of losing aptamer functionality.

Not only were aptamers M1 and M6-2 able to bind to multiple human NoV VLPs, they also bound to stool samples previously confirmed as positive for human NoV as evaluated by both the ELASA and AMC assay. The stool specimens were purified and diluted in order to achieve reliable detection signals; matrix-associated interference with ligand binding may occur when samples are too "dirty." This may be due to a degree of non-specific binding and/or association of the aptamers with the extracted stool matrix. This phenomenon has been observed in similar types of assays done by other investigators for both aptamers (Escudero-Abarca et al., *PLoS One* 9:e106805 (2014); see Example 1) and other ligands (Burton-MacLeod et al., *J. Clin. Microbiol.* 42:2587-2595 (2004); Huang et al., *Protein Eng. Des. Sel.* 27:339-349 (2014); Li et al., *J. Food. Prot.* 75:1350-1354 (2012)). Interestingly, the dilution of the chloroform-extracted stool to about 0.2% original stool content for GII.4 New Orleans is similar to the optimal 1% stool dilution reported by Huang et al. (2014) when detecting NoV GII.4 in ELISA using phages displaying single-chain antibodies. When it comes to AMC, non-specific binding to the paramagnetic beads is commonly observed, as has been reported by others for bacteria (Rijpens et al., *Int. J. Food Microbiol.* 46:37-44 (1999); Tomoyasu, *Appl. Environ. Microbiol.* 64:376-382 (1998)) and NoV (Escudero-Abarca et al., *PLoS One* 9:e106805 (2014); Gilpatrick et al., *J. Virol. Methods* 90:69-78 (2000)). All told, regardless of the ligand or assay design, non-specific binding often impacts analytical sensitivity and this remains a recalcitrant issue for development of rapid, reliable, and sensitive human NoV detection methods.

The human NoV capsid protein is under constant selective pressure, especially GII.4 strains, and strain emergence occurs every few years (Bull et al., *PLoS Pathog.* 6:e1000831 (2010); Debbink et al., *J. Virol.* 86:1214-1226 (2012)). With respect to development of advanced detection and vaccination strategies that can cover emerging strains, it is important to have a readily available target for product development purposes. A functional human NoV P domain can be easily cloned, expressed and purified in *E. coli* with only capsid sequence information needed, thus resulting in the production of high concentrations of protein at low cost with relative ease. In short, the method described here can provide a cost-effective, rapid, and easily implemented means to create large quantities of ligands with high affinity to emerging human NoV strains. As rapid, microfluidic SELEX processes emerge, this may become an even simpler and faster means by which to select ligands with binding specificity to protein targets (Huang et al., *Biosens. Bioelectron.* 25:1761-1766 (2010); Lou et al., *Proc. Natl. Acad. Sci. U.S.A.* 106:2989-2994 (2009)).

In summary, we isolated and characterized ssDNA aptamers with binding specificity to a broad range of human NoV VLPs and outbreak strains using an *E. coli*-expressed viral capsid protein, and demonstrated that they could be used as capture ligands in both ELISA-type and aptamer-mediated magnetic capture-RT-qPCR assays. The aptamers reported here are among the broadest reacting ligands to human NoV identified to date (Escudero-Abarca et al., *PLoS One* 9:e106805 (2014) (see Example 1); Hardy et al., *Virology* 217:252-261 (1996); Huang et al., *Protein Eng. Des. Sel.* 27:339-349 (2014); Kitamoto et al., *J. Clin. Microbiol.* 40:2459-2465 (2002); Kou et al., *Clin. Vaccine Immunol.* 3849 (2014); Li et al., *Virus Res.* 151:142-147 (2010); Shiota et al., *J. Virol.* 81:12298-12306 (2007); Yoda et al., *J. Clin. Microbiol.* 41:2367-2371 (2003); Yoda et al., *BMC Microbiol.* 1:24 (2001)). With further development, the aptamers may be useful in novel detection platforms such as biosensors (reviewed in Torres-Chavolla & Alocilja, *Biosens. Bioelectron.* 24:3175-3182 (2009)) and also may have relevance in antiviral or therapeutic applications (Jeon et al., *J. Biol. Chem.* 279:48410-48419 (2004); Khati et al., *J. Virol.* 77:12692-12698 (2003); Yoon et al., *Antiviral Res.* 88:19-24 (2010)). This is the first report to demonstrate that broadly reactive aptamers binding human NoV can be easily and cheaply produced using SELEX directed against the P domain of these viruses.

Example 4: Selection and Characterization of Aptamers with Binding Affinity to the Norwalk Virus P Protein Materials and Methods Preparation of Targets for Aptamer Selection Virus Suspensions.

Norwalk virus (NV) was obtained as fecal extracts suspended 20% in phosphate-buffered saline (PBS) originating from human challenge studies. NV was used without further purifications.

Construction, Expression, and Purification of P Particles.

Norwalk virus P domain (corresponding to capsid amino acid residues 226-530) was amplified using primers P493 and P494 (Table 9) (Tan et al., *J. Virol.* 78:6233-6242 (2004)). The resulting PCR product was cloned as a BamH1-NotI fragment into vector pGEX-4T-3 (GE Healthcare, Piscataway, N.J.) resulting in vector pHR140; pGEX-4T-3 is a GST expression vector which contains a multiple cloning site downstream of glutathione S-transferase which is under the control of the plac promoter. The insertion of the P domain into the pGEX-4T-3 vector was confirmed by restriction digest and sequence analysis.

TABLE 9

Oligonucleotides Used in Selection and Characterization of Aptamers with Binding Affinity to Noroviruses

| Name | Sequence (5'-3') | SEQ ID NO |
|---|---|---|
| DNA Aptamer Library Sequence | AGTATACGTATTACCTGCAGC-$(N)_{40}$-CGATATCTCGGAGATCTTGC | 146 |
| FAM-Forward Constant Region | FAM-AGTATACGTATTACCTGCAGC | 147 |
| Biotin-Reverse Constant Region | Biotin-GCAAGATCTCCGAGATATCG | 148 |
| Forward Constant Region | AGTATACGTATTACCTGCAGC | 147 |
| Reverse Constant Region | GCAAGATCTCCGAGATATCG | 148 |
| P493* | GCAC<u>GGATCC</u>TTTTTAGTCCCTCCTACGGTG | 156 |
| P494* | GGA<u>CGCGGCCGC</u>TTATCGGCGCAGACCAAG | 157 |

*The underlined bases in P493 and P494 correspond to BamH1 and Not1 enzyme sites, respectively.

For expression of the P protein, pHR140 was electroporated into *E. coli* BL21 cells (Invitrogen, Carlsbad, Calif.) following the manufacturer's instructions. Transformants were selected for on LB media containing 100 µg/ml ampicillin. A 10 ml overnight culture of cells was diluted 1/10 in 2×YT (Yeast extract-tryptone) broth and grown to an $OD_{600nm}$ of 0.6-0.9; 0.5 mM IPTG was added to induce expression, and the culture was left to grow at 37° C. for 3-4 hr in a shaking (250 rpm) incubator. The cells were harvested by centrifugation, and the supernatant was removed. The cell pellet was then resuspended in PBS containing 1 mM phenylmethanesulfonylfluoride. The cells were transferred to 2 ml screw cap tubes to which 500 µl of 106 micron acid-washed glass beads were added. The protein was extracted by beating for 30 s at maximum speed in a Biospec mini bead beater (Biospec Products Inc., Bartlesville, Okla.) followed by 30 s on ice; this was repeated 3 more times. Thereafter, samples were placed on ice and centrifuged at 18,500×g for 5 min (Eppendorf 5424 microcentrifuge, Eppendorf, Westbury, N.Y.) to remove the glass beads and cellular debris.

The P protein was purified using a GSTrapFF column (GE Healthcare, Piscataway, N.J.) following the manufacturer's protocol with minor changes. Briefly, the column was equilibrated with 5 column volumes of binding buffer (I×PBS; 140 mM NaCl, 2.7 mM KCl, 10 mM $Na_2HPO_4$, 1.8 mM $KH_2PO_4$, pH 7.3). The sample was applied to the column at a flow rate of 0.2-1 ml/min. The column was capped and the protein was allowed to bind overnight at 4° C. The column then was uncapped and washed with 5-10 column volumes of binding buffer at a flow rate of 1-2 ml/min. The protein was eluted in 5 column volumes of elution buffer (50 mM Tris-HCl, 10 mM reduced glutathione, pH 8.0) at a flow rate of 1-2 ml/min. Confirmation of the P-protein identity was done using Western blotting and a NV (GI.I) mouse-derived antibody (Abcam, Cambridge, Mass.) that was diluted 1/400 prior to application to the membrane. After washing, the membrane was treated with a 1/5000 dilution of anti-mouse IgG conjugated to alkaline phosphatase (Sigma Aldrich, St Louis, Mo.), with color development done using BCIP/NBT liquid substrate (Sigma Aldrich, St Louis, Mo.).

Aptamer Selection (SELEX)

Preparation of DNA Library (FAM-Labeling).

An 81-base combinatorial DNA library was constructed (as described below) by producing an 81 bp dsDNA molecule that was labeled at the 5' end with FAM and the 3' end with biotin. This enabled the preparation of FAM-labeled ssDNA through biotin coupling at the 3' end of the 81 bp dsDNA to paramagnetic particles (see below for method). The diluted aptamer library (10 µM initial concentration) was amplified in a 50 µl PCR reaction containing 1×GOTAQ Buffer (Promega Corp., Madison, Wis.), 0.2 mM GENEAMP dNTPs mix (Applied Biosystems, Foster City Calif.), 2 U GOTAQ DNA polymerase (Promega), 500 nM FAM-Forward Constant Region primer and 500 nM Biotin-Reverse Constant Region primer (Table 9). The PCR was performed in a DNA engine Peltier Thermal Cycler 200 (MJ Research/Bio-Rad Laboratories, Hercules, Calif.) using a 3-step thermal protocol consisting of an initial denaturation at 95° C. for 2 mM followed by 30 cycles of 95° C. for 30 s, 55° C. for 30 s and 72° C. for 15 s, and a final extension at 72° C. for 5 min.

Separation of FAM-Labeled, Single-Stranded DNA (FAM-ssDNA) During SELEX.

Prior to each round of SELEX, it was necessary to separate single-stranded, FAM-labeled DNA from its complementary biotinylated strand. To do this, Streptavidin MAGNESPHERE paramagnetic particles (Promega) were washed 3 times in 0.5×SSC buffer before use. The FAM:Biotin-labeled, double-stranded DNA (dsDNA) was coupled with the Streptavidin MAGNESPHERE paramagnetic particles by incubating at room temperature for 30 min with end-over-end mixing. The dsDNA-coupled magnetic beads were washed 3 times with 0.IX SSC buffer. The FAM-labeled ssDNA moieties were separated from the immobilized biotin-labeled strains by alkaline denaturation in 0.15M NaOH at room temperature for 3-5 min. The biotin-ssDNA strands attached to the magnetic beads were captured using a Dynal MPC-M magnetic particle concentrator (Dynal A.S. Oslo, Norway). The FAM-ssDNA was removed and the NaOH was neutralized with 0.15M HCl. The FAM-ssDNA was then recovered by ethanol precipitation and resuspended in $dH_2O$.

SELEX Applied to Norwalk Virus (NV) P Protein.

Prior to SELEX, purified P protein was bound to glutathione sepharose 4B (GS4B) (GE Healthcare, Piscataway, N.J.) following manufacturer's instructions. Briefly, the GS4B was spun down at 500×g for 5 min, and the storage buffer was removed. The GS4B was washed in PBS twice, each time centrifuging at 500×g for 5 min, and the final pellet was resuspended in PBS. The P protein was overexpressed as described above, and the protein was extracted by bead beating. The extracted proteins were mixed with the washed GS4B and allowed to incubate at room temperature for 1 h with end-over-end rotation. The GS4B was washed 3 times with PBS at 500×g for 5 min to remove the unbound proteins and stored at 4° C. until required. About 300-500 pmol of ssDNA aptamers were heated at 90° C. for 10 min and cooled on ice. The cooled aptamers were added to a 250 µl aliquot of P-protein-bound GS4B and allowed to mix gently at room temperature for 1 h. The GS4B was then washed 3 times with PBS at 700×g for 5 min to remove any unbound aptamers. Bound aptamers were eluted from the GS4B with 500 µl elution buffer (50 mM Tris-HCL, 10 mM reduced glutathione, pH8.0) and recovered by phenol:chloroform extraction and ethanol precipitation. The aptamer pool was then regenerated by PCR. Counter-SELEX was performed before round 1 of SELEX and after rounds 5 and 10. The initial round of counter-SELEX was performed with protein bound to the GS4B from *E. coli* containing the pGEX-4T-3 vector. This removed any aptamers that could bind to the GS4B or the GST region of the fusion protein. After round 5, the counter-SELEX was performed using a 20% human stool suspension previously screened negative for HuNoV. After SELEX round 10, the counter-SELEX was performed with GS4B only.

Identification of Aptamer Sequences

After the final round of SELEX, the dsDNA was regenerated as described above; however, unlabeled Forward Constant primer and Reverse Constant primer were utilized in the PCR reaction. The PCR product was then cleaned using the QiaQuick PCR purification kit following the manufacturer's instructions (Qiagen, Valencia, Calif.). The purified PCR product was ligated into the pCR2.1 TOPO vector (Invitrogen, Carlsbad, Calif.) according to the manufacturer's instructions and electroporated into *E. coli* Top10 cells. Transformants were selected for as white colonies on LB-Xgal plates containing 50 µg/ml kanamycin. The selected transformants were grown overnight, and the plasmid DNA was extracted using the QlAprep Spin plasmid miniprep kit (Qiagen Inc., Valencia, Calif.). The plasmid DNA was then sent to Genewiz (South Plainfield, N.J.) for sequencing.

Prediction of Aptamer Structural Folding and Characterization of Aptamer Binding The structural folding analysis of the NV and SMV candidate aptamer sequences was done using the DNA Mfold online server (found at the website located at mfold.ma.albany.eduno=mfold/DNA-Foldirw-Form). A binding assay was developed and used to characterize binding affinities of candidate aptamers to NV.

Norwalk:Aptamer Binding Assay

This assay is similar to the two-site binding assay described above. Specifically, mouse GI.I (NV) antibody (Abcam) was biotinylated using an EZ-Link Sulfo-NHS-LC-Biotin and biotinylation kit according to the manufacturer's instructions (Pierce Biotechnology, Inc. Rockford Ill.). Streptavidin MAGNESPHERE paramagnetic particles (Promega) were washed as described above in 0.5×SSC and bound to the biotinylated GI.I antibody. After washing, a 50 µl aliquot of 20% NV stool suspension was added to the antibody:bead complex, and the suspension was mixed for 1 h at room temperature with end-over-end rotation. The bead:antibody:virus complex was then washed 3 times with PBS to remove unbound virus and fecal material. The aptamer was heated at 90° C. for 10 min, cooled on ice, 1 nM of the aptamer was added to the bead:antibody:virus complex, and the samples were mixed for 2 h at room temperature with end-over-end rotation. The bead:antibody:virus:aptamer complex was washed 3 times with PBS to remove any unbound aptamer. This was followed by a heat release to elute the aptamers from the surface of the virus. The recovered suspension was used in a SYBR green real-time PCR reaction targeting the aptamer. The real-time PCR assay was performed in a SmartCycler (Cepheid, Sunnyvale Calif.) using 200 nM unlabeled Forward Constant Region primer, 200 nM unlabeled Reverse Constant Region primer and IX SYBR green master mix (Applied Biosystems, Foster City Calif.). The PCR protocol was as follows: 95° C. 10 min followed by 95° C. for 15 s, 55° C. for 15 s, and 72° C. for 15 s for 40 cycles.

Aptamers with Binding Affinity to the Norwalk Virus P Protein

After five rounds of SELEX and two rounds of counter-SELEX (done using the pGEX-4T-3 vector only, and norovirus-negative stool), a total of 22 candidate aptamer sequences were identified (representative sequences shown in Table 10). Several of these were chosen for further characterization, based in part on frequency in which that aptamer was identified (e.g., aptamer NV 1-1) and unique structure (e.g., aptamer NV1-24). The free energies (dG) of NV 2-1, NV 2-9, NV 2-3, NV 1-1, NV 1-24, and NV 1-15 were −13.09, −13.11, −5.82, −9.94, −5.05, and −5.05 Kcal/mol, respectively.

TABLE 10

Representative Aptamer Sequences Obtained from 5th and 10th Rounds of SELEX for Norwalk Virus (NV)

| Round of SELEX | Random Region Sequence | SEQ ID NO | # Repeats | Aptamer Identifier |
|---|---|---|---|---|
| 5 | GGGGTGGTGCCGGAGTGGGGTGGCGGTGCGGATTCCCTGGCTATGCC | 41 | 8 | NV 1-1 |
| 5 | TGGGGGGTGGTGCGGTGTGTGACAAGGGAGCATAGCCGGGGCCAGT | 42 | 2 | NV 1-15 |
| 5 | TTGGTTGGTGCTCGCTGTAAGGTTAACACCGTCTAATCGGGACCGT | 43 | 2 | |
| 5 | GGGGAGCTCGTGGGTAGAGTGGGGCCGGGGTGTGGTATAGTGCGGCC | 44 | 1 | |
| 5 | TCGTCCTAGTGTGGGATATAGCTATGAAATCAACTTTCCC | 45 | 1 | |
| 5 | TGTAGGGAGTTGTTACATCGGCACTGGTCTGTTGAATTCT | 46 | 1 | |
| 5 | GGGGAATGTTCTTGTGGCCTACCGGGGAGTGGCCTTTATGTCCCTT | 47 | 1 | |
| 5 | GGTGGGGGGGTGCGGCATGTGGAGGCGGCGGGCAGGAGGGGACAGTG | 48 | 1 | |
| 5 | TGGGGGGGAGGGGAGATGGGTGGCGGTGGTGGGGCTTAGGGCTATCC | 49 | 1 | |
| 5 | GTGGACGGTAGTCGTTGTGGGCGCGGTGCGGGGGGGTTCGGGCGTG | 50 | 1 | |
| 5 | TGGGAAAGGGAAGTGTGGGCAGGGGAGGGAGGGGGGTGGCTACATCA | 51 | 1 | |
| 5 | TAGGGCAATATGTTAGTTAGGCGACTTGCTTAGACTACTG | 52 | 1 | |
| 5 | TTTGATGGTGCGGTGGCTTACATATGCGTTCTACATTGCGTTCGG | 53 | 1 | NV 1-24 |
| 10 | TAATTGTGTGTCGCAGCATGGTGGTGCCGGGCCTTGCATCCACCTTCGG | 54 | 14 | |
| 10 | TGGGGGGGGGGGCTGCTAAAGGTTTGTGGAGGGTTAACATGTACCTCCCC | 55 | 7 | NV 2-9 |
| 10 | TGGGAAAGGGAAGTGTGGGCAGGGGAGGGAGGGGGGTGGCTACATCA | 56 | 9 | NV 2-3 |
| 10 | TGGATGGGTGATGCTGGGTGGAAGAGGGGGCCGGACCCGCCGTCCGTG | 57 | 2 | |
| 10 | TTGGTTGGTGCTCGCTGTAAGGTTAACACCGTCTAATCGGGACCGT | 58 | 2 | |
| 10 | TGGGGGGTGGTGCGGTGTGTGACAAGGGAGCATAGCCGGGGCCAGT | 59 | 4 | |
| 10 | GGGGTGGTGCCGGAGTGGGGTGGCGGTGCGGATTCCCTGGCTATGCC | 60 | 3 | |
| 10 | TGGGGGGTGGTGCGGCATGTGGAGGCGGCGGGCAGGAGGGGACAGTG | 61 | 1 | |
| 10 | GGTGGGGGTGTGACCGGTGTGAGTCCGGTCCCGACGCGTGGATTCGG | 62 | 1 | NV 2-1 |
| 10 | TGGGAATAGGGAAGTGTGGATGAGTTCTGAGGATACCACGCCTTACCC | 63 | 1 | |

TABLE 10-continued

Representative Aptamer Sequences Obtained from 5th and
10th Rounds of SELEX for Norwalk Virus (NV)

| Round of SELEX | Random Region Sequence | SEQ ID NO | # Repeats | Aptamer Identifier |
|---|---|---|---|---|
| 10 | TTGAATGGTGGCAGTTGTTGAGGGGAGGTGTCGGGGGGGCGTTCGT | 64 | 1 | |
| 10 | TGGGAAAGGGGGAGAGTTGTGTGGCGAGCGTTGGACGGTGTGCCCCC | 65 | 1 | |

The norovirus:aptamer binding assay was utilized to confirm that aptamers NV 1-1 and NV 1-24 were able to bind to the surface of the NV. Using this protocol, we were able to confirm that Aptamers NV1-1 and NV 1-24 did bind to NV, as evidenced by successful amplification (with low Ct value) using the SELEX constant primers, and a corresponding shift in $T_m$. In the absence of virus, the aptamers were not amplified, and the associated $T_m$ values corresponded to those observed for primer-dimer, not target-specific PCR amplification (Table 11).

TABLE 11

Real-Time RT-PCR Data Obtained for
Norovirus:Aptamer Binding Assay

| Sample | PCR Product Seen | Melting Temperature ($T_m$) |
|---|---|---|
| NV 1-1 with virus | + (Ct 13.84) | 84.75 |
| NV 1-24 with virus | + (Ct 16.80) | 79.25 |
| NV 1-1 without virus | − | 62.5 |
| NV 1-24 without virus | − | 62.65 |
| No template control | − | 63.44 |

Example 5: Multiple Graphene Oxide (GO)-SELEX for Efficient Screening of Aptamers for Norovirus Genogroup GI Graphene and its derivative graphene oxide (GO) are promising molecules for a variety of biotechnological uses, with features such as fluorescence quenching, ability to protect biomolecules from enzymatic cleavage, ssDNA adsorption, and desorption of ssDNA in the presence of a specific target (Nguyen et al., *Chem. Commun.* (Camb) September 18; 50(72):10513-10516 (2014); Chen et al., *J. Agric. Food Chem.* 62(42):10368-10374 (2014); Park, *Chem. Commun.* (Camb) February 18; 48(15):2071-2073 (2012)). The use of GO-Selex method for virus particles offers a simple to use, cost effective and immobilization-free platform for screening of aptamers that bind to their target with high affinity and specificity. Herein, we report a simple aptamer screening method for a group of norovirus GI VLPs using graphene oxide (Multi-GO-Selex) without immobilizing targets.

Three hundred picomoles of the pool of aptamers were incubated with 400 μg of GO in 1 ml of 1×PBS buffer for 45 min at room temperature. The unadsorbed aptamers were discarded in the supernatant by centrifugation at 10,000×g, 7 min. The pellet with the bound aptamers was incubated with 5 different GI VLPs (GI.1, GI.4, GI.6, GI.7 and GI.8) as targets for specific desorption of the aptamers with a concentration of $10^{13}$ particles. After 2 h incubation at RT, the pool of aptamers bound to VLPs were recovered in the supernatant by centrifugation at 10,000×g, for 7 min. The pool was amplified and purified as described previously (Escudero-Abarca et al., *PLoS One* 9:e106805 (2014). This constituted one selection round.

After four rounds of GO-Selex, the enriched pool was cloned and 9 clones were sequenced. Three copies were found to have identical copies (AP6-GI), thus a total of 6 candidates were obtained. The structural folding analysis of GI candidate aptamer sequences was done using the DNA Mfold online server. The secondary structures predicted at room temperature (RT) in the presence of 137 mM NaCl which is the concentration of the salt in the buffer PBS used during the Selex process, showed free energy (dG) values of dG=−10.67 (AP-GI); dG=−8.74 (AP2-GI); dG=−5.78 (AP3-GI); dG=−9.26 (AP4-GI); dG=−6.98 (AP5-GI) and dG-10.99 (AP6-GI). See Table 12 and FIGS. 23-28.

TABLE 12

Aptamer Sequences Obtained from 4th Round of SELEX for GI-VLPs

| Aptamer | Random Region Sequence | # Repeats in Pool | SEQ ID NO |
|---|---|---|---|
| AP1-GI | CAGGATTAGTCATGGAATAGCCGACGATCATGACCCATTG | 1 | 176 |
| AP2-GI | CAGCGAAGGGACAGTTCTACGAATGTGAACATGAGGTAGC | 1 | 177 |
| AP3-GI | TGTTGGATTGATCCTAATTACGGATATTTACACGAATG | 1 | 178 |
| AP4-GI | TCACGGCGAATCGAAGGGACGCCGCGAAGTGTACCAAGTG | 1 | 179 |
| AP5-GI | CTGGTCCAGTCAAGGGGATTAGATGAGGGGTAATGGAGAG | 1 | 180 |
| AP6-GI | CCGAGTAGGGCCGGTCGTCACGGAGAAGCAGGGTGAGCGT | 3 | 181 |

Common sequence identification of the random regions of the aptamers in the sequence pool was conducted using the MEME server for analysis of only the input aptamer strands with a minimum motif length of 6 bases (Bailey & Elkan, *Proc. Int. Conf. Intell. Syst. Mol. Biol.* 2:28-36 (1994); Bailey et al., *Nucleic Acids Res.* 37:W202-W208 (2009)). Motifs of at least 6 bases with no more than two mismatches were selected as candidate motifs. The motifs are provided in Table 13.

TABLE 13

Motifs for GI SELEX Round 4 Sequences

| Motif | Sequence | SEQ ID NO | Aptamers |
|---|---|---|---|
| 15 | ACGAATG | 182 | AP2-GI, AP3-GI |
| 16 | ACGGAT | 183 | AP3-GI* |
| 17 | CGAAGGGAC | 184 | AP2-GI, AP4-GI |
| 18 | CGAAGTGTAC | 185 | AP4-GI |
| 19 | GGNGAGCG | 186 | AP5-GI, AP6-GI |
| 20 | NGTNGG | 187 | AP3-GI, AP6-GI |
| 21 | NGGTNG | 188 | AP2-GI, AP6-GI |
| 22 | GGATTAG | 189 | AP1-GI, APS-GI |
| 23 | GGAATAG | 190 | AP1-GI |

*Occurs twice in same aptamer.

Example 6: Discriminating Between Infectious and Non-Infectious Norovirus

Capsid Integrity and Functionality

The inability to culture HuNoV prevents the direct detection of infectious virus by molecular methods such as RT-qPCR. The reason for this is that naked or even partially degraded RNA may persist in the environment long after inactivation of the viral capsid or whole genome, and hence could be amplified by RT-qPCR after the virus has lost its ability to infect a host cell. This is of particular concern in foods and water, as various physical and chemical methods (e.g., heat, high hydrostatic pressure, ultraviolet light, ozone, chlorine, ionizing radiation, etc.) are commonly used to inactivate microorganisms of concern. In the case of viruses, the presence of a positive molecular amplification signal may erroneously imply the failure of the method to inactivate HuNoV.

In an effort to use molecular methods to aid in predicting viral infectivity, some have capitalized on specific properties of an infectious virus. One of these is the integrity of the viral capsid, which should theoretically protect the viral RNA from damage or degradation. The viral capsid is frequently the first to be degraded when viruses are subjected to inactivation methods. One approach in this regard is to precede RT-qPCR with a proteinase K and/or RNase digestion treatment, the idea being that partially degraded capsids will be fully degraded by the former enzyme, while exposed RNA will be degraded by the latter. Another approach is to precede RT-qPCR by a virus capture step using an immobilized ligand with affinity to HuNoV. Such ligands can include antibodies, histo-blood group antigens (HBGAs; the putative receptors/co-factors for HuNoV), or porcine mucin. Purportedly, these methods are intended to discriminate infectivity status based on the integrity of the viral capsid assuming that non-intact capsids would not be able to bind to the appropriate ligands. Further information on these types of methods can be found in Knight et al., *Crit. Rev. Microbiol.* 39:295-309 (2012). We maintain that aptamers could be a candidate ligand in these types of assays.

The most commonly used ligands for virus capture prior to RT-qPCR is HBGAs or porcine gastric mucin (which contains some HBGAs). These receptors are fairly costly, require purification from animals, and cannot be easily functionally modified with chemical groups. Because HuNoV binding is strain-specific, no HBGA broadly reacts with all HuNoV strains, and some HuNoV do not bind any HBGAs (see Murakami et al., PLoS One 8(6):e66534; Donaldson et al., Immunol. Rev. 225:190-211 (2008)). This further complicates detection and diagnosis of HuNoV. Despite reports of some broadly reactive antibodies, no antibody has been identified capable of binding all HuNoV strains (see Huang et al., Prot. Eng. Design & Sel. 27(10): 339-349 (2014); Kou et al. Clin. Vaccine Immunol. 22(2): 160-167 (2015); Shiota et al. (2007)). Nucleic acid aptamers are an interesting alternative but have not yet been used in this application. Multiple aptamers have been generated against noroviruses, some of which are broadly reactive (see Beier et al., FEMS Micro. Let. 351(2):162-169 (2014); Escudero-Abarca et al., PLoS One 9(9):e106805 (2014); Giamberardino et al., PLoS One 8(11):e79087 (2013); Moore et al., J. Biotech. Accepted Manuscript). In this study, we investigated whether loss of aptamer binding correlates with loss of HBGA or antibody binding for heat-treated HuNoV capsids as a potential proxy for estimating capsid integrity/functionality.

Materials and Methods

Virus-Like Particles (VLPs)

VLPs consisting of the assembled recombinant HuNoV capsid proteins of different HuNoV strains were used to investigate HuNoV capsid integrity. Specifically, GII.2 Snow Mountain (SMV), GII.4 Houston (HOV), and GII.4 Sydney (SDV) strains from human norovirus genogroup II were generously provided in purified form by R. Atmar (Baylor College of Medicine, Houston, Tex.). VLPs were stored in buffer at >1.0 mg/ml concentration and 4° C. until use.

Nucleic Acid Aptamers

Biotinylated versions of two ssDNA aptamers previously reported to be broadly reactive to HuNoV strains were selected for use in the study. One aptamer, SMV-19, was generated with a FAM label against infectious SMV from patient stool isolates (see Escudero-Abarca et al., PLoS One 9(9):e106805 (2014)). The other aptamer, M6-2, was generated with a biotin label against the P domain of a GII.4 2006b HuNoV strain expressed in *Escherichia coli* (see Moore et al., J. Biotech. Accepted Manuscript).

Heat Treatment of VLPs

VLP suspensions were diluted to 50 μg/ml in 1× phosphate-buffered saline (PBS; pH 7.2) or 10 mM HEPES (pH 7.4) for plate assays and electron microscopy, respectively. Samples were placed in 15 μl aliquots in 0.2 ml PCR tubes and heated using a T100 Thermal Cycler (Bio-Rad, Hercules, Calif.) at different temperatures [60° C., 65° C., 70° C., 75° C., 80° C.] for 1 min and at selected temperatures [63° C., 65° C., 68° C., 70° C., 72° C.] for 2.5-100 min, depending upon strain and experimental design. In other experiments, VLPs were treated at 80° C. for 5 min (completely denatured) or left untreated for use as negative and positive controls, respectively.

Immediately after heat treatment, samples were placed in a DNA Engine (PTC-200) Peltier Thermal Cycler (MJ Research, Hercules, Calif.) running at 4° C. for 5 min to cool. For plate assays. VLP aliquots were briefly centrifuged and diluted in 1×PBS to 3 μg/ml. One hundred μl of the dilutions were then applied to Costar 3591 medium-binding polystyrene 96-well plates (Fisher, Pittsburgh, Pa.) overnight at 4° C. with light shaking using an orbital shaker. Plates were processed by aptamer, HBGA, and/or antibody binding assays as described below.

Enzyme-Linked Aptamer Sorbent Assay (ELASA)

Aptamer binding to treated VLPs was probed using a previously established assay (see Escudero-Abarca et al., *PLoS One* 9(9):e106805 (2014); Rogers et al., *J. Clin. Micro.* 51(6):1803-1808 (2013)). Briefly, the wells containing the VLPs or PBS were blocked with 200 µl of 5% skim milk in PBS-Tween 20 (0.05% v/v; PBST) with a 10 nM mix of unrelated PCR primers (*Listeria monocytogenes* primers hlyQF/R and L23 SQF/R) (Rodriguez-Lazaro et al., *FEMS Microbiol. Lett.* 233:257-267 (2004)) for 2 h at room temperature with shaking. The plates were washed thrice with 200 µl of PBST and then incubated with 100 µl of 1 uM biotinylated M6-2 or SMV-19 aptamer for 1 h. Plates were washed 4 times with PBST and incubated with 100 µl/well of a 1 mg/ml streptavidin-horseradish peroxidase diluted 1:5,000 (v/v; Invitrogen, Carlsbad, Calif.) in PBS for 15 min. Residual conjugate was removed with 3 wash steps of PBST and plate signal developed with 100 µl/well of the 3,3',5,5'-Tetramethylbenzidine (TMB) microwell peroxidase substrate system (KPL, Gaithersburg, Md.) per manufacturer's instructions. Signal was allowed to develop for 2-7 min before reactions were stopped with the addition of TMB stop solution (KPL). The absorbance at 450 nm was then recorded using a Tecan Infinity M200pro microplate reader (Tecan Group Ltd., Männedorf, Switzerland). For all plate-based assays, a minimum of two wells per treatment per plate and three replicate plates for each treatment experiment were conducted. Signal development time was kept consistent within 30 seconds for each replicate.

ELISA-Like Histo Blood Group Antigen (HBGA Binding) Assay

Binding of heat-treated VLPs to HBGAs was observed simultaneously and in parallel to aptamer binding of heat-treated VLPs to aptamers. The HBGA binding assay has been previously reported (see Manuel et al., *Appl. Environ. Micro.* In Press) for observing capsid degradation and is similar to the ELASA except for the following: wells were washed twice with PBST after blocking and incubated with 30 µg/ml biotinylated blood type A HBGA (#01-032, GlycoTech, Gaithersburg, Md.) in 100 µl blocking buffer for 1 h. Wells were subsequently washed thrice and the signal determined as above using the streptavidin-horseradish peroxidase as above. Signal was developed for 10-20 min before stopping and reading at 450 nm.

Enzyme-Linked Immuno-Sorbent Assay (ELISA)

For the GII.4 Sydney VLPs, aptamer and HBGA binding was compared to antibody binding for heat treatments using a previously described ELISA method (see Hansman et al., *J. Virol.* 86(7):3635-46 (2012); Koho et al., *J. Virol. Meth.* 179(1):1-7 (2012)). Briefly, VLPs were blocked for 2 h as above and washed thrice with PBST. Wells were then incubated with 100 µl of 0.137 µg NS14 antibody (kindly provided by R. Atmar, Baylor College of Medicine, Houston, Tex.) (see Kitamoto et al., *J. Clin. Micro.* (2002)) in 0.1% skim milk-PBST for 1 h. Plates were washed thrice with PBST and wells incubated with 0.1 µg goat anti-mouse-horseradish peroxidase antibody (#62-6520, Invitrogen) in 100 µl of 0.1% skim milk for 1 h. Wells were washed thrice with PBST and signal developed as above with the TMB substrate system for 1-5 minutes before reactions were stopped and read.

Plate Data Analysis

For plate analysis, absorbances of negative control wells for each ligand seeded with completely heat denatured VLP (80° C., 5 min) were subtracted from sample well absorbances to remove nonspecific and primary sequence-based ligand interaction. Negative-adjusted absorbances of the samples for different temperature/time points were then taken as a percentage of the negative-adjusted absorbances of untreated positive control VLPs. At least two wells per temperature-time point per plate and three replicate plates were performed. For each VLP degradation at a specific temperature, a range of times where the approximate linear portions of the aforementioned signal degradation based on the HBGA binding loss were selected and linear trendlines were drawn and equations with $R^2$ values calculated using Microsoft Excel. Slopes for the lines for each ligand at the same selected time points—which indicates the apparent rate of signal loss—were calculated for each plate replicate. Average rates of apparent signal loss with standard deviation were calculated and unpaired t-tests with Welch correction were conducted comparing the three ligands for each temperature using GraphPad Prism version 5.0d (San Diego, Calif.). To estimate the apparent percentage of signal attributable to VLP protein sequence-dependent versus confirmation-dependent binding for all three ligands, three replicates of GII.4 Sydney VLP plates were completed. Instead of subtracting the absorbance values of denatured capsid (80° C. for 5 min), the absorbance value of a no VLP well (accounting for signal due to the plate apparatus) was subtracted. The subtracted values of positive control (untreated) and completely denatured VLP (80° C., 5 min) were used in the equation below to estimate the percentage of signal attributable to completely denatured capsid (sequence-dependent binding): [(80° C. 5 min wells average absorbance)−(No VLP wells average absorbance)]/[(Untreated VLP wells average absorbance)−(No VLP wells average absorbance)]*100 The apparent percentage of ligand binding to completely denatured capsid for each replicate plate were then averaged and their standard deviations determined using Microsoft Excel 2013.

Transmission Electron Microscopy

In order to confirm VLP degradation and observe morphological changes for VLPs after different degrees of heat treatment, TEM images were taken corresponding to different heat treatments relevant to those conducted for binding assays. VLPs were heat treated and cooled at 50 µg/ml in 10 mM HEPES (pH 7.4) as described above, and then applied to carbon-coated nickel grids (Ladd Research, Williston, Vt.) for 10 min. Samples were stained with 2% uranyl acetate (SPI Supplies, West Chester, Pa.) for 45 seconds, dried in a desiccator, and viewed using a JEOL 1210 transmission electron microscope (JEOL-USA Inc., Peabody, Mass.) at 80 kV and 50,000×.

Results

Behavior of Two Different Aptamers with Snow Mountain Virus (SMV)

Figure 19:
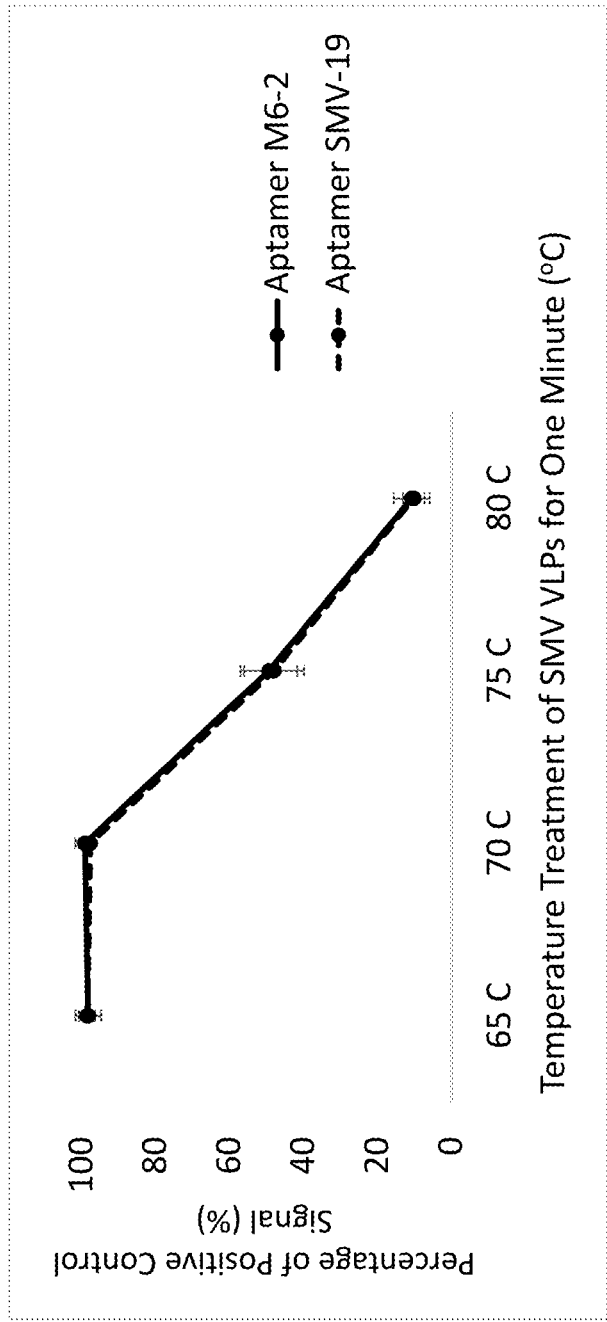
FIG. 19 shows a binding comparison of two different human NoV aptamers to SMV VLPs treated at different temperatures for one minute as a percentage of untreated SMV VLPs. Percentages have absorbance of completely denatured SMV subtracted.

Initial tests were done to compare the binding behavior of two previously selected aptamers to heat-treated VLPs. Specifically, aptamer SMV-19, selected against whole virus (see Escudero-Abarca et al., PLoS One 9(9):e106805 (2014)), and M6-2, produced against the P domain of a GII.4 2006b HuNoV strain (see Moore et al., J. Biotech. Accepted Manuscript) were used. Snow Mountain Virus (SMV; representing a GII.2 strain) was exposed to various temperatures (65-80° C.) for one min followed by detection using ELASA. VLP binding to the aptamers was virtually unaffected by treatments at 65° C. and 70° C. Some signal loss occurred at 75° C., and nearly all signal (~90%) was lost with treatment at 80° C. for one min. Both aptamers behaved nearly identically in terms of degree of signal loss at each temperature treatment (FIG. 19). Corresponding EM data showed gradual changes capsid structure and the number of intact VLPs at intermediate temperatures, and complete loss of capsid integrity when ELASA signal was lost (<90% signal reduction).

Further Observation of SMV VLP Degradation Using Aptamer M6-2

Figures 20A, 20B:
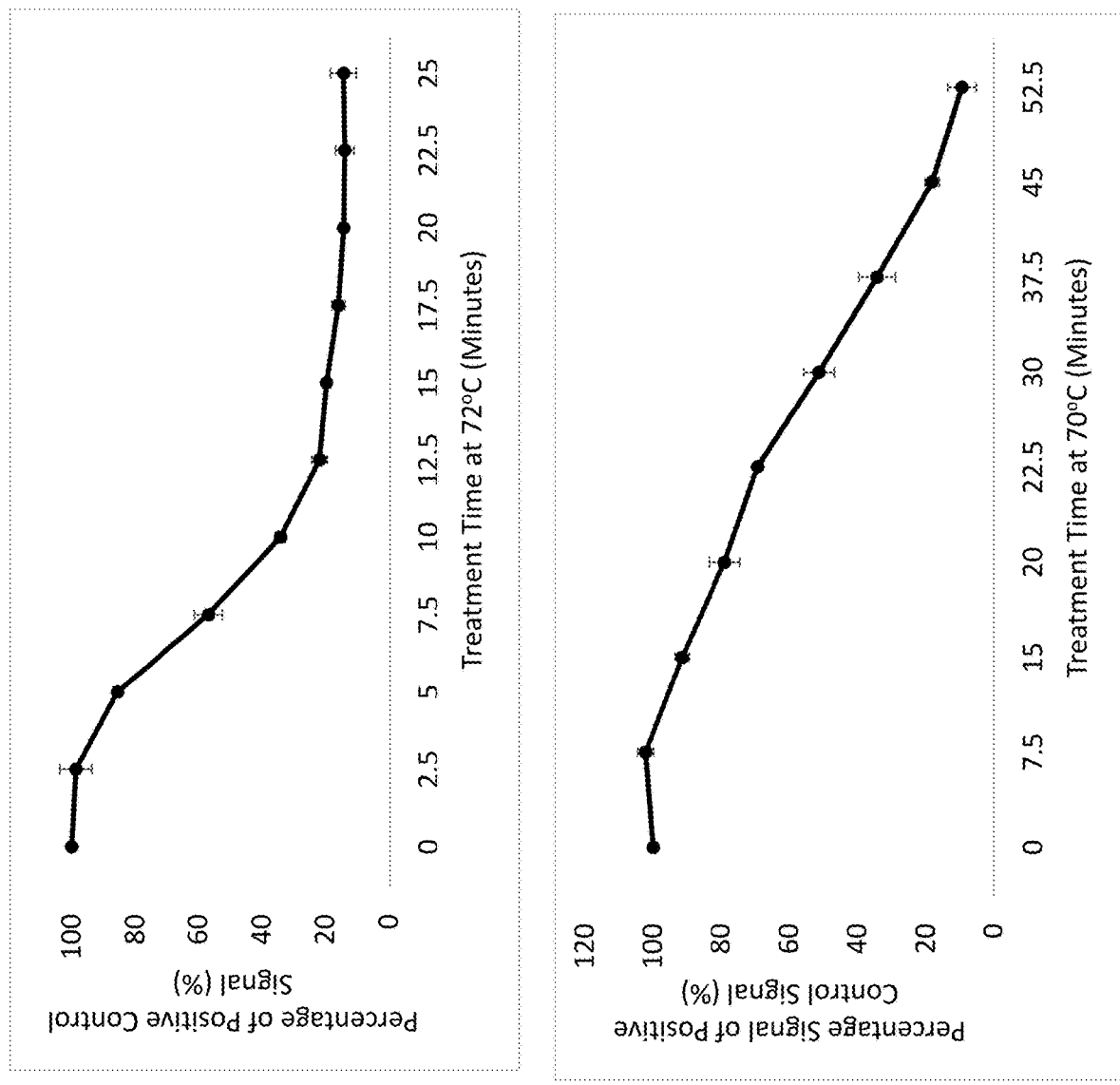
FIG. 20A-B shows degradation of SMV VLPs at two selected temperatures.
Figure 21A:
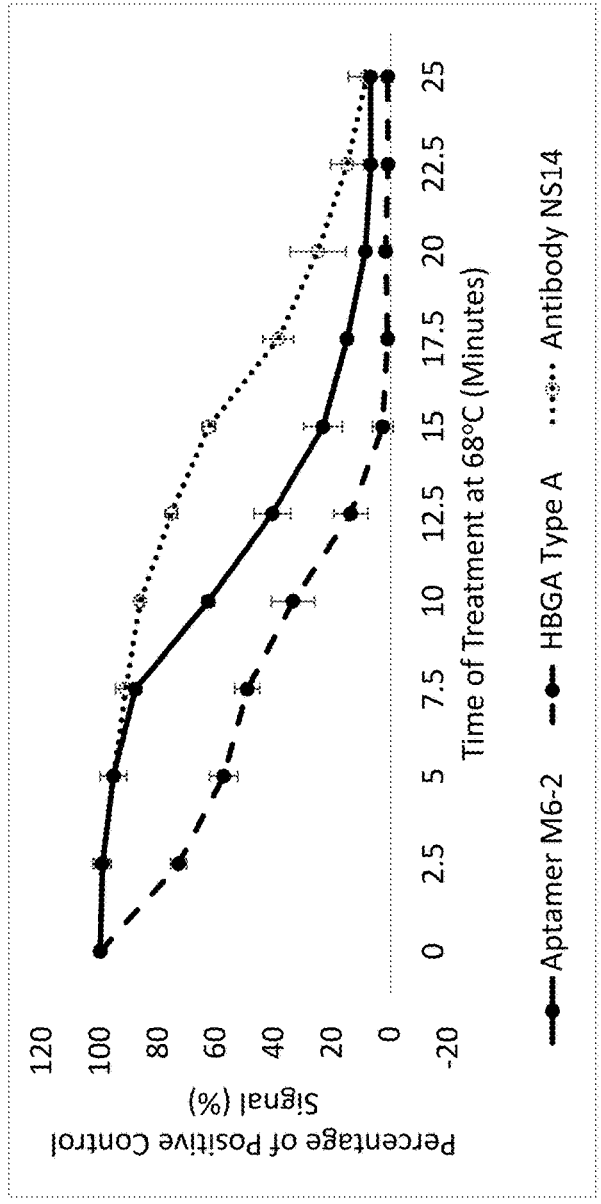
FIG. 21A-B shows binding behaviour of three different ligands (aptamer M6-2, HBGA type A, and antibody NS14) to GII.4 Sydney Virus VLPs treated at selected temperatures for different times.
Figure 21B:
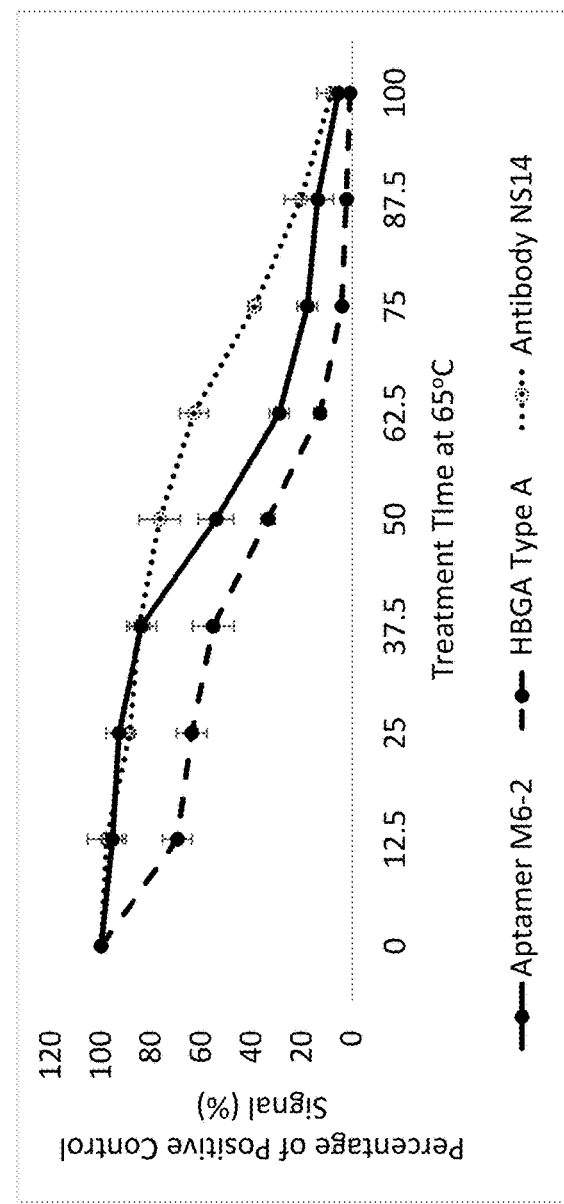
Figure 22:
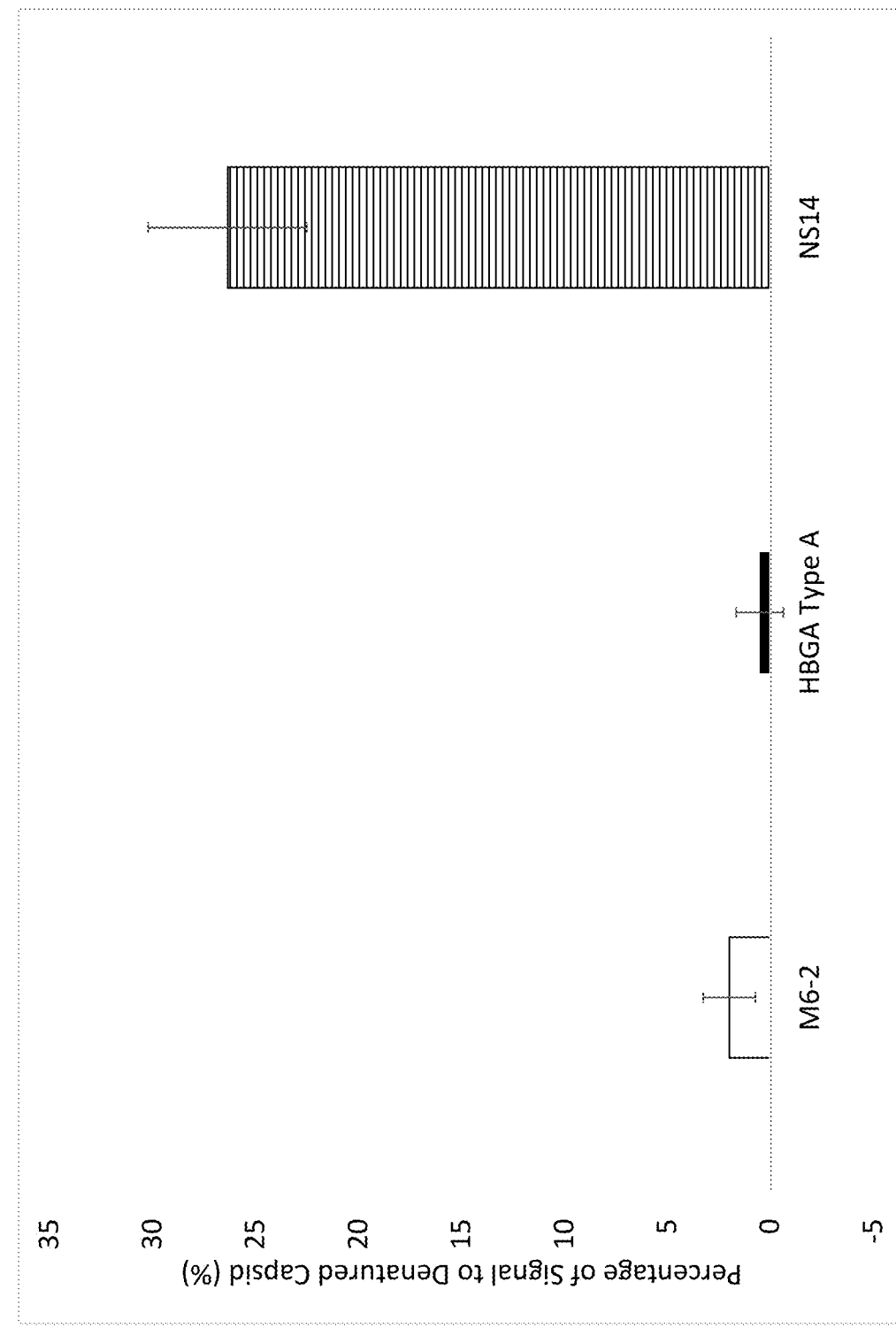
FIG. 22 shows binding signal of three human NoV ligands (aptamer M6-2, HBGA type A, and antibody NS14) to completely denatured GII.4 Sydney Virus VLPs as a percentage of untreated GII.4 Sydney Virus VLPs. Background signal as measured by no VLP wells was subtracted from all absorbances.
Figure 23:
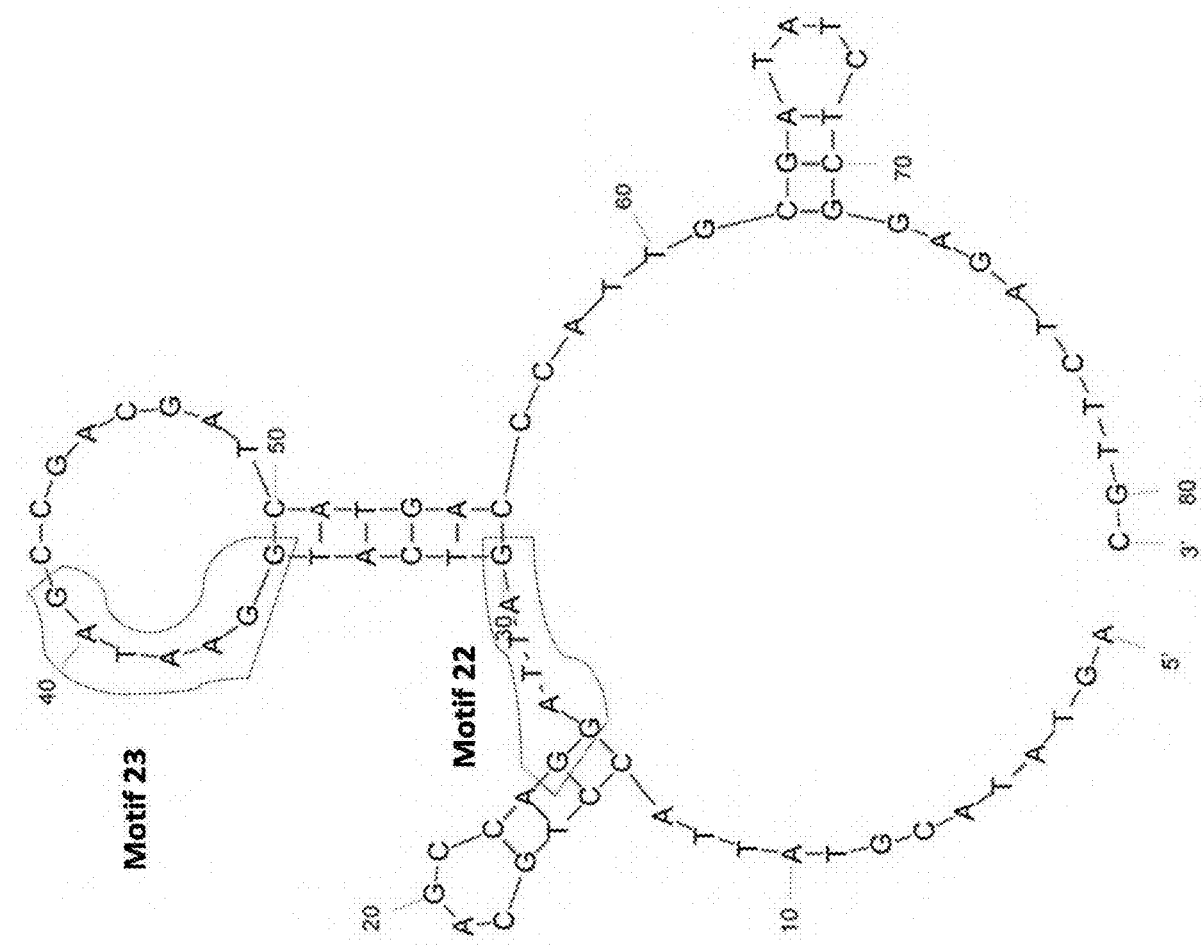
FIG. 23 shows the predicted structural folding of aptamer Apt-GI (SEQ ID NO: 176).
Figure 24:
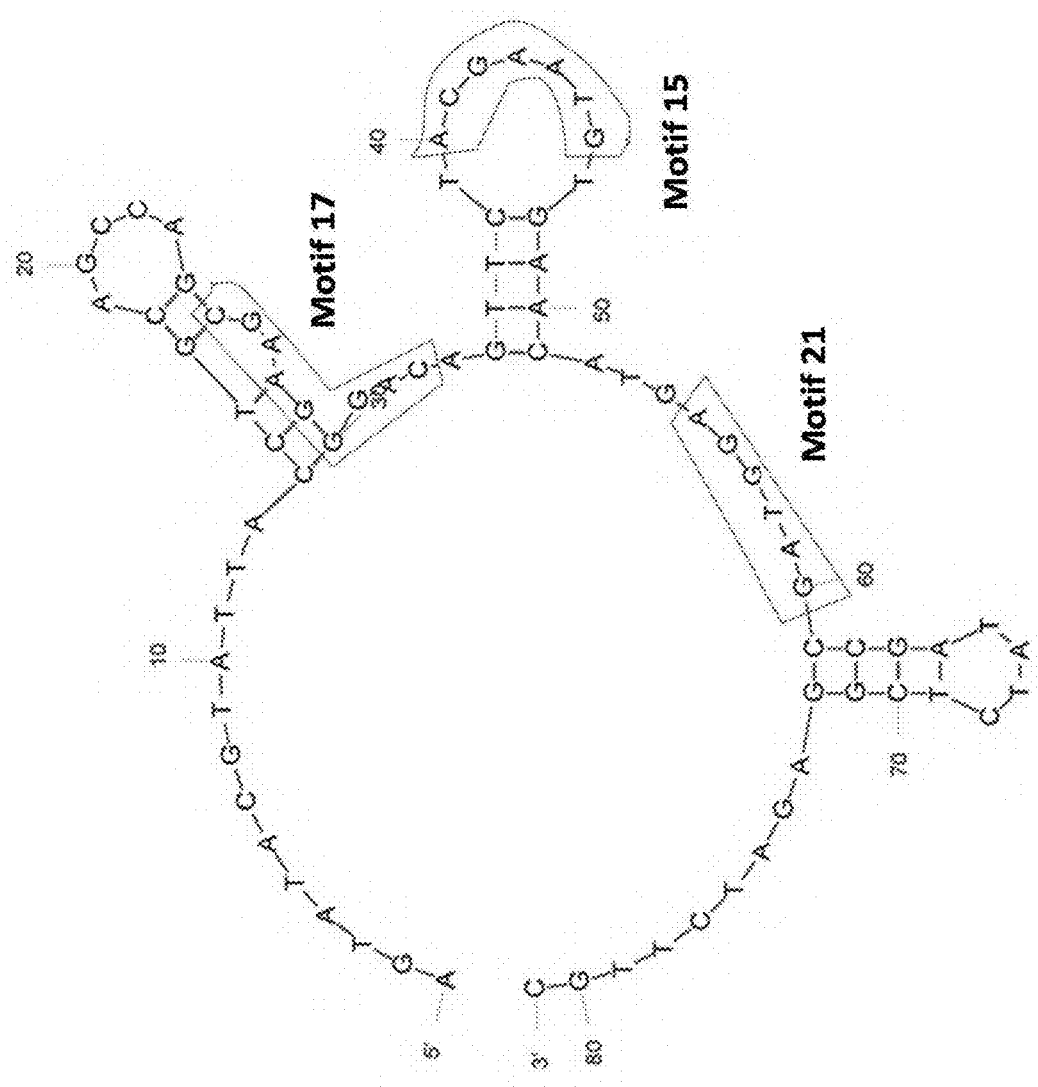
FIG. 24 shows the predicted structural folding of aptamer Ap2-GI (SEQ ID NO: 177).
Figure 25:
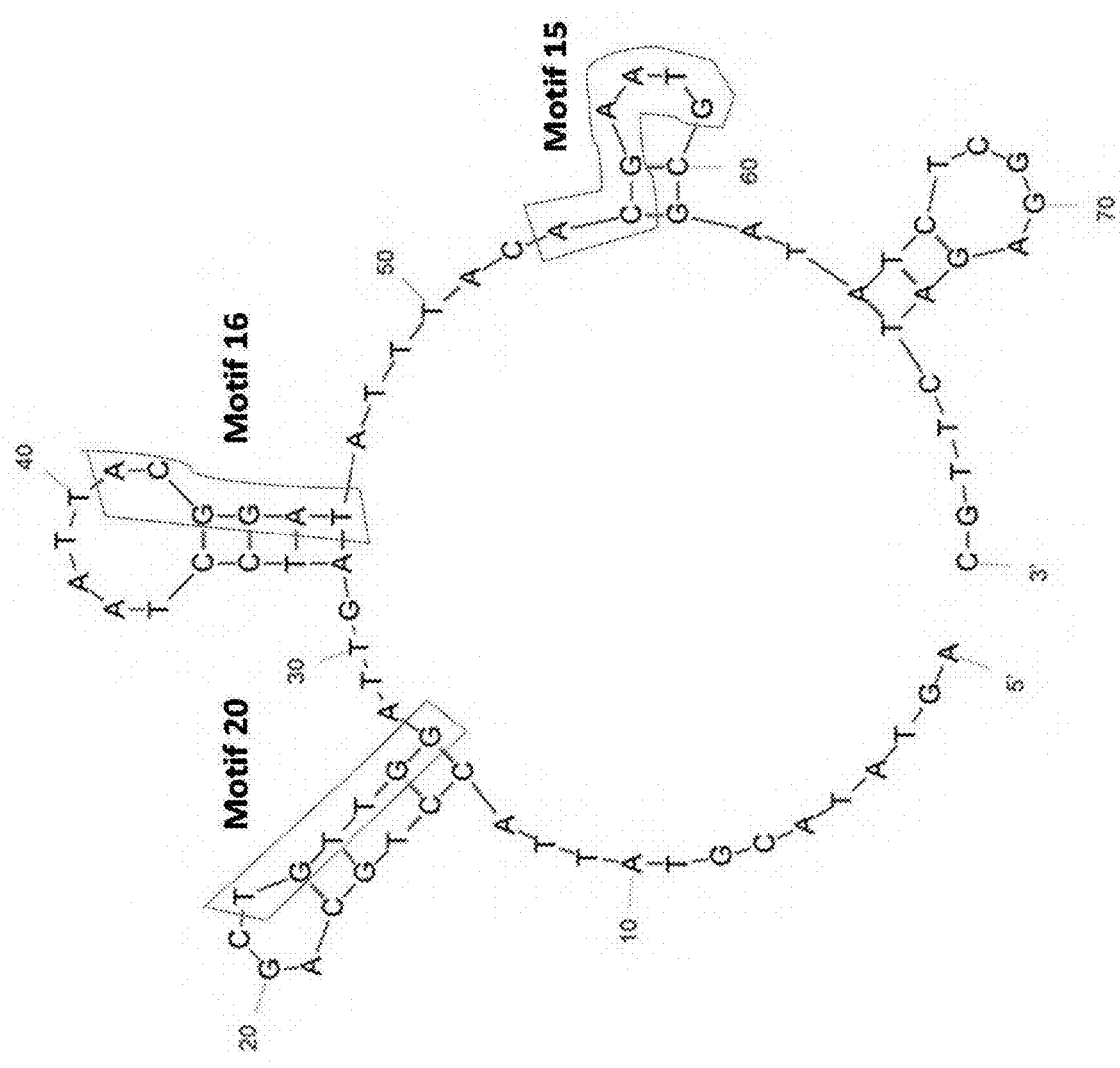
FIG. 25 shows the predicted structural folding of aptamer Ap3-GI (SEQ ID NO: 178).
Figure 26:
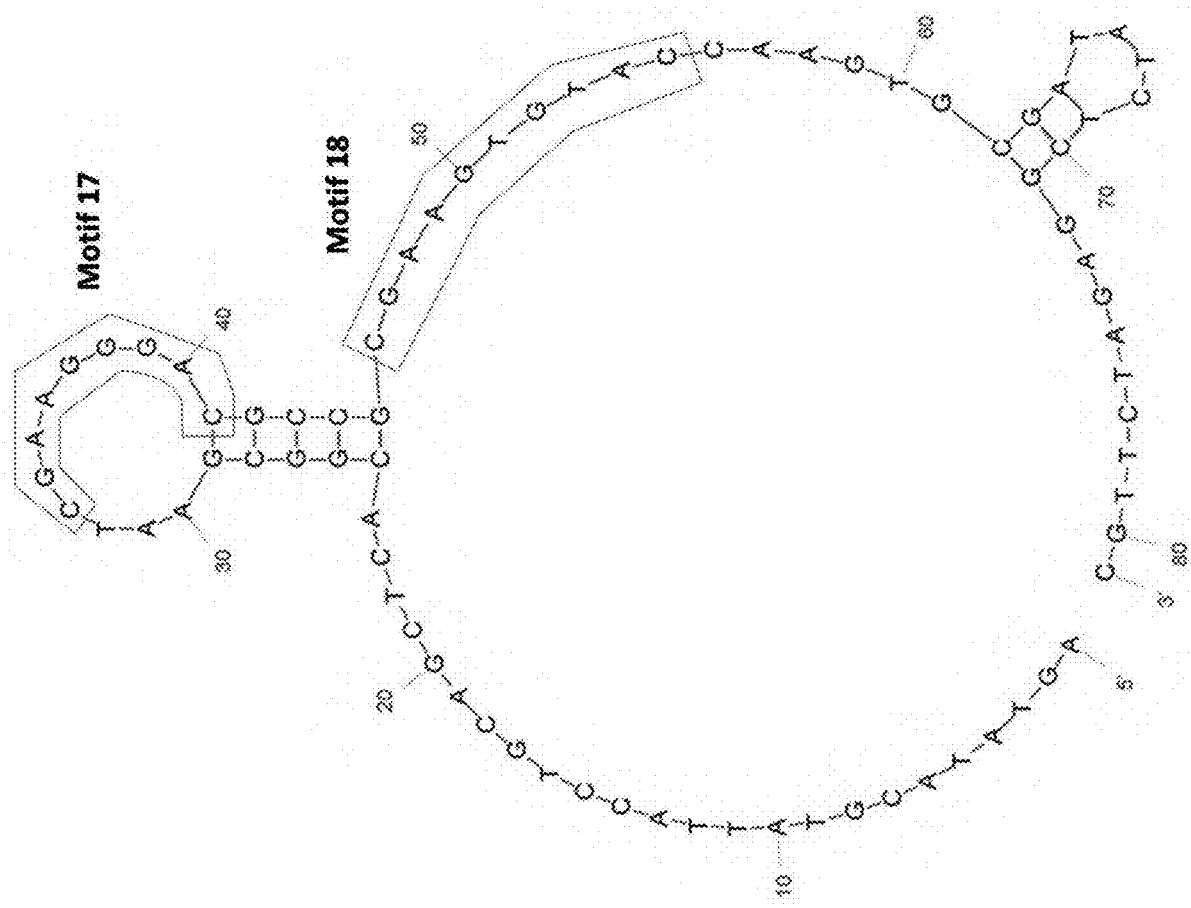
FIG. 26 shows the predicted structural folding of aptamer Ap4-GI (SEQ ID NO: 179).
Figure 27:
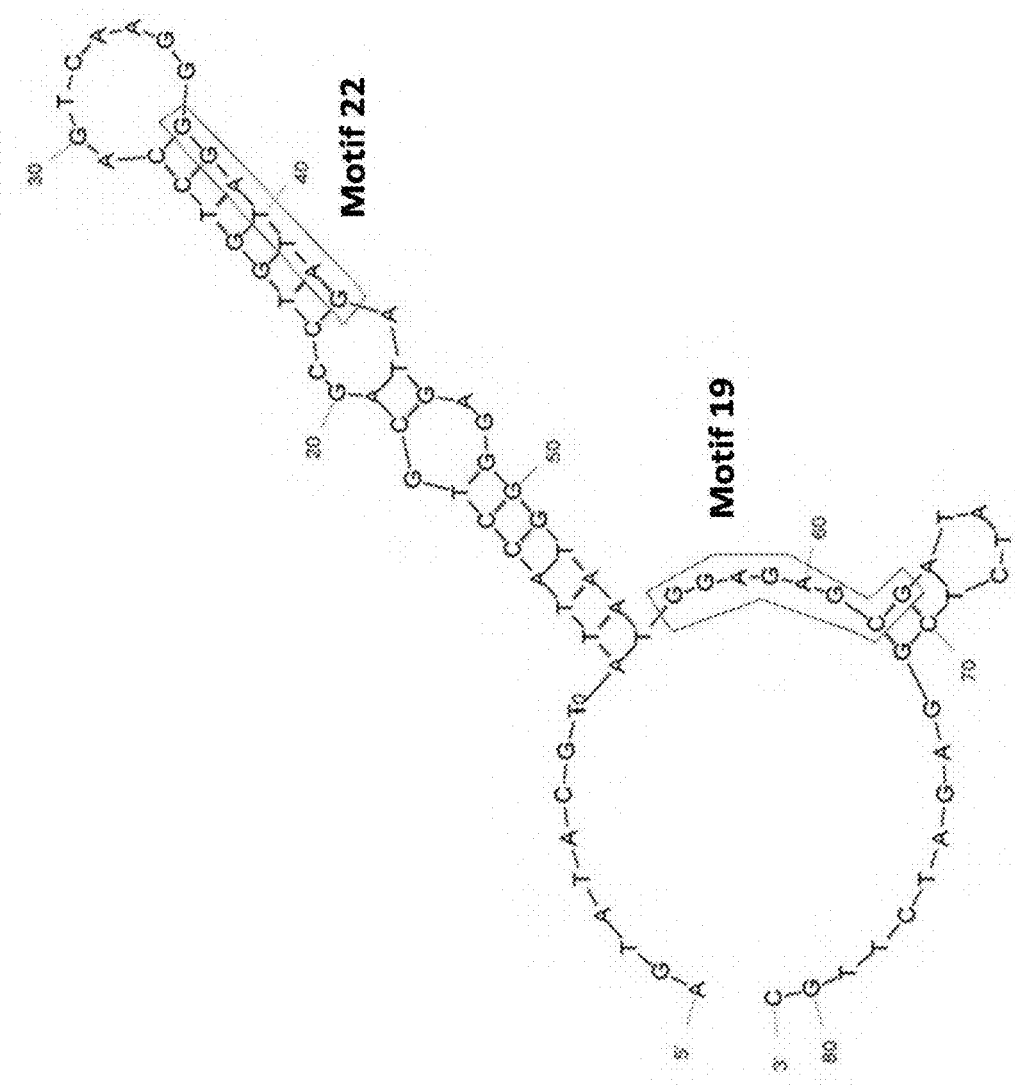
FIG. 27 shows the predicted structural folding of aptamer Ap5-GI (SEQ ID NO: 180).
Figure 28:
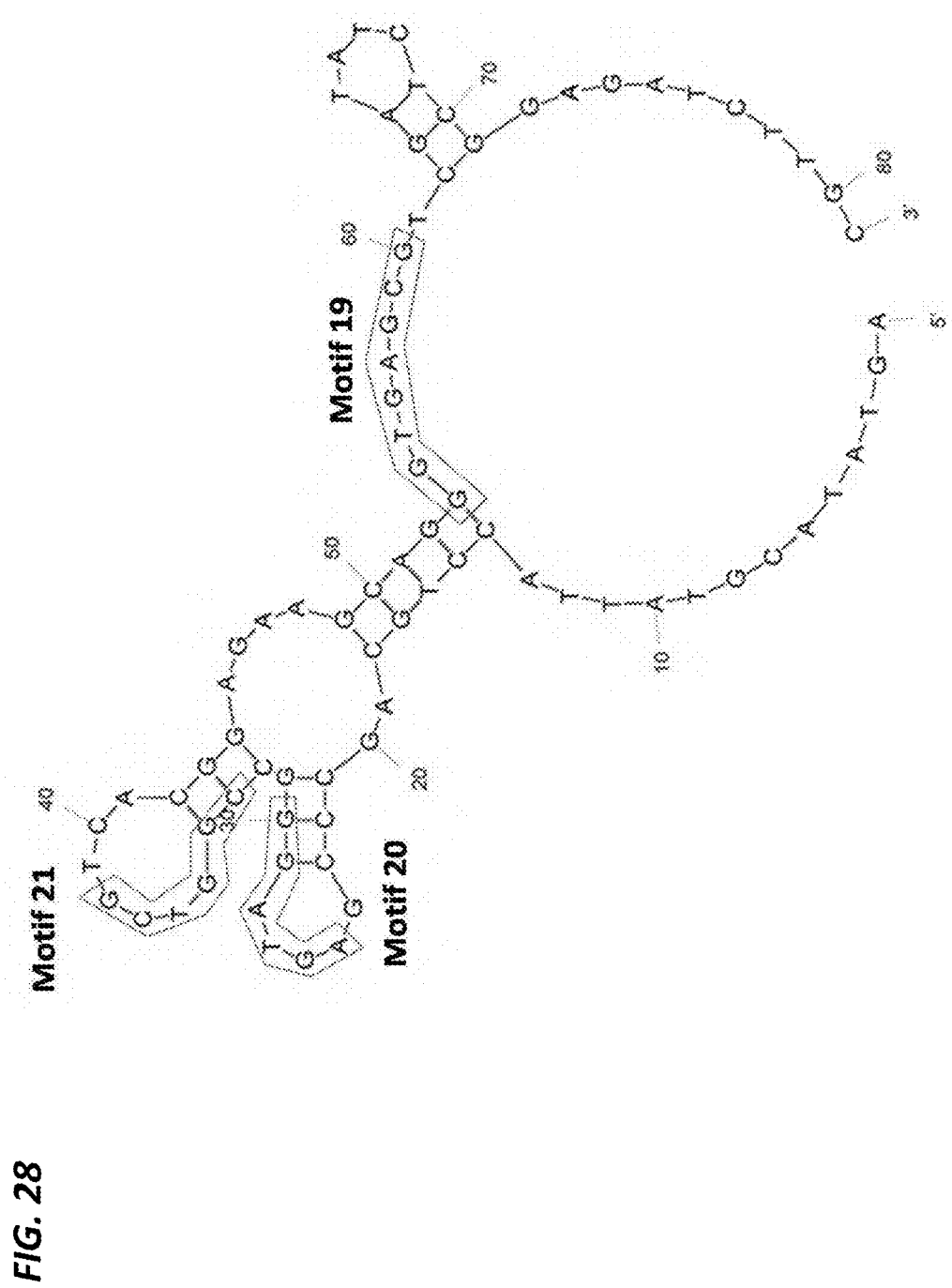
FIG. 28 shows the predicted structural folding of aptamer Ap6-GI (SEQ ID NO: 181).

To further investigate aptamer binding with SMV VLPs over more intermediate treatment intensities, temperatures of 70° C. and 72° C. were used with differing exposure times (0-52.5 min). Samples were then tested using ELASA and in some instances, TEM (e.g., 72° C. treatment). At 70° C., ELASA signal loss began within 7.5-15 min of heating, with complete signal loss (>90%) observed after 52.5 minutes (FIG. 20B). At 72° C., initial signal loss was observed after 2.5 min of heating, and a majority of signal (>85%) was lost after over 17.5 min (FIG. 20A). EM data resembled that described above (data not shown).

Comparison of Aptamer and HBGA Binding to Houston Virus (HOV) VLPs

In the next set of experiments, aptamer and HBGA binding were compared as applied to heat-treated HOV VLPs. HOV VLPs were chosen for this work as they have been reported to bind well with both type A HBGA and aptamer M6-2 in direct plate assay formats (see Manuel et al., Appl. Environ. Micro. In Press; Moore et al., J. Biotech. Accepted Manuscript). Initially, VLPs were exposed to temperatures ranging from 60-80° C. for one min followed by ELASA or HBGA-binding assay. Parallel EM was done for each sample. Decreases in ELASA signal occurred between 65 and 75° C., with HBGA and aptamer curves similar although not identical (FIG. 17). EM revealed slight morphological changes for treatment at 75° C., and VLP integrity was completely lost after exposure to 80° C. for 1 min.

When HOV VLPs were exposed to various time-temperature combinations (63° C. and 65° C. for up to 30 min), both aptamer and HBGA binding signals were quite similar (FIGS. 18A and 18B). In most cases, there were no statistically significant differences (p>0.05) in signals at any one time-temperature combination. For 63° C. over the range of 0-15 min, rates of degradation of VLPs measured by binding assay using either ligand were not statistically significantly different (Table 14). Notable morphological changes in the form of disfigured capsids were observed in increasing proportion as treatment time was lengthened, although intact capsids could still be observed after most of the HBGA or aptamer signal was lost.

TABLE 14

Degradation Rates of Different Human NoV VLPs as Measured by Three Different Ligands

| VLP | Ligand | Temperature (° C.) | Treatment Times Used (min) | Degradation Rate (-% Signal/min) | $R^2$ |
|---|---|---|---|---|---|
| SDV | Aptamer M6-2 | 65 | 0-75 | 1.20 ± 0.03 | 0.90 ± 0.04 |
| SDV | HBGA Type A | 65 | 0-75 | 1.23 ± 0.02 | 0.97 ± 0.01 |
| SDV | Antibody NS14 | 65 | 0-75 | 0.76 ± 0.09 | 0.87 ± 0.07 |
| SDV | Aptamer M6-2 | 68 | 0-17.5 | 5.55 ± 0.13 | 0.92 ± 0.01 |
| SDV | HBGA Type A | 68 | 0-17.5 | 5.68 ± 0.10 | 0.96 ± 0.01 |
| SDV | Antibody NS14 | 68 | 0-17.5 | 3.24 ± 0.24 | 0.85 ± 0.04 |
| HOV | Aptamer M6-2 | 63 | 0-15 | 5.96 ± 0.32 | 0.97 ± 0.01 |
| HOV | HBGA Type A | 63 | 0-15 | 5.87 ± 0.13 | 0.97 ± 0.02 |
| HOV | Aptamer M6-2 | 65 | 0-6 | 16.20 ± 1.00 | 0.98 ± 0.02 |
| HOV | HBGA Type A | 65 | 0-6 | 16.51 ± 2.97 | 0.96 ± 0.01 |

Comparison of Aptamer, HBGA, and Antibody Binding for GIL4 Sydney VLPs

Aptamer, HBGA, and antibody binding were compared for GII.4 Sydney (SDV) VLPs exposed to 65° C. for up to 100 min, and 68° C. for up to 25 min. A broadly reactive GII antibody, NS14 was used in these studies (see Kitamoto et al., J. Clin. Micro. (2002)). Gradual signal reduction with increasing exposure time to heat was observed for all binding assays, and complete loss of signal (>90%) occurred at the maximum exposure time. However, signal reduction, when assessed by HBGA binding assay occurred earlier (beginning almost immediately after initial exposure to heat), followed by that for aptamer and then antibody (FIGS. 21A and 21B). The rates of ELASA signal loss generally mimicked that of the HBGA binding assay, whereas the data for the antibody binding assay were different. This is supported by the difference in the apparent rates observed over the 0-75 min range at 65° C., as aptamer and HBGA signal degradation rates were not significantly different, but the NS14 antibody signal degradation rate was significantly different from both HBGA and aptamer M6-2 (p<0.05) (FIG. 21B). A similar result was observed for the 68° C. treatment (Table 14).

Degree of Sequence—Versus Conformation-Dependent Binding of Ligands

To evaluate the ability of each ligand to bind to completely destroyed capsid, GII.4 Sydney VLPs were completely inactivated by treatment at 80° C. for 5 min and assayed using HBGA, antibody, and aptamer binding assays. Results were expressed as the ratio (%) of ligand binding signal of the heated VLPs to the untreated control VLPs. Aptamer M6-2 (1.98±1.27%) and HBGA (0.50±1.15%) bound very poorly to completely denatured GII.4 Sydney VLP (<3% of positive control signal), but antibody NS14 displayed a much higher degree of binding (26.35±3.85% or positive control signal) (FIG. 22).

Discussion

In this study, the ability of ssDNA aptamers to bind various HuNoV VLPs, which were partially or completely inactivated by heat, was assessed. The performance of the aptamers was directly compared to that of type A HBGA and a HuNoV antibody, as these are common ligands used for virus binding and to aid in discrimination of virus infectivity status by preceding RT-qPCR with a specific virus capture step. In this way, ligand binding can serve as a proxy for HuNoV capsid integrity. Representative VLPs were treated at time-temperature combinations that produced varying degrees of capsid disruption and/or destruction. When comparing two aptamers to one another, both performed equivalently for heat-treated SMV VLPs, suggesting that they can be used interchangeably. The similar performance of the two aptamers may be a function of similarities in aptamer size, structure, binding affinity, and/or virus-ligand binding site, among other possible factors.

In the second phase of work, the binding of heat-treated GII.4 Houston (HOV) VLPs to aptamer and type A HBGA were compared. Capsid degradation profiles for HOV exposed to heat were very similar when comparing aptamer M6-2 and HBGA binding results, suggesting that aptamer M6-2 might be an alternative to HBGA for use in studies in which consideration of capsid integrity is necessary.

When aptamer, HBGA, and antibody binding were compared for heat-treated GII.4 Sydney VLPs, a relationship between treatment time-temperature and ligand biding was observed for all three ligands. The rates of aptamer signal loss as a function of time-temperature generally mimicked those of HBGA, whereas the rate of signal loss for the antibody-based assay was significantly different. This would imply that both aptamer M6-2 and HBGA binding to GII.4 Sydney VLPs strongly depends on higher order protein conformation.

Indeed, a high degree of conformational dependence has been demonstrated using heat denatured Norwalk Virus VLPs and synthetic HBGA (see Harrington et al., J. Virol. 76(23):12335-12343 (2002)) and has been observed for other treatments (see Manuel et al., Appl. Environ. Micro. In Press), as HBGAs and receptor binding have been found to approximate capsid functionality and infectivity for heat-treated virus (see Dancho et al., Intl. J. Food Micro. 155(3): 222-226 (2012); Hirneisen & Kniel, J. Virol. Meth. (2012)). Additionally, similar observations of aptamer dependence on nondenatured target protein have been observed (see Takemura et al., Exp. Bio. Med. 231(2): 204-214 (2006)). Others have found that the nature of aptamer binding interactions with targets can be notably different than interactions with protein ligands like antibodies (see Hermann & Patel, Sci. 287:820-825 (2000)). Collectively, this literature is consistent with our finding that that the aptamer and HBGA bound very poorly to completely denatured GII.4 Sydney VLP, but antibody NS14 displayed a much higher degree of binding to the denatured VLPs.

Comparatively speaking, different VLPs showed different thermal inactivation profiles. Overall, SMV VLPs were most heat resistant, followed by GII.4 Sydney VLPs and then HOV VLPs. The fact that two different GII.4 VLPs (NOV and Sydney) have different thermal inactivation profiles is interesting as both represent epidemic strains, albeit having emerged at different times. Strain-specific differences in capsid structure likely mediate this observation. These results have practical significance as thermal inactivation data collected for one human NoV strain may not necessarily reflect the behavior of another.

TEM images of capsid integrity roughly correlated with loss of HBGA binding at broader treatments (such as the different temperature treatments), but capsids appeared to retain structure after loss of capsid integrity when observed at more gradual heat treatments (such as set temperatures for different times). This is consistent with the observations of other studies (see Lou et al., Appl. Environ. Micro. 78(15): 5320-5327 (2012); Manuel et al. Appl. Environ. Micro. In Press) and is somewhat expected given the highly conformation-dependent nature of HBGA binding discussed above. This phenomenon has implications for proper quantification of infectious human NoV particles in detection, as RNase pre-treatment of samples prior to RT-qPCR are not likely to account for particles that remain intact but have lost HBGA binding functionality. Shortcomings in the ability to properly predict infectious human NoV particles have been discussed elsewhere (see Moore et al., Annual Rev. Food Sci. & Tech. 6(1):411-433 (2015); Knight et al., Crit. Rev. Micro. 39(3):295-309 (2013)).

Although the plate-based assays allow for direct comparison of capsid integrity estimation, absolute quantification (i.e., $\log_{10}$ reductions) is not possible due to assay design, relatively high assay detection limits, and variations in VLP solution purity. However, the plate-based methods do allow for relative quantification, and results were supported by TEM, providing additional support to the validity of the comparisons made in this study.

This study demonstrated that loss of aptamer binding correlates with loss of HBGA binding (and to some extent, loss of antibody binding) to HuNoV capsids subjected to sublethal or lethal damage by heat. HBGAs and antibodies are frequently used to capture intact HuNoV prior to detection using RT-qPCR. It is believed that a ligand binding step excludes non-binding (and hence, non-infectious) virus particles, and subsequent RT-qPCR is more discriminatory for infectious virus. In short, ligand binding is used as proxy for estimating capsid integrity/functionality. The results presented here show suggest that some virus particles remained intact after non-lethal heat treatment, but capsid regions with which the aptamer-virus interaction occurred may have been altered. Hence, capsid integrity/functionality could have been impacted. Such a phenomenon would likely impact virus infectivity, in which case aptamer binding could be a promising means by which to assesss HuNoV infectivity prior to detection using molecular amplification. However, in the absence of a HuNoV cultivation method, this cannot yet be definitively proven. A study similar to this one using a cultivable surrogate to which an aptamer has been produced, would be a logical next step.

HuNoV Nonstructural Polyprotein

In addition to the requirement of capsid integrity and functionality, the correct expression and presence of the HuNoV nonstructural polyprotein (encoded in ORF1) is required for HuNoV to be infectious. ORF1 is first translated as a polyprotein that cleaves into six different nonstructural proteins. One of these proteins, the VPg, is covalently bound to the 5' end of HuNoV genomic and subgenomic RNA, and it is suspected to be involved in translation of viral RNA (Daughenbaugh et al., Virol. J. 3:33 (2006); Goodfellow et al., EMBO Rep. 6:968-972 (2005)), as well as potentially serving a role in initiating transcription (Belliot et al., Virol. 374:33-49 (2008); Machin et al., J. Biol. Chem. 276:27787-27792 (2001)). It has been demonstrated that the VPg is required for cultivable surrogates of HuNoV to be infectious (Guix et al., J. Virol. 81:12238-12248 (2007)). Additionally, HuNoV VPg is under less selective pressure than the viral capsid, which may make it a more suitable target for the creation of a broadly reactive ligand.

Because the VPg is required for replication of the virus, it is expected that it must also be functional (in addition to the capsid) for infectious viruses. Therefore, the previously discussed capsid integrity and binding functionality methods and RNase treatment methods could be combined with an aptamer-based capture step targeting the intact VPg in an effort to discriminate between infectious and non-infectious virus. This might be called an "integrated" method to discriminate virus infectivity status. Because of the aforementioned advantages of modification for aptamers, this approach can be amenable to a microfluidic device.

Aptamers targeting both HuNoV GI.1 Norwalk Virus (NV) and Tulane Virus (TV) VPgs were created using the same process used for the GII.4 P protein. This approach was taken so that the behavior of aptamers targeting HuNoV VPg could be compared directly to those targeting the VPg of a cultivable surrogate virus (TV), the latter of which would be necessary to make direct correlations between the proposed VPg-based assay and virus infectivity. Additionally, the fact that TV also binds HBGAs means that it would be possible to combine ligand-based virus capture (using HBGAs) with aptamer-mediated VPg capture in an effort to produce a truly "integrated" approach to discriminating virus infectivity status.

For the cloning and expression of VPgs, Norwalk Virus (GI.1; NV) clinical stool specimens were used. Tulane Virus (TV), a novel surrogate of norovirus, was cultured as previously reported and a lysate containing viral capsid was obtained. The fact that aptamers were created against HuNoV and a cultivable surrogate mean that infectivity assays can be validated and developed.

Genomic RNA from both viruses was extracted using a viral extraction kit (Qiagen), reverse transcribed using the Ambion RETROScript kit with 5 μM of primers designed to the VPg region of the cDNA, and product cleaned with Qiagen Qiaquick kit. Primers for NV were taken from previously performed work (Daughenbaugh et al., *EMBO J.* 22:2852-2859 (2003)) and are listed in Table 15 below. TV primers were designed using the genome and cleavage sites estimated by Farkas et al., *J. Virol.* 82:5408-5416 (2008) and are also listed in Table 15 below. The VPg sequences were amplified by PCR, product cleaned using Qiagen Qiaquick kit, and digested with EcoRI and XhoI restriction enzymes. Sequences were ligated into digested pGEX 4T-1 plasmid vector using the Epicentre Fast-Link kit at a 2:1 insert:vector ratio then electroporated into *E. coli* BL21 cells (Lucigen E. CLONI electrocompetent cells). Successful transformants were confirmed by sequencing (Genewiz Inc.). VPg was overexpressed by diluting an incubation of overnight cells 1:10 into fresh 2×YT-ampicillin broth and incubated at 37° C. with shaking until $OD_{600}$=0.6-0.9, after which IPTG was added to a final concentration of 1 mM. Samples were left to incubate overnight with shaking at 25° C. The cells were then pelleted, and lysate was made using a bead beater with acid-washed beads (Sigma). Lysate was divided into one-time use aliquots and stored at −80° C. for use in the same SELEX process as described for the P Protein. Eight rounds of SELEX and two rounds of counter-SELEX (against SELEX equipment and negative stool) were performed prior to sequencing for both NV and TV VPgs. Sequences obtained are in Tables 16 and 17.

TABLE 15

Oligonucleotides Used for VPg Cloning

| Name | Sequence (5'-3')* | SEQ ID NO |
|---|---|---|
| Norwalk VPg Forward | CCGGAATTCGGAAAGAACAAAGGCAAGACC | 158 |
| Norwalk VPg Reverse | CCGCTCGAGTTCAAAATTGATCTTTTCATTATAAT | 159 |
| Tulane VPg Forward | CCGGAATTCGCCAAGGGCAAGACAAAAAGG | 160 |
| Tulane VPg Reverse | CCGCTCGAGCTACTCGTCGTAATAATCATCACTGGG | 161 |

TABLE 16

Representative Norwalk Virus (GI.1) VPg Aptamer Candidates

| Round of SELEX | Random Region Sequence* | SEQ ID NO | # Repeats | Aptamer Identifier |
|---|---|---|---|---|
| 8 | CAGAGTTGATGTAAGCTTCGTGTTAGCTCAACTCTTATCG | 66 | 10/19 | N6 |
| 8 | AGGGATGTGTTGGATGCATGCCAGGCTTGGTAACATTGTA | 67 | 1/19 | N3 |
| 8 | TCTTCGGTTTAATAAAGTTGGCTAGGAAAGTTTAAAACCG | 68 | 3/19 | N1 |
| 8 | AGTGGGTGGTGATGAATTCTGGTCGCGCTGACAACCCGCG | 69 | 1/19 | N14 |
| 8 | CGGGTCTCGTCTATGCAGTACTCAAAACGCTT-GAGGTACCGA | 70 | 1/19 | N1-2 |
| 8 | AAGGCTTTTTTAAAGGCTAGGCTTGATAATCGGTTAACTC | 71 | 1/19 | N4-2 |
| 8 | TGTCGATAAAGTGAGTTAAGTCACCGGCCCGGCCTATTCG | 72 | 1/19 | N11-2 |
| 8 | TCACACTCGTTTCTATTACTAAAACATCGTTCCTTTCAGC | 73 | 1/19 | N12-2 |

*Bolded sequence also occurs in Tulane virus VPg aptamer pool

TABLE 17

Representative Tulane Virus VPg Aptamer Candidates

| Round of SELEX | Random Region Sequence | SEQ ID NO | # Repeats | Aptamer Identifier |
|---|---|---|---|---|
| 8 | TCACACTCGTTTCTATTACTAAAACATCGTTCCTTTCAGC | 74 | 13/17 | T5 |
| 8 | TGGAAGGCGGGAAGATTTTTGGTCGACCTGACAACCCGGT | 75 | 1/17 | T9 |

TABLE 17-continued

Representative Tulane Virus VPg Aptamer Candidates

| Round of SELEX | Random Region Sequence | SEQ ID NO | # Repeats | Aptamer Identifier |
|---|---|---|---|---|
| 8 | TAGTAACGATTACCAAAATTCTCCCGAGGCTGACAACCCG | 76 | 1/17 | T1-2 |
| 8 | TCGAGGTATGGCCTTGTCTAGGCGCACCTGACAACCCGGTG | 77 | 1/17 | T9-2 |
| 8 | TGTCGTTAATTATTCGTGATCTGACAACCCGATCACTCTC | 78 | 1/17 | T10-2 |

*Bolded sequence also occurs in Norwalk virus VPg aptamer pool.

The VPg aptamers could be used to design a more stringent "integrated" in vitro process for discriminating infectious from non-infectious virus, especially if combined with an intact capsid recognition step (such as capture with an antibody or HBGA). The combination of these two steps would allow the simultaneous confirmation of capsid and genome integrity. Since some disinfection methods degrade the capsid, and others degrade the genome, this approach could also be used to investigate the mechanism of action of existing and new chemical or physical disinfectants or sanitizers. For example, no one has studied the heat stability of VPg; theoretically the capsid, which is composed of quite stable dimers, may be more heat tolerant than the VPg (which must first be cleaved, and has unstructured regions flanking a core of alpha helices as seen in FCV and MNV proteins using NMR).

In addition, the VPg aptamers could be a potentially more sensitive clinical detection platform because a copy of the VPg is covalently linked to genomic and subgenomic RNA. Hence, there are more VPgs in each virus-infected cell than there are accessible binding sites for a ligand on a capsid. Moreover, because the VPg is under less selection pressure than the capsid, the more conserved nature of it is likely to make aptamers against it more cross-reactive and thus effective against a wider range of HuNoV strains in clinical detection. Additionally, these aptamers could be relevant in studying virus-infected cells as a cheaper alternative to VPg antibodies (which do not exist commercially currently) for certain applications.

Similarly, the aptamers could be used as the recognition element in a biosensor that may be more sensitive than any other recognition elements. Due to the ease with which they can be chemically modified, their high stability, and lower cost, such aptamers are more attractive as candidates for ligands in biosensors, especially for point-of-care and in-field testing applications.

What is claimed is:

1. A method of detecting the presence of at least one norovirus strain in a test sample, the method comprising:
   (a) contacting said test sample with a norovirus-binding aptamer comprising:
      (i) a norovirus-binding motif wherein said norovirus-binding motif comprises one or more of SEQ ID NOS: 113, 114, 116-118, 120, or 101-106; and/or
      (ii) the nucleic acid sequence of SEQ ID NO: 27, 30, 31, 35, or 39, or variants thereof having at least 90% sequence identity and having norovirus-binding activity; and
   (b) detecting the presence of said norovirus-binding aptamer bound to norovirus in said test sample, wherein detection of bound aptamer indicates the presence of at least one norovirus strain.

2. The method of claim 1, further comprising removing unbound norovirus-binding aptamer prior to detecting the presence of said norovirus-binding aptamer bound to norovirus in said test sample.

3. The method of claim 1, further comprising comparing the presence of said norovirus-binding aptamer bound to norovirus in said test sample with the presence of said norovirus-binding aptamer bound to norovirus in a control sample, whereby increased presence of said norovirus-binding aptamer bound to norovirus in said test sample relative to said control sample indicates the presence of at least one norovirus strain in said test sample.

4. The method of claim 1, wherein said test sample is a clinical sample.

5. The method of claim 1, wherein said test sample is an environmental sample or a food sample.

6. The method of claim 1, wherein the detecting step comprises amplifying the bound aptamer.

7. The method of claim 1, further comprising capturing said at least one norovirus strain from said test sample by substantially separating the aptamer-bound norovirus from the remainder of said test sample.

8. The method of claim 1, wherein said norovirus-binding aptamer preferentially binds to norovirus strains from genogroup I; genogroup I, genotype 1; genogroup II; genogroup II, genotype 2; and/or genogroup II, genotype 4.

9. The method of claim 1, wherein said norovirus-binding aptamer preferentially binds to an epitope within the VPg protein, the VP1 protein, the P domain of the VP1 protein, the PI subdomain of the VP1 protein, the P2 subdomain of the VP1 protein, the S domain of the VP1 protein, and/or the VP2 protein of said at least one norovirus strain.

10. The method of claim 1, wherein said norovirus-binding aptamer is a single-stranded DNA aptamer.

11. The method of claim 1, wherein said norovirus binding aptamer comprises the nucleic acid sequence of SMV-21 (SEQ ID NO: 27), SMV-25 (SEQ ID NO: 30), SMV-26 (SEQ ID NO: 31), M1 (SEQ ID NO: 35), or M6-2 (SEQ ID NO: 39).

12. The method of claim 1, wherein said norovirus-binding motif comprises two or more of SEQ ID NOS: 113, 114, 116-118, 120, or 101-106.

13. The method of claim 1, wherein said norovirus-binding aptamer is tethered to a solid support or immobilized on a magnetic bead.

14. The method of claim 1, wherein said norovirus-binding aptamer further comprises a label.

15. The method of claim 1, wherein said norovirus-binding aptamer comprises an aptamer mixture comprising a first aptamer and at least one different aptamer.

* * * * *

SEQUENCE LISTING

```
<160> NUMBER OF SEQ ID NOS: 199

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
tgttggattt tacgaaaaac gtgcttactt catagcggcc                              40

<210> SEQ ID NO 2
<211> LENGTH: 40
<212> TYPE: DNA
<213> ORGANISM: Artificial Sequence
<220> FEATURE:
<223> OTHER INFORMATION: Synthetic

<400> SEQUENCE: 2
ggttgggtaa gggggtctgg tcaggtaggg cggggggggg                              40

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3
tcgtaaaccc cttatccgtg aaccttcagc ggtagacgct                              40
```

<210> SEQ ID NO 4
<211> LENGTH: 40
<212> TYPE: DNA
<213> ORGANISM: Artificial Sequence
<220> FEATURE:
<223> OTHER INFORMATION: Synthetic

<400> SEQUENCE: 4
ctccctccag cctgcctatt ttgcttggtt acgcatctgt                              40

<210> SEQ ID NO 5
<211> LENGTH: 40
<212> TYPE: DNA
<213> ORGANISM: Artificial Sequence
<220> FEATURE:
<223> OTHER INFORMATION: Synthetic

<400> SEQUENCE: 5
ccagcgaagg aaagtcttgg ttggtctagt ttttcgtgtg                              40

<210> SEQ ID NO 6
<211> LENGTH: 40
<212> TYPE: DNA
<213> ORGANISM: Artificial Sequence
<220> FEATURE:
<223> OTHER INFORMATION: Synthetic

<400> SEQUENCE: 6
ctacgtgtgc gttccgattg tttaaattgc tcaatgtatg                              40

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
cacaccacct gaattccagc acactggcgg ccgttactag                              40

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
cactcgacct tcagggcggc ttctcagcgt gtagtggtga                              40

<210> SEQ ID NO 9
<211> LENGTH: 40
<212> TYPE: DNA
<213> ORGANISM: Artificial Sequence
<220> FEATURE:
<223> OTHER INFORMATION: Synthetic

<400> SEQUENCE: 9
ctcgactgat agacctagcg tcaatcctca ttgttcgctg                              40

<210> SEQ ID NO 10
<211> LENGTH: 40
<212> TYPE: DNA
<213> ORGANISM: Artificial Sequence
<220> FEATURE:
<223> OTHER INFORMATION: Synthetic

<400> SEQUENCE: 10
ccagtattag agtcctactt tacaccgctc ttggcatcgt                              40

<210> SEQ ID NO 11
<211> LENGTH: 40
<212> TYPE: DNA
<213> ORGANISM: Artificial Sequence
<220> FEATURE:
<223> OTHER INFORMATION: Synthetic

<400> SEQUENCE: 11
cacatgataa ggtcgcgtga ctgtgagtta gttgttacac                              40

<210> SEQ ID NO 12
<211> LENGTH: 40
<212> TYPE: DNA
<213> ORGANISM: Artificial Sequence
<220> FEATURE:
<223> OTHER INFORMATION: Synthetic

<400> SEQUENCE: 12
tcggcatagg tcaagtcgct tcatttggat taagttgagg                              40

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
cacataccaa agtattggtc gctaactttc gcccaattga                              40

<210> SEQ ID NO 14
<211> LENGTH: 40
<212> TYPE: DNA
<213> ORGANISM: Artificial Sequence
<220> FEATURE:
<223> OTHER INFORMATION: Synthetic

<400> SEQUENCE: 14
ctacgaggtg gttataagag aacttatccg tgttggttgc                              40

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
tggtagtggg atatagtttt tccaagcgta cccagttctg                              40

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
ctatcagcca tgaattgcat tacctttgtt ctcccttgc                               40

<210> SEQ ID NO 17

```
<211> LENGTH: 40
<212> TYPE: DNA
<213> ORGANISM: Artificial Sequence
<220> FEATURE:
<223> OTHER INFORMATION: Synthetic

<400> SEQUENCE: 17
cccctcggaa gatagatttt gcgagagtct tgggttgagg                              40

<210> SEQ ID NO 18
<211> LENGTH: 40
<212> TYPE: DNA
<213> ORGANISM: Artificial Sequence
<220> FEATURE:
<223> OTHER INFORMATION: Synthetic

<400> SEQUENCE: 18
ccagatagca gcacctaatc ttatcccttt tattttggt                               40

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19 tcgggggag gaggggaat gggaagaagg aggtcgaggg                                40

<210> SEQ ID NO 20
<211> LENGTH: 40
<212> TYPE: DNA
<213> ORGANISM: Artificial Sequence
<220> FEATURE:
<223> OTHER INFORMATION: Synthetic

<400> SEQUENCE: 20
tggattacac ggctaacttc cctggttctt ttctttgatg                              40

<210> SEQ ID NO 21
<211> LENGTH: 40
<212> TYPE: DNA
<213> ORGANISM: Artificial Sequence
<220> FEATURE:
<223> OTHER INFORMATION: Synthetic

<400> SEQUENCE: 21
tggacgttat ttgcactcgt cgaaccctat catgcctcct                              40

<210> SEQ ID NO 22
<211> LENGTH: 40
<212> TYPE: DNA
<213> ORGANISM: Artificial Sequence
<220> FEATURE:
<223> OTHER INFORMATION: Synthetic

<400> SEQUENCE: 22
cctcatgcac aaaggcttat tacggtctaa ttctttataa                              40

<210> SEQ ID NO 23
<211> LENGTH: 40
<212> TYPE: DNA
<213> ORGANISM: Artificial Sequence
<220> FEATURE:
<223> OTHER INFORMATION: Synthetic

<400> SEQUENCE: 23
```
tcgacattat gtttgacatc gattgttaat gtttctttgc                                    40

<210> SEQ ID NO 24
<211> LENGTH: 40
<212> TYPE: DNA
<213> ORGANISM: Artificial Sequence
<220> FEATURE:
<223> OTHER INFORMATION: Synthetic

<400> SEQUENCE: 24
cccctacaca gtaaaattct ttaacaccta gatcttcgac                                    40

<210> SEQ ID NO 25
<211> LENGTH: 40
<212> TYPE: DNA
<213> ORGANISM: Artificial Sequence
<220> FEATURE:
<223> OTHER INFORMATION: Synthetic

<400> SEQUENCE: 25
caccagtgtg ttgaggtttg agcacactga tagagtgtca                                    40

<210> SEQ ID NO 26
<211> LENGTH: 40
<212> TYPE: DNA
<213> ORGANISM: Artificial Sequence
<220> FEATURE:
<223> OTHER INFORMATION: Synthetic

<400> SEQUENCE: 26
tgagcctccg ttttagtgat cagaagggat gtgtggcgta                                    40

<210> SEQ ID NO 27
<211> LENGTH: 40
<212> TYPE: DNA
<213> ORGANISM: Artificial Sequence
<220> FEATURE:
<223> OTHER INFORMATION: Synthetic

<400> SEQUENCE: 27
ccatgttttg taggtgtaat aggtcatgtt agggtttctg                                    40

<210> SEQ ID NO 28
<211> LENGTH: 40
<212> TYPE: DNA
<213> ORGANISM: Artificial Sequence
<220> FEATURE:
<223> OTHER INFORMATION: Synthetic

<400> SEQUENCE: 28
cgagggatac atgctgacta tggaattatt tgaattccca                                    40

<210> SEQ ID NO 29
<211> LENGTH: 40
<212> TYPE: DNA
<213> ORGANISM: Artificial Sequence
<220> FEATURE:
<223> OTHER INFORMATION: Synthetic

<400> SEQUENCE: 29
ctacaggagt tcatctggga gagtgtaaag gatgaggtgg                                    40

<210> SEQ ID NO 30
<211> LENGTH: 40
<212> TYPE: DNA

```
<213> ORGANISM: Artificial Sequence
<220> FEATURE:
<223> OTHER INFORMATION: Synthetic

<400> SEQUENCE: 30
catctgtgtg aagactatat ggcgctcaca tatttctttc                                40

<210> SEQ ID NO 31
<211> LENGTH: 40
<212> TYPE: DNA
<213> ORGANISM: Artificial Sequence
<220> FEATURE:
<223> OTHER INFORMATION: Synthetic

<400> SEQUENCE: 31
tgaccgagtg tctggtcatt ttcgatgtct gttgttaggc                                40

<210> SEQ ID NO 32
<211> LENGTH: 40
<212> TYPE: DNA
<213> ORGANISM: Artificial Sequence
<220> FEATURE:
<223> OTHER INFORMATION: Synthetic

<400> SEQUENCE: 32
ccctccttat ctctgctaat ggttgatccg tgtcccgtac                                40

<210> SEQ ID NO 33
<211> LENGTH: 40
<212> TYPE: DNA
<213> ORGANISM: Artificial Sequence
<220> FEATURE:
<223> OTHER INFORMATION: Synthetic

<400> SEQUENCE: 33
ccctgttatc cttatccaac gagcttaatg taacttggac                                40

<210> SEQ ID NO 34
<211> LENGTH: 40
<212> TYPE: DNA
<213> ORGANISM: Artificial Sequence
<220> FEATURE:
<223> OTHER INFORMATION: Synthetic

<400> SEQUENCE: 34
tgggggagtg gtaggtgtgc tgtgaagggg agggttgggg                                40

<210> SEQ ID NO 35
<211> LENGTH: 40
<212> TYPE: DNA
<213> ORGANISM: Artificial Sequence
<220> FEATURE:
<223> OTHER INFORMATION: Synthetic

<400> SEQUENCE: 35
tgtttatggg gataaacgta tctaattcgt gtactaatca                                40

<210> SEQ ID NO 36
<211> LENGTH: 40
<212> TYPE: DNA
<213> ORGANISM: Artificial Sequence
<220> FEATURE:
<223> OTHER INFORMATION: Synthetic

<400> SEQUENCE: 36
tgttaagggg aattaataat gataatccgt ctactaatca                                40
```

<210> SEQ ID NO 37
<211> LENGTH: 41
<212> TYPE: DNA
<213> ORGANISM: Artificial Sequence
<220> FEATURE:
<223> OTHER INFORMATION: Synthetic

<400> SEQUENCE: 37
tgttaggggg aattaataat ggataatccg tctactaatc a                41

<210> SEQ ID NO 38
<211> LENGTH: 48
<212> TYPE: DNA
<213> ORGANISM: Artificial Sequence
<220> FEATURE:
<223> OTHER INFORMATION: Synthetic

<400> SEQUENCE: 38
tggggggtgg tgcggtgtgt ggcaggggag catagccggg ggcccct         48

<210> SEQ ID NO 39
<211> LENGTH: 39
<212> TYPE: DNA
<213> ORGANISM: Artificial Sequence
<220> FEATURE:
<223> OTHER INFORMATION: Synthetic

<400> SEQUENCE: 39
tgggaagagg tccggtaaat gcagggtcag cccggagag                  39

<210> SEQ ID NO 40
<211> LENGTH: 48
<212> TYPE: DNA
<213> ORGANISM: Artificial Sequence
<220> FEATURE:
<223> OTHER INFORMATION: Synthetic

<400> SEQUENCE: 40
tggggggtgg tgcggtgtgt gacaagggag catagccggg ggcccct         48

<210> SEQ ID NO 41
<211> LENGTH: 47
<212> TYPE: DNA
<213> ORGANISM: Artificial Sequence
<220> FEATURE:
<223> OTHER INFORMATION: Synthetic

<400> SEQUENCE: 41
ggggtggtgc cggagtgggg tggcggtgcg gattccctgg ctatgcc         47

<210> SEQ ID NO 42
<211> LENGTH: 47
<212> TYPE: DNA
<213> ORGANISM: Artificial Sequence
<220> FEATURE:
<223> OTHER INFORMATION: Synthetic

<400> SEQUENCE: 42
tggggggtgg tgcggtgtgt gacaagggag catagccggg ggccagt         47

<210> SEQ ID NO 43
<211> LENGTH: 46
<212> TYPE: DNA
<213> ORGANISM: Artificial Sequence
<220> FEATURE:

<223> OTHER INFORMATION: Synthetic

<400> SEQUENCE: 43
ttggttggtg ctcgctgtaa ggttaacacc gtctaatcgg gaccgt					46

<210> SEQ ID NO 44
<211> LENGTH: 47
<212> TYPE: DNA
<213> ORGANISM: Artificial Sequence
<220> FEATURE:
<223> OTHER INFORMATION: Synthetic

<400> SEQUENCE: 44
ggggagctcg tgggtagagt ggggccgggg tgtggtatag tgcggcc					47

<210> SEQ ID NO 45
<211> LENGTH: 40
<212> TYPE: DNA
<213> ORGANISM: Artificial Sequence
<220> FEATURE:
<223> OTHER INFORMATION: Synthetic

<400> SEQUENCE: 45
tcgtcctagt gtgggatata gctatgaaat caactttccc					40

<210> SEQ ID NO 46
<211> LENGTH: 40
<212> TYPE: DNA
<213> ORGANISM: Artificial Sequence
<220> FEATURE:
<223> OTHER INFORMATION: Synthetic

<400> SEQUENCE: 46
tgtagggagt tgttacatcg gcactggtct gttgaattct					40

<210> SEQ ID NO 47
<211> LENGTH: 46
<212> TYPE: DNA
<213> ORGANISM: Artificial Sequence
<220> FEATURE:
<223> OTHER INFORMATION: Synthetic

<400> SEQUENCE: 47
ggggaatgtt cttgtggcct accggggagt ggcctttatg tccctt					46

<210> SEQ ID NO 48
<211> LENGTH: 48
<212> TYPE: DNA
<213> ORGANISM: Artificial Sequence
<220> FEATURE:
<223> OTHER INFORMATION: Synthetic

<400> SEQUENCE: 48
ggtggggggg tgcggcatgt ggaggcggcg ggcaggaggg ggacagtg					48

<210> SEQ ID NO 49
<211> LENGTH: 47
<212> TYPE: DNA
<213> ORGANISM: Artificial Sequence
<220> FEATURE:
<223> OTHER INFORMATION: Synthetic

<400> SEQUENCE: 49
tgggggggag gggagatggg tggcggtggt ggggcttagg gctatcc					47

<210> SEQ ID NO 50
<211> LENGTH: 47
<212> TYPE: DNA
<213> ORGANISM: Artificial Sequence
<220> FEATURE:
<223> OTHER INFORMATION: Synthetic

<400> SEQUENCE: 50
gtggacggta gtcgttgtgg ggcgcggtgc ggggggttc gggcgtg        47

<210> SEQ ID NO 51
<211> LENGTH: 47
<212> TYPE: DNA
<213> ORGANISM: Artificial Sequence
<220> FEATURE:
<223> OTHER INFORMATION: Synthetic

<400> SEQUENCE: 51
tgggaaaggg aagtgtgggc agggagggga gggggtggc tacatca        47

<210> SEQ ID NO 52
<211> LENGTH: 40
<212> TYPE: DNA
<213> ORGANISM: Artificial Sequence
<220> FEATURE:
<223> OTHER INFORMATION: Synthetic

<400> SEQUENCE: 52
tagggcaata tgttagttag gcgacttgct tagactactg        40

<210> SEQ ID NO 53
<211> LENGTH: 45
<212> TYPE: DNA
<213> ORGANISM: Artificial Sequence
<220> FEATURE:
<223> OTHER INFORMATION: Synthetic

<400> SEQUENCE: 53
tttgatggtg cggtggctta catatgcgtt ctacattgcg ttcgg        45

<210> SEQ ID NO 54
<211> LENGTH: 49
<212> TYPE: DNA
<213> ORGANISM: Artificial Sequence
<220> FEATURE:
<223> OTHER INFORMATION: Synthetic

<400> SEQUENCE: 54
taattgtgtg tcgcagcatg gtggtgccgg gccttgcatc caccttcgg        49

<210> SEQ ID NO 55
<211> LENGTH: 50
<212> TYPE: DNA
<213> ORGANISM: Artificial Sequence
<220> FEATURE:
<223> OTHER INFORMATION: Synthetic

<400> SEQUENCE: 55 tgggggggg ggctgctaaa ggtttgtgga gggttaacat gtacctcccc        50

<210> SEQ ID NO 56
<211> LENGTH: 47
<212> TYPE: DNA
<213> ORGANISM: Artificial Sequence
<220> FEATURE:
<223> OTHER INFORMATION: Synthetic

<400> SEQUENCE: 56
tgggaaaggg aagtgtgggc aggggaggga gggggggtggc tacatca                                    47

<210> SEQ ID NO 57
<211> LENGTH: 49
<212> TYPE: DNA
<213> ORGANISM: Artificial Sequence
<220> FEATURE:
<223> OTHER INFORMATION: Synthetic

<400> SEQUENCE: 57
tggatggggt gatgctgggt ggaagagggg gccggacccg ccgtccgtg                                   49

<210> SEQ ID NO 58
<211> LENGTH: 46
<212> TYPE: DNA
<213> ORGANISM: Artificial Sequence
<220> FEATURE:
<223> OTHER INFORMATION: Synthetic

<400> SEQUENCE: 58
ttggttggtg ctcgctgtaa ggttaacacc gtctaatcgg gaccgt                                       46

<210> SEQ ID NO 59
<211> LENGTH: 47
<212> TYPE: DNA
<213> ORGANISM: Artificial Sequence
<220> FEATURE:
<223> OTHER INFORMATION: Synthetic

<400> SEQUENCE: 59 tgggggggtgg tgcggtgtgt gacaagggag catagccggg ggccagt                                     47

<210> SEQ ID NO 60
<211> LENGTH: 47
<212> TYPE: DNA
<213> ORGANISM: Artificial Sequence
<220> FEATURE:
<223> OTHER INFORMATION: Synthetic

<400> SEQUENCE: 60
ggggtggtgc cggagtgggg tggcggtgcg gattccctgg ctatgcc                                      47

<210> SEQ ID NO 61
<211> LENGTH: 48
<212> TYPE: DNA
<213> ORGANISM: Artificial Sequence
<220> FEATURE:
<223> OTHER INFORMATION: Synthetic

<400> SEQUENCE: 61 tgggggggtgg tgcggcatgt ggaggcggcg ggcaggaggg ggacagtg                                    48

<210> SEQ ID NO 62
<211> LENGTH: 47
<212> TYPE: DNA
<213> ORGANISM: Artificial Sequence
<220> FEATURE:
<223> OTHER INFORMATION: Synthetic

<400> SEQUENCE: 62
ggtgggggtg tgaccggtgt gagtccggtc ccgacgcgtg gattcgg                                      47

<210> SEQ ID NO 63
<211> LENGTH: 48

```
<212> TYPE: DNA
<213> ORGANISM: Artificial Sequence
<220> FEATURE:
<223> OTHER INFORMATION: Synthetic

<400> SEQUENCE: 63
tgggaatagg gaagtgtgga tgagttctga ggataccacg ccttaccc          48

<210> SEQ ID NO 64
<211> LENGTH: 47
<212> TYPE: DNA
<213> ORGANISM: Artificial Sequence
<220> FEATURE:
<223> OTHER INFORMATION: Synthetic

<400> SEQUENCE: 64
ttgaatggtg gcagttgttg aggggaggtg tcgggggggg cgttcgt           47

<210> SEQ ID NO 65
<211> LENGTH: 47
<212> TYPE: DNA
<213> ORGANISM: Artificial Sequence
<220> FEATURE:
<223> OTHER INFORMATION: Synthetic

<400> SEQUENCE: 65
tgggaaaggg ggagagttgt gtggcgagcg ttggacggtg tgccccc           47

<210> SEQ ID NO 66
<211> LENGTH: 40
<212> TYPE: DNA
<213> ORGANISM: Artificial Sequence
<220> FEATURE:
<223> OTHER INFORMATION: Synthetic

<400> SEQUENCE: 66
cagagttgat gtaagcttcg tgttagctca actcttatcg                   40

<210> SEQ ID NO 67
<211> LENGTH: 40
<212> TYPE: DNA
<213> ORGANISM: Artificial Sequence
<220> FEATURE:
<223> OTHER INFORMATION: Synthetic

<400> SEQUENCE: 67
agggatgtgt tggatgcatg ccaggcttgg taacattgta                   40

<210> SEQ ID NO 68
<211> LENGTH: 40
<212> TYPE: DNA
<213> ORGANISM: Artificial Sequence
<220> FEATURE:
<223> OTHER INFORMATION: Synthetic

<400> SEQUENCE: 68
tcttcggttt aataaagttg gctaggaaag tttaaaaccg                   40

<210> SEQ ID NO 69
<211> LENGTH: 40
<212> TYPE: DNA
<213> ORGANISM: Artificial Sequence
<220> FEATURE:
<223> OTHER INFORMATION: Synthetic

<400> SEQUENCE: 69
```
agtgggtggt gatgaattct ggtcgcgctg acaacccgcg                40

<210> SEQ ID NO 70
<211> LENGTH: 42
<212> TYPE: DNA
<213> ORGANISM: Artificial Sequence
<220> FEATURE:
<223> OTHER INFORMATION: Synthetic

<400> SEQUENCE: 70
cgggtctcgt ctatgcagta ctcaaaacgc ttgaggtacc ga             42

<210> SEQ ID NO 71
<211> LENGTH: 40
<212> TYPE: DNA
<213> ORGANISM: Artificial Sequence
<220> FEATURE:
<223> OTHER INFORMATION: Synthetic

<400> SEQUENCE: 71
aaggcttttt taaaggctag gcttgataat cggttaactc                40

<210> SEQ ID NO 72
<211> LENGTH: 40
<212> TYPE: DNA
<213> ORGANISM: Artificial Sequence
<220> FEATURE:
<223> OTHER INFORMATION: Synthetic

<400> SEQUENCE: 72
tgtcgataaa gtgagttaag tcaccggccc ggcctattcg                40

<210> SEQ ID NO 73
<211> LENGTH: 40
<212> TYPE: DNA
<213> ORGANISM: Artificial Sequence
<220> FEATURE:
<223> OTHER INFORMATION: Synthetic

<400> SEQUENCE: 73
tcacactcgt ttctattact aaaacatcgt tcctttcagc                40

<210> SEQ ID NO 74
<211> LENGTH: 40
<212> TYPE: DNA
<213> ORGANISM: Artificial Sequence
<220> FEATURE:
<223> OTHER INFORMATION: Synthetic

<400> SEQUENCE: 74
tcacactcgt ttctattact aaaacatcgt tcctttcagc                40

<210> SEQ ID NO 75
<211> LENGTH: 40
<212> TYPE: DNA
<213> ORGANISM: Artificial Sequence
<220> FEATURE:
<223> OTHER INFORMATION: Synthetic

<400> SEQUENCE: 75
tggaaggcgg gaagattttt ggtcgacctg acaacccggt                40

<210> SEQ ID NO 76
<211> LENGTH: 40
<212> TYPE: DNA
<213> ORGANISM: Artificial Sequence
<220> FEATURE:
<223> OTHER INFORMATION: Synthetic

<400> SEQUENCE: 76
tagtaacgat taccaaaatt ctcccgaggc tgacaacccg                                40

<210> SEQ ID NO 77
<211> LENGTH: 41
<212> TYPE: DNA
<213> ORGANISM: Artificial Sequence
<220> FEATURE:
<223> OTHER INFORMATION: Synthetic

<400> SEQUENCE: 77
tcgaggtatg gccttgtcta ggcgcacctg acaacccggt g                              41

<210> SEQ ID NO 78
<211> LENGTH: 40
<212> TYPE: DNA
<213> ORGANISM: Artificial Sequence
<220> FEATURE:
<223> OTHER INFORMATION: Synthetic

<400> SEQUENCE: 78
tgtcgttaat tattcgtgat ctgacaaccc gatcactctc                                40

<210> SEQ ID NO 79
<211> LENGTH: 81
<212> TYPE: DNA
<213> ORGANISM: Artificial Sequence
<220> FEATURE:
<223> OTHER INFORMATION: Synthetic

<400> SEQUENCE: 79
agtatacgta ttacctgcag ccaccagtgt gttgaggttt gagcacactg atagagtgtc          60
acgatatctc ggagatcttg c                                                    81

<210> SEQ ID NO 80
<211> LENGTH: 81
<212> TYPE: DNA
<213> ORGANISM: Artificial Sequence
<220> FEATURE:
<223> OTHER INFORMATION: Synthetic

<400> SEQUENCE: 80
agtatacgta ttacctgcag cccatgtttt gtaggtgtaa taggtcatgt tagggtttct          60
gcgatatctc ggagatcttg c                                                    81

<210> SEQ ID NO 81
<211> LENGTH: 81
<212> TYPE: DNA
<213> ORGANISM: Artificial Sequence
<220> FEATURE:
<223> OTHER INFORMATION: Synthetic

<400> SEQUENCE: 81
agtatacgta ttacctgcag ccatctgtgt gaagactata tggcgctcac atatttcttt          60
ccgatatctc ggagatcttg c                                                    81

<210> SEQ ID NO 82
<211> LENGTH: 81
<212> TYPE: DNA
<213> ORGANISM: Artificial Sequence
<220> FEATURE:

<223> OTHER INFORMATION: Synthetic

<400> SEQUENCE: 82
agtatacgta ttacctgcag ctgaccgagt gtctggtcat tttcgatgtc tgttgttagg    60
ccgatatctc ggagatcttg c    81

<210> SEQ ID NO 83
<211> LENGTH: 81
<212> TYPE: DNA
<213> ORGANISM: Artificial Sequence
<220> FEATURE:
<223> OTHER INFORMATION: Synthetic

<400> SEQUENCE: 83
agtatacgta ttacctgcag ctgtttatgg ggataaacgt atctaattcg tgtactaatc    60
acgatatctc ggagatcttg c    81

<210> SEQ ID NO 84
<211> LENGTH: 80
<212> TYPE: DNA
<213> ORGANISM: Artificial Sequence
<220> FEATURE:
<223> OTHER INFORMATION: Synthetic

<400> SEQUENCE: 84
agtatacgta ttacctgcag ctgggaagag gtccggtaaa tgcagggtca gcccggagag    60
cgatatctcg gagatcttgc    80

<210> SEQ ID NO 85
<211> LENGTH: 88
<212> TYPE: DNA
<213> ORGANISM: Artificial Sequence
<220> FEATURE:
<223> OTHER INFORMATION: Synthetic

<400> SEQUENCE: 85
agtatacgta ttacctgcag cggtgggggt gtgaccggtg tgagtccggt cccgacgcgt    60
ggattcggcg atatctcgga gatcttgc    88

<210> SEQ ID NO 86
<211> LENGTH: 91
<212> TYPE: DNA
<213> ORGANISM: Artificial Sequence
<220> FEATURE:
<223> OTHER INFORMATION: Synthetic

<400> SEQUENCE: 86
agtatacgta ttacctgcag ctgggggggg gggctgctaa aggtttgtgg agggttaaca    60
tgtacctccc ccgatatctc ggagatcttg c    91

<210> SEQ ID NO 87
<211> LENGTH: 88
<212> TYPE: DNA
<213> ORGANISM: Artificial Sequence
<220> FEATURE:
<223> OTHER INFORMATION: Synthetic

<400> SEQUENCE: 87
agtatacgta ttacctgcag ctgggaaagg gaagtgtggg caggggaggg aggggggtgg    60
ctacatcacg atatctcgga gatcttgc    88

<210> SEQ ID NO 88
<211> LENGTH: 88
<212> TYPE: DNA
<213> ORGANISM: Artificial Sequence
<220> FEATURE:
<223> OTHER INFORMATION: Synthetic

<400> SEQUENCE: 88
agtatacgta ttacctgcag cggggtggtg ccggagtggg gtggcggtgc ggattccctg    60
gctatgcccg atatctcgga gatcttgc                                      88

<210> SEQ ID NO 89
<211> LENGTH: 86
<212> TYPE: DNA
<213> ORGANISM: Artificial Sequence
<220> FEATURE:
<223> OTHER INFORMATION: Synthetic

<400> SEQUENCE: 89
agtatacgta ttacctgcag ctttgatggt gcggtggctt acatatgcgt tctacattgc    60
gttcggcgat atctcggaga tcttgc                                        86

<210> SEQ ID NO 90
<211> LENGTH: 88
<212> TYPE: DNA
<213> ORGANISM: Artificial Sequence
<220> FEATURE:
<223> OTHER INFORMATION: Synthetic

<400> SEQUENCE: 90
agtatacgta ttacctgcag ctgggggtg gtgcggtgtg tgacaaggga gcatagccgg    60
gggccagtcg atatctcgga gatcttgc                                      88

<210> SEQ ID NO 91
<211> LENGTH: 81
<212> TYPE: DNA
<213> ORGANISM: Artificial Sequence
<220> FEATURE:
<223> OTHER INFORMATION: Synthetic

<400> SEQUENCE: 91
agtatacgta ttacctgcag cccagcgaag gaaagtcttg gttggtctag tttttcgtgt    60
gcgatatctc ggagatcttg c                                             81

<210> SEQ ID NO 92
<211> LENGTH: 81
<212> TYPE: DNA
<213> ORGANISM: Artificial Sequence
<220> FEATURE:
<223> OTHER INFORMATION: Synthetic

<400> SEQUENCE: 92
agtatacgta ttacctgcag cctacgtgtg cgttccgatt gtttaaattg ctcaatgtat    60
gcgatatctc ggagatcttg c                                             81

<210> SEQ ID NO 93
<211> LENGTH: 81
<212> TYPE: DNA
<213> ORGANISM: Artificial Sequence
<220> FEATURE:
<223> OTHER INFORMATION: Synthetic

<400> SEQUENCE: 93

```
agtatacgta ttacctgcag ccacaccacc tgaattccag cacactggcg gccgttacta      60
gcgatatctc ggagatcttg c                                                81

<210> SEQ ID NO 94
<211> LENGTH: 81
<212> TYPE: DNA
<213> ORGANISM: Artificial Sequence
<220> FEATURE:
<223> OTHER INFORMATION: Synthetic

<400> SEQUENCE: 94
agtatacgta ttacctgcag ctcggcatag gtcaagtcgc ttcatttgga ttaagttgag      60
gcgatatctc ggagatcttg c                                                81

<210> SEQ ID NO 95
<211> LENGTH: 81
<212> TYPE: DNA
<213> ORGANISM: Artificial Sequence
<220> FEATURE:
<223> OTHER INFORMATION: Synthetic

<400> SEQUENCE: 95
agtatacgta ttacctgcag ccgagggata catgctgact atggaattat ttgaattccc      60
acgatatctc ggagatcttg c                                                81

<210> SEQ ID NO 96
<211> LENGTH: 81
<212> TYPE: DNA
<213> ORGANISM: Artificial Sequence
<220> FEATURE:
<223> OTHER INFORMATION: Synthetic

<400> SEQUENCE: 96
agtatacgta ttacctgcag ctcgacatta tgtttgacat cgattgttaa tgtttctttg      60
ccgatatctc ggagatcttg c                                                81

<210> SEQ ID NO 97
<211> LENGTH: 89
<212> TYPE: DNA
<213> ORGANISM: Artificial Sequence
<220> FEATURE:
<223> OTHER INFORMATION: Synthetic

<400> SEQUENCE: 97
agtatacgta ttacctgcag ctgggggtg gtgcggtgtg tgacaaggga gcatagccgg       60
gggccccctc gatatctcgg agatcttgc                                        89

<210> SEQ ID NO 98
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3, 4, 7, 8
<223> OTHER INFORMATION: n = A,T,C or G

<400> SEQUENCE: 98 tgnnagnn                                                                8

<210> SEQ ID NO 99
<211> LENGTH: 10
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1, 2, 3, 7, 8, 9
<223> OTHER INFORMATION: n = A,T,C or G

<400> SEQUENCE: 99 nnntgtnnng                                                                  10

<210> SEQ ID NO 100
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: n = A,T,C or G

<400> SEQUENCE: 100 aggtnt                                                                       6

<210> SEQ ID NO 101
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: n = A,T,C or G

<400> SEQUENCE: 101 tgggna                                                                       6

<210> SEQ ID NO 102
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 2, 5
<223> OTHER INFORMATION: n = A,T,C or G

<400> SEQUENCE: 102 gnganaa                                                                      7

<210> SEQ ID NO 103
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6
<223> OTHER INFORMATION: n = A,T,C or G

<400> SEQUENCE: 103 tgggnng                                                                      7

<210> SEQ ID NO 104
```

```
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3, 4
<223> OTHER INFORMATION: n = A,T,C or G

<400> SEQUENCE: 104 tcnngta                                                                    7

<210> SEQ ID NO 105
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 4
<223> OTHER INFORMATION: n = A,T,C or G

<400> SEQUENCE: 105 ggtncggt                                                                   8

<210> SEQ ID NO 106
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 7
<223> OTHER INFORMATION: n = A,T,C or G

<400> SEQUENCE: 106 taaangna                                                                   8

<210> SEQ ID NO 107
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6, 7, 11, 14
<223> OTHER INFORMATION: n = A,T,C or G

<400> SEQUENCE: 107
tgttnnnggg natnaa                                                         16

<210> SEQ ID NO 108
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 9
<223> OTHER INFORMATION: n = A,T,C or G

<400> SEQUENCE: 108
taatncgtnt actaatca                                                       18
```

```
<210> SEQ ID NO 109
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6, 8, 12
<223> OTHER INFORMATION: n = A,T,C or G

<400> SEQUENCE: 109
tgggnngngg tncggt                                                      16

<210> SEQ ID NO 110
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6
<223> OTHER INFORMATION: r = G or A
<220> FEATURE:
<221> NAME/KEY: misc_feature
<222> LOCATION: 7
<223> OTHER INFORMATION: k = G or T

<400> SEQUENCE: 110 tgggrrk                                                                7

<210> SEQ ID NO 111
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6, 9, 10, 14
<223> OTHER INFORMATION: r = G or A
<220> FEATURE:
<221> NAME/KEY: misc_feature
<222> LOCATION: 7, 15
<223> OTHER INFORMATION: k = G or T
<220> FEATURE:
<221> NAME/KEY: misc_feature
<222> LOCATION: 8
<223> OTHER INFORMATION: w = A or T
<220> FEATURE:
<221> NAME/KEY: misc_feature
<222> LOCATION: 11, 13, 16
<223> OTHER INFORMATION: y = T or C
<220> FEATURE:
<221> NAME/KEY: misc_feature
<222> LOCATION: 12
<223> OTHER INFORMATION: s = G or C

<400> SEQUENCE: 111
tgggrrkwrr ysyrky                                                      16

<210> SEQ ID NO 112
<211> LENGTH: 8
<212> TYPE: DNA
<213> ORGANISM: Artificial Sequence
<220> FEATURE:
<223> OTHER INFORMATION: Synthetic

<400> SEQUENCE: 112 tgatagag                                                               8
```

<210> SEQ ID NO 113
<211> LENGTH: 8
<212> TYPE: DNA
<213> ORGANISM: Artificial Sequence
<220> FEATURE:
<223> OTHER INFORMATION: Synthetic

<400> SEQUENCE: 113 tgttaggg                                                                 8

<210> SEQ ID NO 114
<211> LENGTH: 8
<212> TYPE: DNA
<213> ORGANISM: Artificial Sequence
<220> FEATURE:
<223> OTHER INFORMATION: Synthetic

<400> SEQUENCE: 114 tgttaggc                                                                 8

<210> SEQ ID NO 115
<211> LENGTH: 10
<212> TYPE: DNA
<213> ORGANISM: Artificial Sequence
<220> FEATURE:
<223> OTHER INFORMATION: Synthetic

<400> SEQUENCE: 115
cagtgtgttg                                                              10

<210> SEQ ID NO 116
<211> LENGTH: 10
<212> TYPE: DNA
<213> ORGANISM: Artificial Sequence
<220> FEATURE:
<223> OTHER INFORMATION: Synthetic

<400> SEQUENCE: 116
ccatgttttg                                                              10

<210> SEQ ID NO 117
<211> LENGTH: 10
<212> TYPE: DNA
<213> ORGANISM: Artificial Sequence
<220> FEATURE:
<223> OTHER INFORMATION: Synthetic

<400> SEQUENCE: 117
ctgtgtgaag                                                              10

<210> SEQ ID NO 118
<211> LENGTH: 10
<212> TYPE: DNA
<213> ORGANISM: Artificial Sequence
<220> FEATURE:
<223> OTHER INFORMATION: Synthetic

<400> SEQUENCE: 118
gagtgtctgg                                                              10

<210> SEQ ID NO 119
<211> LENGTH: 6
<212> TYPE: DNA
<213> ORGANISM: Artificial Sequence
<220> FEATURE:
<223> OTHER INFORMATION: Synthetic

```
<400> SEQUENCE: 119 aggttt                                                              6

<210> SEQ ID NO 120
<211> LENGTH: 6
<212> TYPE: DNA
<213> ORGANISM: Artificial Sequence
<220> FEATURE:
<223> OTHER INFORMATION: Synthetic

<400> SEQUENCE: 120 aggtgt                                                              6

<210> SEQ ID NO 121
<211> LENGTH: 6
<212> TYPE: DNA
<213> ORGANISM: Artificial Sequence
<220> FEATURE:
<223> OTHER INFORMATION: Synthetic

<400> SEQUENCE: 121 tgggga                                                              6

<210> SEQ ID NO 122
<211> LENGTH: 6
<212> TYPE: DNA
<213> ORGANISM: Artificial Sequence
<220> FEATURE:
<223> OTHER INFORMATION: Synthetic

<400> SEQUENCE: 122 tgggaa                                                              6

<210> SEQ ID NO 123
<211> LENGTH: 7
<212> TYPE: DNA
<213> ORGANISM: Artificial Sequence
<220> FEATURE:
<223> OTHER INFORMATION: Synthetic

<400> SEQUENCE: 123 gggataa                                                             7

<210> SEQ ID NO 124
<211> LENGTH: 7
<212> TYPE: DNA
<213> ORGANISM: Artificial Sequence
<220> FEATURE:
<223> OTHER INFORMATION: Synthetic

<400> SEQUENCE: 124 gtgacaa                                                             7

<210> SEQ ID NO 125
<211> LENGTH: 7
<212> TYPE: DNA
<213> ORGANISM: Artificial Sequence
<220> FEATURE:
<223> OTHER INFORMATION: Synthetic

<400> SEQUENCE: 125 tgggggg                                                             7

<210> SEQ ID NO 126
```

```
<211> LENGTH: 7
<212> TYPE: DNA
<213> ORGANISM: Artificial Sequence
<220> FEATURE:
<223> OTHER INFORMATION: Synthetic

<400> SEQUENCE: 126 tgggaag                                                                    7

<210> SEQ ID NO 127
<211> LENGTH: 7
<212> TYPE: DNA
<213> ORGANISM: Artificial Sequence
<220> FEATURE:
<223> OTHER INFORMATION: Synthetic

<400> SEQUENCE: 127 tcgtgta                                                                    7

<210> SEQ ID NO 128
<211> LENGTH: 7
<212> TYPE: DNA
<213> ORGANISM: Artificial Sequence
<220> FEATURE:
<223> OTHER INFORMATION: Synthetic

<400> SEQUENCE: 128 tccggta                                                                    7

<210> SEQ ID NO 129
<211> LENGTH: 8
<212> TYPE: DNA
<213> ORGANISM: Artificial Sequence
<220> FEATURE:
<223> OTHER INFORMATION: Synthetic

<400> SEQUENCE: 129 ggtgcggt                                                                   8

<210> SEQ ID NO 130
<211> LENGTH: 8
<212> TYPE: DNA
<213> ORGANISM: Artificial Sequence
<220> FEATURE:
<223> OTHER INFORMATION: Synthetic

<400> SEQUENCE: 130 ggtccggt                                                                   8

<210> SEQ ID NO 131
<211> LENGTH: 8
<212> TYPE: DNA
<213> ORGANISM: Artificial Sequence
<220> FEATURE:
<223> OTHER INFORMATION: Synthetic

<400> SEQUENCE: 131 taaacgta                                                                   8

<210> SEQ ID NO 132
<211> LENGTH: 8
<212> TYPE: DNA
<213> ORGANISM: Artificial Sequence
<220> FEATURE:
<223> OTHER INFORMATION: Synthetic

<400> SEQUENCE: 132
``` taaatgca                                                          8

<210> SEQ ID NO 133
<211> LENGTH: 16
<212> TYPE: DNA
<213> ORGANISM: Artificial Sequence
<220> FEATURE:
<223> OTHER INFORMATION: Synthetic

<400> SEQUENCE: 133
tgtttatggg gataaa                                                 16

<210> SEQ ID NO 134
<211> LENGTH: 16
<212> TYPE: DNA
<213> ORGANISM: Artificial Sequence
<220> FEATURE:
<223> OTHER INFORMATION: Synthetic

<400> SEQUENCE: 134
tgttaagggg aattaa                                                 16

<210> SEQ ID NO 135
<211> LENGTH: 16
<212> TYPE: DNA
<213> ORGANISM: Artificial Sequence
<220> FEATURE:
<223> OTHER INFORMATION: Synthetic

<400> SEQUENCE: 135
tgttaggggg aattaa                                                 16

<210> SEQ ID NO 136
<211> LENGTH: 18
<212> TYPE: DNA
<213> ORGANISM: Artificial Sequence
<220> FEATURE:
<223> OTHER INFORMATION: Synthetic

<400> SEQUENCE: 136
taattcgtgt actaatca                                               18

<210> SEQ ID NO 137
<211> LENGTH: 18
<212> TYPE: DNA
<213> ORGANISM: Artificial Sequence
<220> FEATURE:
<223> OTHER INFORMATION: Synthetic

<400> SEQUENCE: 137
taatccgtct actaatca                                               18

<210> SEQ ID NO 138
<211> LENGTH: 16
<212> TYPE: DNA
<213> ORGANISM: Artificial Sequence
<220> FEATURE:
<223> OTHER INFORMATION: Synthetic

<400> SEQUENCE: 138 tgggggtgg tgcggt                                                  16

<210> SEQ ID NO 139
<211> LENGTH: 16
<212> TYPE: DNA

```
<213> ORGANISM: Artificial Sequence
<220> FEATURE:
<223> OTHER INFORMATION: Synthetic

<400> SEQUENCE: 139
tgggaagagg tccggt                                                    16

<210> SEQ ID NO 140
<211> LENGTH: 7
<212> TYPE: DNA
<213> ORGANISM: Artificial Sequence
<220> FEATURE:
<223> OTHER INFORMATION: Synthetic

<400> SEQUENCE: 140 tggggat                                                               7

<210> SEQ ID NO 141
<211> LENGTH: 7
<212> TYPE: DNA
<213> ORGANISM: Artificial Sequence
<220> FEATURE:
<223> OTHER INFORMATION: Synthetic

<400> SEQUENCE: 141 tgggggg                                                               7

<210> SEQ ID NO 142
<211> LENGTH: 7
<212> TYPE: DNA
<213> ORGANISM: Artificial Sequence
<220> FEATURE:
<223> OTHER INFORMATION: Synthetic

<400> SEQUENCE: 142 tgggaag                                                               7

<210> SEQ ID NO 143
<211> LENGTH: 16
<212> TYPE: DNA
<213> ORGANISM: Artificial Sequence
<220> FEATURE:
<223> OTHER INFORMATION: Synthetic

<400> SEQUENCE: 143
tggggataaa cgtatc                                                    16

<210> SEQ ID NO 144
<211> LENGTH: 16
<212> TYPE: DNA
<213> ORGANISM: Artificial Sequence
<220> FEATURE:
<223> OTHER INFORMATION: Synthetic

<400> SEQUENCE: 144 tgggggtgg tgcggt                                                     16

<210> SEQ ID NO 145
<211> LENGTH: 16
<212> TYPE: DNA
<213> ORGANISM: Artificial Sequence
<220> FEATURE:
<223> OTHER INFORMATION: Synthetic

<400> SEQUENCE: 145
tgggaagagg tccggt                                                    16
```

<210> SEQ ID NO 146
<211> LENGTH: 81
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 22, 23, 24, 25, 26, 27, 28, 29, 30, 31, 32, 33, 34, 35,
      36, 37, 38, 39, 40, 41, 42, 43, 44, 45, 46, 47, 48, 49, 50,
      51, 52, 53, 54, 55, 56, 57, 58, 59, 60, 61
<223> OTHER INFORMATION: n = A,T,C or G

<400> SEQUENCE: 146
agtatacgta ttacctgcag cnnnnnnnnn nnnnnnnnnn nnnnnnnnnn nnnnnnnnnn    60
ncgatatctc ggagatcttg c                                              81

<210> SEQ ID NO 147
<211> LENGTH: 21
<212> TYPE: DNA
<213> ORGANISM: Artificial Sequence
<220> FEATURE:
<223> OTHER INFORMATION: Synthetic

<400> SEQUENCE: 147
agtatacgta ttacctgcag c                                              21

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
gcaagatctc cgagatatcg                                                20

<210> SEQ ID NO 149
<211> LENGTH: 26
<212> TYPE: DNA
<213> ORGANISM: Artificial Sequence
<220> FEATURE:
<223> OTHER INFORMATION: Synthetic

<400> SEQUENCE: 149
caagagtcaa tgtttaggtg gatgag                                         26

<210> SEQ ID NO 150
<211> LENGTH: 21
<212> TYPE: DNA
<213> ORGANISM: Artificial Sequence
<220> FEATURE:
<223> OTHER INFORMATION: Synthetic

<400> SEQUENCE: 150
tcgacgccat cttcattcac a                                              21

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
tgggagggcg atcgcaatct                                              20

<210> SEQ ID NO 152
<211> LENGTH: 34
<212> TYPE: DNA
<213> ORGANISM: Artificial Sequence
<220> FEATURE:
<223> OTHER INFORMATION: Synthetic

<400> SEQUENCE: 152
gcacggatcc tcaagaacta aaccatttac tgtc                              34

<210> SEQ ID NO 153
<211> LENGTH: 33
<212> TYPE: DNA
<213> ORGANISM: Artificial Sequence
<220> FEATURE:
<223> OTHER INFORMATION: Synthetic

<400> SEQUENCE: 153
ggacgcggcc gcttataaag cacgtctacg ccc                               33

<210> SEQ ID NO 154
<211> LENGTH: 45
<212> TYPE: DNA
<213> ORGANISM: Artificial Sequence
<220> FEATURE:
<223> OTHER INFORMATION: Synthetic

<400> SEQUENCE: 154
taatacgact caactatagc aagagtcaat gtttaggtgg atgag                  45

<210> SEQ ID NO 155
<211> LENGTH: 22
<212> TYPE: DNA
<213> ORGANISM: Artificial Sequence
<220> FEATURE:
<223> OTHER INFORMATION: Synthetic

<400> SEQUENCE: 155
gttgggaaat tcggtgggac tg                                           22

<210> SEQ ID NO 156
<211> LENGTH: 31
<212> TYPE: DNA
<213> ORGANISM: Artificial Sequence
<220> FEATURE:
<223> OTHER INFORMATION: Synthetic

<400> SEQUENCE: 156
gcacggatcc tttttagtcc ctcctacggt g                                 31

<210> SEQ ID NO 157
<211> LENGTH: 30
<212> TYPE: DNA
<213> ORGANISM: Artificial Sequence
<220> FEATURE:
<223> OTHER INFORMATION: Synthetic

<400> SEQUENCE: 157
ggacgcggcc gcttatcggc gcagaccaag                                   30

<210> SEQ ID NO 158
<211> LENGTH: 30
<212> TYPE: DNA
<213> ORGANISM: Artificial Sequence
<220> FEATURE:
<223> OTHER INFORMATION: Synthetic

<400> SEQUENCE: 158
ccggaattcg gaaagaacaa aggcaagacc					30

<210> SEQ ID NO 159
<211> LENGTH: 35
<212> TYPE: DNA
<213> ORGANISM: Artificial Sequence
<220> FEATURE:
<223> OTHER INFORMATION: Synthetic

<400> SEQUENCE: 159
ccgctcgagt tcaaaattga tcttttcatt ataat					35

<210> SEQ ID NO 160
<211> LENGTH: 30
<212> TYPE: DNA
<213> ORGANISM: Artificial Sequence
<220> FEATURE:
<223> OTHER INFORMATION: Synthetic

<400> SEQUENCE: 160
ccggaattcg ccaagggcaa gacaaaaagg					30

<210> SEQ ID NO 161
<211> LENGTH: 36
<212> TYPE: DNA
<213> ORGANISM: Artificial Sequence
<220> FEATURE:
<223> OTHER INFORMATION: Synthetic

<400> SEQUENCE: 161
ccgctcgagc tactcgtcgt aataatcatc actggg					36

<210> SEQ ID NO 162
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3
<223> OTHER INFORMATION: w = A or T
<220> FEATURE:
<221> NAME/KEY: misc_feature
<222> LOCATION: 4
<223> OTHER INFORMATION: k = G or T
<220> FEATURE:
<221> NAME/KEY: misc_feature
<222> LOCATION: 7
<223> OTHER INFORMATION: v = A or G or C
<220> FEATURE:
<221> NAME/KEY: misc_feature
<222> LOCATION: 8
<223> OTHER INFORMATION: s = G or C

<400> SEQUENCE: 162 tgwkagvs					8

<210> SEQ ID NO 163
<211> LENGTH: 10
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: 1
<223> OTHER INFORMATION: s = G or C
<220> FEATURE:
<221> NAME/KEY: misc_feature
<222> LOCATION: 2
<223> OTHER INFORMATION: h = A or C or T
<220> FEATURE:
<221> NAME/KEY: misc_feature
<222> LOCATION: 3
<223> OTHER INFORMATION: r = G or A
<220> FEATURE:
<221> NAME/KEY: misc_feature
<222> LOCATION: 7
<223> OTHER INFORMATION: b = G or C or T
<220> FEATURE:
<221> NAME/KEY: misc_feature
<222> LOCATION: 8
<223> OTHER INFORMATION: w = A or T
<220> FEATURE:
<221> NAME/KEY: misc_feature
<222> LOCATION: (9)...(9)
<223> OTHER INFORMATION: d = A or G or T

<400> SEQUENCE: 163 shrtgtbwdg                                                              10

<210> SEQ ID NO 164
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: k = G or T

<400> SEQUENCE: 164 aggtkt                                                                   6

<210> SEQ ID NO 165
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: r = G or A

<400> SEQUENCE: 165 tgggra                                                                   6

<210> SEQ ID NO 166
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 2
<223> OTHER INFORMATION: k = G or T
<220> FEATURE:
<221> NAME/KEY: misc_feature
<222> LOCATION: 5
<223> OTHER INFORMATION: y = T or C

<400> SEQUENCE: 166 gkgayaa                                                                  7
```

```
<210> SEQ ID NO 167
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6
<223> OTHER INFORMATION: r = G or A

<400> SEQUENCE: 167 tgggrrg                                                                 7

<210> SEQ ID NO 168
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3
<223> OTHER INFORMATION: s = G or C
<220> FEATURE:
<221> NAME/KEY: misc_feature
<222> LOCATION: 4
<223> OTHER INFORMATION: k = G or T

<400> SEQUENCE: 168 tcskgta                                                                 7

<210> SEQ ID NO 169
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 4
<223> OTHER INFORMATION: s = G or C

<400> SEQUENCE: 169 ggtscggt                                                                8

<210> SEQ ID NO 170
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 7
<223> OTHER INFORMATION: y = T or C

<400> SEQUENCE: 170 taaaygya                                                                8

<210> SEQ ID NO 171
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 14
```

```
<223> OTHER INFORMATION: w = A or T
<220> FEATURE:
<221> NAME/KEY: misc_feature
<222> LOCATION: 6, 11
<223> OTHER INFORMATION: r = G or A
<220> FEATURE:
<221> NAME/KEY: misc_feature
<222> LOCATION: 7
<223> OTHER INFORMATION: k = G or T

<400> SEQUENCE: 171
tgttwrkggg ratwaa                                                        16

<210> SEQ ID NO 172
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: y = T or C
<220> FEATURE:
<221> NAME/KEY: misc_feature
<222> LOCATION: 9
<223> OTHER INFORMATION: s = G or C

<400> SEQUENCE: 172
taatycgtst actaatca                                                      18

<210> SEQ ID NO 173
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6
<223> OTHER INFORMATION: r = G or A
<220> FEATURE:
<221> NAME/KEY: misc_feature
<222> LOCATION: 8
<223> OTHER INFORMATION: w = A or T
<220> FEATURE:
<221> NAME/KEY: misc_feature
<222> LOCATION: 12
<223> OTHER INFORMATION: s = G or C

<400> SEQUENCE: 173
tgggrrgwgg tscggt                                                        16

<210> SEQ ID NO 174
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5, 6
<223> OTHER INFORMATION: r = G or A
<220> FEATURE:
<221> NAME/KEY: misc_feature
<222> LOCATION: 8
<223> OTHER INFORMATION: w = A or T
<220> FEATURE:
<221> NAME/KEY: misc_feature
<222> LOCATION: 12
<223> OTHER INFORMATION: s = G or C

<400> SEQUENCE: 174
```
tgggrrgwgg tscggt                                                16

<210> SEQ ID NO 175
<211> LENGTH: 19
<212> TYPE: DNA
<213> ORGANISM: Artificial Sequence
<220> FEATURE:
<223> OTHER INFORMATION: Synthetic

<400> SEQUENCE: 175
gacgccatct tcattcaca                                             19

<210> SEQ ID NO 176
<211> LENGTH: 40
<212> TYPE: DNA
<213> ORGANISM: Artificial Sequence
<220> FEATURE:
<223> OTHER INFORMATION: Synthetic

<400> SEQUENCE: 176
caggattagt catggaatag ccgacgatca tgacccattg                      40

<210> SEQ ID NO 177
<211> LENGTH: 40
<212> TYPE: DNA
<213> ORGANISM: Artificial Sequence
<220> FEATURE:
<223> OTHER INFORMATION: Synthetic

<400> SEQUENCE: 177
cagcgaaggg acagttctac gaatgtgaac atgaggtagc                      40

<210> SEQ ID NO 178
<211> LENGTH: 38
<212> TYPE: DNA
<213> ORGANISM: Artificial Sequence
<220> FEATURE:
<223> OTHER INFORMATION: Synthetic

<400> SEQUENCE: 178
tgttggattg atcctaatta cggatattta cacgaatg                        38

<210> SEQ ID NO 179
<211> LENGTH: 40
<212> TYPE: DNA
<213> ORGANISM: Artificial Sequence
<220> FEATURE:
<223> OTHER INFORMATION: Synthetic

<400> SEQUENCE: 179
tcacggcgaa tcgaagggac gccgcgaagt gtaccaagtg                      40

<210> SEQ ID NO 180
<211> LENGTH: 40
<212> TYPE: DNA
<213> ORGANISM: Artificial Sequence
<220> FEATURE:
<223> OTHER INFORMATION: Synthetic

<400> SEQUENCE: 180
ctggtccagt caaggggatt agatgagggg taatggagag                      40

<210> SEQ ID NO 181
<211> LENGTH: 40
<212> TYPE: DNA

```
<213> ORGANISM: Artificial Sequence
<220> FEATURE:
<223> OTHER INFORMATION: Synthetic

<400> SEQUENCE: 181
ccgagtaggg ccggtcgtca cggagaagca gggtgagcgt                           40

<210> SEQ ID NO 182
<211> LENGTH: 7
<212> TYPE: DNA
<213> ORGANISM: Artificial Sequence
<220> FEATURE:
<223> OTHER INFORMATION: Synthetic

<400> SEQUENCE: 182 acgaatg                                                                7

<210> SEQ ID NO 183
<211> LENGTH: 6
<212> TYPE: DNA
<213> ORGANISM: Artificial Sequence
<220> FEATURE:
<223> OTHER INFORMATION: Synthetic

<400> SEQUENCE: 183 acggat                                                                 6

<210> SEQ ID NO 184
<211> LENGTH: 9
<212> TYPE: DNA
<213> ORGANISM: Artificial Sequence
<220> FEATURE:
<223> OTHER INFORMATION: Synthetic

<400> SEQUENCE: 184 cgaagggac                                                              9

<210> SEQ ID NO 185
<211> LENGTH: 10
<212> TYPE: DNA
<213> ORGANISM: Artificial Sequence
<220> FEATURE:
<223> OTHER INFORMATION: Synthetic

<400> SEQUENCE: 185
cgaagtgtac                                                            10

<210> SEQ ID NO 186
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3
<223> OTHER INFORMATION: n = A,T,C or G

<400> SEQUENCE: 186 ggngagcg                                                               8

<210> SEQ ID NO 187
<211> LENGTH: 6
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: 1,4
<223> OTHER INFORMATION: n = A,T,C or G

<400> SEQUENCE: 187 ngtngg                                                                        6

<210> SEQ ID NO 188
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1,5
<223> OTHER INFORMATION: n = A,T,C or G

<400> SEQUENCE: 188 nggtng                                                                        6

<210> SEQ ID NO 189
<211> LENGTH: 7
<212> TYPE: DNA
<213> ORGANISM: Artificial Sequence
<220> FEATURE:
<223> OTHER INFORMATION: Synthetic

<400> SEQUENCE: 189 ggattag                                                                       7

<210> SEQ ID NO 190
<211> LENGTH: 7
<212> TYPE: DNA
<213> ORGANISM: Artificial Sequence
<220> FEATURE:
<223> OTHER INFORMATION: Synthetic

<400> SEQUENCE: 190 ggaatag                                                                       7

<210> SEQ ID NO 191
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3
<223> OTHER INFORMATION: w = A or T

<400> SEQUENCE: 191 ggwgagcg                                                                      8

<210> SEQ ID NO 192
<211> LENGTH: 8
<212> TYPE: DNA
<213> ORGANISM: Artificial Sequence
<220> FEATURE:
<223> OTHER INFORMATION: Synthetic

<400> SEQUENCE: 192 ggagagcg                                                                      8

<210> SEQ ID NO 193
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 193 ggtgagcg                                                                    8

<210> SEQ ID NO 194
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1,4
<223> OTHER INFORMATION: w = A or T

<400> SEQUENCE: 194 wgtwgg                                                                      6

<210> SEQ ID NO 195
<211> LENGTH: 6
<212> TYPE: DNA
<213> ORGANISM: Artificial Sequence
<220> FEATURE:
<223> OTHER INFORMATION: Synthetic

<400> SEQUENCE: 195 agtagg                                                                      6

<210> SEQ ID NO 196
<211> LENGTH: 6
<212> TYPE: DNA
<213> ORGANISM: Artificial Sequence
<220> FEATURE:
<223> OTHER INFORMATION: Synthetic

<400> SEQUENCE: 196 tgttgg                                                                      6

<210> SEQ ID NO 197
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1,5
<223> OTHER INFORMATION: m = A or C

<400> SEQUENCE: 197 mggtmg                                                                      6

<210> SEQ ID NO 198
<211> LENGTH: 6
<212> TYPE: DNA
<213> ORGANISM: Artificial Sequence
<220> FEATURE:
<223> OTHER INFORMATION: Synthetic

<400> SEQUENCE: 198 aggtag                                                                      6
```

```
<210> SEQ ID NO 199
<211> LENGTH: 6
<212> TYPE: DNA
<213> ORGANISM: Artificial Sequence
<220> FEATURE:
<223> OTHER INFORMATION: Synthetic

<400> SEQUENCE: 199 cggtcg                                                                    6
```